(12) United States Patent
Johnson et al.

(10) Patent No.: US 10,294,504 B2
(45) Date of Patent: *May 21, 2019

(54) MUTANT ENDOGLYCOCERAMIDASES WITH ENHANCED SYNTHETIC ACTIVITY

(71) Applicants: La Jolla Pharmaceutical Company, San Diego, CA (US); The University of British Columbia, Vancouver (CA)

(72) Inventors: Karl F. Johnson, Willow Grove, PA (US); Shawn Defrees, San Marcos, CA (US); Stephen Withers, Vancouver (CA); Mark Vaughan, Vancouver (CA)

(73) Assignees: La Jolla Pharmaceutical Company, San Diego, CA (US); The University of British Columbia, Vancouver (CA)

(*) Notice: Subject to any disclaimer, the term of this patent is extended or adjusted under 35 U.S.C. 154(b) by 344 days.

This patent is subject to a terminal disclaimer.

(21) Appl. No.: 14/754,310

(22) Filed: Jun. 29, 2015

(65) Prior Publication Data

US 2016/0032342 A1  Feb. 4, 2016

Related U.S. Application Data

(60) Continuation of application No. 13/950,259, filed on Jul. 24, 2013, now Pat. No. 9,068,208, which is a division of application No. 11/596,942, filed as application No. PCT/US2005/019451 on Jun. 1, 2005, now abandoned.

(60) Provisional application No. 60/666,765, filed on Mar. 29, 2005, provisional application No. 60/626,791, filed on Nov. 10, 2004, provisional application No. 60/576,316, filed on Jun. 1, 2004.

(51) Int. Cl.
*C12N 9/24* (2006.01)
*C12P 19/26* (2006.01)

(52) U.S. Cl.
CPC ............ *C12P 19/26* (2013.01); *C12N 9/2402* (2013.01); *C12Y 302/01123* (2013.01)

(58) Field of Classification Search
CPC combination set(s) only.
See application file for complete search history.

(56) References Cited

U.S. PATENT DOCUMENTS 5,716,812 A  2/1998  Withers et al.

FOREIGN PATENT DOCUMENTS

WO  WO 03/018605 A2  3/2003

OTHER PUBLICATIONS

Hilden, Lars, et al, "Recent Developments of Cellulases and Carbohydrate-Binding Modules with Cellulose Affinity", Biotechnology Letters, vol. 26, p. 1683-1693 (2004).
Horibata Y., et al, "Transglycosylation and Reverse Hydrolysis Reactions of Endoglycoceramidase from the Jellyfish, *Cyanea nozakii*", J. Biochem. vol. 130, No. 2, p. 263-268 (2001).
Izu, H., et al, "Molecular Cloning, Expression, and Sequence Analysis of the Endoglycoceramidase II Gene from *Rhodococcus* Species", J. of Biol. Chem., vol. 272, No. 32, p. 19846-19850 (1997).
Mackenzie, L., et al., "Glycosynthases: Mutant glycosidases for oligosaccharide synthesis," J. Am. Chem. Soc., vol. 120, pp. 5583-5584 (1998).
Malet, C. et al., "From β-glucanase to β-glucansynthase: glycosyl transfer to α-glycosyl fluorides catalyzed by a mutant endoglucanase lacking its catalytic nucleophile," FEBS Letters, vol. 440, p. 108-212 (1998).
Perugino, G., et al., "Oligosaccharide synthesis by glycosynthases," Trends in Biotechnology, vol. 22, No. 1, p. 31-37 (Jan. 2004).
Sakaguchi, K., et al., "Cloning and Expression of Gene Encoding a Novel Endoglycoceramidase of *Rhodococcus* sp. Strain C9," J. Biochem, vol. 128, p. 145-152 (2000).
Sakaguchi, K., et al., "The Glu Residue in the Conserved Asn-Glu-Pro Sequence of Endoglycoceramidase is Essential for Enzymatic Activity," Biochemical and Biophysical Research Communications, vol. 260, p. 89-93 (1999).
Sonnino, S., et al., "Ganglioside Molecular Species Containing C18- and C20-Sphingosine in Mammalian Nervous Tissues and Neuronal Cell Cultures", Biochimica et Biophysica Acta (BBA), vol. 1469, issue 2, p. 63-77 (Sep. 18, 2000).
Vaughan, M., et al., "Glycosynthase-mediated synthesis of glycosphingolipids," J. Am. Chem. Soc., vol. 128, No. 17, p. 6300-6301 (2006).
Wang, Q., et al., "Glu$^{280}$ is the nucleophile in the active site of *Clostridium thermocellum* CelC, a family A endo-β-1,4-glucanase," J. Biol. Chem., vol. 268, No. 19, p. 14096-14102 (1993).
Williams, S. et al., "Glycosyl Fluorides in Enzymatic Reactions", Carbohydrate Research, vol. 327, p. 27-46 (2000).

*Primary Examiner* — Kagnew H Gebreyesus
(74) *Attorney, Agent, or Firm* — Foley Hoag LLP; David P. Halstead; Lucas P. Watkins

(57) ABSTRACT

The present invention relates to a novel endoglycoceramidase whose hydrolytic activity has been substantially reduced or eliminated, such that the enzyme is useful for synthesis of glycolipids from a monosaccharide or oligosaccharide and a ceramide. More specifically, the endoglycoceramidase is a mutant version of a naturally occurring endoglycoceramidase, preferably comprising a mutation within the active site or the nucleophilic site of the enzyme and more preferably comprising a substitution mutation of the Glu residue within the active site or the nucleophilic site. Also disclosed are a method for generating the mutant endoglycoceramidase and a method for enzymatically synthesizing glycolipids using this mutant enzyme.

16 Claims, 31 Drawing Sheets

Specification includes a Sequence Listing.

$R_1$ = H, alkyl, fatty acid, hydroxyfatty acid, unsaturated fatty acid, unsaturatedhydroxyfatty acid.
n = 0-40.

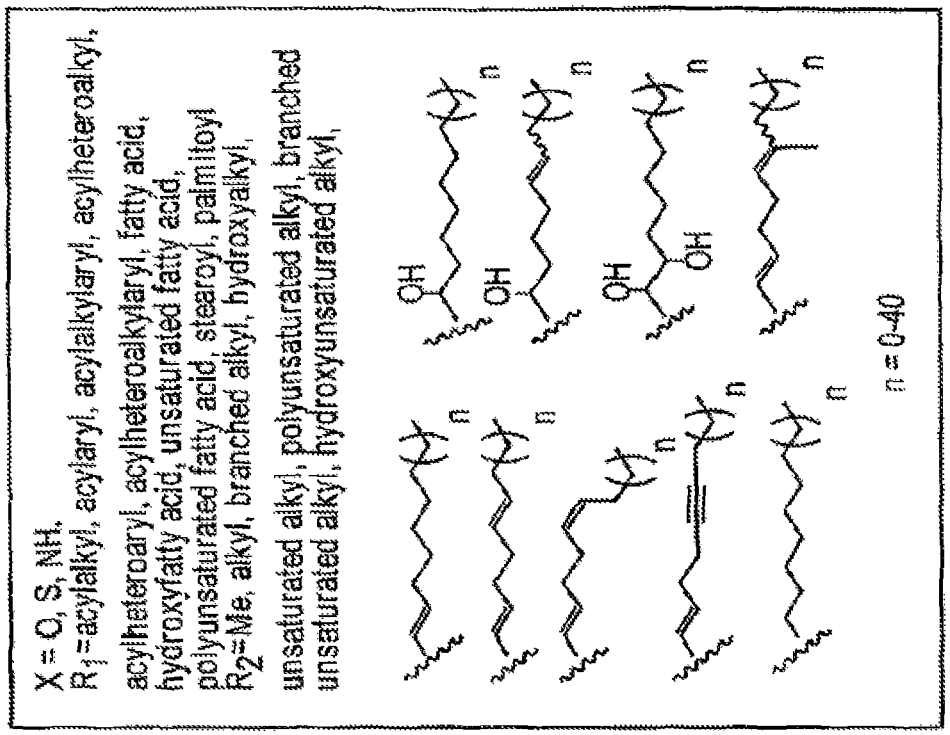
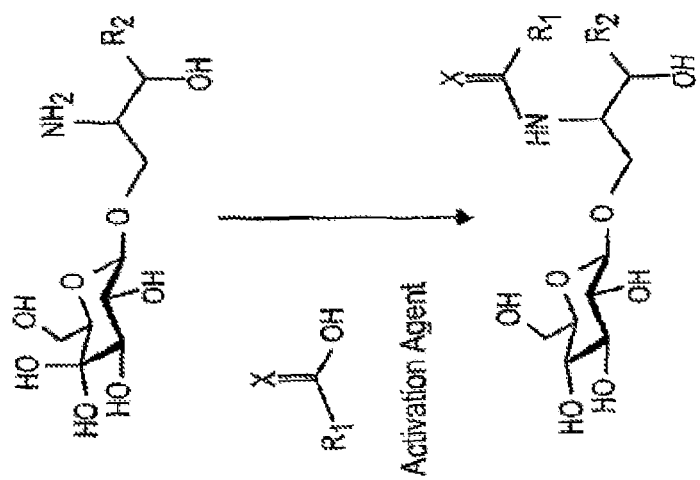
FIG. 5

Aglycone= linker, alkyl, alkylaryl, aryl, arylalkyl, aminoacid, cholesterol, steroid, peptide, flavanoid, Sphingoid, Scheme 7.
X = O, S, NH, N-alkyl, N-aryl, NHC-linker
Sphingoid =

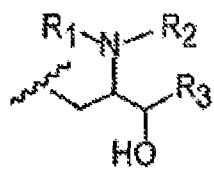

$R_1$ = H, alkyl, fatty acid, hydroxyfatty acid, unsaturated fatty acid, unsaturatedhydroxyfatty acid
$R_2$ = H, alkyl, fatty acid, hydroxyfatty acid, unsaturated fatty acid, unsaturatedhydroxyfatty acid
$R_3$ = H, -$(CH_2)_n CH_3$, -CH=CH-$(CH_2)_n CH_3$, -CHOH-$(CH_2)_n CH_3$, -CH=CH-$(CH_2)_2$-CH=CH-$(CH_2)_n CH_3$, -CH=CH-$(CH_2)_2$-C=C-$(CH_2)_n CH_3$, -CHOH-$(CH_2)_3$-CH=CH-$(CH_2)_n CH_3$, aryl, alkylaryl, linker.
n = 0-40.

FIG. 12C

Sphingoid =

$R_1$ = H, alkyl, fatty acid, hydroxyfatty acid, unsaturated fatty acid, unsaturatedhydroxyfatty acid
$R_2$ = H, alkyl, fatty acid, hydroxyfatty acid, unsaturated fatty acid, unsaturatedhydroxyfatty acid
$R_3$ = H, -$(CH_2)_n CH_3$, -CH=CH-$(CH_2)_n CH_3$, -CHOH-$(CH_2)_n CH_3$, -CH=CH-$(CH_2)_2$-CH=CH-$(CH_2)_n CH_3$, -CH=CH-$(CH_2)_2$-C=C-$(CH_2)_n CH_3$, -CHOH-$(CH_2)_3$-CH=CH-$(CH_2)_n CH_3$, aryl, alkylaryl, linker.
n = 0-40.

```
Rh. M-777 EGC II            1   ------------------------------MRRTRLVSLIVTGSLVFGGG
Rh. C9 EGC                  1   ------------------------------MRRTRIASLAVAGSLVLGAG
P. acnes EGCa               1   ------------------------------MRRKSALGFVALSLFATGMG
P. acnes EGCb               1   --------------------MYHHSWHSPDARRRGVTRWATTFIAALTAA
Dictostelium hyp. EGC       1   ------------------------------------MNKKKQIITTTIT
C. nozakii EGC              1   ---------------------------------MAETQPLVFVIMSISA
Schistosoma japonicum hyp. EGC  1  ----------------------------------------MWSIFILTF
Leptospira interrogans hyp. EG  1  ------------------------------MEELFVKNGHFASKEG
Hydra magnipapillata EGC    1   ---------------------------------MISVALIILFLAK
Streptomyces avermitilis hyp. 1 MRKNAKLTHESEVLTFHRSARTVVDMSKLRARLLGVLVSLTGLLG
Neurospora crassus hyp. EGC 1   ------------------------------MAGFRLTIENGSFRDVHG Rh. M-777 EGC II           36   GSGTALTP--------------SYLKDDDGRSLILRGFNTASSAKS
Rh. C9 EGC                 36   SEWSAS----------------AYLTDDAGRSLILRGFNTASSAKS
P. acnes EGCa              36   AFVHVDASRWTTQG--------RWVTDTQHRVVITQGINEVAKSAP
P. acnes EGCb              46   AAPHIATSKTITDAGPIGQSGRWYTDGQGRAILTAGVNMVSKRHP
Dictostelium hyp. EGC      27   IKVNPAN---------------QFFIDQYNRVRLFHGVNVVYKIPP
C. nozakii EGC             32   ISVNPET---------------QQLVDSLGRERFFHGTNVVVKHKP
Schistosoma japonicum hyp. EGC 25 IHLNSDG---------------LFTDSRGFIKLFRGFNNVHKHFP
Leptospira interrogans hyp. EG 32 LPLKPDG---------------TTHFDQT--TTFDNHKNVSFVGRP
Hydra magnipapillata EGC   23   ISVNPET---------------NMLIDGYGRERFFHGTNVVVKHFP
Streptomyces avermitilis hyp. 61 LWFDASASAAFTVQN-------GRFSDGLGREVVLRGYNVSGETKL
Neurospora crassus hyp. EGC 34  YPNKFEQ---------------PSHVGEN----FFDGDNVKFTGRP Rh. M-777 EGC II           77   EADLAREYADMGTNFVRFLISWRSVEPA-PGVYDQQYLDRVEDRV
Rh. C9 EGC                 75   ESDLDREHADMGTNFVRFLISWRSVEPE-PGQYDQAYLDRVEQRV
P. acnes EGCa              83   EDDAA-FLEAQGFTSVRLGVLWAGVEPR-PGVYDDAYLARVERTV
P. acnes EGCb             100   DADAA-WLQKNGFDSVRLGVIWKGVEPK-PGEYDDAYLASITRTV
Dictostelium hyp. EGC      73   SQDIE-NLVEWGFNAVRLGVMWPGVEPV-KDEYNQTYLDVMSKLV
C. nozakii EGC             77   EVDMK-ILQDLGLNTIRLGMMLPGYVPT-RGNYNETYLKIIQEIV
Schistosoma japonicum hyp. EGC 62 NITQLEMFKNWGLNVVRLGVMWSGVKPT-ISIVNTTYLDVIENVI
Leptospira interrogans hyp. EG 67 EEHFD-RLRKWGFNFLRFLITWEAIEHKGPGKYDMEYIDYVERMV
Hydra magnipapillata EGC   68   EDDMK-ILQKFGLNSIRLGMMLPGYVPK-REEYNETYIKVIQSIV
Streptomyces avermitilis hyp. 114 RKSATALRTLGGGNSVRFLLSWAHAEPV-RGQVDTAYLAAATAQM
Neurospora crassus hyp. EGC 67  HLHFS-RLKRFGYNTIRYVFTWEAIEAAGPGIYDEEWIQHTIDVL Rh. M-777 EGC II          136   QDVYSGAI-TPEGNSGNGAGAIGNGAPAWATY--------MDGLPV
Rh. C9 EGC                134   QDLYSGAI-TPDGKTG--------NGAPAWATY--------MDGLPV
P. acnes EGCa             141   QDMVNEKY-QGEGW~~~~~~~~~~PAWAALD-------HGMPNIV
P. acnes EGCb             158   QDMYNEKF-EGEGA~~~~~~~~~~PDWAVLD------KGAFNLL
Dictostelium hyp. EGC     131   QDLLSRKY-CGEGL~~~~~~~~~~PDWIVSNDTNDSFPSFVAH
C. nozakii EGC            135   QDVMSAKF-CVEGF~~~~~~~~~~PDWAVNTGNADNFPFPLED
Schistosoma japonicum hyp. EGC 121 QDVLSSLYGLYDGI~~~~~~~~~~PLWLIEK------FKRFPHH
Leptospira interrogans hyp. EG 126 QDVWSRFT-GGDGA~~~~~~~~~~PGWTLEELGMNISKIRNSE
Hydra magnipapillata EGC  126   QDVFSPKF-CVEGM~~~~~~~~~~PDWIVNTQGAKDFPMFLHK
Streptomyces avermitilis hyp. 173 QDLYSRYL-FNSGS---WYTGD---GAFEWAVDAG----DYPAESC
Neurospora crassus hyp. EGC 126 QDVWSRFS-GGSGA~~~~~~~~~~PMWTLYAAGLNPQSFAATE Rh. M-777 EGC II          184   -PGVMRAFDNFWN----------TTGKH~~~~~~~~~~~~PELV
Rh. C9 EGC                175   -PGVIRAFDNFWN----------TTGKH~~~~~~~~~~~~PELV
P. acnes EGCa             169   ---GFPGNYFLN-EAVKYSFDSFYDNTKASDGIG~~~~~~~~~~
P. acnes EGCb             186   ---GFPANQVFN-LGLIKAYDSFLDNAKGPGGVG~~~~~~~~~~
Dictostelium hyp. EGC     177   CLNKDFGVYYFS-EDVNREFQNLYDNVNG~~~~~~~~~~~~~~
C. nozakii EGC            182   CAKHAWGDYYFT-EAAAAAFQNFYN-NTDG~~~~~~~~~~~~~
Schistosoma japonicum hyp. EGC 157 KKPDFWVMSYLT-YECANGAQQLYN--NVSG~~~~~~~~~~~~
Leptospira interrogans hyp. EG 171 ---MSWPLNYQK~~~~~~YSCATMFSLFFGGKEFAPDTKIDGRN
Hydra magnipapillata EGC  173   CAKFSWADYYFT-EAAGQAFQNLYD--NVDG~~~~~~~~~~~~
Streptomyces avermitilis hyp. 223 VTQASHDFWH----------NAYG~~~~~~~~~~~~~~~~~VQ
Neurospora crassus hyp. EGC 173 KMIWSTNYYR-LAAATMFTLFFAGR~~DFAPKCIIDGVNIQDYLQ
```

FIG. 15A

```
Rh. M-777 EGC II              221  DN------DAVVAYDLMNEPFGG-SLQG-----PAFEAG-PLAA-
Rh. C9 EGC                    212  DN------ETVVAYDLMNEPWGG-SLQG-----PAFEAG-PLTS-
P. acnes EGCa                 211  VAEHFRNVPGVQGYDLFNEPFPGHRYTR-----CLTQLG-CRAAD
P. acnes EGCb                 228  VAQVVGQEPGVMGYDIINEPWPGHHYPI-----CYVAFGWCGRAM
Dictostelium hyp. EGC         216  VVNTFKSYDTVIGYEIINEPWGGDIYQN-----PEYLLKLGYADS
C. nozakii EGC                221  TAQGFKDYKSVIGYELINEPFAGDIYRD-----PSLMIP-GVADE
Schistosoma japonicum hyp. EGC 196 VARRFGGKSNVIGYELINEPPPGNFYTN-----PLRGLP-GYAGR
Leptospira interrogans hyp. EG 222 IVRKLKKYKNVIGFDTLNEPSPGWIGKKNLGEFDGFGFG-KVVKS
Hydra magnipapillata EGC      212  TADVFKEEPSVIGYELINEPFCGNVFKH-----PTLLIP-GVADY
Streptomyces avermitilis hyp. 254  QNLSADEFNGVVGFDPYNEPHAGTYDSG-----ETSRTWEQNVLW
Neurospora crassus hyp. EGC   230  EAG-DIENDVVFGWESLNEPNKGMIAYEDISVIPKEQNLKKGTCP Rh. M-777 EGC II              262  QVDQDTWVCVAPQA-------------IGV--------------
Rh. C9 EGC                    253  QVDQDSWVCVAPQA--------------VGV--------------
P. acnes EGCa                 265  SVDKATTVWYEP-----------MQFFN-----------------
P. acnes EGCb                 283  SVDPDGIVTYEP-------------YS------------------
Dictostelium hyp. EGC         271  ELDDQHCVYY---------------EKA-----------------
C. nozakii EGC                275  TVDEQHSIFF---------------EGV-----------------
Schistosoma japonicum hyp. EGC 250 KYDNSTLIFYEP----------VTYGVFTP---------------
Leptospira interrogans hyp. EG 281 AAQAYMLGFWSLPFGKVRLNPEGVPLWE-----------------
Hydra magnipapillata EGC      266  QVDEEHNIFF---------------EGV-----------------
Streptomyces avermitilis hyp. 309  QTKPAFIEPN-----------------------------------
Neurospora crassus hyp. EGC   289  VDTWDMGGMGPYKVGRALIDPSGEQAWLPADYDESRYGYKRDPGW Rh. M-777 EGC II              278  -----------------NQG-------------------------
Rh. C9 EGC                    269  -----------------NQG-------------------------
P. acnes EGCa                 281  ----------------IGVG-------------------------
P. acnes EGCb                 296  ----------------TWNMG------------------------
Dictostelium hyp. EGC         283  -----------------LTDL------------------------
C. nozakii EGC                287  -----------------TWDY------------------------
Schistosoma japonicum hyp. EGC 269 -----------------VRSSG-----------------------
Leptospira interrogans hyp. EG 313 CIWRNHGVWDYDPNGAPMMLKPEYFYKKNGRKYEFYSDFMYPFIK
Hydra magnipapillata EGC      278  -----------------TWDF------------------------
Streptomyces avermitilis hyp. 318  -----------------LFWN------------------------
Neurospora crassus hyp. EGC   349  ATDSLLKKDYFGKHPATGEHVDYPYFSNRYFMDFFRKYRDTIRSI Rh. M-777 EGC II              287  TK--------IDD----------------PRAGQQRIAYCPHLYPL
Rh. C9 EGC                    278  GT--------IAD----------------PRQGARRIAYCPHLYPL
P. acnes EGCa                 292  ----SNLG---------------------LSFHDYCTSQATLHSYVG
P. acnes EGCb                 309  ----SSPK---------------------AAISWHVYCPMNAIFGSYVG
Dictostelium hyp. EGC         295  -----TPG---------------------GVQYNDRQVLSYHIYCA
C. nozakii EGC                298  -----VPG---------------------GDAYRNRSVLSYHYYEP
Schistosoma japonicum hyp. EGC 282 -----VPG---------------------AHRDKSAPSKSVLSYHYYCWI
Leptospira interrogans hyp. EG 373 FIESDPSKLELEWKEIPKKNQGSVINATHWYDISVLMLKRYLPWF
Hydra magnipapillata EGC      289  -----VPG---------------------GKQYQNRSVLSYHYYEP
Streptomyces avermitilis hyp. 329  -----QEG---------------------GLLDAGTLGPRYVLNTHFYDQ
Neurospora crassus hyp. EGC   409  PPKIIGTPDGDDPLLVYAPHWYDGITLMTKKWNRVWNVDVIGILR Rh. M-777 EGC II              324  TDVTIDAWR--ANTAHTARVLGDVPIILGEFGLDTTLPGARDYIE
Rh. C9 EGC                    315  TDATIETWR-TSIEHVADTVLEGAPVILGEFGLDTTLPGAQDYLD
P. acnes EGCa                 315  CTAPDNRVFTNAEKHSRQTGSGL---MLTEFGAIT--------TP
P. acnes EGCb                 334  CNLPDTRTFHNADQAAQFNNSAS----LLSEFGATK--------DP
Dictostelium hyp. EGC         328  CDGEDDIFLVSAMKDLKQTGGGG---FMTEFGAVS-----NGTNS
C. nozakii EGC                319  -DFNKKFQFEVRMEDLRRLKCGG----FLTELLTVGD-----TAKDM
Schistosoma japonicum hyp. EGC 322 VICDRLLLPNVISNAIRATKSTGGGRFLTEFGLCGDDGNPRSVNT
Leptospira interrogans hyp. EG 432 NIDNAYEETIRMIREMSEKKMGNCPTVIGETGIPMDLNHRVAYLK
Hydra magnipapillata EGC      310  -DFSKKLNFEARLLDLKRLKCGG---FLTEMFTVG--------TDF
Streptomyces avermitilis hyp. 363  -KAADGQYATDFGKVRDRAAGAGTAAVVSEFGHPLSGSVSDKAPT
Neurospora crassus hyp. EGC   469  AIRNCFKNQHATMRQEGLDYIGNHPCVMTEFGIPYDMDDKNAYKT
```

FIG. 15B

```
Rh. M-777 EGC II              370  GTAREMGAGVSYWSSDPGP---------W-------------------
Rh. C9 EGC                    362  TVARDMGAGVSYWSSDRGP---------W-------------------
P. acnes EGCa                 362  RVGVQW--------------WAYTAGDPTTAGPGTEQALVDDP-----
P. acnes EGCb                 381  LVGWLY--------------WTYNGNSDPTTQNAADEELVRHIN----
Dictostelium hyp. EGC         379  LQSWTY--------------WQLKYYNDITTAGSTESLY---------
C. nozakii EGC                370  KQSWMG--------------WLYKSYGCYKQHLGCLTDS---------
Schistosoma japonicum hyp. EGC 371 NILNEADKHFESWTYWDSN-----------------------------
Leptospira interrogans hyp. EG 491 KAVEKNFVNLALWNYTPDHTHSLGDRWNEEDLSIY-------------
Hydra magnipapillata EGC      358  KQSWHG--------------WMYKSYGCIEQNLGCLNMS---------
Streptomyces avermitilis hyp. 423  STWWSDPTGSGPVLSGAQWQWDIYNGRHHELENGNPDKVLTSG-----
Neurospora crassus hyp. EGC   529  GVEGAGLEGYTLWLYMTKNDHELGDWNGEDLSIFSVDDKLLPES Rh. M-777 EGC II              389  -----------------------------------GPYLPDG
Rh. C9 EGC                    381  -----------------------------------GPYLEDG
P. acnes EGCa                 390  ------------------------------------------
P. acnes EGCb                 410  ------------------------------------------
Dictostelium hyp. EGC         403  ------------------------------------------
C. nozakii EGC                394  ------------------------------------------
Schistosoma japonicum hyp. EGC 389 -----------------------------------LLDLSGN
Leptospira interrogans hyp. EG 525 ---------------------------------SQDTPSSYDE
Hydra magnipapillata EGC      382  ------------------------------------------
Streptomyces avermitilis hyp. 474  ------------------------------------------
Neurospora crassus hyp. EGC   589  ATPTGTKDDDLDDDSSVTPANIKRTLTNPSISSVSTQRQPELTNS Rh. M-777 EGC II              412  AVAGTPTEWSS---TSDRLQLTIEPDAAITAP----------
Rh. C9 EGC                    404  AVAGMPVRWSS---TSDRLDLTYRNDPAVTAP----------
P. acnes EGCa                 393  PPQGTNVESAKLTLIAVPHPDRVAGTPSAYHHDRSRRVFTMTWTA
P. acnes EGCb                 414  PVTDEQVDHTKLAILAVPHLRAAAGTPTSTTWDQSTRTYQATWTA
Dictostelium hyp. EGC         405  PNGE--LDIPKITALSRTYAQAIAGVPLSMSFNPANSDFSFSYNI
C. nozakii EGC                396  HDETGHLRDIVLQNTTRTYPQAVAGHTIGYKFDRITKKFDLSFVV
Schistosoma japonicum hyp. EGC 412 SIRGVFRKQQFDHKTGDFHLSFIANTTKEQNNEKQTLI-------
Leptospira interrogans hyp. EG 551 RTKGFPVALTFDMERSLFKYAFRQEGDLFPE--------------
Hydra magnipapillata EGC      384  PGKE--S--IQIANTSRTYPQAVAGRTQSYAFDIKTKVFTLVYET
Streptomyces avermitilis hyp. 479  NDSGTAVLRQDARLLDRLYPSATAGATVAFTYEDRSRDGSTTLTW
Neurospora crassus hyp. EGC   649  ATAGTVKKYGFDLRSCQFHVTIQAPEAAKPDTP------------

Rh. M-777 EGC II              450  FPG------DVHVEG-ADVVGWDRQ--SRLLTVRTPADSGN-VTVT
Rh. C9 EGC                    442  FPG------DIAVQG-ADVVGWDSQ--SRLLTVRSAPDAGE-VTVT
P. acnes EGCa                 450  ------------TTVVVPAIS-APHGY---DVQASG-AHVTSHPGD
P. acnes EGCb                 472  ------------SEIAVPAIH-YPNGY---KVEVKG-AKVISKAGD
Dictostelium hyp. EGC         454  ------------TQIYLNQDIYYPNGF---TTNIITGTATVSIPQK
C. nozakii EGC                448  ------------SIVYFNKDLHYSNGY---DVTVFP-KDSVTWKQV
Schistosoma japonicum hyp. EGC 460 YPNGF----SMSVKPDNLSTKMNEN---MMYVYLPSGVSNASVFVR
Leptospira interrogans hyp. EG 591 YKKGF----EVLVN--AGTYQYDFR--SRVLKFKGEKGILD-YGIT
Hydra magnipapillata EGC      432  ------------TIVYFNKNLHYPNGY---RYEINP-NFKVTPSEN
Streptomyces avermitilis hyp. 539  SGQYGLLVWRSNGSTAPTELHLPASFPAASTTVVSDLGTTSGLPA
Neurospora crassus hyp. EGC   692  PKDAC---QVEVSSGKWEIRSDEEETTPLQKLRWWHGEGEQTLRV Rh. M-777 EGC II              490  --------------------.........
Rh. C9 EGC                    482  --------------------.........
P. acnes EGCa                 492  T-AKVTITLR---------
P. acnes EGCb                 512  GPVSVTITPAGQA------
Dictostelium hyp. EGC         499  Q-STITITILKK-------
C. nozakii EGC                492  AGTTVTFSLVAK-------
Schistosoma japonicum hyp. EGC 507 ..........
Leptospira interrogans hyp. EG 643 KVVPKTQKRKTQ-------
Hydra magnipapillata EGC      476  N-TVVTFKLFPLSFTDSEDIHPVTVMGDKHLSENHNENEKKKK--
Streptomyces avermitilis hyp. 599  TGSHRLLLTAADSGTVHYALVTNGATAPSAGLLSAARAELSSWAA
Neurospora crassus hyp. EGC   749  EVGYYDQVFNQAKGFLDACVIM-----..........
```

FIG. 15C

SEQUENCE LISTING

<160> NUMBER OF SEQ ID NOS: 85

<210> SEQ ID NO 1
<211> LENGTH: 2012
<212> TYPE: DNA
<213> ORGANISM: Rhodococcus sp. -M777
<220> FEATURE:
<221> NAME/KEY: CDS
<222> LOCATION: (391)..(1863)

<400> SEQUENCE: 1

```
cctgaccatg ttgggcccca acggtttcag gagggagttc gccggggcga ccgacggggc      60
cgcggccgaa ctcgagctgt cctcgacgat cgtcgccggg acgcgatctc tcgctctgag     120
cgtgaacaac cgtggaacgc acgagctgac ggtcgcggtc gacggtcaac ggcgccgggt     180 cgcggccac  gggtcggaat cactgacggt gtcctcggtg aacggttggt acgaggccgc     240
cgtgaccgtc gacgaggacc ccgacttccg gcgacggctc gtcgggcaca tcgagaacgg     300
gcaggacagc gtcagtcagc cgagctgacg gggtgtcgcc ggtaccccgg caaggaacgt     360
gatcgaacca agagtccagt aggaggacac gtg cgt cgc acc cgg ctc gta tcg      414
                                 Val Arg Arg Thr Arg Leu Val Ser
                                  1               5 ctg atc gtg aca ggt tcg ctg gtg ttc ggc ggc ggc gtt gcc gcc gct      462
Leu Ile Val Thr Gly Ser Leu Val Phe Gly Gly Gly Val Ala Ala Ala
    10              15                  20 cag agc agc ttg gcc gca tcc gga agc gga agt ggc agt ggt acc gcg      510
Gln Ser Ser Leu Ala Ala Ser Gly Ser Gly Ser Gly Ser Gly Thr Ala
25              30                  35                  40 ctg acg ccg tcc tac ctg aag gac gat gac ggc cgc tca ctg atc ctg      558
Leu Thr Pro Ser Tyr Leu Lys Asp Asp Asp Gly Arg Ser Leu Ile Leu
                45                  50                  55 cgc ggg ttc aac acg gca tcg agc gcg aag agc gcg ccg gac ggc atg      606
Arg Gly Phe Asn Thr Ala Ser Ser Ala Lys Ser Ala Pro Asp Gly Met
            60                  65                  70 ccg cag ttc acc gag gcg gac ctg gcg cgc gag tat gca gac atg gga      654
Pro Gln Phe Thr Glu Ala Asp Leu Ala Arg Glu Tyr Ala Asp Met Gly
        75                  80                  85 acc aac ttc gtt cgg ttc ctc atc tcg tgg cgg tcg gtc gaa cca gca      702
Thr Asn Phe Val Arg Phe Leu Ile Ser Trp Arg Ser Val Glu Pro Ala
    90                  95                  100 ccg ggc gtg tac gac cag cag tat ctg gac cgt gtc gaa gat cgg gtc      750
Pro Gly Val Tyr Asp Gln Gln Tyr Leu Asp Arg Val Glu Asp Arg Val
105                 110                 115                 120 ggc tgg tac gcc gag cgc ggc tac aag gtg atg ctc gac atg cac cag      798
Gly Trp Tyr Ala Glu Arg Gly Tyr Lys Val Met Leu Asp Met His Gln
                125                 130                 135 gac gtg tac tcc ggc gcg atc acc ccg gag ggc aac agc ggc aac ggt      846
Asp Val Tyr Ser Gly Ala Ile Thr Pro Glu Gly Asn Ser Gly Asn Gly
            140                 145                 150 gcc ggc gcc atc ggc aac ggc gca ccg gcc tgg gcg acc tac atg gac      894
Ala Gly Ala Ile Gly Asn Gly Ala Pro Ala Trp Ala Thr Tyr Met Asp
        155                 160                 165 ggc ctt ccg gtc gag ccg cag ccc cgg tgg gag ctg tac tac atc cag      942
Gly Leu Pro Val Glu Pro Gln Pro Arg Trp Glu Leu Tyr Tyr Ile Gln
    170                 175                 180
```

| | | |
|---|---|---|
| ccc ggc gtg atg cgc gcg ttc gac aac ttc tgg aac acc acc ggc aag<br>Pro Gly Val Met Arg Ala Phe Asp Asn Phe Trp Asn Thr Thr Gly Lys<br>185                              190                    195                   200 | | 990 |
| cac ccc gaa ctc gtc gag cac tac gcg aaa gcg tgg cgg gcg gtc gcc<br>His Pro Glu Leu Val Glu His Tyr Ala Lys Ala Trp Arg Ala Val Ala<br>                      205                    210                    215 | | 1038 |
| gac cga ttc gcc gac aac gac gcc gtc gtg gcc tac gac ctg atg aac<br>Asp Arg Phe Ala Asp Asn Asp Ala Val Val Ala Tyr Asp Leu Met Asn<br>              220                    225                  230 | | 1086 |
| gag ccg ttc gga gga tcc ctg cag gga ccg gcg ttc gag gca ggg ccg<br>Glu Pro Phe Gly Gly Ser Leu Gln Gly Pro Ala Phe Glu Ala Gly Pro<br>        235                    240                  245 | | 1134 |
| ctc gcc gcg atg tac cag cgc acc acc gac gcc atc cgg cag gta gac<br>Leu Ala Ala Met Tyr Gln Arg Thr Thr Asp Ala Ile Arg Gln Val Asp<br>250                              255                    260 | | 1182 |
| cag gac acc tgg gtc tgc gtg gcc ccg cag gcg atc ggc gtc aac cag<br>Gln Asp Thr Trp Val Cys Val Ala Pro Gln Ala Ile Gly Val Asn Gln<br>265                              270                    275                   280 | | 1230 |
| ggt ctc ccc agc ggg ctc acc aag atc gac gac cct cgt gcg ggt caa<br>Gly Leu Pro Ser Gly Leu Thr Lys Ile Asp Asp Pro Arg Ala Gly Gln<br>                          285                    290                   295 | | 1278 |
| cag cgc atc gcg tac tgc ccg cac ctc tac cca ctg ccg ctg gat atc<br>Gln Arg Ile Ala Tyr Cys Pro His Leu Tyr Pro Leu Pro Leu Asp Ile<br>            300                    305                  310 | | 1326 |
| ggt gac ggc cac gag ggc ctg gcc cgg acg ctc acc gac gtg acc atc<br>Gly Asp Gly His Glu Gly Leu Ala Arg Thr Leu Thr Asp Val Thr Ile<br>        315                    320                  325 | | 1374 |
| gac gcc tgg cgt gcc aac acc gcc cac acc gcc cgt gtg ctg ggt gac<br>Asp Ala Trp Arg Ala Asn Thr Ala His Thr Ala Arg Val Leu Gly Asp<br>330                              335                    340 | | 1422 |
| gtg ccc atc atc ctc ggc gag ttc ggc ctg gac aca acg ctg ccc ggg<br>Val Pro Ile Ile Leu Gly Glu Phe Gly Leu Asp Thr Thr Leu Pro Gly<br>345                              350                    355                   360 | | 1470 |
| gcc cgg gat tac atc gaa cgc gtc tac ggg acc gcg cga gag atg ggg<br>Ala Arg Asp Tyr Ile Glu Arg Val Tyr Gly Thr Ala Arg Glu Met Gly<br>                      365                    370                   375 | | 1518 |
| gcc gga gtc tcg tac tgg tcc agc gat ccc ggc ccc tgg ggc ccg tac<br>Ala Gly Val Ser Tyr Trp Ser Ser Asp Pro Gly Pro Trp Gly Pro Tyr<br>              380                    385                  390 | | 1566 |
| ctg cct gac ggc acg cag acg ctg ctc gtc gac acc ctg aac aag ccg<br>Leu Pro Asp Gly Thr Gln Thr Leu Leu Val Asp Thr Leu Asn Lys Pro<br>        395                    400                  405 | | 1614 |
| tac ccc cgc gca gtg gcc ggc aca ccc acc gag tgg tcg tcg acc tcc<br>Tyr Pro Arg Ala Val Ala Gly Thr Pro Thr Glu Trp Ser Ser Thr Ser<br>410                              415                    420 | | 1662 |
| gat cgc ctc caa ttg acg atc gag ccg gac gcc gcg atc acc gct ccc<br>Asp Arg Leu Gln Leu Thr Ile Glu Pro Asp Ala Ala Ile Thr Ala Pro<br>425                              430                    435                   440 | | 1710 |
| acc gag atc tac ctc ccg gag gca gga ttc ccg ggc gac gtc cac gtc<br>Thr Glu Ile Tyr Leu Pro Glu Ala Gly Phe Pro Gly Asp Val His Val<br>                      445                    450                   455 | | 1758 |
| gaa ggc gcc gac gtc gtg ggg tgg gat cgg cag agt cga ctg ctc acg<br>Glu Gly Ala Asp Val Val Gly Trp Asp Arg Gln Ser Arg Leu Leu Thr<br>              460                    465                  470 | | 1806 |
| gtg cgc act ccg gcc gac tcg ggc aac gtg acc gtg acg gtc act ccg<br>Val Arg Thr Pro Ala Asp Ser Gly Asn Val Thr Val Thr Val Thr Pro<br>        475                    480                  485 | | 1854 |
| gca gcc tga tccggccgac gcgacgaccg ccgtcggtg cgacgatgac<br>Ala Ala<br>        490 | | 1903 |

```
tgcatggatg aagtggtctc ggtctacgac gcagacggca ccgtgatcgg cacggcgcca    1963
cgctcgcgcg tgtacgccga ggggctgtgg catgccagtg cgggcgtgc               2012
```

<210> SEQ ID NO 2
<211> LENGTH: 490
<212> TYPE: PRT
<213> ORGANISM: Rhodococcus sp. -M777

<400> SEQUENCE: 2

Val Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
            20                  25                  30

Ser Gly Ser Gly Ser Gly Thr Ala Leu Thr Pro Ser Tyr Leu Lys Asp
        35                  40                  45

Asp Asp Gly Arg Ser Leu Ile Leu Arg Gly Phe Asn Thr Ala Ser Ser
    50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
            100                 105                 110

Leu Asp Arg Val Glu Asp Arg Val Gly Trp Tyr Ala Glu Arg Gly Tyr
        115                 120                 125

Lys Val Met Leu Asp Met His Gln Asp Val Tyr Ser Gly Ala Ile Thr
    130                 135                 140

Pro Glu Gly Asn Ser Gly Asn Gly Ala Gly Ala Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
            180                 185                 190

Asn Phe Trp Asn Thr Thr Gly Lys His Pro Glu Leu Val Glu His Tyr
        195                 200                 205

Ala Lys Ala Trp Arg Ala Val Ala Asp Arg Phe Ala Asp Asn Asp Ala
    210                 215                 220

Val Val Ala Tyr Asp Leu Met Asn Glu Pro Phe Gly Gly Ser Leu Gln
225                 230                 235                 240

Gly Pro Ala Phe Glu Ala Gly Pro Leu Ala Ala Met Tyr Gln Arg Thr
                245                 250                 255

Thr Asp Ala Ile Arg Gln Val Asp Gln Asp Thr Trp Val Cys Val Ala
            260                 265                 270

Pro Gln Ala Ile Gly Val Asn Gln Gly Leu Pro Ser Gly Leu Thr Lys
        275                 280                 285

Ile Asp Asp Pro Arg Ala Gly Gln Gln Arg Ile Ala Tyr Cys Pro His
    290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

```
Gly Leu Asp Thr Thr Leu Pro Gly Ala Arg Asp Tyr Ile Glu Arg Val
            355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
            435                 440                 445

Gly Phe Pro Gly Asp Val His Val Glu Gly Ala Asp Val Val Gly Trp
    450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 3
<211> LENGTH: 490
<212> TYPE: PRT
<213> ORGANISM: Rhodococcus sp.

<400> SEQUENCE: 3

Met Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
                20                  25                  30

Ser Gly Ser Gly Ser Gly Thr Ala Leu Thr Pro Ser Tyr Leu Lys Asp
            35                  40                  45

Asp Asp Gly Arg Ser Leu Ile Leu Arg Gly Phe Asn Thr Ala Ser Ser
50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
            100                 105                 110

Leu Asp Arg Val Glu Asp Arg Val Gly Trp Tyr Ala Glu Arg Gly Tyr
        115                 120                 125

Lys Val Met Leu Asp Met His Gln Asp Val Tyr Ser Gly Ala Ile Thr
    130                 135                 140

Pro Glu Gly Asn Ser Gly Asn Gly Ala Gly Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
            180                 185                 190

Asn Phe Trp Asn Thr Thr Gly Lys His Pro Glu Leu Val Glu His Tyr
        195                 200                 205

Ala Lys Ala Trp Arg Ala Val Ala Asp Arg Phe Ala Asp Asn Asp Ala
    210                 215                 220

Val Val Ala Tyr Asp Leu Met Asn Glu Pro Phe Gly Gly Ser Leu Gln
225                 230                 235                 240
```

```
Gly Pro Ala Phe Glu Ala Gly Pro Leu Ala Ala Met Tyr Gln Arg Thr
                245                 250                 255

Thr Asp Ala Ile Arg Gln Val Asp Gln Asp Thr Trp Val Cys Val Ala
            260                 265                 270

Pro Gln Ala Ile Gly Val Asn Gln Gly Leu Pro Ser Gly Leu Thr Lys
        275                 280                 285

Ile Asp Asp Pro Arg Ala Gly Gln Gln Arg Ile Ala Tyr Cys Pro His
    290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

Gly Leu Asp Thr Thr Leu Pro Gly Ala Arg Asp Tyr Ile Glu Arg Val
        355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
        435                 440                 445

Gly Phe Pro Gly Asp Val His Val Glu Gly Ala Asp Val Val Gly Trp
    450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 4
<211> LENGTH: 2012
<212> TYPE: DNA
<213> ORGANISM: Rhodococcus sp.
<220> FEATURE:
<221> NAME/KEY: CDS
<222> LOCATION: (414)..(1862)
<223> OTHER INFORMATION: EGCase

<400> SEQUENCE: 4
gggcccgaac ggattccgcc gcgagttcgc cgggtcgacg gacggcccgg ccgcgagggt      60
ctcggtctcg acgacggtcg acgcgggcgg acgcaccctc gacctggtcg tgacgaacgg     120
aggaacccgg gatgtgacgg tcgtcgtcga cggccgcgt ggaacgctgg gtcccggcgc     180
ccgacgctcg tggacggtgc cgtcgacgga cggctggtac cggtgcgccg tgaccgtcga     240
cgaggacacg gacttccggc gcacgctggc cggacacatc gagaacggcg aggacagcgt     300
cagccaaccc acctgacgcg gcacctgcca ccgtgcgggc acggccgc acgaccgcca       360 tctgatccac acaacccgta ggaggagcga cagtgcgtcc aggaggaacg aca gtg       416
                                                              Val
                                                               1 cgt cga aca aga atc gcg tcc ctt gcc gtg gcg ggg tcg ctc gta ctc      464
Arg Arg Thr Arg Ile Ala Ser Leu Ala Val Ala Gly Ser Leu Val Leu
```

-continued

|   | 5 | | | | 10 | | | | 15 | | | | | |
|---|---|---|---|---|---|---|---|---|---|---|---|---|---|---|

```
ggg gcc ggt gtg gcc acc gcg cag agc agc ttg ccg gcc acc ggg agt    512
Gly Ala Gly Val Ala Thr Ala Gln Ser Ser Leu Pro Ala Thr Gly Ser
         20                  25                  30 gac tcg agc gag tgg agc gca tcg gcc tac ctg acg gac gac gcg ggc    560
Asp Ser Ser Glu Trp Ser Ala Ser Ala Tyr Leu Thr Asp Asp Ala Gly
     35                  40                  45 cga tcc ctg atc ctg cgt ggg ttc aac acg gca tcg agc gcg aag agc    608
Arg Ser Leu Ile Leu Arg Gly Phe Asn Thr Ala Ser Ser Ala Lys Ser
 50                  55                  60                  65 acc ccg gac ggc atg ccg atc ttc acc gag tcc gac ctg gac cgc gag    656
Thr Pro Asp Gly Met Pro Ile Phe Thr Glu Ser Asp Leu Asp Arg Glu
                     70                  75                  80 cac gcc gac atg gga acc aac ttc gtg cgc ttc ctg atc tcc tgg cgt    704
His Ala Asp Met Gly Thr Asn Phe Val Arg Phe Leu Ile Ser Trp Arg
                 85                  90                  95 tcg gtg gaa ccc gaa ccg gga cag tac gac cag gcg tat ctg gac cgg    752
Ser Val Glu Pro Glu Pro Gly Gln Tyr Asp Gln Ala Tyr Leu Asp Arg
             100                 105                 110 gtc gag cag cgc gtc ggc tgg tat gcc gaa cgc ggc tac aag gtc atg    800
Val Glu Gln Arg Val Gly Trp Tyr Ala Glu Arg Gly Tyr Lys Val Met
         115                 120                 125 ctc gac atg cac cag gac ctc tac tcc ggc gcg atc acc ccc gac ggc    848
Leu Asp Met His Gln Asp Leu Tyr Ser Gly Ala Ile Thr Pro Asp Gly
130                 135                 140                 145 aag acc ggc aac ggc gcg ccg gca tgg gcg acg tac atg gac ggt ctc    896
Lys Thr Gly Asn Gly Ala Pro Ala Trp Ala Thr Tyr Met Asp Gly Leu
                     150                 155                 160 ccc gtc aac gag cgg gac agc tgg gag ctg tac tac atc gag ccc ggc    944
Pro Val Asn Glu Arg Asp Ser Trp Glu Leu Tyr Tyr Ile Glu Pro Gly
                 165                 170                 175 gtg atc cgc gcg ttc gac aac ttc tgg aac acc acc gga aag cac ccc    992
Val Ile Arg Ala Phe Asp Asn Phe Trp Asn Thr Thr Gly Lys His Pro
             180                 185                 190 gaa ctc gtc gac cac tac gtg aat gcc tgg aag gcc gtc gcg gac cgg    1040
Glu Leu Val Asp His Tyr Val Asn Ala Trp Lys Ala Val Ala Asp Arg
         195                 200                 205 ttc gcc gac aac gag act gtc gtc gcc tac gac ctg atg aac gag ccg    1088
Phe Ala Asp Asn Glu Thr Val Val Ala Tyr Asp Leu Met Asn Glu Pro
210                 215                 220                 225 tgg ggc gga tcc ttg cag gga ccg gcg ttc gag gca gga cca ctc acc    1136
Trp Gly Gly Ser Leu Gln Gly Pro Ala Phe Glu Ala Gly Pro Leu Thr
                     230                 235                 240 tcg atg tac cag cgg acc acc gac gcc atc cga cag gtc gac cag gac    1184
Ser Met Tyr Gln Arg Thr Thr Asp Ala Ile Arg Gln Val Asp Gln Asp
                 245                 250                 255 agc tgg gtc tgc gtc gcc ccg cag gct gtc ggc gtc aac cag ggc att    1232
Ser Trp Val Cys Val Ala Pro Gln Ala Val Gly Val Asn Gln Gly Ile
             260                 265                 270 ccg agc gca ctc ggc acg atc gcc gat ccc cgc cag ggc gct cgg cgc    1280
Pro Ser Ala Leu Gly Thr Ile Ala Asp Pro Arg Gln Gly Ala Arg Arg
         275                 280                 285 atc gcc tac tgc ccg cac ctg tat ccc ctc ccc ctc gac ctc ggt gac    1328
Ile Ala Tyr Cys Pro His Leu Tyr Pro Leu Pro Leu Asp Leu Gly Asp
290                 295                 300                 305 ggg tac tcg ggg ttc tcg aag acc ctc acc gac gcc acc atc gaa acc    1376
Gly Tyr Ser Gly Phe Ser Lys Thr Leu Thr Asp Ala Thr Ile Glu Thr
                     310                 315                 320 tgg cgc acg agc atc gaa cac gtc gcc gac acc gtt ctc gag ggt gca    1424
```

```
Trp Arg Thr Ser Ile Glu His Val Ala Asp Thr Val Leu Glu Gly Ala
            325                 330                 335 ccg gtg atc ctc gga gag ttc ggg ctc gac acc acc ctg ccc ggc gcc    1472
Pro Val Ile Leu Gly Glu Phe Gly Leu Asp Thr Thr Leu Pro Gly Ala
        340                 345                 350 cag gac tac ctc gat cgc gtc tac acc gtc gct cgc gac atg ggt gcg    1520
Gln Asp Tyr Leu Asp Arg Val Tyr Thr Val Ala Arg Asp Met Gly Ala
355                 360                 365 ggt gtc tcg tac tgg tcg agc gat cgc ggt ccc tgg ggt ccc tac ctg    1568
Gly Val Ser Tyr Trp Ser Ser Asp Arg Gly Pro Trp Gly Pro Tyr Leu
370                 375                 380                 385 gag gac ggg acg cag acc atc ctc gtc gac acc gtg aac aag ccg tat    1616
Glu Asp Gly Thr Gln Thr Ile Leu Val Asp Thr Val Asn Lys Pro Tyr
            390                 395                 400 ccg cgg gcc gtg gcg ggc atg ccc gtc cgg tgg tcg tcg acc tcc gat    1664
Pro Arg Ala Val Ala Gly Met Pro Val Arg Trp Ser Ser Thr Ser Asp
        405                 410                 415 cga ctg gac ctg acg tac cgc aac gat ccc gcg gtg acc gcg ccc acc    1712
Arg Leu Asp Leu Thr Tyr Arg Asn Asp Pro Ala Val Thr Ala Pro Thr
    420                 425                 430 gag atc tac ctt ccg gca gca gga ttc ccc ggc gac atc gcc gtc cag    1760
Glu Ile Tyr Leu Pro Ala Ala Gly Phe Pro Gly Asp Ile Ala Val Gln
435                 440                 445 ggg gcg gac gtg gtc gga tgg gac tca cag agt cgg ctc ctg acc gtt    1808
Gly Ala Asp Val Val Gly Trp Asp Ser Gln Ser Arg Leu Leu Thr Val
450                 455                 460                 465 cgg tcc gcg ccc gac gcg ggt gag gtg acc gtg acg gtg acg ccc gcg    1856
Arg Ser Ala Pro Asp Ala Gly Glu Val Thr Val Thr Val Thr Pro Ala
            470                 475                 480 gcg tga ccccgtacct gcggccggcc ggtcaggccg ccgcgggtg gtgtcacatg      1912
Ala tcgaggccga ggtccagcac cgtcaccgaa tgggtgagag cgccgacggc gaggtagtcg  1972
acaccggtcg ccgcgtagtc ggccgcgacg cccagggtca                        2012

<210> SEQ ID NO 5
<211> LENGTH: 482
<212> TYPE: PRT
<213> ORGANISM: Rhodococcus sp.

<400> SEQUENCE: 5

Val Arg Arg Thr Arg Ile Ala Ser Leu Ala Val Ala Gly Ser Leu Val
1               5                   10                  15

Leu Gly Ala Gly Val Ala Thr Ala Gln Ser Ser Leu Pro Ala Thr Gly
            20                  25                  30

Ser Asp Ser Ser Glu Trp Ser Ala Ser Ala Tyr Leu Thr Asp Asp Ala
        35                  40                  45

Gly Arg Ser Leu Ile Leu Arg Gly Phe Asn Thr Ala Ser Ser Ala Lys
    50                  55                  60

Ser Thr Pro Asp Gly Met Pro Ile Phe Thr Glu Ser Asp Leu Asp Arg
65                  70                  75                  80

Glu His Ala Asp Met Gly Thr Asn Phe Val Arg Phe Leu Ile Ser Trp
                85                  90                  95

Arg Ser Val Glu Pro Glu Pro Gly Gln Tyr Asp Gln Ala Tyr Leu Asp
            100                 105                 110

Arg Val Glu Gln Arg Val Gly Trp Tyr Ala Glu Arg Gly Tyr Lys Val
        115                 120                 125

Met Leu Asp Met His Gln Asp Leu Tyr Ser Gly Ala Ile Thr Pro Asp
```

```
            130                 135                 140
Gly Lys Thr Gly Asn Gly Ala Pro Ala Trp Ala Thr Tyr Met Asp Gly
145                 150                 155                 160

Leu Pro Val Asn Glu Arg Asp Ser Trp Glu Leu Tyr Tyr Ile Glu Pro
                165                 170                 175

Gly Val Ile Arg Ala Phe Asp Asn Phe Trp Asn Thr Thr Gly Lys His
            180                 185                 190

Pro Glu Leu Val Asp His Tyr Val Asn Ala Trp Lys Ala Val Ala Asp
        195                 200                 205

Arg Phe Ala Asp Asn Glu Thr Val Val Ala Tyr Asp Leu Met Asn Glu
    210                 215                 220

Pro Trp Gly Gly Ser Leu Gln Gly Pro Ala Phe Glu Ala Gly Pro Leu
225                 230                 235                 240

Thr Ser Met Tyr Gln Arg Thr Asp Ala Ile Arg Gln Val Asp Gln
                245                 250                 255

Asp Ser Trp Val Cys Val Ala Pro Gln Ala Val Gly Val Asn Gln Gly
            260                 265                 270

Ile Pro Ser Ala Leu Gly Thr Ile Ala Asp Pro Arg Gln Gly Ala Arg
        275                 280                 285

Arg Ile Ala Tyr Cys Pro His Leu Tyr Pro Leu Pro Leu Asp Leu Gly
    290                 295                 300

Asp Gly Tyr Ser Gly Phe Ser Lys Thr Leu Thr Asp Ala Thr Ile Glu
305                 310                 315                 320

Thr Trp Arg Thr Ser Ile Glu His Val Ala Asp Thr Val Leu Glu Gly
                325                 330                 335

Ala Pro Val Ile Leu Gly Glu Phe Gly Leu Asp Thr Leu Pro Gly
            340                 345                 350

Ala Gln Asp Tyr Leu Asp Arg Val Tyr Thr Val Ala Arg Asp Met Gly
        355                 360                 365

Ala Gly Val Ser Tyr Trp Ser Ser Asp Arg Gly Pro Trp Gly Pro Tyr
    370                 375                 380

Leu Glu Asp Gly Thr Gln Thr Ile Leu Val Asp Thr Val Asn Lys Pro
385                 390                 395                 400

Tyr Pro Arg Ala Val Ala Gly Met Pro Val Arg Trp Ser Ser Thr Ser
                405                 410                 415

Asp Arg Leu Asp Leu Thr Tyr Arg Asn Asp Pro Ala Val Thr Ala Pro
            420                 425                 430

Thr Glu Ile Tyr Leu Pro Ala Ala Gly Phe Pro Gly Asp Ile Ala Val
        435                 440                 445

Gln Gly Ala Asp Val Val Gly Trp Asp Ser Gln Ser Arg Leu Leu Thr
    450                 455                 460

Val Arg Ser Ala Pro Asp Ala Gly Glu Val Thr Val Thr Val Thr Pro
465                 470                 475                 480

Ala Ala

<210> SEQ ID NO 6
<211> LENGTH: 482
<212> TYPE: PRT
<213> ORGANISM: Rhodococcus sp.

<400> SEQUENCE: 6

Met Arg Arg Thr Arg Ile Ala Ser Leu Ala Val Ala Gly Ser Leu Val
1               5                   10                  15

Leu Gly Ala Gly Val Ala Thr Ala Gln Ser Ser Leu Pro Ala Thr Gly
```

```
             20                  25                  30
Ser Asp Ser Ser Glu Trp Ser Ala Ser Ala Tyr Leu Thr Asp Asp Ala
             35                  40                  45
Gly Arg Ser Leu Ile Leu Arg Gly Phe Asn Thr Ala Ser Ser Ala Lys
             50                  55                  60
Ser Thr Pro Asp Gly Met Pro Ile Phe Thr Glu Ser Asp Leu Asp Arg
 65                  70                  75                  80
Glu His Ala Asp Met Gly Thr Asn Phe Val Arg Phe Leu Ile Ser Trp
                         85                  90                  95
Arg Ser Val Glu Pro Glu Pro Gly Gln Tyr Asp Gln Ala Tyr Leu Asp
                100                 105                 110
Arg Val Glu Gln Arg Val Gly Trp Tyr Ala Glu Arg Gly Tyr Lys Val
                115                 120                 125
Met Leu Asp Met His Gln Asp Leu Tyr Ser Gly Ala Ile Thr Pro Asp
                130                 135                 140
Gly Lys Thr Gly Asn Gly Ala Pro Ala Trp Ala Thr Tyr Met Asp Gly
145                 150                 155                 160
Leu Pro Val Asn Glu Arg Asp Ser Trp Glu Leu Tyr Tyr Ile Glu Pro
                165                 170                 175
Gly Val Ile Arg Ala Phe Asp Asn Phe Trp Asn Thr Thr Gly Lys His
                180                 185                 190
Pro Glu Leu Val Asp His Tyr Val Asn Ala Trp Lys Ala Val Ala Asp
                195                 200                 205
Arg Phe Ala Asp Asn Glu Thr Val Val Ala Tyr Asp Leu Met Asn Glu
                210                 215                 220
Pro Trp Gly Gly Ser Leu Gln Gly Pro Ala Phe Glu Ala Gly Pro Leu
225                 230                 235                 240
Thr Ser Met Tyr Gln Arg Thr Thr Asp Ala Ile Arg Gln Val Asp Gln
                245                 250                 255
Asp Ser Trp Val Cys Val Ala Pro Gln Ala Val Gly Val Asn Gln Gly
                260                 265                 270
Ile Pro Ser Ala Leu Gly Thr Ile Ala Asp Pro Arg Gln Gly Ala Arg
                275                 280                 285
Arg Ile Ala Tyr Cys Pro His Leu Tyr Pro Leu Pro Leu Asp Leu Gly
                290                 295                 300
Asp Gly Tyr Ser Gly Phe Ser Lys Thr Leu Thr Asp Ala Thr Ile Glu
305                 310                 315                 320
Thr Trp Arg Thr Ser Ile Glu His Val Ala Asp Thr Val Leu Glu Gly
                325                 330                 335
Ala Pro Val Ile Leu Gly Glu Phe Gly Leu Asp Thr Thr Leu Pro Gly
                340                 345                 350
Ala Gln Asp Tyr Leu Asp Arg Val Tyr Thr Val Ala Arg Asp Met Gly
                355                 360                 365
Ala Gly Val Ser Tyr Trp Ser Ser Asp Arg Gly Pro Trp Gly Pro Tyr
                370                 375                 380
Leu Glu Asp Gly Thr Gln Thr Ile Leu Val Asp Thr Val Asn Lys Pro
385                 390                 395                 400
Tyr Pro Arg Ala Val Ala Gly Met Pro Val Arg Trp Ser Ser Thr Ser
                405                 410                 415
Asp Arg Leu Asp Leu Thr Tyr Arg Asn Asp Pro Ala Val Thr Ala Pro
                420                 425                 430
Thr Glu Ile Tyr Leu Pro Ala Ala Gly Phe Pro Gly Asp Ile Ala Val
                435                 440                 445
```

```
Gln Gly Ala Asp Val Val Gly Trp Asp Ser Gln Ser Arg Leu Leu Thr
    450                 455                 460

Val Arg Ser Ala Pro Asp Ala Gly Glu Val Thr Val Thr Val Thr Pro
465                 470                 475                 480

Ala Ala

<210> SEQ ID NO 7
<211> LENGTH: 1503
<212> TYPE: DNA
<213> ORGANISM: Propionibacterium acnes
<220> FEATURE:
<221> NAME/KEY: CDS
<222> LOCATION: (1)..(1503)
<223> OTHER INFORMATION: EGCase

<400> SEQUENCE: 7 atg cgt cga aag tct gcc ctc gga ttt gta gct ttg tcc ctg ttc gcc      48
Met Arg Arg Lys Ser Ala Leu Gly Phe Val Ala Leu Ser Leu Phe Ala
1               5                   10                  15 aca ggg atg ggc gtt gcc gca gca aca ccg gca act gcc tcg ccg gcg      96
Thr Gly Met Gly Val Ala Ala Ala Thr Pro Ala Thr Ala Ser Pro Ala
            20                  25                  30 gat acg gca gcg cca gtt cac gtc gac gct tca cgg tgg acc acc cag     144
Asp Thr Ala Ala Pro Val His Val Asp Ala Ser Arg Trp Thr Thr Gln
        35                  40                  45 ggg cgt tgg gtg acc gac acc cag cac cgc gtg gtc atc acg cag ggg     192
Gly Arg Trp Val Thr Asp Thr Gln His Arg Val Val Ile Thr Gln Gly
    50                  55                  60 atc aac gag gtc gcc aag agc gcc ccc tac gcc ccc gat gcc gtc ggt     240
Ile Asn Glu Val Ala Lys Ser Ala Pro Tyr Ala Pro Asp Ala Val Gly
65                  70                  75                  80 ttc ggt gaa gac gac gca gcc ttc ctc gag gcg cag ggg ttc acc agc     288
Phe Gly Glu Asp Asp Ala Ala Phe Leu Glu Ala Gln Gly Phe Thr Ser
                85                  90                  95 gtc cgg ctg ggg gtg ctg tgg gcc ggc gtc gag cct cgg ccg ggc gtc     336
Val Arg Leu Gly Val Leu Trp Ala Gly Val Glu Pro Arg Pro Gly Val
            100                 105                 110 tac gac gac gct tac ctg gcc cgg gtc gaa cgc acc gtg cgg atc ctc     384
Tyr Asp Asp Ala Tyr Leu Ala Arg Val Glu Arg Thr Val Arg Ile Leu
        115                 120                 125 aac gcc cac ggc atc gcc agt gtc ctc gac ttc cat cag gac atg gtc     432
Asn Ala His Gly Ile Ala Ser Val Leu Asp Phe His Gln Asp Met Val
    130                 135                 140 aac gag aag tac cag ggg gag ggg tgg cct gcc tgg gcc gcg ctc gac     480
Asn Glu Lys Tyr Gln Gly Glu Gly Trp Pro Ala Trp Ala Ala Leu Asp
145                 150                 155                 160 cac ggc atg ccc aac atc gtc aag acg ggc ttc ccc ggc aac tat ttc     528
His Gly Met Pro Asn Ile Val Lys Thr Gly Phe Pro Gly Asn Tyr Phe
                165                 170                 175 ctc aac gag gcc gtc aaa tac tcc ttc gac tcc ttc tac gac aac acc     576
Leu Asn Glu Ala Val Lys Tyr Ser Phe Asp Ser Phe Tyr Asp Asn Thr
            180                 185                 190 aag gcc tcc gac ggc atc ggt gtt gcc gac cac tac gcc agc gcc tgg     624
Lys Ala Ser Asp Gly Ile Gly Val Ala Asp His Tyr Ala Ser Ala Trp
        195                 200                 205 cga cat gtg gcc gag cat ttc cga aac gtg ccc ggc gtg cag ggc tac     672
Arg His Val Ala Glu His Phe Arg Asn Val Pro Gly Val Gln Gly Tyr
    210                 215                 220 gac ctg ttc aac gag ccg ttc ccg ggc cac cgc tac acg cgg tgc ctc     720
Asp Leu Phe Asn Glu Pro Phe Pro Gly His Arg Tyr Thr Arg Cys Leu
```

```
                225                 230                 235                 240
acg cag ctc ggt tgc cgc gct gct gac gcg cga ctg tcg gcc gtc cag              768
Thr Gln Leu Gly Cys Arg Ala Ala Asp Ala Arg Leu Ser Ala Val Gln
                    245                 250                 255 cag aag act gtc gac gcg atc cgc tcg gtc gac aag gcc acc act gtc              816
Gln Lys Thr Val Asp Ala Ile Arg Ser Val Asp Lys Ala Thr Thr Val
                260                 265                 270 tgg tac gag ccg atg cag ttc ttc aat ata ggt gtc ggg acc aac gtc              864
Trp Tyr Glu Pro Met Gln Phe Phe Asn Ile Gly Val Gly Thr Asn Val
            275                 280                 285 cgg ctc acg gga tcc aac ctg ggg ttg agc ttc cac gac tac tgc acc              912
Arg Leu Thr Gly Ser Asn Leu Gly Leu Ser Phe His Asp Tyr Cys Thr
        290                 295                 300 agc cag gcc acc ctc cac tcc tat gtc ggg tgc act gcg ccc gac aac              960
Ser Gln Ala Thr Leu His Ser Tyr Val Gly Cys Thr Ala Pro Asp Asn
305                 310                 315                 320 cgg gtc ttc act aac gca gag aag cat tca cgt cag acc ggg tcg ggg             1008
Arg Val Phe Thr Asn Ala Glu Lys His Ser Arg Gln Thr Gly Ser Gly
                325                 330                 335 ctg atg ctc acc gag ttc ggc gcc atc acg acc ccc gcg gtg atc acg             1056
Leu Met Leu Thr Glu Phe Gly Ala Ile Thr Thr Pro Ala Val Ile Thr
            340                 345                 350 tcc cag atg gac ctg gca gct cgc aac cgg gtc ggc gtc cag tgg tgg             1104
Ser Gln Met Asp Leu Ala Ala Arg Asn Arg Val Gly Val Gln Trp Trp
        355                 360                 365 gcc tac act gcc ggt gat ccc acc aca gcc ggc ccg ggc acc gag caa             1152
Ala Tyr Thr Ala Gly Asp Pro Thr Thr Ala Gly Pro Gly Thr Glu Gln
    370                 375                 380 gcc ctc gtc gac gac cca gct cgg cca ccc cag ggg acc aac gtc gaa             1200
Ala Leu Val Asp Asp Pro Ala Arg Pro Pro Gln Gly Thr Asn Val Glu
385                 390                 395                 400 agc gcc aag ctg acg ctg atc gcc gtt ccc cac ccg gac cgt gtc gcg             1248
Ser Ala Lys Leu Thr Leu Ile Ala Val Pro His Pro Asp Arg Val Ala
                405                 410                 415 ggc acc cca tcc gcg tac cac cac gac cgg tcc cga cgc gtg ttc acc             1296
Gly Thr Pro Ser Ala Tyr His His Asp Arg Ser Arg Arg Val Phe Thr
            420                 425                 430 atg acc tgg acc gcc cag cgg ccc gac ggg tcg cgc gcg gag gag tcg             1344
Met Thr Trp Thr Ala Gln Arg Pro Asp Gly Ser Arg Ala Glu Glu Ser
        435                 440                 445 gac gag acg act gtg gtg gtc cct gcc atc tca gcg ccc cac ggg tac             1392
Asp Glu Thr Thr Val Val Val Pro Ala Ile Ser Ala Pro His Gly Tyr
    450                 455                 460 gac gtg cag gca tcc ggc gcc cac gtc acc tcc cac cca ggc gac cgg             1440
Asp Val Gln Ala Ser Gly Ala His Val Thr Ser His Pro Gly Asp Arg
465                 470                 475                 480 gtg gcg cgg ttg cac ctc aac caa ggc agt gcc acg gcg aag gtc acg             1488
Val Ala Arg Leu His Leu Asn Gln Gly Ser Ala Thr Ala Lys Val Thr
                485                 490                 495 atc acc ctg cgc taa                                                          1503
Ile Thr Leu Arg
            500

<210> SEQ ID NO 8
<211> LENGTH: 500
<212> TYPE: PRT
<213> ORGANISM: Propionibacterium acnes

<400> SEQUENCE: 8

Met Arg Arg Lys Ser Ala Leu Gly Phe Val Ala Leu Ser Leu Phe Ala
```

```
1               5                   10                  15
Thr Gly Met Gly Val Ala Ala Thr Pro Ala Thr Ala Ser Pro Ala
            20                  25                  30
Asp Thr Ala Ala Pro Val His Val Asp Ala Ser Arg Trp Thr Thr Gln
            35                  40                  45
Gly Arg Trp Val Thr Asp Thr Gln His Arg Val Val Ile Thr Gln Gly
            50                  55                  60
Ile Asn Glu Val Ala Lys Ser Ala Pro Tyr Ala Pro Asp Ala Val Gly
65                  70                  75                  80
Phe Gly Glu Asp Asp Ala Ala Phe Leu Glu Ala Gln Gly Phe Thr Ser
                85                  90                  95
Val Arg Leu Gly Val Leu Trp Ala Gly Val Glu Pro Arg Pro Gly Val
                100                 105                 110
Tyr Asp Asp Ala Tyr Leu Ala Arg Val Glu Arg Thr Val Arg Ile Leu
                115                 120                 125
Asn Ala His Gly Ile Ala Ser Val Leu Asp Phe His Gln Asp Met Val
                130                 135                 140
Asn Glu Lys Tyr Gln Gly Glu Gly Trp Pro Ala Trp Ala Ala Leu Asp
145                 150                 155                 160
His Gly Met Pro Asn Ile Val Lys Thr Gly Phe Pro Gly Asn Tyr Phe
                165                 170                 175
Leu Asn Glu Ala Val Lys Tyr Ser Phe Asp Ser Phe Tyr Asp Asn Thr
                180                 185                 190
Lys Ala Ser Asp Gly Ile Gly Val Ala Asp His Tyr Ala Ser Ala Trp
                195                 200                 205
Arg His Val Ala Glu His Phe Arg Asn Val Pro Gly Val Gln Gly Tyr
                210                 215                 220
Asp Leu Phe Asn Glu Pro Phe Pro Gly His Arg Tyr Thr Arg Cys Leu
225                 230                 235                 240
Thr Gln Leu Gly Cys Arg Ala Ala Asp Ala Arg Leu Ser Ala Val Gln
                245                 250                 255
Gln Lys Thr Val Asp Ala Ile Arg Ser Val Asp Lys Ala Thr Thr Val
                260                 265                 270
Trp Tyr Glu Pro Met Gln Phe Phe Asn Ile Gly Val Gly Thr Asn Val
                275                 280                 285
Arg Leu Thr Gly Ser Asn Leu Gly Leu Ser Phe His Asp Tyr Cys Thr
                290                 295                 300
Ser Gln Ala Thr Leu His Ser Tyr Val Gly Cys Thr Ala Pro Asp Asn
305                 310                 315                 320
Arg Val Phe Thr Asn Ala Glu Lys His Ser Arg Gln Thr Gly Ser Gly
                325                 330                 335
Leu Met Leu Thr Glu Phe Gly Ala Ile Thr Thr Pro Ala Val Ile Thr
                340                 345                 350
Ser Gln Met Asp Leu Ala Ala Arg Asn Arg Val Gly Val Gln Trp Trp
                355                 360                 365
Ala Tyr Thr Ala Gly Asp Pro Thr Thr Ala Gly Pro Gly Thr Glu Gln
                370                 375                 380
Ala Leu Val Asp Asp Pro Ala Arg Pro Gln Gly Thr Asn Val Glu
385                 390                 395                 400
Ser Ala Lys Leu Thr Leu Ile Ala Val Pro His Pro Asp Arg Val Ala
                405                 410                 415
Gly Thr Pro Ser Ala Tyr His His Asp Arg Ser Arg Arg Val Phe Thr
                420                 425                 430
```

```
Met Thr Trp Thr Ala Gln Arg Pro Asp Gly Ser Arg Ala Glu Glu Ser
            435                 440                 445

Asp Glu Thr Thr Val Val Pro Ala Ile Ser Ala Pro His Gly Tyr
450                 455                 460

Asp Val Gln Ala Ser Gly Ala His Val Thr Ser His Pro Gly Asp Arg
465                 470                 475                 480

Val Ala Arg Leu His Leu Asn Gln Gly Ser Ala Thr Ala Lys Val Thr
                485                 490                 495

Ile Thr Leu Arg
            500

<210> SEQ ID NO 9
<211> LENGTH: 500
<212> TYPE: PRT
<213> ORGANISM: Propionibacterium acnes

<400> SEQUENCE: 9

Met Arg Arg Lys Ser Ala Leu Gly Phe Val Ala Leu Ser Leu Phe Ala
1               5                   10                  15

Thr Gly Met Gly Val Ala Ala Ala Thr Pro Ala Thr Ala Ser Pro Ala
            20                  25                  30

Asp Thr Ala Ala Pro Val His Val Asp Ala Ser Arg Trp Thr Thr Gln
        35                  40                  45

Gly Arg Trp Val Thr Asp Thr Gln His Arg Val Val Ile Thr Gln Gly
    50                  55                  60

Ile Asn Glu Val Ala Lys Ser Ala Pro Tyr Ala Pro Asp Ala Val Gly
65              70                  75                  80

Phe Gly Glu Asp Ala Ala Phe Leu Glu Ala Gln Gly Phe Thr Ser
                85                  90                  95

Val Arg Leu Gly Val Leu Trp Ala Gly Val Glu Pro Arg Pro Gly Val
            100                 105                 110

Tyr Asp Asp Ala Tyr Leu Ala Arg Val Glu Arg Thr Val Arg Ile Leu
        115                 120                 125

Asn Ala His Gly Ile Ala Ser Val Leu Asp Phe His Gln Asp Met Val
130                 135                 140

Asn Glu Lys Tyr Gln Gly Glu Gly Trp Pro Ala Trp Ala Ala Leu Asp
145                 150                 155                 160

His Gly Met Pro Asn Ile Val Lys Thr Gly Phe Pro Gly Asn Tyr Phe
                165                 170                 175

Leu Asn Glu Ala Val Lys Tyr Ser Phe Asp Ser Phe Tyr Asp Asn Thr
            180                 185                 190

Lys Ala Ser Asp Gly Ile Gly Val Ala Asp His Tyr Ala Ser Ala Trp
        195                 200                 205

Arg His Val Ala Glu His Phe Arg Asn Val Pro Gly Val Gln Gly Tyr
210                 215                 220

Asp Leu Phe Asn Glu Pro Phe Pro Gly His Arg Tyr Thr Arg Cys Leu
225                 230                 235                 240

Thr Gln Leu Gly Cys Arg Ala Ala Asp Ala Arg Leu Ser Ala Val Gln
                245                 250                 255

Gln Lys Thr Val Asp Ala Ile Arg Ser Val Asp Lys Ala Thr Thr Val
            260                 265                 270

Trp Tyr Glu Pro Met Gln Phe Phe Asn Ile Gly Val Gly Thr Asn Val
        275                 280                 285

Arg Leu Thr Gly Ser Asn Leu Gly Leu Ser Phe His Asp Tyr Cys Thr
```

```
                    290                 295                 300
Ser Gln Ala Thr Leu His Ser Tyr Val Gly Cys Thr Ala Pro Asp Asn
305                 310                 315                 320

Arg Val Phe Thr Asn Ala Glu Lys His Ser Arg Gln Thr Gly Ser Gly
                325                 330                 335

Leu Met Leu Thr Glu Phe Gly Ala Ile Thr Thr Pro Ala Val Ile Thr
            340                 345                 350

Ser Gln Met Asp Leu Ala Ala Arg Asn Arg Val Gly Val Gln Trp Trp
        355                 360                 365

Ala Tyr Thr Ala Gly Asp Pro Thr Thr Ala Gly Pro Gly Thr Glu Gln
    370                 375                 380

Ala Leu Val Asp Asp Pro Ala Arg Pro Pro Gln Gly Thr Asn Val Glu
385                 390                 395                 400

Ser Ala Lys Leu Thr Leu Ile Ala Val Pro His Pro Asp Arg Val Ala
                405                 410                 415

Gly Thr Pro Ser Ala Tyr His His Asp Arg Ser Arg Arg Val Phe Thr
            420                 425                 430

Met Thr Trp Thr Ala Gln Arg Pro Asp Gly Ser Arg Ala Glu Glu Ser
        435                 440                 445

Asp Glu Thr Thr Val Val Val Pro Ala Ile Ser Ala Pro His Gly Tyr
    450                 455                 460

Asp Val Gln Ala Ser Gly Ala His Val Thr Ser His Pro Gly Asp Arg
465                 470                 475                 480

Val Ala Arg Leu His Leu Asn Gln Gly Ser Ala Thr Ala Lys Val Thr
                485                 490                 495

Ile Thr Leu Arg
            500

<210> SEQ ID NO 10
<211> LENGTH: 1575
<212> TYPE: DNA
<213> ORGANISM: Propionibacterium acnes
<220> FEATURE:
<221> NAME/KEY: CDS
<222> LOCATION: (1)..(1575)
<223> OTHER INFORMATION: EGCase

<400> SEQUENCE: 10 atg tat cac cat tca tgg cat tcc ccg gat gca cga cgc cga ggc gtc      48
Met Tyr His His Ser Trp His Ser Pro Asp Ala Arg Arg Arg Gly Val
1               5                   10                  15 acc cgg tgg gcg acc acc ttc att gct gcc ctt act gcc gcc tgc atg      96
Thr Arg Trp Ala Thr Thr Phe Ile Ala Ala Leu Thr Ala Ala Cys Met
            20                  25                  30 gca cag atg cct gca cag gcc tcg ccc cat acc agc gac gcc gct ccc     144
Ala Gln Met Pro Ala Gln Ala Ser Pro His Thr Ser Asp Ala Ala Pro
        35                  40                  45 cac atc gca acg tca aag acc atc acc gac gcc ggc ccc atc ggg cag     192
His Ile Ala Thr Ser Lys Thr Ile Thr Asp Ala Gly Pro Ile Gly Gln
    50                  55                  60 tcc ggc cgt tgg tac acc gac ggt cag ggt cgc gct atc ctc acc gcc     240
Ser Gly Arg Trp Tyr Thr Asp Gly Gln Gly Arg Ala Ile Leu Thr Ala
65                  70                  75                  80 ggc gtc aac atg gtc tct aaa cgt cac cca tac agt ccc gaa gcc gat     288
Gly Val Asn Met Val Ser Lys Arg His Pro Tyr Ser Pro Glu Ala Asp
                85                  90                  95 gga ttc gat gac gcc gac gct gcc tgg tta cag aag aac ggc ttc gat     336
Gly Phe Asp Asp Ala Asp Ala Ala Trp Leu Gln Lys Asn Gly Phe Asp
```

-continued

```
                100                 105                 110
tcg gtg cgc ctg gga gtc ata tgg aag ggg gtc gag ccc aag ccc gga    384
Ser Val Arg Leu Gly Val Ile Trp Lys Gly Val Glu Pro Lys Pro Gly
        115                 120                 125 gag tac gac gac gcc tac ctg gcc agc atc acc cgc aca gta aga aca    432
Glu Tyr Asp Asp Ala Tyr Leu Ala Ser Ile Thr Arg Thr Val Arg Thr
    130                 135                 140 ctt cgc gct cac ggc ata atg acc ctc ttg gac gct cac cag gac atg    480
Leu Arg Ala His Gly Ile Met Thr Leu Leu Asp Ala His Gln Asp Met
145                 150                 155                 160 tat aac gag aag ttc gag ggt gag gga gcc ccc gac tgg gcc gtt ctc    528
Tyr Asn Glu Lys Phe Glu Gly Glu Gly Ala Pro Asp Trp Ala Val Leu
                165                 170                 175 gac aag gga gca ccg aat ctg ctc aag gtt ggc ttc ccc gcc aac cag    576
Asp Lys Gly Ala Pro Asn Leu Leu Lys Val Gly Phe Pro Ala Asn Gln
            180                 185                 190 gtc ttc aac ctc gga ctc atc aag gct tac gac agt ttc ctg gac aat    624
Val Phe Asn Leu Gly Leu Ile Lys Ala Tyr Asp Ser Phe Leu Asp Asn
        195                 200                 205 gcc aag ggc ccg ggc gga gtg ggc ttg cag gat cgt tac gcg gcc atg    672
Ala Lys Gly Pro Gly Gly Val Gly Leu Gln Asp Arg Tyr Ala Ala Met
    210                 215                 220 tgg aag cac gtc gca cag gtc gtc ggg cag gaa ccc ggc gtc atg gga    720
Trp Lys His Val Ala Gln Val Val Gly Gln Glu Pro Gly Val Met Gly
225                 230                 235                 240 tac gac att atc aac gag cct tgg ccg gga cat cac tac ccc atc tgc    768
Tyr Asp Ile Ile Asn Glu Pro Trp Pro Gly His His Tyr Pro Ile Cys
                245                 250                 255 tac gtt gcc ttc ggc tgg tgc ggc cga gcg atg gtg tcc ttg gac acc    816
Tyr Val Ala Phe Gly Trp Cys Gly Arg Ala Met Val Ser Leu Asp Thr
            260                 265                 270 ttg tac gag aaa gtc ggc aga gcc atc acc tcg gtc gac ccc gac ggc    864
Leu Tyr Glu Lys Val Gly Arg Ala Ile Thr Ser Val Asp Pro Asp Gly
        275                 280                 285 atc gtc acc tac gag ccc tac tca acg tgg aac atg ggg ctg gac agc    912
Ile Val Thr Tyr Glu Pro Tyr Ser Thr Trp Asn Met Gly Leu Asp Ser
    290                 295                 300 cgc cca gcc cgc cca tcc tca ccg aag gct gcc att tct tgg cac gtc    960
Arg Pro Ala Arg Pro Ser Ser Pro Lys Ala Ala Ile Ser Trp His Val
305                 310                 315                 320 tac tgc ccc atg aac gca atc ttc ggc tcc tac gtc ggg tgc aat ctc   1008
Tyr Cys Pro Met Asn Ala Ile Phe Gly Ser Tyr Val Gly Cys Asn Leu
                325                 330                 335 ccc gac act cgc acc ttc cac aac gcc gac cag gca gcc cag ttc aac   1056
Pro Asp Thr Arg Thr Phe His Asn Ala Asp Gln Ala Ala Gln Phe Asn
            340                 345                 350 aac tca gcc tcc ttg ctc agt gaa ttc ggg gcc acc aaa gac ccc ggc   1104
Asn Ser Ala Ser Leu Leu Ser Glu Phe Gly Ala Thr Lys Asp Pro Gly
        355                 360                 365 act ctc atg ggg gtc aca tcc aag gct cgc gcc cat ctg gtc ggc tgg   1152
Thr Leu Met Gly Val Thr Ser Lys Ala Arg Ala His Leu Val Gly Trp
    370                 375                 380 ctg tac tgg acg tac aac gga aac tcc gac ccg aca acc cag aat gct   1200
Leu Tyr Trp Thr Tyr Asn Gly Asn Ser Asp Pro Thr Thr Gln Asn Ala
385                 390                 395                 400 gca gac gag gag ctc gtc cgt cat atc aac cgt ccg gga cct gtc acc   1248
Ala Asp Glu Glu Leu Val Arg His Ile Asn Arg Pro Gly Pro Val Thr
                405                 410                 415 gac gaa caa gtg gac cac acc aag ctc gcc att ctg gcg gta ccg cac   1296
```

```
                Asp Glu Gln Val Asp His Thr Lys Leu Ala Ile Leu Ala Val Pro His
                                420                 425                 430 ctg cgc gcc gct gcg ggc acc ccg acc tcg acg acc tgg gac cag tcc         1344
Leu Arg Ala Ala Ala Gly Thr Pro Thr Ser Thr Thr Trp Asp Gln Ser
        435                 440                 445 acc cgg acg tac cag gcc acg tgg acg gct aaa cgt gtc gcc ggt gac         1392
Thr Arg Thr Tyr Gln Ala Thr Trp Thr Ala Lys Arg Val Ala Gly Asp
450                 455                 460 ggt gac ttc gcg gca gga tcc gtc tcc gag atc gcc gtc ccg gct atc         1440
Gly Asp Phe Ala Ala Gly Ser Val Ser Glu Ile Ala Val Pro Ala Ile
465                 470                 475                 480 cac tac ccc aat ggt tac aag gtc gag gtg aag ggc gcc aag gtc att         1488
His Tyr Pro Asn Gly Tyr Lys Val Glu Val Lys Gly Ala Lys Val Ile
                485                 490                 495 tcc aaa gcc gga gac aca cgc ctg cag gtc agc tcc acc gga gaa ggc         1536
Ser Lys Ala Gly Asp Thr Arg Leu Gln Val Ser Ser Thr Gly Glu Gly
                500                 505                 510 ccg gta agc gtc acc atc acc cct gcc ggt cag gcc taa                     1575
Pro Val Ser Val Thr Ile Thr Pro Ala Gly Gln Ala
                515                 520

<210> SEQ ID NO 11
<211> LENGTH: 524
<212> TYPE: PRT
<213> ORGANISM: Propionibacterium acnes

<400> SEQUENCE: 11

Met Tyr His His Ser Trp His Ser Pro Asp Ala Arg Arg Gly Val
1               5                   10                  15

Thr Arg Trp Ala Thr Thr Phe Ile Ala Ala Leu Thr Ala Ala Cys Met
                20                  25                  30

Ala Gln Met Pro Ala Gln Ala Ser Pro His Thr Ser Asp Ala Ala Pro
            35                  40                  45

His Ile Ala Thr Ser Lys Thr Ile Thr Asp Ala Gly Pro Ile Gly Gln
        50                  55                  60

Ser Gly Arg Trp Tyr Thr Asp Gly Gln Gly Arg Ala Ile Leu Thr Ala
65                  70                  75                  80

Gly Val Asn Met Val Ser Lys Arg His Pro Tyr Ser Pro Glu Ala Asp
                85                  90                  95

Gly Phe Asp Asp Ala Asp Ala Ala Trp Leu Gln Lys Asn Gly Phe Asp
            100                 105                 110

Ser Val Arg Leu Gly Val Ile Trp Lys Gly Val Glu Pro Lys Pro Gly
        115                 120                 125

Glu Tyr Asp Asp Ala Tyr Leu Ala Ser Ile Thr Arg Thr Val Arg Thr
    130                 135                 140

Leu Arg Ala His Gly Ile Met Thr Leu Leu Asp Ala His Gln Asp Met
145                 150                 155                 160

Tyr Asn Glu Lys Phe Glu Gly Glu Gly Ala Pro Asp Trp Ala Val Leu
                165                 170                 175

Asp Lys Gly Ala Pro Asn Leu Leu Lys Val Gly Phe Pro Ala Asn Gln
            180                 185                 190

Val Phe Asn Leu Gly Leu Ile Lys Ala Tyr Asp Ser Phe Leu Asp Asn
        195                 200                 205

Ala Lys Gly Pro Gly Gly Val Gly Leu Gln Asp Arg Tyr Ala Ala Met
    210                 215                 220

Trp Lys His Val Ala Gln Val Val Gly Gln Glu Pro Gly Val Met Gly
225                 230                 235                 240
```

```
Tyr Asp Ile Ile Asn Glu Pro Trp Pro Gly His His Tyr Pro Ile Cys
                245                 250                 255
Tyr Val Ala Phe Gly Trp Cys Gly Arg Ala Met Val Ser Leu Asp Thr
            260                 265                 270
Leu Tyr Glu Lys Val Gly Arg Ala Ile Thr Ser Val Asp Pro Asp Gly
        275                 280                 285
Ile Val Thr Tyr Glu Pro Tyr Ser Thr Trp Asn Met Gly Leu Asp Ser
    290                 295                 300
Arg Pro Ala Arg Pro Ser Ser Pro Lys Ala Ala Ile Ser Trp His Val
305                 310                 315                 320
Tyr Cys Pro Met Asn Ala Ile Phe Gly Ser Tyr Val Gly Cys Asn Leu
                325                 330                 335
Pro Asp Thr Arg Thr Phe His Asn Ala Asp Gln Ala Ala Gln Phe Asn
            340                 345                 350
Asn Ser Ala Ser Leu Leu Ser Glu Phe Gly Ala Thr Lys Asp Pro Gly
        355                 360                 365
Thr Leu Met Gly Val Thr Ser Lys Ala Arg Ala His Leu Val Gly Trp
    370                 375                 380
Leu Tyr Trp Thr Tyr Asn Gly Asn Ser Asp Pro Thr Thr Gln Asn Ala
385                 390                 395                 400
Ala Asp Glu Glu Leu Val Arg His Ile Asn Arg Pro Gly Pro Val Thr
                405                 410                 415
Asp Glu Gln Val Asp His Thr Lys Leu Ala Ile Leu Ala Val Pro His
            420                 425                 430
Leu Arg Ala Ala Ala Gly Thr Pro Thr Ser Thr Thr Trp Asp Gln Ser
        435                 440                 445
Thr Arg Thr Tyr Gln Ala Thr Trp Thr Ala Lys Arg Val Ala Gly Asp
    450                 455                 460
Gly Asp Phe Ala Ala Gly Ser Val Ser Glu Ile Ala Val Pro Ala Ile
465                 470                 475                 480
His Tyr Pro Asn Gly Tyr Lys Val Glu Val Lys Gly Ala Lys Val Ile
                485                 490                 495
Ser Lys Ala Gly Asp Thr Arg Leu Gln Val Ser Ser Thr Gly Glu Gly
            500                 505                 510
Pro Val Ser Val Thr Ile Thr Pro Ala Gly Gln Ala
        515                 520

<210> SEQ ID NO 12
<211> LENGTH: 524
<212> TYPE: PRT
<213> ORGANISM: Propionibacterium acnes

<400> SEQUENCE: 12

Met Tyr His His Ser Trp His Ser Pro Asp Ala Arg Arg Arg Gly Val
1               5                   10                  15
Thr Arg Trp Ala Thr Thr Phe Ile Ala Ala Leu Thr Ala Ala Cys Met
            20                  25                  30
Ala Gln Met Pro Ala Gln Ala Ser Pro His Thr Ser Asp Ala Ala Pro
        35                  40                  45
His Ile Ala Thr Ser Lys Thr Ile Thr Asp Ala Gly Pro Ile Gly Gln
    50                  55                  60
Ser Gly Arg Trp Tyr Thr Asp Gly Gln Gly Arg Ala Ile Leu Thr Ala
65                  70                  75                  80
Gly Val Asn Met Val Ser Lys Arg His Pro Tyr Ser Pro Glu Ala Asp
```

```
                 85                  90                  95
Gly Phe Asp Asp Ala Asp Ala Ala Trp Leu Gln Lys Asn Gly Phe Asp
            100                 105                 110

Ser Val Arg Leu Gly Val Ile Trp Lys Gly Val Glu Pro Lys Pro Gly
        115                 120                 125

Glu Tyr Asp Asp Ala Tyr Leu Ala Ser Ile Thr Arg Thr Val Arg Thr
    130                 135                 140

Leu Arg Ala His Gly Ile Met Thr Leu Leu Asp Ala His Gln Asp Met
145                 150                 155                 160

Tyr Asn Glu Lys Phe Glu Gly Glu Gly Ala Pro Asp Trp Ala Val Leu
                165                 170                 175

Asp Lys Gly Ala Pro Asn Leu Leu Lys Val Gly Phe Pro Ala Asn Gln
            180                 185                 190

Val Phe Asn Leu Gly Leu Ile Lys Ala Tyr Asp Ser Phe Leu Asp Asn
        195                 200                 205

Ala Lys Gly Pro Gly Gly Val Gly Leu Gln Asp Arg Tyr Ala Ala Met
    210                 215                 220

Trp Lys His Val Ala Gln Val Gly Gln Glu Pro Gly Val Met Gly
225                 230                 235                 240

Tyr Asp Ile Ile Asn Glu Pro Trp Pro Gly His His Tyr Pro Ile Cys
                245                 250                 255

Tyr Val Ala Phe Gly Trp Cys Gly Arg Ala Met Val Ser Leu Asp Thr
            260                 265                 270

Leu Tyr Glu Lys Val Gly Arg Ala Ile Thr Ser Val Asp Pro Asp Gly
        275                 280                 285

Ile Val Thr Tyr Glu Pro Tyr Ser Thr Trp Asn Met Gly Leu Asp Ser
    290                 295                 300

Arg Pro Ala Arg Pro Ser Ser Pro Lys Ala Ala Ile Ser Trp His Val
305                 310                 315                 320

Tyr Cys Pro Met Asn Ala Ile Phe Gly Ser Tyr Val Gly Cys Asn Leu
                325                 330                 335

Pro Asp Thr Arg Thr Phe His Asn Ala Asp Gln Ala Ala Gln Phe Asn
            340                 345                 350

Asn Ser Ala Ser Leu Leu Ser Glu Phe Gly Ala Thr Lys Asp Pro Gly
        355                 360                 365

Thr Leu Met Gly Val Thr Ser Lys Ala Arg Ala His Leu Val Gly Trp
    370                 375                 380

Leu Tyr Trp Thr Tyr Asn Gly Asn Ser Asp Pro Thr Thr Gln Asn Ala
385                 390                 395                 400

Ala Asp Glu Glu Leu Val Arg His Ile Asn Arg Pro Gly Pro Val Thr
                405                 410                 415

Asp Glu Gln Val Asp His Thr Lys Leu Ala Ile Leu Ala Val Pro His
            420                 425                 430

Leu Arg Ala Ala Ala Gly Thr Pro Thr Ser Thr Thr Trp Asp Gln Ser
        435                 440                 445

Thr Arg Thr Tyr Gln Ala Thr Trp Thr Ala Lys Arg Val Ala Gly Asp
    450                 455                 460

Gly Asp Phe Ala Ala Gly Ser Val Ser Glu Ile Ala Val Pro Ala Ile
465                 470                 475                 480

His Tyr Pro Asn Gly Tyr Lys Val Glu Val Lys Gly Ala Lys Val Ile
                485                 490                 495

Ser Lys Ala Gly Asp Thr Arg Leu Gln Val Ser Ser Thr Gly Glu Gly
            500                 505                 510
```

```
                                                    Pro Val Ser Val Thr Ile Thr Pro Ala Gly Gln Ala
                                                            515                 520

<210> SEQ ID NO 13
<211> LENGTH: 1730
<212> TYPE: DNA
<213> ORGANISM: Cyanella capensis
<220> FEATURE:
<221> NAME/KEY: CDS
<222> LOCATION: (12)..(1523)
<223> OTHER INFORMATION: EGCase

<400> SEQUENCE: 13
ggcgatttgc a atg gct gaa aca caa cca ttg gtg ttt gtc ttg atg agc            50
             Met Ala Glu Thr Gln Pro Leu Val Phe Val Leu Met Ser
             1               5                   10 att tca gct att tta acg gca gga ctt cca ata aac gat gat gca tca            98
Ile Ser Ala Ile Leu Thr Ala Gly Leu Pro Ile Asn Asp Asp Ala Ser
 15              20                  25 ttg ttg ata agc gtc aat cct gaa aca caa cag ttg gtt gat agt ttg           146
Leu Leu Ile Ser Val Asn Pro Glu Thr Gln Gln Leu Val Asp Ser Leu
 30              35                  40                  45 ggg aga gag aga ttt ttt cat gga acg aac gtt gtt gtc aaa cat aaa           194
Gly Arg Glu Arg Phe Phe His Gly Thr Asn Val Val Val Lys His Lys
                 50                  55                  60 cct tat cat cca tca gtt gag ggt tat gac aat acg tct ttc tca gaa           242
Pro Tyr His Pro Ser Val Glu Gly Tyr Asp Asn Thr Ser Phe Ser Glu
             65                  70                  75 gtt gat atg aag att ttg caa gat ctt ggc ctc aat aca att cgc ctt           290
Val Asp Met Lys Ile Leu Gln Asp Leu Gly Leu Asn Thr Ile Arg Leu
         80                  85                  90 ggt atg atg ctg cca ggc tac gtg cct acc cga ggt aat tac aat gaa           338
Gly Met Met Leu Pro Gly Tyr Val Pro Thr Arg Gly Asn Tyr Asn Glu
     95                 100                 105 aca tac ttg aag atc ata cag gaa att gta tca aag gca gct aaa tat           386
Thr Tyr Leu Lys Ile Ile Gln Glu Ile Val Ser Lys Ala Ala Lys Tyr
110                 115                 120                 125 ggc att tat act tta ctg gat atg cac cag gat gtt atg tct gca aag           434
Gly Ile Tyr Thr Leu Leu Asp Met His Gln Asp Val Met Ser Ala Lys
                130                 135                 140 ttt tgc gtt gaa gga ttt cct gat tgg gct gtt aat aca ggc aat gca           482
Phe Cys Val Glu Gly Phe Pro Asp Trp Ala Val Asn Thr Gly Asn Ala
            145                 150                 155 gac aat ttc cct ttt cca ctt gaa gac aaa tac ccc ctg aat ctg cag           530
Asp Asn Phe Pro Phe Pro Leu Glu Asp Lys Tyr Pro Leu Asn Leu Gln
        160                 165                 170 act gga tac cct tat cca aaa gac tgt gca aag cat gcc tgg ggg gac           578
Thr Gly Tyr Pro Tyr Pro Lys Asp Cys Ala Lys His Ala Trp Gly Asp
    175                 180                 185 tac tac ttc acg gaa gca gcc gcc gca gct ttc cag aac ttc tac aat           626
Tyr Tyr Phe Thr Glu Ala Ala Ala Ala Ala Phe Gln Asn Phe Tyr Asn
190                 195                 200                 205 aac act gac ggg cta tta gat gca tgg gcg gac ttc tgg aag aaa aca           674
Asn Thr Asp Gly Leu Leu Asp Ala Trp Ala Asp Phe Trp Lys Lys Thr
                210                 215                 220 gca cag ggt ttc aaa gat tat aaa agt gtc att gga tat gaa ctt att           722
Ala Gln Gly Phe Lys Asp Tyr Lys Ser Val Ile Gly Tyr Glu Leu Ile
            225                 230                 235 aat gaa cca ttt gct ggc gat ata tac agg gat cct tca ctc atg att           770
Asn Glu Pro Phe Ala Gly Asp Ile Tyr Arg Asp Pro Ser Leu Met Ile
        240                 245                 250
```

| | | | | | | | | | | | | | | | |
|---|---|---|---|---|---|---|---|---|---|---|---|---|---|---|---|
| cct | ggc | gtt | gcg | gac | gaa | aga | aac | ctc | gcg | cca | gcc | tat | gac | gtc | atc | 818 |
| Pro | Gly | Val | Ala | Asp | Glu | Arg | Asn | Leu | Ala | Pro | Ala | Tyr | Asp | Val | Ile | |
| | 255 | | | | 260 | | | | | 265 | | | | | | |
| cat | aaa | gcc | att | cgt | acg | gtg | gat | gaa | caa | cac | agc | ata | ttt | ttc | gag | 866 |
| His | Lys | Ala | Ile | Arg | Thr | Val | Asp | Glu | Gln | His | Ser | Ile | Phe | Phe | Glu | |
| 270 | | | | | 275 | | | | | 280 | | | | | 285 | |
| ggc | gta | acg | tgg | gat | tat | ttc | gcg | gcg | gga | ttc | agt | aaa | gta | cca | ggc | 914 |
| Gly | Val | Thr | Trp | Asp | Tyr | Phe | Ala | Ala | Gly | Phe | Ser | Lys | Val | Pro | Gly | |
| | | | | 290 | | | | | 295 | | | | | 300 | | |
| ggt | gac | gca | tac | cgt | aat | cgg | agc | gtt | tta | agc | tat | cat | tat | tac | gag | 962 |
| Gly | Asp | Ala | Tyr | Arg | Asn | Arg | Ser | Val | Leu | Ser | Tyr | His | Tyr | Tyr | Glu | |
| | | | 305 | | | | | 310 | | | | | 315 | | | |
| cct | cca | gat | ttc | aat | aag | aag | ttt | cag | ttc | gag | gtg | cgt | atg | gaa | gat | 1010 |
| Pro | Pro | Asp | Phe | Asn | Lys | Lys | Phe | Gln | Phe | Glu | Val | Arg | Met | Glu | Asp | |
| | | 320 | | | | | 325 | | | | | 330 | | | | |
| ctt | agg | cgt | tta | aaa | tgt | ggc | ggt | ttc | ttg | acc | gaa | ctt | ctt | acg | gtt | 1058 |
| Leu | Arg | Arg | Leu | Lys | Cys | Gly | Gly | Phe | Leu | Thr | Glu | Leu | Leu | Thr | Val | |
| | 335 | | | | | 340 | | | | | 345 | | | | | |
| ggc | gat | acg | gcg | aaa | gat | atg | agc | gat | atg | ctc | gaa | ctt | ttc | gac | att | 1106 |
| Gly | Asp | Thr | Ala | Lys | Asp | Met | Ser | Asp | Met | Leu | Glu | Leu | Phe | Asp | Ile | |
| 350 | | | | | 355 | | | | | 360 | | | | | 365 | |
| tgc | gat | caa | cat | aag | cag | tcc | tgg | atg | gga | tgg | cta | tac | aaa | tcc | tac | 1154 |
| Cys | Asp | Gln | His | Lys | Gln | Ser | Trp | Met | Gly | Trp | Leu | Tyr | Lys | Ser | Tyr | |
| | | | | 370 | | | | | 375 | | | | | 380 | | |
| ggt | tgc | tac | aag | caa | cat | ctg | ggc | tgt | cta | acg | gac | tct | atg | cat | gac | 1202 |
| Gly | Cys | Tyr | Lys | Gln | His | Leu | Gly | Cys | Leu | Thr | Asp | Ser | Met | His | Asp | |
| | | | 385 | | | | | 390 | | | | | 395 | | | |
| gaa | aca | gga | cat | tta | cgc | gat | atc | gtc | ctt | caa | aac | act | act | cgc | acc | 1250 |
| Glu | Thr | Gly | His | Leu | Arg | Asp | Ile | Val | Leu | Gln | Asn | Thr | Thr | Arg | Thr | |
| | | 400 | | | | | 405 | | | | | 410 | | | | |
| tac | ccg | caa | gct | gtc | gca | gga | cac | aca | att | gga | tat | aag | ttt | gac | agg | 1298 |
| Tyr | Pro | Gln | Ala | Val | Ala | Gly | His | Thr | Ile | Gly | Tyr | Lys | Phe | Asp | Arg | |
| | 415 | | | | | 420 | | | | | 425 | | | | | |
| att | acg | aaa | aag | ttc | gat | ttg | agt | ttc | gtc | gtt | act | gca | gat | tgt | cga | 1346 |
| Ile | Thr | Lys | Lys | Phe | Asp | Leu | Ser | Phe | Val | Val | Thr | Ala | Asp | Cys | Arg | |
| 430 | | | | | 435 | | | | | 440 | | | | | 445 | |
| agc | acg | gag | tct | atc | gtc | tac | ttc | aac | aaa | gat | tta | cat | tac | tcg | aat | 1394 |
| Ser | Thr | Glu | Ser | Ile | Val | Tyr | Phe | Asn | Lys | Asp | Leu | His | Tyr | Ser | Asn | |
| | | | | 450 | | | | | 455 | | | | | 460 | | |
| ggt | tac | gac | gtt | acg | gtt | ttt | ccg | aaa | gat | tcc | gtt | acg | tgg | aag | caa | 1442 |
| Gly | Tyr | Asp | Val | Thr | Val | Phe | Pro | Lys | Asp | Ser | Val | Thr | Trp | Lys | Gln | |
| | | | 465 | | | | | 470 | | | | | 475 | | | |
| gta | gag | aag | aaa | ata | atc | atc | aac | cat | tcg | caa | aag | ctt | tct | gct | ggc | 1490 |
| Val | Glu | Lys | Lys | Ile | Ile | Ile | Asn | His | Ser | Gln | Lys | Leu | Ser | Ala | Gly | |
| | | 480 | | | | | 485 | | | | | 490 | | | | |
| acg | act | gtg | act | ttc | tct | ctc | gtt | gct | aag | tag | ctattgccat | ggaaacaaat | | | | 1543 |
| Thr | Thr | Val | Thr | Phe | Ser | Leu | Val | Ala | Lys | | | | | | | |
| | 495 | | | | | 500 | | | | | | | | | | | attctgctgt tggtgattca aatctgaaaa ggactgcgta ttatatcagt gtcatgattt 1603 atattaaaac gaggctaatc caaaatggct gggtagattt tgttgctaat agtgaacaat 1663 agtgaaaacc aagatatgcc ataaaaagtt tgttttaaaa aaaaaaaaaa aaaaaaaaa 1723 aaaaaaa 1730

<210> SEQ ID NO 14
<211> LENGTH: 503
<212> TYPE: PRT
<213> ORGANISM: Cyanella capensis

<400> SEQUENCE: 14

```
Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

Ser Val Asn Pro Glu Thr Gln Gln Leu Val Asp Ser Leu Gly Arg Glu
            35                  40                  45

Arg Phe Phe His Gly Thr Asn Val Val Lys His Lys Pro Tyr His
            50                  55                  60

Pro Ser Val Glu Gly Tyr Asp Asn Thr Ser Phe Ser Glu Val Asp Met
65                  70                  75                  80

Lys Ile Leu Gln Asp Leu Gly Leu Asn Thr Ile Arg Leu Gly Met Met
                85                  90                  95

Leu Pro Gly Tyr Val Pro Thr Arg Gly Asn Tyr Asn Glu Thr Tyr Leu
                100                 105                 110

Lys Ile Ile Gln Glu Ile Val Ser Lys Ala Ala Lys Tyr Gly Ile Tyr
            115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Leu Gln Thr Gly Tyr
                165                 170                 175

Pro Tyr Pro Lys Asp Cys Ala Lys His Ala Trp Gly Asp Tyr Tyr Phe
            180                 185                 190

Thr Glu Ala Ala Ala Ala Phe Gln Asn Phe Tyr Asn Asn Thr Asp
    195                 200                 205

Gly Leu Leu Asp Ala Trp Ala Asp Phe Trp Lys Lys Thr Ala Gln Gly
            210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
                245                 250                 255

Ala Asp Glu Arg Asn Leu Ala Pro Ala Tyr Asp Val Ile His Lys Ala
            260                 265                 270

Ile Arg Thr Val Asp Glu Gln His Ser Ile Phe Phe Glu Gly Val Thr
            275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Leu Thr Val Gly Asp Thr
            340                 345                 350

Ala Lys Asp Met Ser Asp Met Leu Glu Leu Phe Asp Ile Cys Asp Gln
    355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415
```

```
Ala Val Ala Gly His Thr Ile Gly Tyr Lys Phe Asp Arg Ile Thr Lys
            420                 425                 430

Lys Phe Asp Leu Ser Phe Val Thr Ala Asp Cys Arg Ser Thr Glu
        435                 440                 445

Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
            485                 490                 495

Thr Phe Ser Leu Val Ala Lys
            500

<210> SEQ ID NO 15
<211> LENGTH: 503
<212> TYPE: PRT
<213> ORGANISM: Cyanella capensis

<400> SEQUENCE: 15

Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

Ser Val Asn Pro Glu Thr Gln Gln Leu Val Asp Ser Leu Gly Arg Glu
        35                  40                  45

Arg Phe Phe His Gly Thr Asn Val Val Val Lys His Lys Pro Tyr His
    50                  55                  60

Pro Ser Val Glu Gly Tyr Asp Asn Thr Ser Phe Ser Glu Val Asp Met
65                  70                  75                  80

Lys Ile Leu Gln Asp Leu Gly Leu Asn Thr Ile Arg Leu Gly Met Met
            85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Ala Lys Tyr Gly Ile Tyr
        115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Leu Gln Thr Gly Tyr
            165                 170                 175

Pro Tyr Pro Lys Asp Cys Ala Lys His Ala Trp Gly Asp Tyr Tyr Phe
            180                 185                 190

Thr Glu Ala Ala Ala Ala Phe Gln Asn Phe Tyr Asn Asn Thr Asp
        195                 200                 205

Gly Leu Leu Asp Ala Trp Ala Asp Phe Trp Lys Lys Thr Ala Gln Gly
    210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
            245                 250                 255

Ala Asp Glu Arg Asn Leu Ala Pro Ala Tyr Asp Val Ile His Lys Ala
            260                 265                 270

Ile Arg Thr Val Asp Glu Gln His Ser Ile Phe Phe Glu Gly Val Thr
```

```
                   275                 280                 285
Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Leu Thr Val Gly Asp Thr
            340                 345                 350

Ala Lys Asp Met Ser Asp Met Leu Glu Leu Phe Asp Ile Cys Asp Gln
        355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415

Ala Val Ala Gly His Thr Ile Gly Tyr Lys Phe Asp Arg Ile Thr Lys
            420                 425                 430

Lys Phe Asp Leu Ser Phe Val Val Thr Ala Asp Cys Arg Ser Thr Glu
        435                 440                 445

Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
                485                 490                 495

Thr Phe Ser Leu Val Ala Lys
            500

<210> SEQ ID NO 16
<211> LENGTH: 1730
<212> TYPE: DNA
<213> ORGANISM: Cyanella capensis
<220> FEATURE:
<221> NAME/KEY: CDS
<222> LOCATION: (12)..(1523)
<223> OTHER INFORMATION: EGCase

<400> SEQUENCE: 16
ggcgatttgc a atg gct gaa aca caa cca ttg gtg ttt gtc ttg atg agc      50
           Met Ala Glu Thr Gln Pro Leu Val Phe Val Leu Met Ser
             1               5                  10 att tca gct att tta acg gca gga ctt cca ata aac gat gat gca tca      98
Ile Ser Ala Ile Leu Thr Ala Gly Leu Pro Ile Asn Asp Asp Ala Ser
 15                  20                  25 ttg tta ata agc gtc aat cct gaa aca caa cag ttg gtt gat agt ttg     146
Leu Leu Ile Ser Val Asn Pro Glu Thr Gln Gln Leu Val Asp Ser Leu
 30                  35                  40                  45 ggg aga gag aga ttt ttc cat gga acg aac gtt gtt gtc aaa cat aaa     194
Gly Arg Glu Arg Phe Phe His Gly Thr Asn Val Val Val Lys His Lys
                 50                  55                  60 cct tat cat cca tca gtt gag ggt tat gac aat acg tct ttc tca gaa     242
Pro Tyr His Pro Ser Val Glu Gly Tyr Asp Asn Thr Ser Phe Ser Glu
             65                  70                  75 gtt gat atg aag att ttg caa gat ctt ggc ctc aat aca att cgc ctt     290
Val Asp Met Lys Ile Leu Gln Asp Leu Gly Leu Asn Thr Ile Arg Leu
         80                  85                  90
```

```
ggt atg atg ctg cca ggc tat gtg cct acc cga ggt aat tac aat gaa    338
Gly Met Met Leu Pro Gly Tyr Val Pro Thr Arg Gly Asn Tyr Asn Glu
     95                 100                 105 aca tac ttg aag atc ata cag gaa att gta tca aag gca gct aaa tat    386
Thr Tyr Leu Lys Ile Ile Gln Glu Ile Val Ser Lys Ala Ala Lys Tyr
110                 115                 120                 125 ggc att tat act tta ctg gat atg cac cag gat gtt atg tct gca aag    434
Gly Ile Tyr Thr Leu Leu Asp Met His Gln Asp Val Met Ser Ala Lys
                130                 135                 140 ttt tgc gtt gaa gga ttt cct gat tgg gct gtt aat aca ggc aat gca    482
Phe Cys Val Glu Gly Phe Pro Asp Trp Ala Val Asn Thr Gly Asn Ala
            145                 150                 155 gac aat ttc cct ttt cca ctt gaa gac aaa tac ccc ctg aat ccg cag    530
Asp Asn Phe Pro Phe Pro Leu Glu Asp Lys Tyr Pro Leu Asn Pro Gln
        160                 165                 170 act gga tac cct tat cca aaa gac tgt gca aag cat gcc tgg ggg gac    578
Thr Gly Tyr Pro Tyr Pro Lys Asp Cys Ala Lys His Ala Trp Gly Asp
    175                 180                 185 tac tac ttc acg gaa gca gcc gcc gca gct ttc cag aac ttc tac aat    626
Tyr Tyr Phe Thr Glu Ala Ala Ala Ala Ala Phe Gln Asn Phe Tyr Asn
190                 195                 200                 205 aac act gac ggg cta tta gat gca tgg gcg gac ttc tgg aag aaa aca    674
Asn Thr Asp Gly Leu Leu Asp Ala Trp Ala Asp Phe Trp Lys Lys Thr
                210                 215                 220 gca cag ggt ttc aaa gat tat aaa agt gtc att gga tat gaa ctt att    722
Ala Gln Gly Phe Lys Asp Tyr Lys Ser Val Ile Gly Tyr Glu Leu Ile
            225                 230                 235 aat gaa cca ttt gct ggc gat ata tac agg gat cct tca ctc atg att    770
Asn Glu Pro Phe Ala Gly Asp Ile Tyr Arg Asp Pro Ser Leu Met Ile
        240                 245                 250 cct ggc gtt gcg gac gaa aga aat ctc gcg cca gcc tat gac gtc atc    818
Pro Gly Val Ala Asp Glu Arg Asn Leu Ala Pro Ala Tyr Asp Val Ile
    255                 260                 265 cat aaa gcc att cgt acg gtg gat gaa caa cac agc ata ttt ttc gag    866
His Lys Ala Ile Arg Thr Val Asp Glu Gln His Ser Ile Phe Phe Glu
270                 275                 280                 285 ggc gta acg tgg gat tat ttc gcg gcg gga ttc agt aaa gta cca ggc    914
Gly Val Thr Trp Asp Tyr Phe Ala Ala Gly Phe Ser Lys Val Pro Gly
                290                 295                 300 ggt gac gca tac cgt aat cgg agc gtt tta agc tat cat tat tac gag    962
Gly Asp Ala Tyr Arg Asn Arg Ser Val Leu Ser Tyr His Tyr Tyr Glu
            305                 310                 315 cct cca gat ttc aat aag aag ttt cag ttc gag gtg cgt atg gaa gat   1010
Pro Pro Asp Phe Asn Lys Lys Phe Gln Phe Glu Val Arg Met Glu Asp
        320                 325                 330 ctt agg cgt tta aaa tgt ggc ggt ttc ttg acc gaa ctt ctt acg gtt   1058
Leu Arg Arg Leu Lys Cys Gly Gly Phe Leu Thr Glu Leu Leu Thr Val
    335                 340                 345 ggc gat acg gcg aaa gat atg agc gat atg ctc gaa ctt ttc gac att   1106
Gly Asp Thr Ala Lys Asp Met Ser Asp Met Leu Glu Leu Phe Asp Ile
350                 355                 360                 365 tgc gat caa cat aag cag tcc tgg atg gga tgg cta tac aaa tcc tac   1154
Cys Asp Gln His Lys Gln Ser Trp Met Gly Trp Leu Tyr Lys Ser Tyr
                370                 375                 380 ggt tgc tac aag caa cat ctg ggc tgt cta acg gac tct atg cat gac   1202
Gly Cys Tyr Lys Gln His Leu Gly Cys Leu Thr Asp Ser Met His Asp
            385                 390                 395 gaa aca gga cat tta cgc gat atc gtc ctt caa aac act act cgc acc   1250
Glu Thr Gly His Leu Arg Asp Ile Val Leu Gln Asn Thr Thr Arg Thr
```

-continued

```
                400             405             410
tac ccg caa gct gtc gca gga cac aca att gga tat aag ttt gac agg    1298
Tyr Pro Gln Ala Val Ala Gly His Thr Ile Gly Tyr Lys Phe Asp Arg
    415             420             425 att acg aaa aag ttc gat ttg agt ttc gtt act gca gat tgt cga        1346
Ile Thr Lys Lys Phe Asp Leu Ser Phe Val Val Thr Ala Asp Cys Arg
430             435             440             445 agc acg gag tct atc gtc tac ttc aac aaa gat tta cat tac tcg aat    1394
Ser Thr Glu Ser Ile Val Tyr Phe Asn Lys Asp Leu His Tyr Ser Asn
                450             455             460 ggt tac gac gtt acg gtt ttt ccg aaa gat tcc gtt acg tgg aag caa    1442
Gly Tyr Asp Val Thr Val Phe Pro Lys Asp Ser Val Thr Trp Lys Gln
            465             470             475 gta gag aag aaa ata atc atc aac cat tcg caa aag ctt tct gct ggc    1490
Val Glu Lys Lys Ile Ile Ile Asn His Ser Gln Lys Leu Ser Ala Gly
        480             485             490 acg act gtg act ttc tct ctc gtt gct aag tag ctattgccat ggaaacaaat  1543
Thr Thr Val Thr Phe Ser Leu Val Ala Lys
    495             500 attctgctgt tggtgattca aatctgaaaa ggactgcgta ttatatcagt gtcatgattt  1603
atattaaaac gaggctaatc caaaatggct gggtagattt tgttgctaat agtgaacaat  1663
agtgaaaacc aagatatgcc ataaaagtt tgttttaaaa aaaaaaaaaa aaaaaaaaa    1723 aaaaaaa                                                             1730
```

<210> SEQ ID NO 17
<211> LENGTH: 503
<212> TYPE: PRT
<213> ORGANISM: Cyanella capensis

<400> SEQUENCE: 17

```
Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

Ser Val Asn Pro Glu Thr Gln Gln Leu Val Asp Ser Leu Gly Arg Glu
        35                  40                  45

Arg Phe Phe His Gly Thr Asn Val Val Lys His Lys Pro Tyr His
    50                  55                  60

Pro Ser Val Glu Gly Tyr Asp Asn Thr Ser Phe Ser Glu Val Asp Met
65                  70                  75                  80

Lys Ile Leu Gln Asp Leu Gly Leu Asn Thr Ile Arg Leu Gly Met Met
                85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Ala Lys Tyr Gly Ile Tyr
        115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Pro Gln Thr Gly Tyr
                165                 170                 175

Pro Tyr Pro Lys Asp Cys Ala Lys His Ala Trp Gly Asp Tyr Tyr Phe
            180                 185                 190

Thr Glu Ala Ala Ala Ala Ala Phe Gln Asn Phe Tyr Asn Asn Thr Asp
```

```
              195                 200                 205
    Gly Leu Leu Asp Ala Trp Ala Asp Phe Trp Lys Lys Thr Ala Gln Gly
        210                 215                 220

Phe Lys Asp Tyr Lys Ser Val Ile Gly Tyr Glu Leu Ile Asn Glu Pro
    225                 230                 235                 240

Phe Ala Gly Asp Ile Tyr Arg Asp Pro Ser Leu Met Ile Pro Gly Val
                    245                 250                 255

Ala Asp Glu Arg Asn Leu Ala Pro Ala Tyr Asp Val Ile His Lys Ala
                260                 265                 270

Ile Arg Thr Val Asp Glu Gln His Ser Ile Phe Phe Glu Gly Val Thr
                    275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
    305                 310                 315                 320

Phe Asn Lys Lys Phe Gln Phe Glu Val Arg Met Glu Asp Leu Arg Arg
                    325                 330                 335

Leu Lys Cys Gly Gly Phe Leu Thr Glu Leu Leu Thr Val Gly Asp Thr
                340                 345                 350

Ala Lys Asp Met Ser Asp Met Leu Glu Leu Phe Asp Ile Cys Asp Gln
                    355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
    385                 390                 395                 400

His Leu Arg Asp Ile Val Leu Gln Asn Thr Thr Arg Thr Tyr Pro Gln
                    405                 410                 415

Ala Val Ala Gly His Thr Ile Gly Tyr Lys Phe Asp Arg Ile Thr Lys
                420                 425                 430

Lys Phe Asp Leu Ser Phe Val Val Thr Ala Asp Cys Arg Ser Thr Glu
                    435                 440                 445

Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
    465                 470                 475                 480

Lys Ile Ile Ile Asn His Ser Gln Lys Leu Ser Ala Gly Thr Thr Val
                    485                 490                 495

Thr Phe Ser Leu Val Ala Lys
                500

<210> SEQ ID NO 18
<211> LENGTH: 503
<212> TYPE: PRT
<213> ORGANISM: Cyanella capensis

<400> SEQUENCE: 18

Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
                20                  25                  30

Ser Val Asn Pro Glu Thr Gln Gln Leu Val Asp Ser Leu Gly Arg Glu
                35                  40                  45

Arg Phe Phe His Gly Thr Asn Val Val Lys His Lys Pro Tyr His
    50                  55                  60
```

```
Pro Ser Val Glu Gly Tyr Asp Asn Thr Ser Phe Ser Glu Val Asp Met
 65                  70                  75                  80

Lys Ile Leu Gln Asp Leu Gly Leu Asn Thr Ile Arg Leu Gly Met Met
                 85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Lys Tyr Gly Ile Tyr
        115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Pro Gln Thr Gly Tyr
            165                 170                 175

Pro Tyr Pro Lys Asp Cys Ala Lys His Ala Trp Gly Asp Tyr Tyr Phe
            180                 185                 190

Thr Glu Ala Ala Ala Ala Phe Gln Asn Phe Tyr Asn Asn Thr Asp
        195                 200                 205

Gly Leu Leu Asp Ala Trp Ala Asp Phe Trp Lys Lys Thr Ala Gln Gly
    210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
            245                 250                 255

Ala Asp Glu Arg Asn Leu Ala Pro Ala Tyr Asp Val Ile His Lys Ala
        260                 265                 270

Ile Arg Thr Val Asp Glu Gln His Ser Ile Phe Phe Glu Gly Val Thr
    275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Thr Val Gly Asp Thr
            340                 345                 350

Ala Lys Asp Met Ser Asp Met Leu Glu Leu Phe Asp Ile Cys Asp Gln
        355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415

Ala Val Ala Gly His Thr Ile Gly Tyr Lys Phe Asp Arg Ile Thr Lys
            420                 425                 430

Lys Phe Asp Leu Ser Phe Val Val Thr Ala Asp Cys Arg Ser Thr Glu
        435                 440                 445

Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
```

Thr Phe Ser Leu Val Ala Lys
            500

<210> SEQ ID NO 19
<211> LENGTH: 1856
<212> TYPE: DNA
<213> ORGANISM: Hydra magnipapillata
<220> FEATURE:
<221> NAME/KEY: CDS
<222> LOCATION: (19)..(1572)
<223> OTHER INFORMATION: EGCase

<400> SEQUENCE: 19

```
atatattaaa aaaaaaaa atg ata agc gtc gca ctt ata ata ctt ttt ctt         51
                    Met Ile Ser Val Ala Leu Ile Ile Leu Phe Leu
                     1               5                  10 gca aaa gtt att tcc gga aaa tcg gat gat ttt ata tct gta aac cct         99
Ala Lys Val Ile Ser Gly Lys Ser Asp Asp Phe Ile Ser Val Asn Pro
             15                  20                  25 gaa aca aat atg ctt att gat ggc tat ggg cga gaa aga ttt ttt cac        147
Glu Thr Asn Met Leu Ile Asp Gly Tyr Gly Arg Glu Arg Phe Phe His
 30                  35                  40 ggt acc aat gtt gtg gtg aag cat ttt cct ttt cat cct gaa act aca        195
Gly Thr Asn Val Val Val Lys His Phe Pro Phe His Pro Glu Thr Thr
 45                  50                  55 ggg ttt aac aaa gac acg ttt tct gaa gat gac atg aaa att cta cag        243
Gly Phe Asn Lys Asp Thr Phe Ser Glu Asp Asp Met Lys Ile Leu Gln
 60                  65                  70                  75 aag ttt gga tta aac tca att cga tta gga atg atg cta cct gga tat        291
Lys Phe Gly Leu Asn Ser Ile Arg Leu Gly Met Met Leu Pro Gly Tyr
                 80                  85                  90 gtg cca aaa aga gag gaa tat aat gaa act tat ata aaa gtt ata caa        339
Val Pro Lys Arg Glu Glu Tyr Asn Glu Thr Tyr Ile Lys Val Ile Gln
             95                 100                 105 agt att gtc act aca gct gca aag tat ggt att tac aca ttg tta gac        387
Ser Ile Val Thr Thr Ala Ala Lys Tyr Gly Ile Tyr Thr Leu Leu Asp
        110                 115                 120 atg cat caa gat gtt ttt tca cca aaa ttt tgt gta gaa ggc atg cct        435
Met His Gln Asp Val Phe Ser Pro Lys Phe Cys Val Glu Gly Met Pro
    125                 130                 135 gat tgg ata gtt aac aca caa gga gca aaa gat ttt cca atg cca ctt        483
Asp Trp Ile Val Asn Thr Gln Gly Ala Lys Asp Phe Pro Met Pro Leu
140                 145                 150                 155 cat aaa ccg ttc aat ttg gat cct aaa aca gga tat cca tac cct gag        531
His Lys Pro Phe Asn Leu Asp Pro Lys Thr Gly Tyr Pro Tyr Pro Glu
                160                 165                 170 gat tgc gcc aag ttt tca tgg gca gac tat tat ttt act gaa gca gca        579
Asp Cys Ala Lys Phe Ser Trp Ala Asp Tyr Tyr Phe Thr Glu Ala Ala
            175                 180                 185 gga caa gct ttt caa aat ctt tac gac aat gtt gat gga ctg cgt gac        627
Gly Gln Ala Phe Gln Asn Leu Tyr Asp Asn Val Asp Gly Leu Arg Asp
        190                 195                 200 gaa tgg gca caa ttt tgg aaa aaa act gct gat gtt ttt aaa gaa gaa        675
Glu Trp Ala Gln Phe Trp Lys Lys Thr Ala Asp Val Phe Lys Glu Glu
    205                 210                 215 cct agc gtt att gga tat gaa ctc ata aac gaa ccg ttt tgt ggc aat        723
Pro Ser Val Ile Gly Tyr Glu Leu Ile Asn Glu Pro Phe Cys Gly Asn
220                 225                 230                 235 gta ttt aaa cac ccg aca ttg ctg att ccc ggt gtt gcc gat tat ctc        771
Val Phe Lys His Pro Thr Leu Leu Ile Pro Gly Val Ala Asp Tyr Leu
```

|     |     |
| --- | --- |
| 240 245 250 | |
| aac cta caa cca aca tat gac gca tta caa aaa gct ata cgt caa gtt<br>Asn Leu Gln Pro Thr Tyr Asp Ala Leu Gln Lys Ala Ile Arg Gln Val<br>255 260 265 | 819 |
| gat gaa gaa cat aac ata ttt ttt gaa gga gtt aca tgg gac ttt ttt<br>Asp Glu Glu His Asn Ile Phe Phe Glu Gly Val Thr Trp Asp Phe Phe<br>270 275 280 | 867 |
| gaa gtt ggt ttt act gaa gtt cct ggc ggt aaa cag tat caa aat cgg<br>Glu Val Gly Phe Thr Glu Val Pro Gly Gly Lys Gln Tyr Gln Asn Arg<br>285 290 295 | 915 |
| agc gtt ctt agt tat cat tat tat gag ccg cca gac ttt tct aaa aaa<br>Ser Val Leu Ser Tyr His Tyr Tyr Glu Pro Pro Asp Phe Ser Lys Lys<br>300 305 310 315 | 963 |
| cta aat ttt gaa gct cgt ttg ctt gat ctt aaa cga ttg aaa tgt ggt<br>Leu Asn Phe Glu Ala Arg Leu Leu Asp Leu Lys Arg Leu Lys Cys Gly<br>320 325 330 | 1011 |
| gga ttt ctt act gaa atg ttt aca gtt gga aca gat ttt aac agc atg<br>Gly Phe Leu Thr Glu Met Phe Thr Val Gly Thr Asp Phe Asn Ser Met<br>335 340 345 | 1059 |
| ttt gaa atg ttt gat tta tgc gat aaa ttc aag caa agt tgg cat gga<br>Phe Glu Met Phe Asp Leu Cys Asp Lys Phe Lys Gln Ser Trp His Gly<br>350 355 360 | 1107 |
| tgg atg tat aaa tca tac ggg tgt ata gag caa aac ctg ggt tgt ttg<br>Trp Met Tyr Lys Ser Tyr Gly Cys Ile Glu Gln Asn Leu Gly Cys Leu<br>365 370 375 | 1155 |
| aat atg tct tct cca ggt aaa gaa tct att caa att gcg aac act tca<br>Asn Met Ser Ser Pro Gly Lys Glu Ser Ile Gln Ile Ala Asn Thr Ser<br>380 385 390 395 | 1203 |
| aga acg tat cca cag gcg gtg gct ggg cgt acg caa tcc tac gca ttt<br>Arg Thr Tyr Pro Gln Ala Val Ala Gly Arg Thr Gln Ser Tyr Ala Phe<br>400 405 410 | 1251 |
| gac ata aag act aaa gta ttc aca ttg gta tac gaa act gtt ggc agt<br>Asp Ile Lys Thr Lys Val Phe Thr Leu Val Tyr Glu Thr Val Gly Ser<br>415 420 425 | 1299 |
| tgc aaa agt ggt aga acc att gtt tac ttt aat aaa aat ctt cat tat<br>Cys Lys Ser Gly Arg Thr Ile Val Tyr Phe Asn Lys Asn Leu His Tyr<br>430 435 440 | 1347 |
| cct aac gga tat cgc tat gag ata aat cca aat ttc aaa gta acc ccc<br>Pro Asn Gly Tyr Arg Tyr Glu Ile Asn Pro Asn Phe Lys Val Thr Pro<br>445 450 455 | 1395 |
| agt gaa aat gaa tac ttt ctt tat tta gat gaa gtt aat aaa gta cca<br>Ser Glu Asn Glu Tyr Phe Leu Tyr Leu Asp Glu Val Asn Lys Val Pro<br>460 465 470 475 | 1443 |
| aac acc gtt gtg aca ttt aaa ctt ttt cca ctc agc ttt act gat agt<br>Asn Thr Val Val Thr Phe Lys Leu Phe Pro Leu Ser Phe Thr Asp Ser<br>480 485 490 | 1491 |
| gaa gat att cat cca gta acg gtg atg ggt gat aaa cat cta tca gaa<br>Glu Asp Ile His Pro Val Thr Val Met Gly Asp Lys His Leu Ser Glu<br>495 500 505 | 1539 |
| aat cat aat gaa aat gaa aaa aaa aag tga aaattatatt tgaaaaaat<br>Asn His Asn Glu Asn Glu Lys Lys Lys<br>510 515 | 1592 |
| aattcgactt taaacacatt ttaaaaatta cttattataa aaacgttttt aaatattttt | 1652 |
| taatgtaaaa ttttaaaaat caatgaagtt aatataagct ttaaataaca tttatggtat | 1712 |
| attatttata aattgtaaca tttaaagcac aggtcagcaa ataatttttt ttttggtttt | 1772 |
| taagatatca ggtatgattt tgtataattt ggtgtgctga atttgagaat aacatttttat | 1832 |
| gaaaaaaaaa aaaaaaaaaa aaaa | 1856 |

<210> SEQ ID NO 20
<211> LENGTH: 517
<212> TYPE: PRT
<213> ORGANISM: Hydra magnipapillata

<400> SEQUENCE: 20

```
Met Ile Ser Val Ala Leu Ile Ile Leu Phe Leu Ala Lys Val Ile Ser
1               5                   10                  15

Gly Lys Ser Asp Asp Phe Ile Ser Val Asn Pro Glu Thr Asn Met Leu
            20                  25                  30

Ile Asp Gly Tyr Gly Arg Glu Arg Phe Phe His Gly Thr Asn Val Val
        35                  40                  45

Val Lys His Phe Pro Phe His Pro Glu Thr Thr Gly Phe Asn Lys Asp
50                  55                  60

Thr Phe Ser Glu Asp Asp Met Lys Ile Leu Gln Lys Phe Gly Leu Asn
65                  70                  75                  80

Ser Ile Arg Leu Gly Met Met Leu Pro Gly Tyr Val Pro Lys Arg Glu
                85                  90                  95

Glu Tyr Asn Glu Thr Tyr Ile Lys Val Ile Gln Ser Ile Val Thr Thr
            100                 105                 110

Ala Ala Lys Tyr Gly Ile Tyr Thr Leu Leu Asp Met His Gln Asp Val
        115                 120                 125

Phe Ser Pro Lys Phe Cys Val Glu Gly Met Pro Asp Trp Ile Val Asn
130                 135                 140

Thr Gln Gly Ala Lys Asp Phe Pro Met Pro Leu His Lys Pro Phe Asn
145                 150                 155                 160

Leu Asp Pro Lys Thr Gly Tyr Pro Tyr Pro Glu Asp Cys Ala Lys Phe
                165                 170                 175

Ser Trp Ala Asp Tyr Tyr Phe Thr Glu Ala Ala Gly Gln Ala Phe Gln
            180                 185                 190

Asn Leu Tyr Asp Asn Val Asp Gly Leu Arg Asp Glu Trp Ala Gln Phe
        195                 200                 205

Trp Lys Lys Thr Ala Asp Val Phe Lys Glu Pro Ser Val Ile Gly
210                 215                 220

Tyr Glu Leu Ile Asn Glu Pro Phe Cys Gly Asn Val Phe Lys His Pro
225                 230                 235                 240

Thr Leu Leu Ile Pro Gly Val Ala Asp Tyr Leu Asn Leu Gln Pro Thr
                245                 250                 255

Tyr Asp Ala Leu Gln Lys Ala Ile Arg Gln Val Asp Glu Glu His Asn
            260                 265                 270

Ile Phe Phe Glu Gly Val Thr Trp Asp Phe Phe Glu Val Gly Phe Thr
        275                 280                 285

Glu Val Pro Gly Gly Lys Gln Tyr Gln Asn Arg Ser Val Leu Ser Tyr
290                 295                 300

His Tyr Tyr Glu Pro Pro Asp Phe Ser Lys Lys Leu Asn Phe Glu Ala
305                 310                 315                 320

Arg Leu Leu Asp Leu Lys Arg Leu Lys Cys Gly Gly Phe Leu Thr Glu
                325                 330                 335

Met Phe Thr Val Gly Thr Asp Phe Asn Ser Met Phe Glu Met Phe Asp
            340                 345                 350

Leu Cys Asp Lys Phe Lys Gln Ser Trp His Gly Trp Met Tyr Lys Ser
        355                 360                 365

Tyr Gly Cys Ile Glu Gln Asn Leu Gly Cys Leu Asn Met Ser Ser Pro
```

```
                    370                 375                 380
Gly Lys Glu Ser Ile Gln Ile Ala Asn Thr Ser Arg Thr Tyr Pro Gln
385                 390                 395                 400

Ala Val Ala Gly Arg Thr Gln Ser Tyr Ala Phe Asp Ile Lys Thr Lys
                405                 410                 415

Val Phe Thr Leu Val Tyr Glu Thr Val Gly Ser Cys Lys Ser Gly Arg
                420                 425                 430

Thr Ile Val Tyr Phe Asn Lys Asn Leu His Tyr Pro Asn Gly Tyr Arg
                435                 440                 445

Tyr Glu Ile Asn Pro Asn Phe Lys Val Thr Pro Ser Glu Asn Glu Tyr
                450                 455                 460

Phe Leu Tyr Leu Asp Glu Val Asn Lys Val Pro Asn Thr Val Val Thr
465                 470                 475                 480

Phe Lys Leu Phe Pro Leu Ser Phe Thr Asp Ser Glu Asp Ile His Pro
                485                 490                 495

Val Thr Val Met Gly Asp Lys His Leu Ser Glu Asn His Asn Glu Asn
                500                 505                 510

Glu Lys Lys Lys Lys
            515

<210> SEQ ID NO 21
<211> LENGTH: 517
<212> TYPE: PRT
<213> ORGANISM: Hydra magnipapillata

<400> SEQUENCE: 21

Met Ile Ser Val Ala Leu Ile Ile Leu Phe Leu Ala Lys Val Ile Ser
1               5                   10                  15

Gly Lys Ser Asp Asp Phe Ile Ser Val Asn Pro Glu Thr Asn Met Leu
                20                  25                  30

Ile Asp Gly Tyr Gly Arg Glu Arg Phe Phe His Gly Thr Asn Val Val
                35                  40                  45

Val Lys His Phe Pro Phe His Pro Glu Thr Thr Gly Phe Asn Lys Asp
            50                  55                  60

Thr Phe Ser Glu Asp Asp Met Lys Ile Leu Gln Lys Phe Gly Leu Asn
65                  70                  75                  80

Ser Ile Arg Leu Gly Met Met Leu Pro Gly Tyr Val Pro Lys Arg Glu
                85                  90                  95

Glu Tyr Asn Glu Thr Tyr Ile Lys Val Ile Gln Ser Ile Val Thr Thr
                100                 105                 110

Ala Ala Lys Tyr Gly Ile Tyr Thr Leu Leu Asp Met His Gln Asp Val
                115                 120                 125

Phe Ser Pro Lys Phe Cys Val Glu Gly Met Pro Asp Trp Ile Val Asn
                130                 135                 140

Thr Gln Gly Ala Lys Asp Phe Pro Met Pro Leu His Lys Pro Phe Asn
145                 150                 155                 160

Leu Asp Pro Lys Thr Gly Tyr Pro Tyr Pro Glu Asp Cys Ala Lys Phe
                165                 170                 175

Ser Trp Ala Asp Tyr Tyr Phe Thr Glu Ala Ala Gly Gln Ala Phe Gln
                180                 185                 190

Asn Leu Tyr Asp Asn Val Asp Gly Leu Arg Asp Glu Trp Ala Gln Phe
                195                 200                 205

Trp Lys Lys Thr Ala Asp Val Phe Lys Glu Pro Ser Val Ile Gly
                210                 215                 220
```

```
Tyr Glu Leu Ile Asn Glu Pro Phe Cys Gly Asn Val Phe Lys His Pro
225                 230                 235                 240

Thr Leu Leu Ile Pro Gly Val Ala Asp Tyr Leu Asn Leu Gln Pro Thr
            245                 250                 255

Tyr Asp Ala Leu Gln Lys Ala Ile Arg Gln Val Asp Glu His Asn
        260                 265                 270

Ile Phe Phe Glu Gly Val Thr Trp Asp Phe Phe Glu Val Gly Phe Thr
    275                 280                 285

Glu Val Pro Gly Gly Lys Gln Tyr Gln Asn Arg Ser Val Leu Ser Tyr
290                 295                 300

His Tyr Tyr Glu Pro Pro Asp Phe Ser Lys Lys Leu Asn Phe Glu Ala
305                 310                 315                 320

Arg Leu Leu Asp Leu Lys Arg Leu Lys Cys Gly Gly Phe Leu Thr Glu
            325                 330                 335

Met Phe Thr Val Gly Thr Asp Phe Asn Ser Met Phe Glu Met Phe Asp
            340                 345                 350

Leu Cys Asp Lys Phe Lys Gln Ser Trp His Gly Trp Met Tyr Lys Ser
        355                 360                 365

Tyr Gly Cys Ile Glu Gln Asn Leu Gly Cys Leu Asn Met Ser Ser Pro
370                 375                 380

Gly Lys Glu Ser Ile Gln Ile Ala Asn Thr Ser Arg Thr Tyr Pro Gln
385                 390                 395                 400

Ala Val Ala Gly Arg Thr Gln Ser Tyr Ala Phe Asp Ile Lys Thr Lys
                405                 410                 415

Val Phe Thr Leu Val Tyr Glu Thr Val Gly Ser Cys Lys Ser Gly Arg
            420                 425                 430

Thr Ile Val Tyr Phe Asn Lys Asn Leu His Tyr Pro Asn Gly Tyr Arg
            435                 440                 445

Tyr Glu Ile Asn Pro Asn Phe Lys Val Thr Pro Ser Glu Asn Glu Tyr
        450                 455                 460

Phe Leu Tyr Leu Asp Glu Val Asn Lys Val Pro Asn Thr Val Val Thr
465                 470                 475                 480

Phe Lys Leu Phe Pro Leu Ser Phe Thr Asp Ser Glu Asp Ile His Pro
            485                 490                 495

Val Thr Val Met Gly Asp Lys His Leu Ser Glu Asn His Asn Glu Asn
            500                 505                 510

Glu Lys Lys Lys Lys
        515
```

<210> SEQ ID NO 22
<211> LENGTH: 1830
<212> TYPE: DNA
<213> ORGANISM: Schistosoma japonicum
<220> FEATURE:
<221> NAME/KEY: CDS
<222> LOCATION: (141)..(1664)
<223> OTHER INFORMATION: EGCase

<400> SEQUENCE: 22

```
agaattgtcg atagccgaga gtagatctat agtataatat agtgttcatt gaaataattg      60
tcactaattc aactactaat tcattaactt ttacaataat acttagtctg gttattatta     120
ccaaacgtag ttattattcc atg tgg tca ata ttc atc ttg aca ttt cta atc     173
               Met Trp Ser Ile Phe Ile Leu Thr Phe Leu Ile
                 1               5                  10 tgg aca tca gtt cag aca aaa cag atc cca ctg agc aaa ata cat ctc       221
Trp Thr Ser Val Gln Thr Lys Gln Ile Pro Leu Ser Lys Ile His Leu
```

```
                    15                  20                  25
aat tca gat gga cta ttc act gat tct cga gga ttc att aaa tta ttt     269
Asn Ser Asp Gly Leu Phe Thr Asp Ser Arg Gly Phe Ile Lys Leu Phe
         30                  35                  40 aga ggg ttt aac aat gtg cat aaa cat ttt cca tgg tat aat gta aat     317
Arg Gly Phe Asn Asn Val His Lys His Phe Pro Trp Tyr Asn Val Asn
 45                  50                  55 tct acg aat atc aca caa tta gaa atg ttt aaa aat tgg ggt tty aat     365
Ser Thr Asn Ile Thr Gln Leu Glu Met Phe Lys Asn Trp Gly Leu Asn
 60                  65                  70                  75 gtt gtt cga tta ggt gta atg tgg agt gga gtg aag ccg aca ata tca     413
Val Val Arg Leu Gly Val Met Trp Ser Gly Val Lys Pro Thr Ile Ser
                 80                  85                  90 ata gtg aat acc aca tac tta gat gtg att gag aat gtg att gat tta     461
Ile Val Asn Thr Thr Tyr Leu Asp Val Ile Glu Asn Val Ile Asp Leu
             95                 100                 105 tat gct gat tat ggg att tat gta ata ttg gat atg cat caa gat gta     509
Tyr Ala Asp Tyr Gly Ile Tyr Val Ile Leu Asp Met His Gln Asp Val
         110                 115                 120 ttg tca tcg ttg tat ggt ctt tat gat ggc att cca cta tgg tta att     557
Leu Ser Ser Leu Tyr Gly Leu Tyr Asp Gly Ile Pro Leu Trp Leu Ile
 125                 130                 135 gaa aaa ttt aag aga cca cct cat cat tta caa tat ccc tgg cca tat     605
Glu Lys Phe Lys Arg Pro Pro His His Leu Gln Tyr Pro Trp Pro Tyr
140                 145                 150                 155 aag aaa aag cca gat ttt tgg gtg atg tct tat tta act tat gaa tgt     653
Lys Lys Lys Pro Asp Phe Trp Val Met Ser Tyr Leu Thr Tyr Glu Cys
                 160                 165                 170 gct aat gga gcc cag caa ttg tat aat aat gtg tcg ggt gca tgg aat     701
Ala Asn Gly Ala Gln Gln Leu Tyr Asn Asn Val Ser Gly Ala Trp Asn
             175                 180                 185 cat tgg ggt gaa ttt tgg gaa ata gtg gct aga cga ttt ggt gga aag     749
His Trp Gly Glu Phe Trp Glu Ile Val Ala Arg Arg Phe Gly Gly Lys
         190                 195                 200 tca aat gtg ctt ggt tat gaa ttg ata aat gaa cca cca cca gga aac     797
Ser Asn Val Leu Gly Tyr Glu Leu Ile Asn Glu Pro Pro Pro Gly Asn
 205                 210                 215 ttt tat acc aat cca ctt cga ggt ctt cca ggt tat gct ggt cga tat     845
Phe Tyr Thr Asn Pro Leu Arg Gly Leu Pro Gly Tyr Ala Gly Arg Tyr
220                 225                 230                 235 aac ttg caa ccg gtt tat gat tat ctc gtt aag aga ata cgc aaa tac     893
Asn Leu Gln Pro Val Tyr Asp Tyr Leu Val Lys Arg Ile Arg Lys Tyr
                 240                 245                 250 gac aat tcg aca ctg ata ttc tat gaa cca gtt aca tat gga gta ttt     941
Asp Asn Ser Thr Leu Ile Phe Tyr Glu Pro Val Thr Tyr Gly Val Phe
             255                 260                 265 acg cca gtg aga tca tca gga tgg tta gga act gga ttc gat cgc gtc     989
Thr Pro Val Arg Ser Ser Gly Trp Leu Gly Thr Gly Phe Asp Arg Val
         270                 275                 280 cct gga gcc cat cgt gac aaa tcg gca cca agt aaa agt gtt cta tct    1037
Pro Gly Ala His Arg Asp Lys Ser Ala Pro Ser Lys Ser Val Leu Ser
 285                 290                 295 tat cat tat tac tgt tgg ata cta caa act gat gca caa aac acg aca    1085
Tyr His Tyr Tyr Cys Trp Ile Leu Gln Thr Asp Ala Gln Asn Thr Thr
300                 305                 310                 315 atg cca ttc tgg aag aaa gtt atc tgt gac agg ctc ctc ttg cct aac    1133
Met Pro Phe Trp Lys Lys Val Ile Cys Asp Arg Leu Leu Leu Pro Asn
                 320                 325                 330 gtc atc tcc aat gca atc aga gca aca aag tca act gga ggt ggc cga    1181
```

```
Val Ile Ser Asn Ala Ile Arg Ala Thr Lys Ser Thr Gly Gly Arg
                335                 340                 345 ttt cta act gaa ttc ggt tta tgt gga gat gac ggg aat cca cgt agt      1229
Phe Leu Thr Glu Phe Gly Leu Cys Gly Asp Asp Gly Asn Pro Arg Ser
        350                 355                 360 gtg aat aca att gaa tgt aat aat ata tta aat gaa gct gat aaa cat      1277
Val Asn Thr Ile Glu Cys Asn Asn Ile Leu Asn Glu Ala Asp Lys His
365                 370                 375 ttt gaa tca tgg acc tac tgg gac agt aat ctc tta gat ttg tca gga      1325
Phe Glu Ser Trp Thr Tyr Trp Asp Ser Asn Leu Leu Asp Leu Ser Gly
380                 385                 390                 395 aat cct ata gta act gag gtg aaa tca ttc att cgt ccg tat cca cat      1373
Asn Pro Ile Val Thr Glu Val Lys Ser Phe Ile Arg Pro Tyr Pro His
            400                 405                 410 tca ata aga gga gta ttt cgg aag caa cag ttc gat cat aaa aca ggg      1421
Ser Ile Arg Gly Val Phe Arg Lys Gln Gln Phe Asp His Lys Thr Gly
        415                 420                 425 gat ttt cac ctc tcc ttc att gct aac aca acc aaa gag cag aac aat      1469
Asp Phe His Leu Ser Phe Ile Ala Asn Thr Thr Lys Glu Gln Asn Asn
        430                 435                 440 gag aag cag acg ttg atc gca gag att tac ata ccg aga tct gtt cat      1517
Glu Lys Gln Thr Leu Ile Ala Glu Ile Tyr Ile Pro Arg Ser Val His
445                 450                 455 tat ccc aat gga ttt tcc atg agt gtg aaa ccg gac aat tta agc acg      1565
Tyr Pro Asn Gly Phe Ser Met Ser Val Lys Pro Asp Asn Leu Ser Thr
460                 465                 470                 475 aag atg aat gag aat atg atg tat gta tac tta cca agt ggt gtc agt      1613
Lys Met Asn Glu Asn Met Met Tyr Val Tyr Leu Pro Ser Gly Val Ser
                480                 485                 490 aat gcg agt gtg ttt gtt cga atc gaa ata gtg aga aaa tcg atc gag      1661
Asn Ala Ser Val Phe Val Arg Ile Glu Ile Val Arg Lys Ser Ile Glu
        495                 500                 505 tga actattctaa ttgtggtggc tatccgctga actaaatgtc attgatgtta           1714
ttcatatgtt atctgtgtta ttgaattcaa caagttgtgt gtttgtttat ttctattgat    1774
ttctactgtt ccgactttt tattttaaa tatatcagtc atccataatc atccat          1830

<210> SEQ ID NO 23
<211> LENGTH: 507
<212> TYPE: PRT
<213> ORGANISM: Schistosoma japonicum

<400> SEQUENCE: 23

Met Trp Ser Ile Phe Ile Leu Thr Phe Leu Ile Trp Thr Ser Val Gln
1               5                   10                  15

Thr Lys Gln Ile Pro Leu Ser Lys Ile His Leu Asn Ser Asp Gly Leu
            20                  25                  30

Phe Thr Asp Ser Arg Gly Phe Ile Lys Leu Phe Arg Gly Phe Asn Asn
        35                  40                  45

Val His Lys His Phe Pro Trp Tyr Asn Val Asn Ser Thr Asn Ile Thr
    50                  55                  60

Gln Leu Glu Met Phe Lys Asn Trp Gly Leu Asn Val Val Arg Leu Gly
65                  70                  75                  80

Val Met Trp Ser Gly Val Lys Pro Thr Ile Ser Ile Val Asn Thr Thr
                85                  90                  95

Tyr Leu Asp Val Ile Glu Asn Val Ile Asp Leu Tyr Ala Asp Tyr Gly
            100                 105                 110

Ile Tyr Val Ile Leu Asp Met His Gln Asp Val Leu Ser Ser Leu Tyr
```

```
            115                 120                 125
Gly Leu Tyr Asp Gly Ile Pro Leu Trp Leu Ile Glu Lys Phe Lys Arg
        130                 135                 140

Pro Pro His His Leu Gln Tyr Pro Trp Pro Tyr Lys Lys Lys Pro Asp
145                 150                 155                 160

Phe Trp Val Met Ser Tyr Leu Thr Tyr Glu Cys Ala Asn Gly Ala Gln
                165                 170                 175

Gln Leu Tyr Asn Asn Val Ser Gly Ala Trp Asn His Trp Gly Glu Phe
            180                 185                 190

Trp Glu Ile Val Ala Arg Arg Phe Gly Gly Lys Ser Asn Val Leu Gly
        195                 200                 205

Tyr Glu Leu Ile Asn Glu Pro Pro Gly Asn Phe Tyr Thr Asn Pro
    210                 215                 220

Leu Arg Gly Leu Pro Gly Tyr Ala Gly Arg Tyr Asn Leu Gln Pro Val
225                 230                 235                 240

Tyr Asp Tyr Leu Val Lys Arg Ile Arg Lys Tyr Asp Asn Ser Thr Leu
                245                 250                 255

Ile Phe Tyr Glu Pro Val Thr Tyr Gly Val Phe Thr Pro Val Arg Ser
            260                 265                 270

Ser Gly Trp Leu Gly Thr Gly Phe Asp Arg Val Pro Gly Ala His Arg
        275                 280                 285

Asp Lys Ser Ala Pro Ser Lys Ser Val Leu Ser Tyr His Tyr Cys
    290                 295                 300

Trp Ile Leu Gln Thr Asp Ala Gln Asn Thr Thr Met Pro Phe Trp Lys
305                 310                 315                 320

Lys Val Ile Cys Asp Arg Leu Leu Leu Pro Asn Val Ile Ser Asn Ala
                325                 330                 335

Ile Arg Ala Thr Lys Ser Thr Gly Gly Arg Phe Leu Thr Glu Phe
            340                 345                 350

Gly Leu Cys Gly Asp Asp Gly Asn Pro Arg Ser Val Asn Thr Ile Glu
        355                 360                 365

Cys Asn Asn Ile Leu Asn Glu Ala Asp Lys His Phe Glu Ser Trp Thr
    370                 375                 380

Tyr Trp Asp Ser Asn Leu Leu Asp Leu Ser Gly Asn Pro Ile Val Thr
385                 390                 395                 400

Glu Val Lys Ser Phe Ile Arg Pro Tyr Pro His Ser Ile Arg Gly Val
                405                 410                 415

Phe Arg Lys Gln Gln Phe Asp His Lys Thr Gly Asp Phe His Leu Ser
            420                 425                 430

Phe Ile Ala Asn Thr Thr Lys Glu Gln Asn Asn Glu Lys Gln Thr Leu
        435                 440                 445

Ile Ala Glu Ile Tyr Ile Pro Arg Ser Val His Tyr Pro Asn Gly Phe
    450                 455                 460

Ser Met Ser Val Lys Pro Asp Asn Leu Ser Thr Lys Met Asn Glu Asn
465                 470                 475                 480

Met Met Tyr Val Tyr Leu Pro Ser Gly Val Ser Asn Ala Ser Val Phe
                485                 490                 495

Val Arg Ile Glu Ile Val Arg Lys Ser Ile Glu
            500                 505

<210> SEQ ID NO 24
<211> LENGTH: 507
<212> TYPE: PRT
<213> ORGANISM: Schistosoma japonicum
```

<400> SEQUENCE: 24

Met Trp Ser Ile Phe Ile Leu Thr Phe Leu Ile Trp Thr Ser Val Gln
1               5                   10                  15

Thr Lys Gln Ile Pro Leu Ser Lys Ile His Leu Asn Ser Asp Gly Leu
            20                  25                  30

Phe Thr Asp Ser Arg Gly Phe Ile Lys Leu Phe Arg Gly Phe Asn Asn
        35                  40                  45

Val His Lys His Phe Pro Trp Tyr Asn Val Asn Ser Thr Asn Ile Thr
    50                  55                  60

Gln Leu Glu Met Phe Lys Asn Trp Gly Leu Asn Val Val Arg Leu Gly
65                  70                  75                  80

Val Met Trp Ser Gly Val Lys Pro Thr Ile Ser Ile Val Asn Thr Thr
                85                  90                  95

Tyr Leu Asp Val Ile Glu Asn Val Ile Asp Leu Tyr Ala Asp Tyr Gly
            100                 105                 110

Ile Tyr Val Ile Leu Asp Met His Gln Asp Val Leu Ser Ser Leu Tyr
        115                 120                 125

Gly Leu Tyr Asp Gly Ile Pro Leu Trp Leu Ile Glu Lys Phe Lys Arg
130                 135                 140

Pro Pro His His Leu Gln Tyr Pro Trp Pro Tyr Lys Lys Lys Pro Asp
145                 150                 155                 160

Phe Trp Val Met Ser Tyr Leu Thr Tyr Glu Cys Ala Asn Gly Ala Gln
                165                 170                 175

Gln Leu Tyr Asn Asn Val Ser Gly Ala Trp Asn His Trp Gly Glu Phe
            180                 185                 190

Trp Glu Ile Val Ala Arg Arg Phe Gly Gly Lys Ser Asn Val Leu Gly
        195                 200                 205

Tyr Glu Leu Ile Asn Glu Pro Pro Gly Asn Phe Tyr Thr Asn Pro
210                 215                 220

Leu Arg Gly Leu Pro Gly Tyr Ala Gly Arg Tyr Asn Leu Gln Pro Val
225                 230                 235                 240

Tyr Asp Tyr Leu Val Lys Arg Ile Arg Lys Tyr Asp Asn Ser Thr Leu
                245                 250                 255

Ile Phe Tyr Glu Pro Val Thr Tyr Gly Val Phe Thr Pro Val Arg Ser
            260                 265                 270

Ser Gly Trp Leu Gly Thr Gly Phe Asp Arg Val Pro Gly Ala His Arg
        275                 280                 285

Asp Lys Ser Ala Pro Ser Lys Ser Val Leu Ser Tyr His Tyr Cys
290                 295                 300

Trp Ile Leu Gln Thr Asp Ala Gln Asn Thr Thr Met Pro Phe Trp Lys
305                 310                 315                 320

Lys Val Ile Cys Asp Arg Leu Leu Pro Asn Val Ile Ser Asn Ala
                325                 330                 335

Ile Arg Ala Thr Lys Ser Thr Gly Gly Arg Phe Leu Thr Glu Phe
            340                 345                 350

Gly Leu Cys Gly Asp Asp Gly Asn Pro Arg Ser Val Asn Thr Ile Glu
        355                 360                 365

Cys Asn Asn Ile Leu Asn Glu Ala Asp Lys His Phe Glu Ser Trp Thr
370                 375                 380

Tyr Trp Asp Ser Asn Leu Leu Asp Leu Ser Gly Asn Pro Ile Val Thr
385                 390                 395                 400

Glu Val Lys Ser Phe Ile Arg Pro Tyr Pro His Ser Ile Arg Gly Val

-continued

```
                405                 410                 415

Phe Arg Lys Gln Gln Phe Asp His Lys Thr Gly Asp Phe His Leu Ser
            420                 425                 430

Phe Ile Ala Asn Thr Thr Lys Glu Gln Asn Asn Glu Lys Gln Thr Leu
        435                 440                 445

Ile Ala Glu Ile Tyr Ile Pro Arg Ser Val His Tyr Pro Asn Gly Phe
    450                 455                 460

Ser Met Ser Val Lys Pro Asp Asn Leu Ser Thr Lys Met Asn Glu Asn
465                 470                 475                 480

Met Met Tyr Val Tyr Leu Pro Ser Gly Val Ser Asn Ala Ser Val Phe
                485                 490                 495

Val Arg Ile Glu Ile Val Arg Lys Ser Ile Glu
            500                 505

<210> SEQ ID NO 25
<211> LENGTH: 509
<212> TYPE: PRT
<213> ORGANISM: Dictyostelium discoideum

<400> SEQUENCE: 25

Met Asn Lys Lys Lys Gln Ile Ile Thr Thr Ile Thr Leu Leu Ser Phe
1               5                   10                  15

Ile Asn Leu Phe Ser Ile Val Asn Ala Ile Ile Lys Val Asn Pro Ala
            20                  25                  30

Asn Gln Phe Phe Ile Asp Gln Tyr Asn Arg Val Arg Leu Phe His Gly
        35                  40                  45

Val Asn Val Val Tyr Lys Ile Pro Pro Phe His Pro Ser Leu Glu Gly
    50                  55                  60

Phe Asp Pro Val Thr Ser Phe Ser Ser Gln Asp Ile Glu Asn Leu Val
65                  70                  75                  80

Glu Trp Gly Phe Asn Ala Val Arg Leu Gly Val Met Trp Pro Gly Val
                85                  90                  95

Glu Pro Val Lys Asp Glu Tyr Asn Gln Thr Tyr Leu Asp Val Met Ser
            100                 105                 110

Lys Leu Val Ser Glu Met Glu Asp Asn Glu Ile Tyr Thr Leu Ile Asp
        115                 120                 125

Phe His Gln Asp Leu Leu Ser Arg Lys Tyr Cys Gly Glu Gly Leu Pro
    130                 135                 140

Asp Trp Ile Val Ser Asn Asp Thr Asn Asp Ser Phe Pro Ser Pro Val
145                 150                 155                 160

Ala His Ser Tyr Pro Lys Asn Asn Glu Ser Tyr Pro Ser Leu Asp Gln
                165                 170                 175

Cys Leu Asn Lys Asp Phe Gly Val Tyr Tyr Phe Ser Glu Asp Val Asn
            180                 185                 190

Arg Glu Phe Gln Asn Leu Tyr Asp Asn Val Asn Gly Val Gln Asp Lys
        195                 200                 205

Phe Ile Asp Tyr Trp Arg Gln Val Val Asn Thr Phe Lys Ser Tyr Asp
    210                 215                 220

Thr Val Leu Gly Tyr Glu Ile Ile Asn Glu Pro Trp Gly Gly Asp Ile
225                 230                 235                 240

Tyr Gln Asn Pro Glu Tyr Leu Leu Lys Leu Gly Tyr Ala Asp Ser Lys
                245                 250                 255

Asn Leu Leu Pro Leu Tyr Gln Ala Val Asn Asn Ala Ile Arg Glu Leu
            260                 265                 270
```

```
Asp Asp Gln His Cys Val Tyr Tyr Glu Lys Ala Leu Thr Asp Leu Phe
            275                 280                 285

His Ser Tyr Phe Pro Ser Gly Thr Pro Gly Gly Val Gln Tyr Asn Asp
290                 295                 300

Arg Gln Val Leu Ser Tyr His Ile Tyr Cys Ala Thr Asp Arg Asp Gly
305                 310                 315                 320

Asn Pro Arg His Glu Tyr Val Cys Asp Gly Glu Asp Asp Ile Phe Leu
                325                 330                 335

Val Ser Ala Met Lys Asp Leu Lys Gln Thr Gly Gly Gly Phe Met
            340                 345                 350

Thr Glu Phe Gly Ala Val Ser Asn Gly Thr Asn Ser Ile Glu Met Leu
            355                 360                 365

Asn Tyr Leu Thr Gly Ser Ala Asp Lys Tyr Leu Gln Ser Trp Thr Tyr
370                 375                 380

Trp Gln Leu Lys Tyr Tyr Asn Asp Ile Thr Thr Ala Gly Ser Thr Glu
385                 390                 395                 400

Ser Leu Tyr Leu Pro Asn Gly Glu Leu Asp Ile Pro Lys Ile Thr Ala
                405                 410                 415

Leu Ser Arg Thr Tyr Ala Gln Ala Ile Ala Gly Val Pro Leu Ser Met
            420                 425                 430

Ser Phe Asn Pro Ala Asn Ser Asp Phe Ser Phe Ser Tyr Asn Ile Asn
435                 440                 445

Thr Thr Ile Thr Gln Pro Thr Gln Ile Tyr Leu Asn Gln Asp Ile Tyr
            450                 455                 460

Tyr Pro Asn Gly Phe Thr Thr Asn Ile Ile Thr Gly Thr Ala Thr Val
465                 470                 475                 480

Ser Ile Pro Gln Lys Asn Leu Ile Tyr Ile Leu Pro Asn Ser Asn Thr
                485                 490                 495

Ile Asn Gln Ser Thr Ile Thr Ile Thr Ile Leu Lys Lys
            500                 505

<210> SEQ ID NO 26
<211> LENGTH: 647
<212> TYPE: PRT
<213> ORGANISM: Streptomyces avermitilis

<400> SEQUENCE: 26

Met Arg Lys Asn Ala Lys Leu Thr His Glu Ser Glu Val Leu Thr Phe
1               5                   10                  15

His Arg Ser Ala Arg Thr Val Val Asp Met Ser Lys Leu Arg Ala Arg
            20                  25                  30

Leu Leu Gly Val Leu Val Ser Leu Thr Gly Leu Leu Gly Ala Thr Gly
        35                  40                  45

Ala Gln Pro Ala Ala Ala Asp Ser Leu Pro Asp Ser Leu Trp Phe Asp
    50                  55                  60

Ala Ser Ala Ser Ala Ala Phe Thr Val Gln Asn Gly Arg Phe Ser Asp
65                  70                  75                  80

Gly Leu Gly Arg Glu Val Val Leu Arg Gly Tyr Asn Val Ser Gly Glu
                85                  90                  95

Thr Lys Leu Glu Glu Asn Ser Gly Leu Pro Phe Ala Ser Val Ala Asp
            100                 105                 110

Ala Arg Lys Ser Ala Thr Ala Leu Arg Thr Leu Gly Gly Gly Asn Ser
        115                 120                 125

Val Arg Phe Leu Leu Ser Trp Ala His Ala Glu Pro Val Arg Gly Gln
    130                 135                 140
```

```
Val Asp Thr Ala Tyr Leu Ala Ala Thr Ala Gln Met Arg Ala Phe
145                 150                 155                 160

Leu Asp Ala Gly Ile Arg Val Phe Pro Asp Phe His Gln Asp Leu Tyr
                165                 170                 175

Ser Arg Tyr Leu Phe Asn Ser Gly Ser Trp Tyr Thr Gly Asp Gly Ala
            180                 185                 190

Pro Glu Trp Ala Val Asp Ala Gly Asp Tyr Pro Ala Glu Ser Cys Gly
            195                 200                 205

Ile Cys Leu Phe Trp Gly Gln Asn Ile Thr Gln Asn Gly Ala Val Thr
210                 215                 220

Gln Ala Ser His Asp Phe Trp His Asn Ala Tyr Gly Val Gln Asp Ala
225                 230                 235                 240

Phe Leu Ala Thr Ala Gln Ala Thr Met Ala Tyr Ile Gln Gln Asn Leu
                245                 250                 255

Ser Ala Asp Glu Phe Asn Gly Val Val Gly Phe Asp Pro Tyr Asn Glu
            260                 265                 270

Pro His Ala Gly Thr Tyr Asp Ser Gly Glu Thr Ser Arg Thr Trp Glu
            275                 280                 285

Gln Asn Val Leu Trp Pro Phe Tyr Lys Lys Phe Arg Ala Arg Met Asp
290                 295                 300

Ala Ala Gly Trp Gln Thr Lys Pro Ala Phe Ile Glu Pro Asn Leu Phe
305                 310                 315                 320

Trp Asn Ala Asn Ile Asp Phe Gln Lys Gln Glu Gly Leu Leu Asp
                325                 330                 335

Ala Gly Thr Leu Gly Pro Arg Tyr Val Leu Asn Thr His Phe Tyr Asp
            340                 345                 350

Gln Lys Ala Ile Ser Gly Val Leu Met Trp Gly Lys Ala Ala Asp Gly
            355                 360                 365

Gln Tyr Ala Thr Asp Phe Gly Lys Val Arg Asp Arg Ala Ala Gly Ala
            370                 375                 380

Gly Thr Ala Ala Val Val Ser Glu Phe Gly His Pro Leu Ser Gly Ser
385                 390                 395                 400

Val Ser Asp Lys Ala Pro Thr Val Val Lys Ala Met Tyr Gln Ala Leu
                405                 410                 415

Asp Ser Arg Leu Pro Gly Ser Thr Trp Trp Ser Asp Pro Thr Gly Ser
            420                 425                 430

Gly Pro Val Leu Ser Gly Ala Gln Trp Gln Trp Asp Ile Tyr Asn Gly
            435                 440                 445

Arg His His Glu Leu Glu Asn Gly Asn Pro Asp Lys Val Leu Thr Ser
            450                 455                 460

Gly Asp Ala Trp Asn Asp Glu Asp Leu Ser Ala Val Ser Leu Asn Asp
465                 470                 475                 480

Ser Gly Thr Ala Val Leu Arg Gln Asp Ala Arg Leu Leu Asp Arg Leu
                485                 490                 495

Tyr Pro Ser Ala Thr Ala Gly Ala Thr Val Ala Phe Thr Tyr Glu Asp
            500                 505                 510

Arg Ser Arg Asp Gly Ser Thr Thr Leu Thr Trp Asn Pro Val Pro Ser
            515                 520                 525

Ser Leu Pro Asn Val Ser Arg Leu Val Gly Ser Gln Tyr Gly Leu
            530                 535                 540

Leu Val Trp Arg Ser Asn Gly Ser Thr Ala Pro Thr Glu Leu His Leu
545                 550                 555                 560
```

```
Pro Ala Ser Phe Pro Ala Ser Thr Thr Val Val Ser Asp Leu Gly
                565                 570                 575

Thr Thr Ser Gly Leu Pro Ala Tyr Thr Arg Thr Thr Pro Val Gly His
            580                 585                 590

Ala Ala Glu Pro Gly Gly Thr Gly Ser His Arg Leu Leu Leu Thr Ala
        595                 600                 605

Ala Asp Ser Gly Thr Val His Tyr Ala Leu Val Thr Asn Gly Ala Thr
    610                 615                 620

Ala Pro Ser Ala Gly Leu Leu Ser Ala Ala Arg Ala Glu Leu Ser Ser
625                 630                 635                 640

Trp Ala Ala Thr Lys Val Gly
                645

<210> SEQ ID NO 27
<211> LENGTH: 654
<212> TYPE: PRT
<213> ORGANISM: Leptospira interrogans

<400> SEQUENCE: 27

Met Glu Glu Leu Phe Val Lys Asn Gly His Phe Ala Ser Lys Glu Gly
1               5                   10                  15

Ala Ile Tyr Gln Leu Arg Gly Val Asn Leu Ser Gly Ser Ala Lys Leu
            20                  25                  30

Pro Leu Lys Pro Asp Gly Thr Thr His Phe Asp Gln Thr Thr Thr Phe
        35                  40                  45

Asp Asn His Lys Asn Val Ser Phe Val Gly Arg Pro Leu Lys Glu Asp
    50                  55                  60

Gln Ala Glu Glu His Phe Asp Arg Leu Arg Lys Trp Gly Phe Asn Phe
65                  70                  75                  80

Leu Arg Phe Leu Ile Thr Trp Glu Ala Ile Glu His Lys Gly Pro Gly
                85                  90                  95

Lys Tyr Asp Asn Glu Tyr Ile Asp Tyr Val Glu Arg Met Val Ser Leu
            100                 105                 110

Ala Ala Lys Lys Gly Phe Tyr Leu Phe Ile Asp Pro His Gln Asp Val
        115                 120                 125

Trp Ser Arg Phe Thr Gly Gly Asp Gly Ala Pro Gly Trp Thr Leu Glu
    130                 135                 140

Glu Leu Gly Met Asn Ile Ser Lys Ile Arg Asn Ser Glu Thr Ala Ile
145                 150                 155                 160

Val His His His Gln Gly Lys Asn Tyr Arg Arg Met Ser Trp Pro Leu
                165                 170                 175

Asn Tyr Gln Lys Tyr Ser Cys Ala Thr Met Phe Ser Leu Phe Phe Gly
            180                 185                 190

Gly Lys Glu Phe Ala Pro Asp Thr Lys Ile Asp Gly Arg Asn Val Gln
        195                 200                 205

Asp Phe Leu Gln Asp His Tyr Ile Asp Ser Val Leu Lys Ile Val Arg
    210                 215                 220

Lys Leu Lys Lys Tyr Lys Asn Val Ile Gly Phe Asp Thr Leu Asn Glu
225                 230                 235                 240

Pro Ser Pro Gly Trp Ile Gly Lys Lys Asn Leu Gly Glu Phe Asp Gly
                245                 250                 255

Phe Gly Phe Gly Lys Val Val Lys Ser Ser Pro Phe Gln Glu Met Tyr
            260                 265                 270

Leu Ser Glu Gly Arg Ala Val Ser Ala Ala Gln Ala Tyr Met Leu Gly
        275                 280                 285
```

Phe Trp Ser Leu Pro Phe Gly Lys Val Arg Leu Asn Pro Glu Gly Val
                290                 295                 300

Pro Leu Trp Glu Arg Gly His Gln Cys Ile Trp Arg Asn His Gly Val
305                 310                 315                 320

Trp Asp Tyr Asp Pro Asn Gly Ala Pro Met Met Leu Lys Pro Glu Tyr
                325                 330                 335

Phe Tyr Lys Lys Asn Gly Arg Lys Tyr Glu Phe Tyr Ser Asp Phe Met
                340                 345                 350

Tyr Pro Phe Ile Lys Lys Phe Lys Glu Arg Val Gln Lys Leu Glu Asn
                355                 360                 365

Arg Phe His Ile Phe Ile Glu Ser Asp Pro Ser Lys Leu Glu Leu Glu
                370                 375                 380

Trp Lys Glu Ile Pro Lys Lys Asn Gln Gly Ser Val Ile Asn Ala Thr
385                 390                 395                 400

His Trp Tyr Asp Ile Ser Val Leu Met Leu Lys Arg Tyr Leu Pro Trp
                405                 410                 415

Phe Gly Val His Val Phe Lys Gln Lys Pro Ile Phe Gly Lys Glu Asn
                420                 425                 430

Ile Asp Asn Ala Tyr Glu Glu Thr Ile Arg Met Ile Arg Glu Met Ser
                435                 440                 445

Glu Lys Lys Met Gly Asn Cys Pro Thr Val Ile Gly Glu Thr Gly Ile
450                 455                 460

Pro Met Asp Leu Asn His Arg Val Ala Tyr Leu Lys Asn Asp Tyr Gly
465                 470                 475                 480

Val Leu Glu Lys Ala Leu Asp Arg Ile Met Lys Ala Val Glu Lys Asn
                485                 490                 495

Phe Val Asn Leu Ala Leu Trp Asn Tyr Thr Pro Asp His Thr His Ser
                500                 505                 510

Leu Gly Asp Arg Trp Asn Glu Glu Asp Leu Ser Ile Tyr Ser Gln Asp
                515                 520                 525

Thr Pro Ser Ser Tyr Asp Glu Asp Gly Gly Arg Ala Val Arg Ala Phe
530                 535                 540

Ser Arg Pro Tyr Pro Ile Arg Thr Lys Gly Phe Pro Val Ala Leu Thr
545                 550                 555                 560

Phe Asp Met Glu Arg Ser Leu Phe Lys Tyr Ala Phe Arg Gln Glu Gly
                565                 570                 575

Asp Leu Phe Pro Glu Thr Glu Ile Phe Ile Pro Glu Ile His Tyr Lys
                580                 585                 590

Lys Gly Phe Glu Val Leu Val Asn Ala Gly Thr Tyr Gln Tyr Asp Phe
                595                 600                 605

Arg Ser Arg Val Leu Lys Phe Lys Gly Glu Lys Gly Ile Leu Asp Tyr
610                 615                 620

Gly Ile Thr Val Tyr Pro Ser Lys Lys Ser Leu Ser Arg Glu Gln Asp
625                 630                 635                 640

Arg Thr Lys Val Val Pro Lys Thr Gln Lys Arg Lys Thr Gln
                645                 650

<210> SEQ ID NO 28
<211> LENGTH: 770
<212> TYPE: PRT
<213> ORGANISM: Neurospora crassa

<400> SEQUENCE: 28

Met Ala Gly Phe Arg Leu Thr Ile Glu Asn Gly Ser Phe Arg Asp Val

-continued

```
1               5                   10                  15
His Gly Arg Gln Ile Thr Leu Arg Gly Ile Asn Val Ala Gly Asp Ala
            20                  25                  30

Lys Tyr Pro Asn Lys Pro Glu Gln Pro Ser His Val Gly Glu Asn Phe
            35                  40                  45

Phe Asp Gly Asp Asn Val Lys Phe Thr Gly Arg Pro Phe Pro Lys Glu
 50                      55                  60

Glu Ala His Leu His Phe Ser Arg Leu Lys Arg Phe Gly Tyr Asn Thr
 65                  70                  75                  80

Ile Arg Tyr Val Phe Thr Trp Glu Ala Ile Glu Ala Ala Gly Pro Gly
                 85                  90                  95

Ile Tyr Asp Glu Glu Trp Ile Gln His Thr Ile Asp Val Leu Arg Val
             100                 105                 110

Ala Lys Arg Tyr Gly Phe Tyr Ile Phe Met Asp Pro His Gln Asp Val
             115                 120                 125

Trp Ser Arg Phe Ser Gly Gly Ser Gly Ala Pro Met Trp Thr Leu Tyr
130                 135                 140

Ala Ala Gly Leu Asn Pro Gln Ser Phe Ala Ala Thr Glu Ala Ala Ile
145                 150                 155                 160

Val His Asn Val Tyr Pro Glu Pro His Asn Phe Pro Lys Met Ile Trp
                 165                 170                 175

Ser Thr Asn Tyr Tyr Arg Leu Ala Ala Ala Thr Met Phe Thr Leu Phe
             180                 185                 190

Phe Ala Gly Arg Asp Phe Ala Pro Lys Cys Ile Ile Asp Gly Val Asn
             195                 200                 205

Ile Gln Asp Tyr Leu Gln Asp His Phe Leu Arg Ala Cys Ala His Leu
210                 215                 220

Ala Gln Arg Ile His Glu Ala Gly Asp Ile Glu Asn Asp Val Val Phe
225                 230                 235                 240

Gly Trp Glu Ser Leu Asn Glu Pro Asn Lys Gly Met Ile Ala Tyr Glu
                 245                 250                 255

Asp Ile Ser Val Ile Pro Lys Glu Gln Asn Leu Lys Lys Gly Thr Cys
             260                 265                 270

Pro Thr Ile Trp Gln Thr Ile Leu Thr Gly Ser Gly Arg Ala Val Glu
             275                 280                 285

Val Asp Thr Trp Asp Met Gly Met Gly Pro Tyr Lys Val Gly Arg
290                 295                 300

Ala Leu Ile Asp Pro Ser Gly Glu Gln Ala Trp Leu Pro Ala Asp Tyr
305                 310                 315                 320

Asp Glu Ser Arg Tyr Gly Tyr Lys Arg Asp Pro Gly Trp Lys Leu Gly
                 325                 330                 335

Gln Cys Ile Trp Ala Gln His Gly Val Trp Asp Pro Ala Thr Asp Ser
             340                 345                 350

Leu Leu Lys Lys Asp Tyr Phe Gly Lys His Pro Ala Thr Gly Glu His
             355                 360                 365

Val Asp Tyr Pro Tyr Phe Ser Asn Arg Tyr Phe Met Asp Phe Phe Arg
370                 375                 380

Lys Tyr Arg Asp Thr Ile Arg Ser Ile His Pro Asn Ala Ile Ile Leu
385                 390                 395                 400

Leu Gln Gly Pro Thr Met Glu Leu Pro Pro Lys Ile Ile Gly Thr Pro
                 405                 410                 415

Asp Gly Asp Asp Pro Leu Leu Val Tyr Ala Pro His Trp Tyr Asp Gly
             420                 425                 430
```

Ile Thr Leu Met Thr Lys Lys Trp Asn Arg Val Trp Asn Val Asp Val
            435                 440                 445

Ile Gly Ile Leu Arg Gly Lys Tyr Trp Ser Pro Ala Phe Gly Ile Lys
450                 455                 460

Ile Gly Glu Thr Ala Ile Arg Asn Cys Phe Lys Asn Gln His Ala Thr
465                 470                 475                 480

Met Arg Gln Glu Gly Leu Asp Tyr Ile Gly Asn His Pro Cys Val Met
                485                 490                 495

Thr Glu Phe Gly Ile Pro Tyr Asp Met Asp Asp Lys Asn Ala Tyr Lys
            500                 505                 510

Thr Gly Asp Tyr Ser Ser Gln Ser Ala Ala Met Asp Ala Asn His Tyr
            515                 520                 525

Gly Val Glu Gly Ala Gly Leu Glu Gly Tyr Thr Leu Trp Leu Tyr Met
            530                 535                 540

Thr Lys Asn Asp His Glu Leu Gly Asp Gln Trp Asn Gly Glu Asp Leu
545                 550                 555                 560

Ser Ile Phe Ser Val Asp Asp Lys Leu Leu Pro Glu Ser Pro Val Pro
                565                 570                 575

Lys Ser His Ser Arg Asp Gly Ser Ser Ser Ile Ala Thr Pro Thr
            580                 585                 590

Gly Thr Lys Asp Asp Asp Leu Asp Asp Asp Ser Ser Val Thr Pro Ala
            595                 600                 605

Asn Ile Lys Arg Thr Leu Thr Asn Pro Ser Ile Ser Ser Val Ser Thr
610                 615                 620

Gln Arg Gln Pro Glu Leu Thr Asn Ser Pro Gly Tyr Arg Ala Ala Glu
625                 630                 635                 640

Ala Tyr Val Arg Pro Ala Pro Ile Ala Thr Ala Gly Thr Val Lys Lys
                645                 650                 655

Tyr Gly Phe Asp Leu Arg Ser Cys Gln Phe His Val Thr Ile Gln Ala
            660                 665                 670

Pro Glu Ala Ala Lys Pro Asp Thr Pro Thr Val Val Phe Leu Pro Asp
            675                 680                 685

Tyr His Phe Pro Lys Asp Ala Cys Gln Val Glu Val Ser Ser Gly Lys
            690                 695                 700

Trp Glu Ile Arg Ser Asp Glu Glu Thr Thr Pro Leu Gln Lys Leu
705                 710                 715                 720

Arg Trp Trp His Gly Glu Gly Glu Gln Thr Leu Arg Val Thr Gly Val
                725                 730                 735

Val Lys Gln Val Asn Gly Asn Ser Ser Glu Gly Ala Glu Val Gly Tyr
            740                 745                 750

Tyr Asp Gln Val Phe Asn Gln Ala Lys Gly Phe Leu Asp Ala Cys Val
            755                 760                 765

Ile Met
    770

<210> SEQ ID NO 29
<211> LENGTH: 490
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) A derived from GenBank
      Accession #AAB67050 (E233A)

<400> SEQUENCE: 29

```
Met Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
            20                  25                  30

Ser Gly Ser Gly Ser Gly Thr Ala Leu Thr Pro Ser Tyr Leu Lys Asp
        35                  40                  45

Asp Asp Gly Arg Ser Leu Ile Leu Arg Gly Phe Asn Thr Ala Ser Ser
    50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
                100                 105                 110

Leu Asp Arg Val Glu Asp Arg Val Gly Trp Tyr Ala Glu Arg Gly Tyr
                115                 120                 125

Lys Val Met Leu Asp Met His Gln Asp Val Tyr Ser Gly Ala Ile Thr
            130                 135                 140

Pro Glu Gly Asn Ser Gly Asn Gly Ala Gly Ala Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
                180                 185                 190

Asn Phe Trp Asn Thr Thr Gly Lys His Pro Glu Leu Val Glu His Tyr
                195                 200                 205

Ala Lys Ala Trp Arg Ala Val Ala Asp Arg Phe Ala Asp Asn Asp Ala
            210                 215                 220

Val Val Ala Tyr Asp Leu Met Asn Ala Pro Phe Gly Gly Ser Leu Gln
225                 230                 235                 240

Gly Pro Ala Phe Glu Ala Gly Pro Leu Ala Ala Met Tyr Gln Arg Thr
                245                 250                 255

Thr Asp Ala Ile Arg Gln Val Asp Gln Asp Thr Trp Val Cys Val Ala
                260                 265                 270

Pro Gln Ala Ile Gly Val Asn Gln Gly Leu Pro Ser Gly Leu Thr Lys
            275                 280                 285

Ile Asp Asp Pro Arg Ala Gly Gln Gln Arg Ile Ala Tyr Cys Pro His
            290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

Gly Leu Asp Thr Thr Leu Pro Gly Ala Arg Asp Tyr Ile Glu Arg Val
            355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
```

```
                420             425             430
Pro Asp Ala Ala Ile Thr Ala Pro Thr Glu Ile Tyr Leu Pro Glu Ala
                435             440             445
Gly Phe Pro Gly Asp Val His Val Glu Gly Ala Asp Val Val Gly Trp
            450             455             460
Asp Arg Gln Ser Arg Leu Leu Thr Val Arg Thr Pro Ala Asp Ser Gly
465             470             475             480
Asn Val Thr Val Thr Val Thr Pro Ala Ala
                485             490

<210> SEQ ID NO 30
<211> LENGTH: 490
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) B derived from GenBank
      Accession #AAB67050 (E233S)

<400> SEQUENCE: 30

Met Arg Arg Thr Arg Leu Val Ser Leu Ile Val Thr Gly Ser Leu Val
1               5                   10                  15
Phe Gly Gly Gly Val Ala Ala Ala Gln Ser Ser Leu Ala Ala Ser Gly
                20                  25                  30
Ser Gly Ser Gly Ser Gly Thr Ala Leu Thr Pro Ser Tyr Leu Lys Asp
            35                  40                  45
Asp Asp Gly Arg Ser Leu Ile Leu Arg Gly Phe Asn Thr Ala Ser Ser
        50                  55                  60
Ala Lys Ser Ala Pro Asp Gly Met Pro Gln Phe Thr Glu Ala Asp Leu
65                  70                  75                  80
Ala Arg Glu Tyr Ala Asp Met Gly Thr Asn Phe Val Arg Phe Leu Ile
                85                  90                  95
Ser Trp Arg Ser Val Glu Pro Ala Pro Gly Val Tyr Asp Gln Gln Tyr
                100                 105                 110
Leu Asp Arg Val Glu Asp Arg Val Gly Trp Tyr Ala Glu Arg Gly Tyr
            115                 120                 125
Lys Val Met Leu Asp Met His Gln Asp Val Tyr Ser Gly Ala Ile Thr
        130                 135                 140
Pro Glu Gly Asn Ser Gly Asn Gly Ala Gly Ala Ile Gly Asn Gly Ala
145                 150                 155                 160
Pro Ala Trp Ala Thr Tyr Met Asp Gly Leu Pro Val Glu Pro Gln Pro
                165                 170                 175
Arg Trp Glu Leu Tyr Tyr Ile Gln Pro Gly Val Met Arg Ala Phe Asp
                180                 185                 190
Asn Phe Trp Asn Thr Thr Gly Lys His Pro Glu Leu Val Glu His Tyr
            195                 200                 205
Ala Lys Ala Trp Arg Ala Val Ala Asp Arg Phe Ala Asp Asn Asp Ala
        210                 215                 220
Val Val Ala Tyr Asp Leu Met Asn Ser Pro Phe Gly Gly Ser Leu Gln
225                 230                 235                 240
Gly Pro Ala Phe Glu Ala Gly Pro Leu Ala Ala Met Tyr Gln Arg Thr
                245                 250                 255
Thr Asp Ala Ile Arg Gln Val Asp Gln Asp Thr Trp Val Cys Val Ala
                260                 265                 270
Pro Gln Ala Ile Gly Val Asn Gln Gly Leu Pro Ser Gly Leu Thr Lys
            275                 280                 285
```

```
Ile Asp Asp Pro Arg Ala Gly Gln Gln Arg Ile Ala Tyr Cys Pro His
            290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

Gly Leu Asp Thr Thr Leu Pro Gly Ala Arg Asp Tyr Ile Glu Arg Val
            355                 360                 365

Tyr Gly Thr Ala Arg Glu Met Gly Ala Gly Val Ser Tyr Trp Ser Ser
370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
            435                 440                 445

Gly Phe Pro Gly Asp Val His Val Glu Gly Ala Asp Val Val Gly Trp
450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 31
<211> LENGTH: 490
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) C derived from GenBank
      Accession #AAB67050 (E233G)

<400> SEQUENCE: 31

Met Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
            20                  25                  30

Ser Gly Ser Gly Ser Gly Thr Ala Leu Thr Pro Ser Tyr Leu Lys Asp
        35                  40                  45

Asp Asp Gly Arg Ser Leu Ile Leu Arg Gly Phe Asn Thr Ala Ser Ser
50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
            100                 105                 110

Leu Asp Arg Val Glu Asp Arg Val Gly Trp Tyr Ala Glu Arg Gly Tyr
        115                 120                 125

Lys Val Met Leu Asp Met His Gln Asp Val Tyr Ser Gly Ala Ile Thr
130                 135                 140
```

```
Pro Glu Gly Asn Ser Gly Asn Gly Ala Gly Ala Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
            180                 185                 190

Asn Phe Trp Asn Thr Thr Gly Lys His Pro Glu Leu Val Glu His Tyr
        195                 200                 205

Ala Lys Ala Trp Arg Ala Val Ala Asp Arg Phe Ala Asp Asn Asp Ala
    210                 215                 220

Val Val Ala Tyr Asp Leu Met Asn Gly Pro Phe Gly Gly Ser Leu Gln
225                 230                 235                 240

Gly Pro Ala Phe Glu Ala Gly Pro Leu Ala Ala Met Tyr Gln Arg Thr
                245                 250                 255

Thr Asp Ala Ile Arg Gln Val Asp Gln Asp Thr Trp Val Cys Val Ala
            260                 265                 270

Pro Gln Ala Ile Gly Val Asn Gln Gly Leu Pro Ser Gly Leu Thr Lys
        275                 280                 285

Ile Asp Asp Pro Arg Ala Gly Gln Gln Arg Ile Ala Tyr Cys Pro His
    290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

Gly Leu Asp Thr Thr Leu Pro Gly Ala Arg Asp Tyr Ile Glu Arg Val
        355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
        435                 440                 445

Gly Phe Pro Gly Asp Val His Val Glu Gly Ala Asp Val Val Gly Trp
    450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490
```

<210> SEQ ID NO 32
<211> LENGTH: 490
<212> TYPE: PRT
<213> ORGANISM: Artificial Sequence
<220> FEATURE:
<223> OTHER INFORMATION: Description of Artificial Sequence:mutant endoglycoceramidase (EGC, EGCase) D derived from GenBank Accession #AAB67050 (E233D)

<400> SEQUENCE: 32

Met Arg Arg Thr Arg Leu Val Ser Leu Ile Val Thr Gly Ser Leu Val

-continued

```
  1               5                   10                  15
Phe Gly Gly Gly Val Ala Ala Gln Ser Ser Leu Ala Ala Ser Gly
          20                  25                  30
Ser Gly Ser Gly Ser Gly Thr Ala Leu Thr Pro Ser Tyr Leu Lys Asp
          35                  40                  45
Asp Asp Gly Arg Ser Leu Ile Leu Arg Gly Phe Asn Thr Ala Ser Ser
 50                  55                  60
Ala Lys Ser Ala Pro Asp Gly Met Pro Gln Phe Thr Glu Ala Asp Leu
 65                  70                  75                  80
Ala Arg Glu Tyr Ala Asp Met Gly Thr Asn Phe Val Arg Phe Leu Ile
              85                  90                  95
Ser Trp Arg Ser Val Glu Pro Ala Pro Gly Val Tyr Asp Gln Gln Tyr
             100                 105                 110
Leu Asp Arg Val Glu Asp Arg Val Gly Trp Tyr Ala Glu Arg Gly Tyr
             115                 120                 125
Lys Val Met Leu Asp Met His Gln Asp Val Tyr Ser Gly Ala Ile Thr
         130                 135                 140
Pro Glu Gly Asn Ser Gly Asn Gly Ala Gly Ala Ile Gly Asn Gly Ala
145                 150                 155                 160
Pro Ala Trp Ala Thr Tyr Met Asp Gly Leu Pro Val Glu Pro Gln Pro
                 165                 170                 175
Arg Trp Glu Leu Tyr Tyr Ile Gln Pro Gly Val Met Arg Ala Phe Asp
             180                 185                 190
Asn Phe Trp Asn Thr Thr Gly Lys His Pro Glu Leu Val Glu His Tyr
             195                 200                 205
Ala Lys Ala Trp Arg Ala Val Ala Asp Arg Phe Ala Asp Asn Asp Ala
         210                 215                 220
Val Val Ala Tyr Asp Leu Met Asn Asp Pro Phe Gly Gly Ser Leu Gln
225                 230                 235                 240
Gly Pro Ala Phe Glu Ala Gly Pro Leu Ala Ala Met Tyr Gln Arg Thr
                 245                 250                 255
Thr Asp Ala Ile Arg Gln Val Asp Gln Asp Thr Trp Val Cys Val Ala
             260                 265                 270
Pro Gln Ala Ile Gly Val Asn Gln Gly Leu Pro Ser Gly Leu Thr Lys
         275                 280                 285
Ile Asp Asp Pro Arg Ala Gly Gln Gln Arg Ile Ala Tyr Cys Pro His
         290                 295                 300
Leu Tyr Pro Leu Pro Leu Asp Ile Gly Asp Gly His Glu Gly Leu Ala
305                 310                 315                 320
Arg Thr Leu Thr Asp Val Thr Ile Asp Ala Trp Arg Ala Asn Thr Ala
                 325                 330                 335
His Thr Ala Arg Val Leu Gly Asp Val Pro Ile Ile Leu Gly Glu Phe
             340                 345                 350
Gly Leu Asp Thr Thr Leu Pro Gly Ala Arg Asp Tyr Ile Glu Arg Val
             355                 360                 365
Tyr Gly Thr Ala Arg Glu Met Gly Ala Gly Val Ser Tyr Trp Ser Ser
         370                 375                 380
Asp Pro Gly Pro Trp Gly Pro Tyr Leu Pro Asp Gly Thr Gln Thr Leu
385                 390                 395                 400
Leu Val Asp Thr Leu Asn Lys Pro Tyr Pro Arg Ala Val Ala Gly Thr
                 405                 410                 415
Pro Thr Glu Trp Ser Ser Thr Ser Asp Arg Leu Gln Leu Thr Ile Glu
             420                 425                 430
```

```
Pro Asp Ala Ala Ile Thr Ala Pro Thr Glu Ile Tyr Leu Pro Glu Ala
        435                 440                 445

Gly Phe Pro Gly Asp Val His Val Glu Gly Ala Asp Val Val Gly Trp
        450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 33
<211> LENGTH: 490
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) E derived from GenBank
      Accession #AAB67050 (E233Q)

<400> SEQUENCE: 33

Met Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
            20                  25                  30

Ser Gly Ser Gly Ser Gly Thr Ala Leu Thr Pro Ser Tyr Leu Lys Asp
        35                  40                  45

Asp Asp Gly Arg Ser Leu Ile Leu Arg Gly Phe Asn Thr Ala Ser Ser
    50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
            100                 105                 110

Leu Asp Arg Val Glu Asp Arg Val Gly Trp Tyr Ala Glu Arg Gly Tyr
        115                 120                 125

Lys Val Met Leu Asp Met His Gln Asp Val Tyr Ser Gly Ala Ile Thr
130                 135                 140

Pro Glu Gly Asn Ser Gly Asn Gly Ala Gly Ala Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
            180                 185                 190

Asn Phe Trp Asn Thr Thr Gly Lys His Pro Glu Leu Val Glu His Tyr
        195                 200                 205

Ala Lys Ala Trp Arg Ala Val Ala Asp Arg Phe Ala Asp Asn Asp Ala
    210                 215                 220

Val Val Ala Tyr Asp Leu Met Asn Gln Pro Phe Gly Gly Ser Leu Gln
225                 230                 235                 240

Gly Pro Ala Phe Glu Ala Gly Pro Leu Ala Ala Met Tyr Gln Arg Thr
                245                 250                 255

Thr Asp Ala Ile Arg Gln Val Asp Gln Asp Thr Trp Val Cys Val Ala
            260                 265                 270

Pro Gln Ala Ile Gly Val Asn Gln Gly Leu Pro Ser Gly Leu Thr Lys
        275                 280                 285
```

```
Ile Asp Asp Pro Arg Ala Gly Gln Gln Arg Ile Ala Tyr Cys Pro His
    290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Glu Phe
            340                 345                 350

Gly Leu Asp Thr Thr Leu Pro Gly Ala Arg Asp Tyr Ile Glu Arg Val
        355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
        435                 440                 445

Gly Phe Pro Gly Asp Val His Val Glu Gly Ala Asp Val Val Gly Trp
    450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:5'Copt PCR
      5' primer for introducing mutations into EGCase gene

<400> SEQUENCE: 34
aattcgattg gatcccatat gagcggaagc g                                      31

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence:3'Asp PstI
      PCR 3' primer for introducing mutations into EGCase gene

<400> SEQUENCE: 35
tcgattctgc agggagccac caaacgggtc attcatcag                              39

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence:3'Gln PstI
      PCR 3' primer for introducing mutations into EGCase gene

<400> SEQUENCE: 36
tcgattctgc agggagccac caaacggctg attcatcag                              39
```

```
<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence:3'Ala
      PstI-11-1 PCR 3' primer for introducing mutations into EGCase gene

<400> SEQUENCE: 37
cggtccctgc agggagccac caaacggcgc attcatcag                              39

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence:3'Gly
      PstI-11-1 PCR 3' primer for introducing mutations into EGCase gene

<400> SEQUENCE: 38
cggtccctgc agggagccac caaacggccc attcatcag                              39

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence:3'Ser
      PstI-11-1 PCR 3' primer for introducing mutations into EGCase gene

<400> SEQUENCE: 39
cggtccctgc agggagccac caaacggcga attcatcag                              39

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351A-forward overlapping PCR primer

<400> SEQUENCE: 40
ctcggtgcgt tcggttaga ttac                                               24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351A-reverse overlapping PCR primer

<400> SEQUENCE: 41
ggtatctaaa ccgaacgcac cgag                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351D-forward overlapping PCR primer

<400> SEQUENCE: 42
ctcggtgatt tcggtttaga tacc                                              24

<210> SEQ ID NO 43
```

```
<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351D-reverse overlapping PCR primer

<400> SEQUENCE: 43
ggtatctaaa ccgaaatcac cgag                                           24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351G-forward overlapping PCR primer

<400> SEQUENCE: 44
ctcggtgggt tcggtttaga tacc                                           24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351G-reverse overlapping PCR primer

<400> SEQUENCE: 45
ggtatctaaa ccgaacccac cgag                                           24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351S-forward overlapping PCR primer

<400> SEQUENCE: 46
ctcggtagtt tcggtttaga tacc                                           24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Rhodococcus
      EGC-E351S-reverse overlapping PCR primer

<400> SEQUENCE: 47
ggtatctaaa ccgaaactac cgag                                           24

<210> SEQ ID NO 48
<211> LENGTH: 1401
<212> TYPE: DNA
<213> ORGANISM: Artificial Sequence
<220> FEATURE:
<223> OTHER INFORMATION: Description of Artificial Sequence:mutant
      endoglycoceramidase (EGC, EGCase) His E351S derived from GenBank
      Accession #U39554

<400> SEQUENCE: 48
catatgggat ccagcggaag cggtagcggt tcgggtaccg cgctgacacc ttcatatctg    60
aaggatgatg acgggcggag cctcattctt cgtggattta atacggcctc atctgcaaaa   120
```

```
agtgccctg acggcatgcc acagttcact gaagcagatt tggcgcgtga atatgcggac      180
atgggtacta attttgtacg ttttctgatc tcttggcgct cggtggaacc ggctcctggc      240
gtatatgatc aacagtacct ggatcgtgta gaagaccgtg taggttggta cgcagagcgt      300
ggttataaag ttatgctgga catgcatcaa gacgtgtact cggggggccat tactccggaa     360
ggcaatagtg gtaatggcgc aggtgcgatt ggtaatgggg caccggcgtg ggccacctat      420
atggatggtc tgccagtgga accccaaccc cgctgggaac tgtattacat ccagccaggc      480
gtgatgcggg cgtttgataa ttttttggaac acgaccggca agcatccgga actggtggaa     540
cattatgcga aagcgtggcg cgcggtagct gaccgcttcg cggataatga tgcggttgtg      600
gcctatgacc tgatgaatga gccgtttggt ggctccctgc agggaccggc attcgaagcg      660
ggcccattag cagcaatgta ccagcgcact actgatgcca tccgtcaggt ggatcaggat      720
acttgggttt gtgtggcacc gcaggccatt ggcgttaatc aaggtttacc atcgggctta      780
actaaaattg atgaccctcg cgccggtcaa caacgcattg cctattgccc gcatctgtac      840
ccgctgccat tggacatcgg cgacggccac gaaggacttg cgcgcactct gaccgatgta      900
accattgatg cctggcgtgc gaacacggct cataccgcgc gcgtcttggg tgatgtgcct      960
atcattctcg gttcgttcgg tttagatacc acgctgcccg gagcacgcga ttacattgaa     1020
cgtgtctatg ggaccgcacg cgaaatgggt gcgggcgtta gttattggtc gagtgatccc     1080
ggcccgtggg gcccgtatct gccggacggt acgcagacct tgttagtgga taccttaaac     1140
aagccatacc ctcgtgcagt ggcggggacc cctaccgaat ggagcagcac ttcggatcgc     1200
ctgcaattga ccattgaacc agatgccgct attaccgcgc ctacagaaat ctacctgcct     1260
gaggctggtt tccccgggga tgtgcatgta aaggggcgg atgtcgttgg ctgggatcgt      1320
caatcgcgtc ttttaaccgt acgcactccc gcggacagtg gtaacgtcac agtgacagtt     1380
acgcccgcag cgtgactcga g                                               1401
```

<210> SEQ ID NO 49
<211> LENGTH: 483
<212> TYPE: PRT
<213> ORGANISM: Artificial Sequence
<220> FEATURE:
<223> OTHER INFORMATION: Description of Artificial Sequence:mutant
endoglycoceramidase (EGC, EGCase) His E351S derived from GenBank
Accession #AAB67050

<400> SEQUENCE: 49

Met Gly Ser Ser His His His His His His Ser Ser Gly Leu Val Pro
1               5                   10                  15

Arg Gly Ser His Met Gly Ser Ser Gly Ser Gly Ser Gly Ser Gly Thr
            20                  25                  30

Ala Leu Thr Pro Ser Tyr Leu Lys Asp Asp Asp Gly Arg Ser Leu Ile
        35                  40                  45

Leu Arg Gly Phe Asn Thr Ala Ser Ser Ala Lys Ser Ala Pro Asp Gly
    50                  55                  60

Met Pro Gln Phe Thr Glu Ala Asp Leu Ala Arg Glu Tyr Ala Asp Met
65                  70                  75                  80

Gly Thr Asn Phe Val Arg Phe Leu Ile Ser Trp Arg Ser Val Glu Pro
                85                  90                  95

Ala Pro Gly Val Tyr Asp Gln Gln Tyr Leu Asp Arg Val Glu Asp Arg
            100                 105                 110

Val Gly Trp Tyr Ala Glu Arg Gly Tyr Lys Val Met Leu Asp Met His
        115                 120                 125

```
Gln Asp Val Tyr Ser Gly Ala Ile Thr Pro Glu Gly Asn Ser Gly Asn
            130                 135                 140

Gly Ala Gly Ala Ile Gly Asn Gly Ala Pro Ala Trp Ala Thr Tyr Met
145                 150                 155                 160

Asp Gly Leu Pro Val Glu Pro Gln Pro Arg Trp Glu Leu Tyr Tyr Ile
            165                 170                 175

Gln Pro Gly Val Met Arg Ala Phe Asp Asn Phe Trp Asn Thr Thr Gly
            180                 185                 190

Lys His Pro Glu Leu Val Glu His Tyr Ala Lys Ala Trp Arg Ala Val
            195                 200                 205

Ala Asp Arg Phe Ala Asp Asn Asp Ala Val Val Ala Tyr Asp Leu Met
            210                 215                 220

Asn Glu Pro Phe Gly Gly Ser Leu Gln Gly Pro Ala Phe Glu Ala Gly
225                 230                 235                 240

Pro Leu Ala Ala Met Tyr Gln Arg Thr Thr Asp Ala Ile Arg Gln Val
            245                 250                 255

Asp Gln Asp Thr Trp Val Cys Val Ala Pro Gln Ala Ile Gly Val Asn
            260                 265                 270

Gln Gly Leu Pro Ser Gly Leu Thr Lys Ile Asp Pro Arg Ala Gly
            275                 280                 285

Gln Gln Arg Ile Ala Tyr Cys Pro His Leu Tyr Pro Leu Pro Leu Asp
            290                 295                 300

Ile Gly Asp Gly His Glu Gly Leu Ala Arg Thr Leu Thr Asp Val Thr
305                 310                 315                 320

Ile Asp Ala Trp Arg Ala Asn Thr Ala His Thr Ala Arg Val Leu Gly
            325                 330                 335

Asp Val Pro Ile Ile Leu Gly Ser Phe Gly Leu Asp Thr Thr Leu Pro
            340                 345                 350

Gly Ala Arg Asp Tyr Ile Glu Arg Val Tyr Gly Thr Ala Arg Glu Met
            355                 360                 365

Gly Ala Gly Val Ser Tyr Trp Ser Ser Asp Pro Gly Pro Trp Gly Pro
            370                 375                 380

Tyr Leu Pro Asp Gly Thr Gln Thr Leu Leu Val Asp Thr Leu Asn Lys
385                 390                 395                 400

Pro Tyr Pro Arg Ala Val Ala Gly Thr Pro Thr Glu Trp Ser Ser Thr
            405                 410                 415

Ser Asp Arg Leu Gln Leu Thr Ile Glu Pro Asp Ala Ala Ile Thr Ala
            420                 425                 430

Pro Thr Glu Ile Tyr Leu Pro Glu Ala Gly Phe Pro Gly Asp Val His
            435                 440                 445

Val Glu Gly Ala Asp Val Val Gly Trp Asp Arg Gln Ser Arg Leu Leu
            450                 455                 460

Thr Val Arg Thr Pro Ala Asp Ser Gly Asn Val Thr Val Thr Val Thr
465                 470                 475                 480

Pro Ala Ala
```

<210> SEQ ID NO 50
<211> LENGTH: 10
<212> TYPE: PRT
<213> ORGANISM: Artificial Sequence
<220> FEATURE:
<223> OTHER INFORMATION: Description of Artificial
      Sequence:endoglycoceramidase (EGC, EGCase) identifying motif A
      located N-terminal to the acid-base sequence region
<220> FEATURE:

```
<221> NAME/KEY: MOD_RES
<222> LOCATION: (1)..(1)
<223> OTHER INFORMATION: Xaa can be any one of Metholionine, Valine or
      Leucine.
<220> FEATURE:
<221> NAME/KEY: MOD_RES
<222> LOCATION: (4)..(4)
<223> OTHER INFORMATION: Xaa can be any one of Methionine,
      Phenylalanine, or Alanine.
<220> FEATURE:
<221> NAME/KEY: MOD_RES
<222> LOCATION: (8)..(8)
<223> OTHER INFORMATION: Xaa can be any one of Metholionine, Valine or
      Leucine.
<220> FEATURE:
<221> NAME/KEY: MOD_RES
<222> LOCATION: (9)..(9)
<223> OTHER INFORMATION: Xaa = any amino acid
<220> FEATURE:
<221> NAME/KEY: MOD_RES
<222> LOCATION: (10)..(10)
<223> OTHER INFORMATION: Xaa and be Serine or Asparagine

<400> SEQUENCE: 50

Xaa Leu Asp Xaa His Gln Asp Xaa Xaa Xaa
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial
      Sequence:endoglycoceramidase (EGC, EGCase) identifying conserved
      motif B, including the acid-base sequence region, conserved
      Asn-Glu-Pro subsequence with acid-base Glu residue
<220> FEATURE:
<221> NAME/KEY: MOD_RES
<222> LOCATION: (2)..(2)
<223> OTHER INFORMATION: Xaa = any amino acid
<220> FEATURE:
<221> NAME/KEY: MOD_RES
<222> LOCATION: (3)..(3)
<223> OTHER INFORMATION: Xaa can be Alanine or Glycine
<220> FEATURE:
<221> NAME/KEY: MOD_RES
<222> LOCATION: (4)..(4)
<223> OTHER INFORMATION: Xaa can be Tyrosine or Phenylalanine
<220> FEATURE:
<221> NAME/KEY: MOD_RES
<222> LOCATION: (5)..(5)
<223> OTHER INFORMATION: Xaa can be any of Aspartic acid or Glutamic
      acid.
<220> FEATURE:
<221> NAME/KEY: MOD_RES
<222> LOCATION: (6)..(6)
<223> OTHER INFORMATION: Xaa can any of Leucine or Ileucine
<220> FEATURE:
<221> NAME/KEY: MOD_RES
<222> LOCATION: (7)..(7)
<223> OTHER INFORMATION: Xaa = any amino acid
<220> FEATURE:
<221> NAME/KEY: MOD_RES
<222> LOCATION: (11)..(12)
<223> OTHER INFORMATION: Xaa = any amino acid

<400> SEQUENCE: 51

Val Xaa Xaa Xaa Xaa Xaa Xaa Asn Glu Pro Xaa Xaa Gly
1               5                   10

<210> SEQ ID NO 52
<211> LENGTH: 6
<212> TYPE: PRT
<213> ORGANISM: Artificial Sequence
<220> FEATURE:
```

```
<223> OTHER INFORMATION: Description of Artificial
      Sequence:endoglycoceramidase (EGC, EGCase) identifying motif C
      located C-terminal to the acid-base sequence region
<220> FEATURE:
<221> NAME/KEY: MOD_RES
<222> LOCATION: (4)..(4)
<223> OTHER INFORMATION: Xaa can be Glutamine, Serine or Threonine.

<400> SEQUENCE: 52

Ala Ile Arg Xaa Val Asp
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial
      Sequence:endoglycoceramidase (EGC, EGCase) identifying conserved
      motif D, including the nucleophilic Glu residue region
<220> FEATURE:
<221> NAME/KEY: MOD_RES
<222> LOCATION: (1)..(1)
<223> OTHER INFORMATION: Xaa can be any one Ileucine, Methionine,
      Leucine, Phenylalanine or Valine.
<220> FEATURE:
<221> NAME/KEY: MOD_RES
<222> LOCATION: (2)..(2)
<223> OTHER INFORMATION: Xaa can be Leucine, Methionie, Ileucine or
      Valine.
<220> FEATURE:
<221> NAME/KEY: MOD_RES
<222> LOCATION: (3)..(3)
<223> OTHER INFORMATION: Xaa can be any of Glycine, Serine or Threonine.
<220> FEATURE:
<221> NAME/KEY: MOD_RES
<222> LOCATION: (5)..(5)
<223> OTHER INFORMATION: Xaa can be any of Phenylalanine, Threonine,
      Methionine or Leucine.
<220> FEATURE:
<221> NAME/KEY: MOD_RES
<222> LOCATION: (6)..(6)
<223> OTHER INFORMATION: Xaa can be Glycine, Leucine or Phenylalanine

<400> SEQUENCE: 53

Xaa Xaa Xaa Glu Xaa Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial
      Sequence:endoglycoceramidase (EGC, EGCase) identifying motif E,
      including nucleophilic carboxylate Glu/Asp residue
<220> FEATURE:
<221> NAME/KEY: MOD_RES
<222> LOCATION: (1)..(1)
<223> OTHER INFORMATION: Xaa can be any one of  Met,hionine, Leucine,
      Phenylalanine or Valine.
<220> FEATURE:
<221> NAME/KEY: MOD_RES
<222> LOCATION: (2)..(2)
<223> OTHER INFORMATION: Xaa can be any one of Leucine, Methiionine,
      Ileucine or Valine.
<220> FEATURE:
<221> NAME/KEY: MOD_RES
<222> LOCATION: (3)..(3)
<223> OTHER INFORMATION: Xaa can be any one of Glycine, Serine or
      Threonine.
<220> FEATURE:
<221> NAME/KEY: MOD_RES
<222> LOCATION: (4)..(4)
<223> OTHER INFORMATION: Xaa any one of Glutamic acid or Aspartic acid.
```

```
<220> FEATURE:
<221> NAME/KEY: MOD_RES
<222> LOCATION: (5)..(5)
<223> OTHER INFORMATION: Xaa can be any one of Phenylalanine, Threonine,
      Metthionine or Leucine.
<220> FEATURE:
<221> NAME/KEY: MOD_RES
<222> LOCATION: (6)..(6)
<223> OTHER INFORMATION: Xaa any one of Glycine, Leucine or
      Phenylalanine

<400> SEQUENCE: 54

Xaa Xaa Xaa Xaa Xaa Xaa
1               5

<210> SEQ ID NO 55
<211> LENGTH: 490
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Rhodococcus sp.
      strain M-777, GenBank Accession #AAB67050
<220> FEATURE:
<221> NAME/KEY: MOD_RES
<222> LOCATION: (351)..(351)
<223> OTHER INFORMATION: Xaa can be any one of Glycine, Alanine,
      Serine, Aspartic acid, Asparagine, Glutamine, Cysteine, Threonine,
      Ileucine,  Leucine or Valine.l

<400> SEQUENCE: 55

Met Arg Arg Thr Arg Leu Val Ser Leu Ile Val Thr Gly Ser Leu Val
1               5                   10                  15

Phe Gly Gly Gly Val Ala Ala Ala Gln Ser Ser Leu Ala Ala Ser Gly
            20                  25                  30

Ser Gly Ser Gly Ser Gly Thr Ala Leu Thr Pro Ser Tyr Leu Lys Asp
        35                  40                  45

Asp Asp Gly Arg Ser Leu Ile Leu Arg Gly Phe Asn Thr Ala Ser Ser
    50                  55                  60

Ala Lys Ser Ala Pro Asp Gly Met Pro Gln Phe Thr Glu Ala Asp Leu
65                  70                  75                  80

Ala Arg Glu Tyr Ala Asp Met Gly Thr Asn Phe Val Arg Phe Leu Ile
                85                  90                  95

Ser Trp Arg Ser Val Glu Pro Ala Pro Gly Val Tyr Asp Gln Gln Tyr
            100                 105                 110

Leu Asp Arg Val Glu Asp Arg Val Gly Trp Tyr Ala Glu Arg Gly Tyr
        115                 120                 125

Lys Val Met Leu Asp Met His Gln Asp Val Tyr Ser Gly Ala Ile Thr
    130                 135                 140

Pro Glu Gly Asn Ser Gly Asn Gly Ala Gly Ala Ile Gly Asn Gly Ala
145                 150                 155                 160

Pro Ala Trp Ala Thr Tyr Met Asp Gly Leu Pro Val Glu Pro Gln Pro
                165                 170                 175

Arg Trp Glu Leu Tyr Tyr Ile Gln Pro Gly Val Met Arg Ala Phe Asp
            180                 185                 190

Asn Phe Trp Asn Thr Thr Gly Lys His Pro Glu Leu Val Glu His Tyr
        195                 200                 205

Ala Lys Ala Trp Arg Ala Val Ala Asp Arg Phe Ala Asp Asn Asp Ala
    210                 215                 220

Val Val Ala Tyr Asp Leu Met Asn Glu Pro Phe Gly Gly Ser Leu Gln
225                 230                 235                 240
```

```
Gly Pro Ala Phe Glu Ala Gly Pro Leu Ala Met Tyr Gln Arg Thr
                245                 250                 255

Thr Asp Ala Ile Arg Gln Val Asp Gln Asp Thr Trp Val Cys Val Ala
        260                 265                 270

Pro Gln Ala Ile Gly Val Asn Gln Gly Leu Pro Ser Gly Leu Thr Lys
    275                 280                 285

Ile Asp Asp Pro Arg Ala Gly Gln Gln Arg Ile Ala Tyr Cys Pro His
290                 295                 300

Leu Tyr Pro Leu Pro Leu Asp Ile Gly Asp Gly His Glu Gly Leu Ala
305                 310                 315                 320

Arg Thr Leu Thr Asp Val Thr Ile Asp Ala Trp Arg Ala Asn Thr Ala
                325                 330                 335

His Thr Ala Arg Val Leu Gly Asp Val Pro Ile Ile Leu Gly Xaa Phe
            340                 345                 350

Gly Leu Asp Thr Thr Leu Pro Gly Ala Arg Asp Tyr Ile Glu Arg Val
        355                 360                 365

Tyr Gly Thr Ala Arg Glu Met Gly Ala Gly Val Ser Tyr Trp Ser Ser
    370                 375                 380

Asp Pro Gly Pro Trp Gly Pro Tyr Leu Pro Asp Gly Thr Gln Thr Leu
385                 390                 395                 400

Leu Val Asp Thr Leu Asn Lys Pro Tyr Pro Arg Ala Val Ala Gly Thr
                405                 410                 415

Pro Thr Glu Trp Ser Ser Thr Ser Asp Arg Leu Gln Leu Thr Ile Glu
            420                 425                 430

Pro Asp Ala Ala Ile Thr Ala Pro Thr Glu Ile Tyr Leu Pro Glu Ala
        435                 440                 445

Gly Phe Pro Gly Asp Val His Val Glu Gly Ala Asp Val Val Gly Trp
    450                 455                 460

Asp Arg Gln Ser Arg Leu Leu Thr Val Arg Thr Pro Ala Asp Ser Gly
465                 470                 475                 480

Asn Val Thr Val Thr Val Thr Pro Ala Ala
                485                 490

<210> SEQ ID NO 56
<211> LENGTH: 482
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Rhodococcus sp.
      strain C9, GenBank Accession #BAB17317
<220> FEATURE:
<221> NAME/KEY: MOD_RES
<222> LOCATION: (343)..(343)
<223> OTHER INFORMATION: Xaa can be any one of Glycine, Alanine,
      Serine, Aspartic acid, Asparagine, Glutamine, Cysteine, Threonine,
      Ileucine, Leucine or Valine.

<400> SEQUENCE: 56

Met Arg Arg Thr Arg Ile Ala Ser Leu Ala Val Ala Gly Ser Leu Val
1               5                   10                  15

Leu Gly Ala Gly Val Ala Thr Ala Gln Ser Ser Leu Pro Ala Thr Gly
            20                  25                  30

Ser Asp Ser Ser Glu Trp Ser Ala Ser Ala Tyr Leu Thr Asp Asp Ala
        35                  40                  45

Gly Arg Ser Leu Ile Leu Arg Gly Phe Asn Thr Ala Ser Ser Ala Lys
    50                  55                  60

Ser Thr Pro Asp Gly Met Pro Ile Phe Thr Glu Ser Asp Leu Asp Arg
```

-continued

```
                65                  70                  75                  80
          Glu His Ala Asp Met Gly Thr Asn Phe Val Arg Phe Leu Ile Ser Trp
                            85                  90                  95
          Arg Ser Val Glu Pro Glu Pro Gly Gln Tyr Asp Gln Ala Tyr Leu Asp
                           100                 105                 110
          Arg Val Glu Gln Arg Val Gly Trp Tyr Ala Glu Arg Gly Tyr Lys Val
                           115                 120                 125
          Met Leu Asp Met His Gln Asp Leu Tyr Ser Gly Ala Ile Thr Pro Asp
                           130                 135                 140
          Gly Lys Thr Gly Asn Gly Ala Pro Ala Trp Ala Thr Tyr Met Asp Gly
          145                 150                 155                 160
          Leu Pro Val Asn Glu Arg Asp Ser Trp Glu Leu Tyr Tyr Ile Glu Pro
                           165                 170                 175
          Gly Val Ile Arg Ala Phe Asp Asn Phe Trp Asn Thr Thr Gly Lys His
                           180                 185                 190
          Pro Glu Leu Val Asp His Tyr Val Asn Ala Trp Lys Ala Val Ala Asp
                           195                 200                 205
          Arg Phe Ala Asp Asn Glu Thr Val Ala Tyr Asp Leu Met Asn Glu
                           210                 215                 220
          Pro Trp Gly Gly Ser Leu Gln Gly Pro Ala Phe Glu Ala Gly Pro Leu
          225                 230                 235                 240
          Thr Ser Met Tyr Gln Arg Thr Thr Asp Ala Ile Arg Gln Val Asp Gln
                           245                 250                 255
          Asp Ser Trp Val Cys Val Ala Pro Gln Ala Val Gly Val Asn Gln Gly
                           260                 265                 270
          Ile Pro Ser Ala Leu Gly Thr Ile Ala Asp Pro Arg Gln Gly Ala Arg
                           275                 280                 285
          Arg Ile Ala Tyr Cys Pro His Leu Tyr Pro Leu Pro Leu Asp Leu Gly
                           290                 295                 300
          Asp Gly Tyr Ser Gly Phe Ser Lys Thr Leu Thr Asp Ala Thr Ile Glu
          305                 310                 315                 320
          Thr Trp Arg Thr Ser Ile Glu His Val Ala Asp Thr Val Leu Glu Gly
                           325                 330                 335
          Ala Pro Val Ile Leu Gly Xaa Phe Gly Leu Asp Thr Thr Leu Pro Gly
                           340                 345                 350
          Ala Gln Asp Tyr Leu Asp Arg Val Tyr Thr Val Ala Arg Asp Met Gly
                           355                 360                 365
          Ala Gly Val Ser Tyr Trp Ser Ser Asp Arg Gly Pro Trp Gly Pro Tyr
                           370                 375                 380
          Leu Glu Asp Gly Thr Gln Thr Ile Leu Val Asp Thr Val Asn Lys Pro
          385                 390                 395                 400
          Tyr Pro Arg Ala Val Ala Gly Met Pro Val Arg Trp Ser Ser Thr Ser
                           405                 410                 415
          Asp Arg Leu Asp Leu Thr Tyr Arg Asn Asp Pro Ala Val Thr Ala Pro
                           420                 425                 430
          Thr Glu Ile Tyr Leu Pro Ala Ala Gly Phe Pro Gly Asp Ile Ala Val
                           435                 440                 445
          Gln Gly Ala Asp Val Val Gly Trp Asp Ser Gln Ser Arg Leu Leu Thr
                           450                 455                 460
          Val Arg Ser Ala Pro Asp Ala Gly Glu Val Thr Val Thr Val Thr Pro
          465                 470                 475                 480
          Ala Ala
```

-continued

<210> SEQ ID NO 57
<211> LENGTH: 500
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Propionibacterium
      acnes KPA171202, GenBank Accession #YP_056771
<220> FEATURE:
<221> NAME/KEY: MOD_RES
<222> LOCATION: (341)..(341)
<223> OTHER INFORMATION: Xaa can be any one of Glycine, Alanine,
      Serine, Aspartic acid, Asparagine Glutamine, Cysteine, Threonine,
      Ileucine, Leucine or Valine.

<400> SEQUENCE: 57

Met Arg Arg Lys Ser Ala Leu Gly Phe Val Ala Leu Ser Leu Phe Ala
1               5                   10                  15

Thr Gly Met Gly Val Ala Ala Ala Thr Pro Ala Thr Ala Ser Pro Ala
            20                  25                  30

Asp Thr Ala Ala Pro Val His Val Asp Ala Ser Arg Trp Thr Thr Gln
        35                  40                  45

Gly Arg Trp Val Thr Asp Thr Gln His Arg Val Val Ile Thr Gln Gly
    50                  55                  60

Ile Asn Glu Val Ala Lys Ser Ala Pro Tyr Ala Pro Asp Ala Val Gly
65                  70                  75                  80

Phe Gly Glu Asp Asp Ala Ala Phe Leu Glu Ala Gln Gly Phe Thr Ser
                85                  90                  95

Val Arg Leu Gly Val Leu Trp Ala Gly Val Glu Pro Arg Pro Gly Val
            100                 105                 110

Tyr Asp Asp Ala Tyr Leu Ala Arg Val Glu Arg Thr Val Arg Ile Leu
        115                 120                 125

Asn Ala His Gly Ile Ala Ser Val Leu Asp Phe His Gln Asp Met Val
130                 135                 140

Asn Glu Lys Tyr Gln Gly Glu Gly Trp Pro Ala Trp Ala Ala Leu Asp
145                 150                 155                 160

His Gly Met Pro Asn Ile Val Lys Thr Gly Phe Pro Gly Asn Tyr Phe
                165                 170                 175

Leu Asn Glu Ala Val Lys Tyr Ser Phe Asp Ser Phe Tyr Asp Asn Thr
            180                 185                 190

Lys Ala Ser Asp Gly Ile Gly Val Ala Asp His Tyr Ala Ser Ala Trp
        195                 200                 205

Arg His Val Ala Glu His Phe Arg Asn Val Pro Gly Val Gln Gly Tyr
    210                 215                 220

Asp Leu Phe Asn Glu Pro Phe Pro Gly His Arg Tyr Thr Arg Cys Leu
225                 230                 235                 240

Thr Gln Leu Gly Cys Arg Ala Ala Asp Ala Arg Leu Ser Ala Val Gln
                245                 250                 255

Gln Lys Thr Val Asp Ala Ile Arg Ser Val Asp Lys Ala Thr Thr Val
            260                 265                 270

Trp Tyr Glu Pro Met Gln Phe Asn Ile Gly Val Gly Thr Asn Val
        275                 280                 285

Arg Leu Thr Gly Ser Asn Leu Gly Leu Ser Phe His Asp Tyr Cys Thr
    290                 295                 300

Ser Gln Ala Thr Leu His Ser Tyr Val Gly Cys Thr Ala Pro Asp Asn
305                 310                 315                 320

Arg Val Phe Thr Asn Ala Glu Lys His Ser Arg Gln Thr Gly Ser Gly

-continued

```
                        325                 330                 335
Leu Met Leu Thr Xaa Phe Gly Ala Ile Thr Thr Pro Ala Val Ile Thr
            340                 345                 350

Ser Gln Met Asp Leu Ala Ala Arg Asn Arg Val Gly Val Gln Trp Trp
            355                 360                 365

Ala Tyr Thr Ala Gly Asp Pro Thr Thr Ala Gly Pro Gly Thr Glu Gln
            370                 375                 380

Ala Leu Val Asp Asp Pro Ala Arg Pro Pro Gln Gly Thr Asn Val Glu
385                 390                 395                 400

Ser Ala Lys Leu Thr Leu Ile Ala Val Pro His Pro Asp Arg Val Ala
                405                 410                 415

Gly Thr Pro Ser Ala Tyr His His Asp Arg Ser Arg Val Phe Thr
                420                 425                 430

Met Thr Trp Thr Ala Gln Arg Pro Asp Gly Ser Arg Ala Glu Glu Ser
                435                 440                 445

Asp Glu Thr Thr Val Val Val Pro Ala Ile Ser Ala Pro His Gly Tyr
                450                 455                 460

Asp Val Gln Ala Ser Gly Ala His Val Thr Ser His Pro Gly Asp Arg
465                 470                 475                 480

Val Ala Arg Leu His Leu Asn Gln Gly Ser Ala Thr Ala Lys Val Thr
                485                 490                 495

Ile Thr Leu Arg
            500

<210> SEQ ID NO 58
<211> LENGTH: 524
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Propionibacterium
      acnes KPA171202, GenBank Accession #YP_055358
<220> FEATURE:
<221> NAME/KEY: MOD_RES
<222> LOCATION: (360)..(360)
<223> OTHER INFORMATION: Xaa can be any one of Glycine, Alanine, Serine,
      Asparagine, Glutamine, Cysteine, Threonine, Isoleucine, or Valine

<400> SEQUENCE: 58

Met Tyr His His Ser Trp His Ser Pro Asp Ala Arg Arg Gly Val
1               5                   10                  15

Thr Arg Trp Ala Thr Thr Phe Ile Ala Ala Leu Thr Ala Ala Cys Met
            20                  25                  30

Ala Gln Met Pro Ala Gln Ala Ser Pro His Thr Ser Asp Ala Ala Pro
            35                  40                  45

His Ile Ala Thr Ser Lys Thr Ile Thr Asp Ala Gly Pro Ile Gly Gln
    50                  55                  60

Ser Gly Arg Trp Tyr Thr Asp Gly Gln Gly Arg Ala Ile Leu Thr Ala
65              70                  75                  80

Gly Val Asn Met Val Ser Lys Arg His Pro Tyr Ser Pro Glu Ala Asp
                85                  90                  95

Gly Phe Asp Asp Ala Asp Ala Trp Leu Gln Lys Asn Gly Phe Asp
            100                 105                 110

Ser Val Arg Leu Gly Val Ile Trp Lys Gly Val Glu Pro Lys Pro Gly
        115                 120                 125

Glu Tyr Asp Asp Ala Tyr Leu Ala Ser Ile Thr Arg Thr Val Arg Thr
    130                 135                 140
```

```
Leu Arg Ala His Gly Ile Met Thr Leu Leu Asp Ala His Gln Asp Met
145                 150                 155                 160

Tyr Asn Glu Lys Phe Glu Gly Glu Gly Ala Pro Asp Trp Ala Val Leu
            165                 170                 175

Asp Lys Gly Ala Pro Asn Leu Leu Lys Val Gly Phe Pro Ala Asn Gln
        180                 185                 190

Val Phe Asn Leu Gly Leu Ile Lys Ala Tyr Asp Ser Phe Leu Asp Asn
    195                 200                 205

Ala Lys Gly Pro Gly Gly Val Gly Leu Gln Asp Arg Tyr Ala Ala Met
210                 215                 220

Trp Lys His Val Ala Gln Val Gly Gln Glu Pro Gly Val Met Gly
225                 230                 235                 240

Tyr Asp Ile Ile Asn Glu Pro Trp Pro Gly His His Tyr Pro Ile Cys
                245                 250                 255

Tyr Val Ala Phe Gly Trp Cys Gly Arg Ala Met Val Ser Leu Asp Thr
            260                 265                 270

Leu Tyr Glu Lys Val Gly Arg Ala Ile Thr Ser Val Asp Pro Asp Gly
        275                 280                 285

Ile Val Thr Tyr Glu Pro Tyr Ser Thr Trp Asn Met Gly Leu Asp Ser
290                 295                 300

Arg Pro Ala Arg Pro Ser Ser Pro Lys Ala Ala Ile Ser Trp His Val
305                 310                 315                 320

Tyr Cys Pro Met Asn Ala Ile Phe Gly Ser Tyr Val Gly Cys Asn Leu
                325                 330                 335

Pro Asp Thr Arg Thr Phe His Asn Ala Asp Gln Ala Ala Gln Phe Asn
            340                 345                 350

Asn Ser Ala Ser Leu Leu Ser Xaa Phe Gly Ala Thr Lys Asp Pro Gly
        355                 360                 365

Thr Leu Met Gly Val Thr Ser Lys Ala Arg Ala His Leu Val Gly Trp
370                 375                 380

Leu Tyr Trp Thr Tyr Asn Gly Asn Ser Asp Pro Thr Thr Gln Asn Ala
385                 390                 395                 400

Ala Asp Glu Glu Leu Val Arg His Ile Asn Arg Pro Gly Pro Val Thr
                405                 410                 415

Asp Glu Gln Val Asp His Thr Lys Leu Ala Ile Leu Ala Val Pro His
            420                 425                 430

Leu Arg Ala Ala Ala Gly Thr Pro Thr Ser Thr Thr Trp Asp Gln Ser
        435                 440                 445

Thr Arg Thr Tyr Gln Ala Thr Trp Thr Ala Lys Arg Val Ala Gly Asp
450                 455                 460

Gly Asp Phe Ala Ala Gly Ser Val Ser Glu Ile Ala Val Pro Ala Ile
465                 470                 475                 480

His Tyr Pro Asn Gly Tyr Lys Val Glu Val Lys Gly Ala Lys Val Ile
                485                 490                 495

Ser Lys Ala Gly Asp Thr Arg Leu Gln Val Ser Ser Thr Gly Glu Gly
            500                 505                 510

Pro Val Ser Val Thr Ile Thr Pro Ala Gly Gln Ala
        515                 520

<210> SEQ ID NO 59
<211> LENGTH: 503
<212> TYPE: PRT
<213> ORGANISM: Artificial Sequence
<220> FEATURE:
<223> OTHER INFORMATION: Description of Artificial Sequence:mutant
```

-continued endoglycoceramidase (EGC, EGCase) derived from Cyanea nozakii,
GenBank Accession #BAB16369
<220> FEATURE:
<221> NAME/KEY: MOD_RES
<222> LOCATION: (361)..(361)
<223> OTHER INFORMATION: Xaa can be any one of Glycine, Alanine, Serine,
Aspartic acid, Asparagine, Glutamine, Cysteine, Threonine,
Ileucine, Leucine or Valine.

<400> SEQUENCE: 59

```
Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

Ser Val Asn Pro Glu Thr Gln Gln Leu Val Asp Ser Leu Gly Arg Glu
        35                  40                  45

Arg Phe Phe His Gly Thr Asn Val Val Val Lys His Lys Pro Tyr His
    50                  55                  60

Pro Ser Val Glu Gly Tyr Asp Asn Thr Ser Phe Ser Glu Val Asp Met
65                  70                  75                  80

Lys Ile Leu Gln Asp Leu Gly Leu Asn Thr Ile Arg Leu Gly Met Met
                85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Ala Lys Tyr Gly Ile Tyr
        115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Leu Gln Thr Gly Tyr
                165                 170                 175

Pro Tyr Pro Lys Asp Cys Ala Lys His Ala Trp Gly Asp Tyr Tyr Phe
            180                 185                 190

Thr Glu Ala Ala Ala Ala Phe Gln Asn Phe Tyr Asn Asn Thr Asp
        195                 200                 205

Gly Leu Leu Asp Ala Trp Ala Asp Phe Trp Lys Lys Thr Ala Gln Gly
    210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
                245                 250                 255

Ala Asp Glu Arg Asn Leu Ala Pro Ala Tyr Asp Val Ile His Lys Ala
            260                 265                 270

Ile Arg Thr Val Asp Glu Gln His Ser Ile Phe Glu Gly Val Thr
        275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Leu Thr Val Gly Asp Thr
            340                 345                 350

Ala Lys Asp Met Ser Asp Met Leu Xaa Leu Phe Asp Ile Cys Asp Gln
        355                 360                 365
```

```
His Lys Gln Ser Trp Met Gly Trp Leu Tyr Lys Ser Tyr Gly Cys Tyr
        370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415

Ala Val Ala Gly His Thr Ile Gly Tyr Lys Phe Asp Arg Ile Thr Lys
            420                 425                 430

Lys Phe Asp Leu Ser Phe Val Val Thr Ala Asp Cys Arg Ser Thr Glu
                435                 440                 445

Ser Ile Val Tyr Phe Asn Lys Asp Leu His Tyr Ser Asn Gly Tyr Asp
            450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
                485                 490                 495

Thr Phe Ser Leu Val Ala Lys
            500
```

<210> SEQ ID NO 60
<211> LENGTH: 503
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Cyanea nozakii,
      GenBank Accession #BAB16370
<220> FEATURE:
<221> NAME/KEY: MOD_RES
<222> LOCATION: (361)..(361)
<223> OTHER INFORMATION: Xaa can be any one of Glycine, Alanine,
      Serine, Aspartic acid, Asparagine, Glutamine, Cysteine,
      Threonine, Ileucine, Leucine or Valine.

<400> SEQUENCE: 60

```
Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

Ser Val Asn Pro Glu Thr Gln Gln Leu Val Asp Ser Leu Gly Arg Glu
        35                  40                  45

Arg Phe Phe His Gly Thr Asn Val Val Lys His Lys Pro Tyr His
    50                  55                  60

Pro Ser Val Glu Gly Tyr Asp Asn Thr Ser Phe Ser Glu Val Asp Met
65                  70                  75                  80

Lys Ile Leu Gln Asp Leu Gly Leu Asn Thr Ile Arg Leu Gly Met Met
                85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Ala Lys Tyr Gly Ile Tyr
        115                 120                 125

Thr Leu Leu Asp Met His Gln Asp Val Met Ser Ala Lys Phe Cys Val
130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Pro Gln Thr Gly Tyr
                165                 170                 175
```

```
Pro Tyr Pro Lys Asp Cys Ala Lys His Ala Trp Gly Asp Tyr Tyr Phe
            180                 185                 190

Thr Glu Ala Ala Ala Ala Phe Gln Asn Phe Tyr Asn Asn Thr Asp
        195                 200                 205

Gly Leu Leu Asp Ala Trp Ala Asp Phe Trp Lys Lys Thr Ala Gln Gly
    210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
                245                 250                 255

Ala Asp Glu Arg Asn Leu Ala Pro Ala Tyr Asp Val Ile His Lys Ala
            260                 265                 270

Ile Arg Thr Val Asp Glu Gln His Ser Ile Phe Phe Glu Gly Val Thr
        275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Leu Thr Val Gly Asp Thr
            340                 345                 350

Ala Lys Asp Met Ser Asp Met Leu Xaa Leu Phe Asp Ile Cys Asp Gln
        355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415

Ala Val Ala Gly His Thr Ile Gly Tyr Lys Phe Asp Arg Ile Thr Lys
            420                 425                 430

Lys Phe Asp Leu Ser Phe Val Val Thr Ala Asp Cys Arg Ser Thr Glu
        435                 440                 445

Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
                485                 490                 495

Thr Phe Ser Leu Val Ala Lys
            500
```

<210> SEQ ID NO 61
<211> LENGTH: 517
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Hydra
      magnipapillata, GenBank Accession #BAD20464
<220> FEATURE:
<221> NAME/KEY: MOD_RES
<222> LOCATION: (349)..(349)
<223> OTHER INFORMATION: Xaa can be any one of Glycine, Alanine,
      Serine, Aspartic acid, Asparagine, Glutamine, Cysteine,
      Threonine, Ileucine, Leucine or Valine.

<400> SEQUENCE: 61

Met Ile Ser Val Ala Leu Ile Ile Leu Phe Leu Ala Lys Val Ile Ser
1               5                   10                  15

Gly Lys Ser Asp Asp Phe Ile Ser Val Asn Pro Glu Thr Asn Met Leu
            20                  25                  30

Ile Asp Gly Tyr Gly Arg Glu Arg Phe Phe His Gly Thr Asn Val Val
        35                  40                  45

Val Lys His Phe Pro Phe His Pro Glu Thr Thr Gly Phe Asn Lys Asp
50                  55                  60

Thr Phe Ser Glu Asp Asp Met Lys Ile Leu Gln Lys Phe Gly Leu Asn
65                  70                  75                  80

Ser Ile Arg Leu Gly Met Met Leu Pro Gly Tyr Val Pro Lys Arg Glu
                85                  90                  95

Glu Tyr Asn Glu Thr Tyr Ile Lys Val Ile Gln Ser Ile Val Thr Thr
            100                 105                 110

Ala Ala Lys Tyr Gly Ile Tyr Thr Leu Leu Asp Met His Gln Asp Val
        115                 120                 125

Phe Ser Pro Lys Phe Cys Val Glu Gly Met Pro Asp Trp Ile Val Asn
130                 135                 140

Thr Gln Gly Ala Lys Asp Phe Pro Met Pro Leu His Lys Pro Phe Asn
145                 150                 155                 160

Leu Asp Pro Lys Thr Gly Tyr Pro Tyr Pro Glu Asp Cys Ala Lys Phe
                165                 170                 175

Ser Trp Ala Asp Tyr Tyr Phe Thr Glu Ala Ala Gly Gln Ala Phe Gln
            180                 185                 190

Asn Leu Tyr Asp Asn Val Asp Gly Leu Arg Asp Glu Trp Ala Gln Phe
        195                 200                 205

Trp Lys Lys Thr Ala Asp Val Phe Lys Glu Pro Ser Val Ile Gly
210                 215                 220

Tyr Glu Leu Ile Asn Glu Pro Phe Cys Gly Asn Val Phe Lys His Pro
225                 230                 235                 240

Thr Leu Leu Ile Pro Gly Val Ala Asp Tyr Leu Asn Leu Gln Pro Thr
                245                 250                 255

Tyr Asp Ala Leu Gln Lys Ala Ile Arg Gln Val Asp Glu Glu His Asn
            260                 265                 270

Ile Phe Phe Glu Gly Val Thr Trp Asp Phe Glu Val Gly Phe Thr
        275                 280                 285

Glu Val Pro Gly Gly Lys Gln Tyr Gln Asn Arg Ser Val Leu Ser Tyr
290                 295                 300

His Tyr Tyr Glu Pro Pro Asp Phe Ser Lys Lys Leu Asn Phe Glu Ala
305                 310                 315                 320

Arg Leu Leu Asp Leu Lys Arg Leu Lys Cys Gly Gly Phe Leu Thr Glu
                325                 330                 335

Met Phe Thr Val Gly Thr Asp Phe Asn Ser Met Phe Xaa Met Phe Asp
            340                 345                 350

Leu Cys Asp Lys Phe Lys Gln Ser Trp His Gly Trp Met Tyr Lys Ser
        355                 360                 365

Tyr Gly Cys Ile Glu Gln Asn Leu Gly Cys Leu Asn Met Ser Ser Pro
        370                 375                 380

Gly Lys Glu Ser Ile Gln Ile Ala Asn Thr Ser Arg Thr Tyr Pro Gln
385                 390                 395                 400

Ala Val Ala Gly Arg Thr Gln Ser Tyr Ala Phe Asp Ile Lys Thr Lys
                405                 410                 415

```
Val Phe Thr Leu Val Tyr Glu Thr Val Gly Ser Cys Lys Ser Gly Arg
            420                 425                 430

Thr Ile Val Tyr Phe Asn Lys Asn Leu His Tyr Pro Asn Gly Tyr Arg
            435                 440                 445

Tyr Glu Ile Asn Pro Asn Phe Lys Val Thr Pro Ser Glu Asn Glu Tyr
450                 455                 460

Phe Leu Tyr Leu Asp Glu Val Asn Lys Val Pro Asn Thr Val Thr
465                 470                 475                 480

Phe Lys Leu Phe Pro Leu Ser Phe Thr Asp Ser Glu Asp Ile His Pro
            485                 490                 495

Val Thr Val Met Gly Asp Lys His Leu Ser Glu Asn His Asn Glu Asn
            500                 505                 510

Glu Lys Lys Lys Lys
            515

<210> SEQ ID NO 62
<211> LENGTH: 507
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Schistosoma
      japonicum, GenBank Accession #AAW25069
<220> FEATURE:
<221> NAME/KEY: MOD_RES
<222> LOCATION: (351)..(351)
<223> OTHER INFORMATION: Xaa can be any one of  Glycine, Alanine,
      Serine, Aspartic acid, Asparagine, Glutamine, Cysteine,
      Threonine, Ileucine, Leucine or Valine.

<400> SEQUENCE: 62

Met Trp Ser Ile Phe Ile Leu Thr Phe Leu Ile Trp Thr Ser Val Gln
1               5                   10                  15

Thr Lys Gln Ile Pro Leu Ser Lys Ile His Leu Asn Ser Asp Gly Leu
            20                  25                  30

Phe Thr Asp Ser Arg Gly Phe Ile Lys Leu Phe Arg Gly Phe Asn Asn
            35                  40                  45

Val His Lys His Phe Pro Trp Tyr Asn Val Asn Ser Thr Asn Ile Thr
50                  55                  60

Gln Leu Glu Met Phe Lys Asn Trp Gly Leu Asn Val Val Arg Leu Gly
65                  70                  75                  80

Val Met Trp Ser Gly Val Lys Pro Thr Ile Ser Ile Val Asn Thr Thr
                85                  90                  95

Tyr Leu Asp Val Ile Glu Asn Val Ile Asp Leu Tyr Ala Asp Tyr Gly
            100                 105                 110

Ile Tyr Val Ile Leu Asp Met His Gln Asp Val Leu Ser Ser Leu Tyr
            115                 120                 125

Gly Leu Tyr Asp Gly Ile Pro Leu Trp Leu Ile Glu Lys Phe Lys Arg
130                 135                 140

Pro Pro His His Leu Gln Tyr Pro Trp Pro Tyr Lys Lys Lys Pro Asp
145                 150                 155                 160

Phe Trp Val Met Ser Tyr Leu Thr Tyr Glu Cys Ala Asn Gly Ala Gln
            165                 170                 175

Gln Leu Tyr Asn Asn Val Ser Gly Ala Trp Asn His Trp Gly Glu Phe
            180                 185                 190

Trp Glu Ile Val Ala Arg Arg Phe Gly Gly Lys Ser Asn Val Leu Gly
            195                 200                 205
```

```
Tyr Glu Leu Ile Asn Glu Pro Pro Gly Asn Phe Tyr Thr Asn Pro
    210                 215                 220

Leu Arg Gly Leu Pro Gly Tyr Ala Gly Arg Tyr Asn Leu Gln Pro Val
225                 230                 235                 240

Tyr Asp Tyr Leu Val Lys Arg Ile Arg Lys Tyr Asp Asn Ser Thr Leu
                245                 250                 255

Ile Phe Tyr Glu Pro Val Thr Tyr Gly Val Phe Thr Pro Val Arg Ser
                260                 265                 270

Ser Gly Trp Leu Gly Thr Gly Phe Asp Arg Val Pro Gly Ala His Arg
                275                 280                 285

Asp Lys Ser Ala Pro Ser Lys Ser Val Leu Ser Tyr His Tyr Tyr Cys
290                 295                 300

Trp Ile Leu Gln Thr Asp Ala Gln Asn Thr Thr Met Pro Phe Trp Lys
305                 310                 315                 320

Lys Val Ile Cys Asp Arg Leu Leu Leu Pro Asn Val Ile Ser Asn Ala
                325                 330                 335

Ile Arg Ala Thr Lys Ser Thr Gly Gly Gly Arg Phe Leu Thr Xaa Phe
                340                 345                 350

Gly Leu Cys Gly Asp Asp Gly Asn Pro Arg Ser Val Asn Thr Ile Glu
                355                 360                 365

Cys Asn Asn Ile Leu Asn Glu Ala Asp Lys His Phe Glu Ser Trp Thr
370                 375                 380

Tyr Trp Asp Ser Asn Leu Leu Asp Leu Ser Gly Asn Pro Ile Val Thr
385                 390                 395                 400

Glu Val Lys Ser Phe Ile Arg Pro Tyr Pro His Ser Ile Arg Gly Val
                405                 410                 415

Phe Arg Lys Gln Gln Phe Asp His Lys Thr Gly Asp Phe His Leu Ser
                420                 425                 430

Phe Ile Ala Asn Thr Thr Lys Glu Gln Asn Glu Lys Gln Thr Leu
                435                 440                 445

Ile Ala Glu Ile Tyr Ile Pro Arg Ser Val His Tyr Pro Asn Gly Phe
                450                 455                 460

Ser Met Ser Val Lys Pro Asp Asn Leu Ser Thr Lys Met Asn Glu Asn
465                 470                 475                 480

Met Met Tyr Val Tyr Leu Pro Ser Gly Val Ser Asn Ala Ser Val Phe
                485                 490                 495

Val Arg Ile Glu Ile Val Arg Lys Ser Ile Glu
                500                 505

<210> SEQ ID NO 63
<211> LENGTH: 509
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Dictyostelium
      discoideum, GenBank Accession #EAL72387
<220> FEATURE:
<221> NAME/KEY: MOD_RES
<222> LOCATION: (354)..(354)
<223> OTHER INFORMATION: Xaa can be any one of Glycine, Alanine,
      Serine, Aspartic acid, Asparagine, Glutamine, Cysteine,
      Threonine, Ileucine, Leucine or Valine.

<400> SEQUENCE: 63

Met Asn Lys Lys Lys Gln Ile Ile Thr Thr Ile Thr Leu Leu Ser Phe
1               5                   10                  15

Ile Asn Leu Phe Ser Ile Val Asn Ala Ile Ile Lys Val Asn Pro Ala
```

```
                    20                  25                  30
Asn Gln Phe Phe Ile Asp Gln Tyr Asn Arg Val Arg Leu Phe His Gly
                35                  40                  45

Val Asn Val Val Tyr Lys Ile Pro Pro Phe His Pro Ser Leu Glu Gly
 50                  55                  60

Phe Asp Pro Val Thr Ser Phe Ser Ser Gln Asp Ile Glu Asn Leu Val
 65                  70                  75                  80

Glu Trp Gly Phe Asn Ala Val Arg Leu Gly Val Met Trp Pro Gly Val
                 85                  90                  95

Glu Pro Val Lys Asp Glu Tyr Asn Gln Thr Tyr Leu Asp Val Met Ser
                100                 105                 110

Lys Leu Val Ser Glu Met Glu Asp Asn Glu Ile Tyr Thr Leu Ile Asp
                115                 120                 125

Phe His Gln Asp Leu Leu Ser Arg Lys Tyr Cys Gly Glu Gly Leu Pro
            130                 135                 140

Asp Trp Ile Val Ser Asn Asp Thr Asn Asp Ser Phe Pro Ser Pro Val
145                 150                 155                 160

Ala His Ser Tyr Pro Lys Asn Asn Glu Ser Tyr Pro Ser Leu Asp Gln
                165                 170                 175

Cys Leu Asn Lys Asp Phe Gly Val Tyr Tyr Phe Ser Glu Asp Val Asn
                180                 185                 190

Arg Glu Phe Gln Asn Leu Tyr Asp Asn Val Asn Gly Val Gln Asp Lys
            195                 200                 205

Phe Ile Asp Tyr Trp Arg Gln Val Val Asn Thr Phe Lys Ser Tyr Asp
            210                 215                 220

Thr Val Leu Gly Tyr Glu Ile Ile Asn Glu Pro Trp Gly Gly Asp Ile
225                 230                 235                 240

Tyr Gln Asn Pro Glu Tyr Leu Leu Lys Leu Gly Tyr Ala Asp Ser Lys
                245                 250                 255

Asn Leu Leu Pro Leu Tyr Gln Ala Val Asn Asn Ala Ile Arg Glu Leu
                260                 265                 270

Asp Asp Gln His Cys Val Tyr Tyr Glu Lys Ala Leu Thr Asp Leu Phe
            275                 280                 285

His Ser Tyr Phe Pro Ser Gly Thr Pro Gly Gly Val Gln Tyr Asn Asp
            290                 295                 300

Arg Gln Val Leu Ser Tyr His Ile Tyr Cys Ala Thr Asp Arg Asp Gly
305                 310                 315                 320

Asn Pro Arg His Glu Tyr Val Cys Asp Gly Glu Asp Ile Phe Leu
                325                 330                 335

Val Ser Ala Met Lys Asp Leu Lys Gln Thr Gly Gly Gly Phe Met
            340                 345                 350

Thr Xaa Phe Gly Ala Val Ser Asn Gly Thr Asn Ser Ile Glu Met Leu
            355                 360                 365

Asn Tyr Leu Thr Gly Ser Ala Asp Lys Tyr Leu Gln Ser Trp Thr Tyr
            370                 375                 380

Trp Gln Leu Lys Tyr Tyr Asn Asp Ile Thr Thr Ala Gly Ser Thr Glu
385                 390                 395                 400

Ser Leu Tyr Leu Pro Asn Gly Glu Leu Asp Ile Pro Lys Ile Thr Ala
                405                 410                 415

Leu Ser Arg Thr Tyr Ala Gln Ala Ile Ala Gly Val Pro Leu Ser Met
            420                 425                 430

Ser Phe Asn Pro Ala Asn Ser Asp Phe Ser Phe Ser Tyr Asn Ile Asn
            435                 440                 445
```

```
Thr Thr Ile Thr Gln Pro Thr Gln Ile Tyr Leu Asn Gln Asp Ile Tyr
    450                 455                 460

Tyr Pro Asn Gly Phe Thr Thr Asn Ile Ile Thr Gly Thr Ala Thr Val
465                 470                 475                 480

Ser Ile Pro Gln Lys Asn Leu Ile Tyr Ile Leu Pro Asn Ser Asn Thr
                485                 490                 495

Ile Asn Gln Ser Thr Ile Thr Ile Thr Ile Leu Lys Lys
            500                 505

<210> SEQ ID NO 64
<211> LENGTH: 647
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Streptomyces
      avermitilis strain MA-4680, GenBank Accession #BAC75219
<220> FEATURE:
<221> NAME/KEY: MOD_RES
<222> LOCATION: (392)..(392)
<223> OTHER INFORMATION: Xaa can be any one of Glycine, Alanine,
      Serine, Aspartic acid, Asparagine, Glutamine, Cysteine,
      Threonine, Ileucine, Leucine or Valine.

<400> SEQUENCE: 64

Met Arg Lys Asn Ala Lys Leu Thr His Glu Ser Glu Val Leu Thr Phe
1               5                   10                  15

His Arg Ser Ala Arg Thr Val Val Asp Met Ser Lys Leu Arg Ala Arg
            20                  25                  30

Leu Leu Gly Val Leu Val Ser Leu Thr Gly Leu Leu Gly Ala Thr Gly
        35                  40                  45

Ala Gln Pro Ala Ala Ala Asp Ser Leu Pro Asp Ser Leu Trp Phe Asp
    50                  55                  60

Ala Ser Ala Ser Ala Ala Phe Thr Val Gln Asn Gly Arg Phe Ser Asp
65                  70                  75                  80

Gly Leu Gly Arg Glu Val Val Leu Arg Gly Tyr Asn Val Ser Gly Glu
                85                  90                  95

Thr Lys Leu Glu Glu Asn Ser Gly Leu Pro Phe Ala Ser Val Ala Asp
            100                 105                 110

Ala Arg Lys Ser Ala Thr Ala Leu Arg Thr Leu Gly Gly Gly Asn Ser
        115                 120                 125

Val Arg Phe Leu Leu Ser Trp Ala His Ala Glu Pro Val Arg Gly Gln
    130                 135                 140

Val Asp Thr Ala Tyr Leu Ala Ala Ala Thr Ala Gln Met Arg Ala Phe
145                 150                 155                 160

Leu Asp Ala Gly Ile Arg Val Phe Pro Asp Phe His Gln Asp Leu Tyr
                165                 170                 175

Ser Arg Tyr Leu Phe Asn Ser Gly Ser Trp Tyr Thr Gly Asp Gly Ala
            180                 185                 190

Pro Glu Trp Ala Val Asp Ala Gly Asp Tyr Pro Ala Glu Ser Cys Gly
        195                 200                 205

Ile Cys Leu Phe Trp Gly Gln Asn Ile Thr Gln Asn Gly Ala Val Thr
    210                 215                 220

Gln Ala Ser His Asp Phe Trp His Asn Ala Tyr Gly Val Gln Asp Ala
225                 230                 235                 240

Phe Leu Ala Thr Ala Gln Ala Thr Met Ala Tyr Ile Gln Gln Asn Leu
                245                 250                 255
```

```
Ser Ala Asp Glu Phe Asn Gly Val Val Gly Phe Asp Pro Tyr Asn Glu
            260                 265                 270

Pro His Ala Gly Thr Tyr Asp Ser Gly Glu Thr Ser Arg Thr Trp Glu
        275                 280                 285

Gln Asn Val Leu Trp Pro Phe Tyr Lys Lys Phe Arg Ala Arg Met Asp
    290                 295                 300

Ala Ala Gly Trp Gln Thr Lys Pro Ala Phe Ile Glu Pro Asn Leu Phe
305                 310                 315                 320

Trp Asn Ala Asn Ile Asp Phe Gln Lys Gln Glu Gly Gly Leu Leu Asp
                325                 330                 335

Ala Gly Thr Leu Gly Pro Arg Tyr Val Leu Asn Thr His Phe Tyr Asp
            340                 345                 350

Gln Lys Ala Ile Ser Gly Val Leu Met Trp Gly Lys Ala Ala Asp Gly
        355                 360                 365

Gln Tyr Ala Thr Asp Phe Gly Lys Val Arg Asp Arg Ala Ala Gly Ala
    370                 375                 380

Gly Thr Ala Ala Val Val Ser Xaa Phe Gly His Pro Leu Ser Gly Ser
385                 390                 395                 400

Val Ser Asp Lys Ala Pro Thr Val Val Lys Ala Met Tyr Gln Ala Leu
                405                 410                 415

Asp Ser Arg Leu Pro Gly Ser Thr Trp Trp Ser Asp Pro Thr Gly Ser
            420                 425                 430

Gly Pro Val Leu Ser Gly Ala Gln Trp Gln Trp Asp Ile Tyr Asn Gly
        435                 440                 445

Arg His His Glu Leu Glu Asn Gly Asn Pro Asp Lys Val Leu Thr Ser
    450                 455                 460

Gly Asp Ala Trp Asn Asp Glu Asp Leu Ser Ala Val Ser Leu Asn Asp
465                 470                 475                 480

Ser Gly Thr Ala Val Leu Arg Gln Asp Ala Arg Leu Leu Asp Arg Leu
                485                 490                 495

Tyr Pro Ser Ala Thr Ala Gly Ala Thr Val Ala Phe Thr Tyr Glu Asp
            500                 505                 510

Arg Ser Arg Asp Gly Ser Thr Thr Leu Thr Trp Asn Pro Val Pro Ser
        515                 520                 525

Ser Leu Pro Asn Val Ser Arg Leu Val Gly Ser Gly Gln Tyr Gly Leu
    530                 535                 540

Leu Val Trp Arg Ser Asn Gly Ser Thr Ala Pro Thr Glu Leu His Leu
545                 550                 555                 560

Pro Ala Ser Phe Pro Ala Ala Ser Thr Thr Val Val Ser Asp Leu Gly
                565                 570                 575

Thr Thr Ser Gly Leu Pro Ala Tyr Thr Arg Thr Thr Pro Val Gly His
            580                 585                 590

Ala Ala Glu Pro Gly Gly Thr Gly Ser His Arg Leu Leu Leu Thr Ala
        595                 600                 605

Ala Asp Ser Gly Thr Val His Tyr Ala Leu Val Thr Asn Gly Ala Thr
    610                 615                 620

Ala Pro Ser Ala Gly Leu Leu Ser Ala Ala Arg Ala Glu Leu Ser Ser
625                 630                 635                 640

Trp Ala Ala Thr Lys Val Gly
                645

<210> SEQ ID NO 65
<211> LENGTH: 654
<212> TYPE: PRT
```

<213> ORGANISM: Artificial Sequence
<220> FEATURE:
<223> OTHER INFORMATION: Description of Artificial Sequence:mutant
endoglycoceramidase (EGC, EGCase) derived from Leptospira
interrogans serovar Copenhageni strain Fiocruz L1-130, GenBank Accession #YP_003582
<220> FEATURE:
<221> NAME/KEY: MOD_RES
<222> LOCATION: (461)..(461)
<223> OTHER INFORMATION: Xaa can be any one of Glycine, Alanine, Serine, Aspartic acid, Asparagine, Glutamine, Cysteine, Threonine, Ileucine, Leucine or Valine.

<400> SEQUENCE: 65

```
Met Glu Glu Leu Phe Val Lys Asn Gly His Phe Ala Ser Lys Glu Gly
1               5                   10                  15

Ala Ile Tyr Gln Leu Arg Gly Val Asn Leu Ser Gly Ser Ala Lys Leu
            20                  25                  30

Pro Leu Lys Pro Asp Gly Thr Thr His Phe Asp Gln Thr Thr Thr Phe
        35                  40                  45

Asp Asn His Lys Asn Val Ser Phe Val Gly Arg Pro Leu Lys Glu Asp
    50                  55                  60

Gln Ala Glu Glu His Phe Asp Arg Leu Arg Lys Trp Gly Phe Asn Phe
65                  70                  75                  80

Leu Arg Phe Leu Ile Thr Trp Glu Ala Ile Glu His Lys Gly Pro Gly
                85                  90                  95

Lys Tyr Asp Asn Glu Tyr Ile Asp Tyr Val Glu Arg Met Val Ser Leu
            100                 105                 110

Ala Ala Lys Lys Gly Phe Tyr Leu Phe Ile Asp Pro His Gln Asp Val
        115                 120                 125

Trp Ser Arg Phe Thr Gly Gly Asp Gly Ala Pro Gly Trp Thr Leu Glu
    130                 135                 140

Glu Leu Gly Met Asn Ile Ser Lys Ile Arg Asn Ser Glu Thr Ala Ile
145                 150                 155                 160

Val His His His Gln Gly Lys Asn Tyr Arg Arg Met Ser Trp Pro Leu
                165                 170                 175

Asn Tyr Gln Lys Tyr Ser Cys Ala Thr Met Phe Ser Leu Phe Phe Gly
            180                 185                 190

Gly Lys Glu Phe Ala Pro Asp Thr Lys Ile Asp Gly Arg Asn Val Gln
        195                 200                 205

Asp Phe Leu Gln Asp His Tyr Ile Asp Ser Val Leu Lys Ile Val Arg
    210                 215                 220

Lys Leu Lys Lys Tyr Lys Asn Val Ile Gly Phe Asp Thr Leu Asn Glu
225                 230                 235                 240

Pro Ser Pro Gly Trp Ile Gly Lys Lys Asn Leu Gly Glu Phe Asp Gly
                245                 250                 255

Phe Gly Phe Gly Lys Val Val Lys Ser Ser Pro Phe Gln Glu Met Tyr
            260                 265                 270

Leu Ser Glu Gly Arg Ala Val Ser Ala Ala Gln Ala Tyr Met Leu Gly
        275                 280                 285

Phe Trp Ser Leu Pro Phe Gly Lys Val Arg Leu Asn Pro Glu Gly Val
    290                 295                 300

Pro Leu Trp Glu Arg Gly His Gln Cys Ile Trp Arg Asn His Gly Val
305                 310                 315                 320

Trp Asp Tyr Asp Pro Asn Gly Ala Pro Met Met Leu Lys Pro Glu Tyr
                325                 330                 335

Phe Tyr Lys Lys Asn Gly Arg Lys Tyr Glu Phe Tyr Ser Asp Phe Met
```

```
                340             345                 350
Tyr Pro Phe Ile Lys Lys Phe Lys Glu Arg Val Gln Lys Leu Glu Asn
            355                 360             365

Arg Phe His Ile Phe Ile Glu Ser Asp Pro Ser Lys Leu Glu Leu Glu
        370                 375             380

Trp Lys Glu Ile Pro Lys Lys Asn Gln Gly Ser Val Ile Asn Ala Thr
385                 390                 395                 400

His Trp Tyr Asp Ile Ser Val Leu Met Leu Lys Arg Tyr Leu Pro Trp
                405                 410                 415

Phe Gly Val His Val Phe Lys Gln Lys Pro Ile Phe Gly Lys Glu Asn
            420                 425             430

Ile Asp Asn Ala Tyr Glu Glu Thr Ile Arg Met Ile Arg Glu Met Ser
        435                 440             445

Glu Lys Lys Met Gly Asn Cys Pro Thr Val Ile Gly Xaa Thr Gly Ile
    450                 455             460

Pro Met Asp Leu Asn His Arg Val Ala Tyr Leu Lys Asn Asp Tyr Gly
465                 470                 475                 480

Val Leu Glu Lys Ala Leu Asp Arg Ile Met Lys Ala Val Glu Lys Asn
                485                 490                 495

Phe Val Asn Leu Ala Leu Trp Asn Tyr Thr Pro Asp His Thr His Ser
                500                 505                 510

Leu Gly Asp Arg Trp Asn Glu Glu Asp Leu Ser Ile Tyr Ser Gln Asp
            515                 520                 525

Thr Pro Ser Ser Tyr Asp Glu Asp Gly Gly Arg Ala Val Arg Ala Phe
        530                 535             540

Ser Arg Pro Tyr Pro Ile Arg Thr Lys Gly Phe Pro Val Ala Leu Thr
545                 550             555                 560

Phe Asp Met Glu Arg Ser Leu Phe Lys Tyr Ala Phe Arg Gln Glu Gly
                565                 570             575

Asp Leu Phe Pro Glu Thr Glu Ile Phe Ile Pro Glu Ile His Tyr Lys
            580                 585             590

Lys Gly Phe Glu Val Leu Val Asn Ala Gly Thr Tyr Gln Tyr Asp Phe
        595                 600             605

Arg Ser Arg Val Leu Lys Phe Lys Gly Glu Lys Gly Ile Leu Asp Tyr
    610                 615             620

Gly Ile Thr Val Tyr Pro Ser Lys Ser Leu Ser Arg Glu Gln Asp
625                 630             635                 640

Arg Thr Lys Val Val Pro Lys Thr Gln Lys Arg Lys Thr Gln
                645                 650
```

<210> SEQ ID NO 66
<211> LENGTH: 770
<212> TYPE: PRT
<213> ORGANISM: Artificial Sequence
<220> FEATURE:
<223> OTHER INFORMATION: Description of Artificial Sequence:mutant
      endoglycoceramidase (EGC, EGCase) derived from Neurospora crassa,
      GenBank Accession #XP_331009
<220> FEATURE:
<221> NAME/KEY: MOD_RES
<222> LOCATION: (498)..(498)
<223> OTHER INFORMATION: Xaa can be any one of Glycine, Alanine, Serine,
      Aspartic acid, Asparagine, Glutamine, Cysteine, Threonine,
      Ileucine, Leucine or Valine.

<400> SEQUENCE: 66

Met Ala Gly Phe Arg Leu Thr Ile Glu Asn Gly Ser Phe Arg Asp Val
1               5                   10                  15

```
His Gly Arg Gln Ile Thr Leu Arg Gly Ile Asn Val Ala Gly Asp Ala
            20                  25                  30

Lys Tyr Pro Asn Lys Pro Glu Gln Pro Ser His Val Gly Glu Asn Phe
            35                  40                  45

Phe Asp Gly Asp Asn Val Lys Phe Thr Gly Arg Pro Phe Pro Lys Glu
50                  55                  60

Glu Ala His Leu His Phe Ser Arg Leu Lys Arg Phe Gly Tyr Asn Thr
65                  70                  75                  80

Ile Arg Tyr Val Phe Thr Trp Glu Ala Ile Glu Ala Ala Gly Pro Gly
                85                  90                  95

Ile Tyr Asp Glu Glu Trp Ile Gln His Thr Ile Asp Val Leu Arg Val
            100                 105                 110

Ala Lys Arg Tyr Gly Phe Tyr Ile Phe Met Asp Pro His Gln Asp Val
            115                 120                 125

Trp Ser Arg Phe Ser Gly Gly Ser Gly Ala Pro Met Trp Thr Leu Tyr
130                 135                 140

Ala Ala Gly Leu Asn Pro Gln Ser Phe Ala Ala Thr Glu Ala Ala Ile
145                 150                 155                 160

Val His Asn Val Tyr Pro Glu Pro His Asn Phe Pro Lys Met Ile Trp
                165                 170                 175

Ser Thr Asn Tyr Tyr Arg Leu Ala Ala Ala Thr Met Phe Thr Leu Phe
            180                 185                 190

Phe Ala Gly Arg Asp Phe Ala Pro Lys Cys Ile Ile Asp Gly Val Asn
            195                 200                 205

Ile Gln Asp Tyr Leu Gln Asp His Phe Leu Arg Ala Cys Ala His Leu
            210                 215                 220

Ala Gln Arg Ile His Glu Ala Gly Asp Ile Glu Asn Asp Val Val Phe
225                 230                 235                 240

Gly Trp Glu Ser Leu Asn Glu Pro Asn Lys Gly Met Ile Ala Tyr Glu
                245                 250                 255

Asp Ile Ser Val Ile Pro Lys Glu Gln Asn Leu Lys Lys Gly Thr Cys
            260                 265                 270

Pro Thr Ile Trp Gln Thr Ile Leu Thr Gly Ser Gly Arg Ala Val Glu
            275                 280                 285

Val Asp Thr Trp Asp Met Gly Gly Met Gly Pro Tyr Lys Val Gly Arg
290                 295                 300

Ala Leu Ile Asp Pro Ser Gly Glu Gln Ala Trp Leu Pro Ala Asp Tyr
305                 310                 315                 320

Asp Glu Ser Arg Tyr Gly Tyr Lys Arg Asp Pro Gly Trp Lys Leu Gly
                325                 330                 335

Gln Cys Ile Trp Ala Gln His Gly Val Trp Asp Pro Ala Thr Asp Ser
            340                 345                 350

Leu Leu Lys Lys Asp Tyr Phe Gly Lys His Pro Ala Thr Gly Glu His
            355                 360                 365

Val Asp Tyr Pro Tyr Phe Ser Asn Arg Tyr Phe Met Asp Phe Phe Arg
            370                 375                 380

Lys Tyr Arg Asp Thr Ile Arg Ser Ile His Pro Asn Ala Ile Ile Leu
385                 390                 395                 400

Leu Gln Gly Pro Thr Met Glu Leu Pro Pro Lys Ile Ile Gly Thr Pro
                405                 410                 415

Asp Gly Asp Asp Pro Leu Leu Val Tyr Ala Pro His Tyr Asp Gly
            420                 425                 430
```

```
Ile Thr Leu Met Thr Lys Lys Trp Asn Arg Val Trp Asn Val Asp Val
            435                 440                 445

Ile Gly Ile Leu Arg Gly Lys Tyr Trp Ser Pro Ala Phe Gly Ile Lys
450                 455                 460

Ile Gly Glu Thr Ala Ile Arg Asn Cys Phe Lys Asn Gln His Ala Thr
465                 470                 475                 480

Met Arg Gln Glu Gly Leu Asp Tyr Ile Gly Asn His Pro Cys Val Met
            485                 490                 495

Thr Xaa Phe Gly Ile Pro Tyr Asp Met Asp Asp Lys Asn Ala Tyr Lys
                500                 505                 510

Thr Gly Asp Tyr Ser Ser Gln Ser Ala Ala Met Asp Ala Asn His Tyr
            515                 520                 525

Gly Val Glu Gly Ala Gly Leu Glu Gly Tyr Thr Leu Trp Leu Tyr Met
            530                 535                 540

Thr Lys Asn Asp His Glu Leu Gly Asp Gln Trp Asn Gly Glu Asp Leu
545                 550                 555                 560

Ser Ile Phe Ser Val Asp Asp Lys Leu Leu Pro Glu Ser Pro Val Pro
                565                 570                 575

Lys Ser His Ser Arg Asp Gly Ser Ser Ser Ile Ala Thr Pro Thr
            580                 585                 590

Gly Thr Lys Asp Asp Asp Leu Asp Asp Asp Ser Ser Val Thr Pro Ala
            595                 600                 605

Asn Ile Lys Arg Thr Leu Thr Asn Pro Ser Ile Ser Ser Val Ser Thr
            610                 615                 620

Gln Arg Gln Pro Glu Leu Thr Asn Ser Pro Gly Tyr Arg Ala Ala Glu
625                 630                 635                 640

Ala Tyr Val Arg Pro Ala Pro Ile Ala Thr Ala Gly Thr Val Lys Lys
                645                 650                 655

Tyr Gly Phe Asp Leu Arg Ser Cys Gln Phe His Val Thr Ile Gln Ala
            660                 665                 670

Pro Glu Ala Ala Lys Pro Asp Thr Pro Thr Val Val Phe Leu Pro Asp
            675                 680                 685

Tyr His Phe Pro Lys Asp Ala Cys Gln Val Glu Val Ser Ser Gly Lys
            690                 695                 700

Trp Glu Ile Arg Ser Asp Glu Glu Thr Thr Pro Leu Gln Lys Leu
705                 710                 715                 720

Arg Trp Trp His Gly Glu Gly Glu Gln Thr Leu Arg Val Thr Gly Val
                725                 730                 735

Val Lys Gln Val Asn Gly Asn Ser Ser Glu Gly Ala Glu Val Gly Tyr
            740                 745                 750

Tyr Asp Gln Val Phe Asn Gln Ala Lys Gly Phe Leu Asp Ala Cys Val
            755                 760                 765

Ile Met
770

<210> SEQ ID NO 67
<211> LENGTH: 24
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Rhodococcus sp. strain
      M-777, GenBank Accession #AAB67050

<400> SEQUENCE: 67
```

Met Arg Arg Thr Arg Leu Val Ser Leu Ile Val Thr Gly Ser Leu Val
1               5                   10                  15

Phe Gly Gly Gly Val Ala Ala Ala
            20

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Rhodococcus sp. strain C9,
      GenBank Accession #BAB17317

<400> SEQUENCE: 68

Met Arg Arg Thr Arg Ile Ala Ser Leu Ala Val Ala Gly Ser Leu Val
1               5                   10                  15

Leu Gly Ala Gly Val Ala Thr Ala
            20

<210> SEQ ID NO 69
<211> LENGTH: 29
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Propionibacterium acnes
      KPA171202, GenBank Accession #YP_056771

<400> SEQUENCE: 69

Met Arg Arg Lys Ser Ala Leu Gly Phe Val Ala Leu Ser Leu Phe Ala
1               5                   10                  15

Thr Gly Met Gly Val Ala Ala Ala Thr Pro Ala Thr Ala
            20                  25

<210> SEQ ID NO 70
<211> LENGTH: 39
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Propionibacterium acnes
      KPA171202, GenBank Accession #YP_055358

<400> SEQUENCE: 70

Met Tyr His His Ser Trp His Ser Pro Asp Arg Arg Arg Gly Val
1               5                   10                  15

Thr Arg Trp Ala Thr Thr Phe Ile Ala Ala Leu Thr Ala Ala Cys Met
            20                  25                  30

Ala Gln Met Pro Ala Gln Ala
        35

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Cyanea nozakii, GenBank
      Accession #BAB16369

<400> SEQUENCE: 71

```
Met Ala Glu Thr Gln Pro Leu Val Phe Val Leu Met Ser Ile Ser Ala
1               5                   10                  15

Ile Leu Thr Ala Gly
            20

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Hydra magnipapillata,
      GenBank Accession #BAD20464

<400> SEQUENCE: 72

Met Ile Ser Val Ala Leu Ile Ile Leu Phe Leu Ala Lys Val Ile Ser
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Schistosoma japonicum,
      GenBank Accession #AAW25069

<400> SEQUENCE: 73

Met Trp Ser Ile Phe Ile Leu Thr Phe Leu Ile Trp Thr Ser Val Gln
1               5                   10                  15

Thr

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Dictyostelium discoideum,
      GenBank Accession #EAL72387

<400> SEQUENCE: 74

Met Asn Lys Lys Lys Gln Ile Ile Thr Thr Ile Thr Leu Leu Ser Phe
1               5                   10                  15

Ile Asn Leu Phe Ser Ile Val Asn Ala
            20                  25

<210> SEQ ID NO 75
<211> LENGTH: 54
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Streptomyces avermitilis
      strain MA-4680, GenBank Accession #BAC75219

<400> SEQUENCE: 75

Met Arg Lys Asn Ala Lys Leu Thr His Glu Ser Glu Val Leu Thr Phe
1               5                   10                  15

His Arg Ser Ala Arg Thr Val Val Asp Met Ser Lys Leu Arg Ala Arg
            20                  25                  30
```

```
Leu Leu Gly Val Leu Val Ser Leu Thr Gly Leu Leu Gly Ala Thr Gly
        35                  40                  45

Ala Gln Pro Ala Ala Ala
    50

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence:predicted
      native N-terminal signal peptide sequence for wild type
      endoglycoceramidase (EGC, EGCase) from Neurospora crassa, GenBank
      Accession #XP_331009

<400> SEQUENCE: 76

Met Ala Gly Phe Arg Leu Thr Ile Glu Asn Gly Ser Phe Arg Asp Val
1               5                   10                  15

His Gly

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence:epitope tag
      for monoclonal anti-FLAG antibody, "FLAG tag"

<400> SEQUENCE: 77

Asp Tyr Lys Asp Asp Asp Asp Lys
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence:DDDDK
      epitope tag

<400> SEQUENCE: 78

Asp Asp Asp Asp Lys
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence:6 residue
      histidine peptide epitope tag

<400> SEQUENCE: 79

His His His His His His
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence:Polyoma
      middle T protein epitope tag

<400> SEQUENCE: 80

Glu Tyr Met Pro Met Glu
```

<210> SEQ ID NO 81
<211> LENGTH: 169
<212> TYPE: DNA
<213> ORGANISM: Artificial Sequence
<220> FEATURE:
<223> OTHER INFORMATION: Description of Artificial Sequence:portion of
      expression vector pT7-7 with T7 promoter and transcription start
      site
<220> FEATURE:
<221> NAME/KEY: CDS
<222> LOCATION: (110)..(169)

<400> SEQUENCE: 81

```
cgattcgaac ttctgataga cttcgaaatt aatacgactc actataggga gaccacaacg      60
gtttccctct agaaataatt ttgtttaact ttaagaagga gatatacat atg gct aga     118
                                                        Met Ala Arg
                                                        1 att cgc gcc cgg gga tcc tct aga gtc gac ctg cag ccc aag ctt atc      166
Ile Arg Ala Arg Gly Ser Ser Arg Val Asp Leu Gln Pro Lys Leu Ile
    5                   10                  15 gat                                                                    169
Asp
20
```

<210> SEQ ID NO 82
<211> LENGTH: 20
<212> TYPE: PRT
<213> ORGANISM: Artificial Sequence
<220> FEATURE:
<223> OTHER INFORMATION: Synthetic Construct

<400> SEQUENCE: 82

Met Ala Arg Ile Arg Ala Arg Gly Ser Ser Arg Val Asp Leu Gln Pro
1               5                   10                  15

Lys Leu Ile Asp
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence:portion of
      expression vector pT7-7 with transcription start site

<400> SEQUENCE: 83

Met Ala Arg Ile Arg Ala Arg Gly Ser Ser Arg Val Asp Leu Gln Pro
1               5                   10                  15

Lys Leu Ile Asp
            20

<210> SEQ ID NO 84
<211> LENGTH: 503
<212> TYPE: PRT
<213> ORGANISM: Artificial Sequence
<220> FEATURE:
<223> OTHER INFORMATION: wild-type endoglycoceramidase

<400> SEQUENCE: 84

Met Ala Glu Thr Gln Pro Leu Val Phe Val Leu Met Ser Ile Ser Ala
1               5                   10                  15

Ile Leu Thr Ala Gly Leu Pro Ile Asn Asp Asp Ala Ser Leu Leu Ile
            20                  25                  30

```
Ser Val Asn Pro Glu Thr Gln Gln Leu Val Asp Ser Leu Gly Arg Glu
            35                  40                  45

Arg Phe Phe His Gly Thr Asn Val Val Lys His Lys Pro Tyr His
 50                  55                  60

Pro Ser Val Glu Gly Tyr Asp Asn Thr Ser Phe Ser Glu Val Asp Met
 65                  70                  75                  80

Lys Ile Leu Gln Asp Leu Gly Leu Asn Thr Ile Arg Leu Gly Met Met
                85                  90                  95

Leu Pro Gly Tyr Val Pro Thr Arg Gly Asn Tyr Asn Glu Thr Tyr Leu
            100                 105                 110

Lys Ile Ile Gln Glu Ile Val Ser Lys Ala Ala Lys Tyr Gly Ile Tyr
        115                 120                 125

Thr Leu Leu Asp Met His Gln Asp Val Met Ser Ala Lys Phe Cys Val
    130                 135                 140

Glu Gly Phe Pro Asp Trp Ala Val Asn Thr Gly Asn Ala Asp Asn Phe
145                 150                 155                 160

Pro Phe Pro Leu Glu Asp Lys Tyr Pro Leu Asn Pro Gln Thr Gly Tyr
                165                 170                 175

Pro Tyr Pro Lys Asp Cys Ala Lys His Ala Trp Gly Tyr Tyr Phe
            180                 185                 190

Thr Glu Ala Ala Ala Ala Phe Gln Asn Phe Tyr Asn Asn Thr Asp
        195                 200                 205

Gly Leu Leu Asp Ala Trp Ala Asp Phe Trp Lys Lys Thr Ala Gln Gly
    210                 215                 220

Phe Lys Asp Tyr Lys Ser Val Ile Gly Tyr Glu Leu Ile Asn Glu Pro
225                 230                 235                 240

Phe Ala Gly Asp Ile Tyr Arg Asp Pro Ser Leu Met Ile Pro Gly Val
                245                 250                 255

Ala Asp Glu Arg Asn Leu Ala Pro Ala Tyr Asp Val Ile His Lys Ala
            260                 265                 270

Ile Arg Thr Val Asp Glu Gln His Ser Ile Phe Phe Glu Gly Val Thr
        275                 280                 285

Trp Asp Tyr Phe Ala Ala Gly Phe Ser Lys Val Pro Gly Gly Asp Ala
    290                 295                 300

Tyr Arg Asn Arg Ser Val Leu Ser Tyr His Tyr Tyr Glu Pro Pro Asp
305                 310                 315                 320

Phe Asn Lys Lys Phe Gln Phe Glu Val Arg Met Glu Asp Leu Arg Arg
                325                 330                 335

Leu Lys Cys Gly Gly Phe Leu Thr Glu Leu Leu Thr Val Gly Asp Thr
            340                 345                 350

Ala Lys Asp Met Ser Asp Met Leu Glu Leu Phe Asp Ile Cys Asp Gln
        355                 360                 365

His Lys Gln Ser Trp Met Gly Trp Leu Tyr Lys Ser Tyr Gly Cys Tyr
    370                 375                 380

Lys Gln His Leu Gly Cys Leu Thr Asp Ser Met His Asp Glu Thr Gly
385                 390                 395                 400

His Leu Arg Asp Ile Val Leu Gln Asn Thr Thr Arg Thr Tyr Pro Gln
                405                 410                 415

Ala Val Ala Gly His Thr Ile Gly Tyr Lys Phe Asp Arg Ile Thr Lys
            420                 425                 430

Lys Phe Asp Leu Ser Phe Val Val Thr Ala Asp Cys Arg Ser Thr Glu
        435                 440                 445
```

```
Ser Ile Val Tyr Phe Asn Lys Asp Leu His Tyr Ser Asn Gly Tyr Asp
    450                 455                 460

Val Thr Val Phe Pro Lys Asp Ser Val Thr Trp Lys Gln Val Glu Lys
465                 470                 475                 480

Lys Ile Ile Ile Asn His Ser Gln Lys Leu Ser Ala Gly Thr Thr Val
                485                 490                 495

Thr Phe Ser Leu Val Ala Lys
                500

<210> SEQ ID NO 85
<211> LENGTH: 517
<212> TYPE: PRT
<213> ORGANISM: Artificial Sequence
<220> FEATURE:
<223> OTHER INFORMATION: wild-type endoglycoceramidase

<400> SEQUENCE: 85

Met Ile Ser Val Ala Leu Ile Ile Leu Phe Leu Ala Lys Val Ile Ser
1               5                   10                  15

Gly Lys Ser Asp Asp Phe Ile Ser Val Asn Pro Glu Thr Asn Met Leu
            20                  25                  30

Ile Asp Gly Tyr Gly Arg Glu Arg Phe Phe His Gly Thr Asn Val Val
        35                  40                  45

Val Lys His Phe Pro Phe His Pro Glu Thr Thr Gly Phe Asn Lys Asp
50                  55                  60

Thr Phe Ser Glu Asp Asp Met Lys Ile Leu Gln Lys Phe Gly Leu Asn
65                  70                  75                  80

Ser Ile Arg Leu Gly Met Met Leu Pro Gly Tyr Val Pro Lys Arg Glu
                85                  90                  95

Glu Tyr Asn Glu Thr Tyr Ile Lys Val Ile Gln Ser Ile Val Thr Thr
            100                 105                 110

Ala Ala Lys Tyr Gly Ile Tyr Thr Leu Leu Asp Met His Gln Asp Val
        115                 120                 125

Phe Ser Pro Lys Phe Cys Val Glu Gly Met Pro Asp Trp Ile Val Asn
130                 135                 140

Thr Gln Gly Ala Lys Asp Phe Pro Met Pro Leu His Lys Pro Phe Asn
145                 150                 155                 160

Leu Asp Pro Lys Thr Gly Tyr Pro Tyr Pro Glu Asp Cys Ala Lys Phe
                165                 170                 175

Ser Trp Ala Asp Tyr Tyr Phe Thr Glu Ala Ala Gly Gln Ala Phe Gln
            180                 185                 190

Asn Leu Tyr Asp Asn Val Asp Gly Leu Arg Asp Glu Trp Ala Gln Phe
        195                 200                 205

Trp Lys Lys Thr Ala Asp Val Phe Lys Glu Pro Ser Val Ile Gly
210                 215                 220

Tyr Glu Leu Ile Asn Glu Pro Phe Cys Gly Asn Val Phe Lys His Pro
225                 230                 235                 240

Thr Leu Leu Ile Pro Gly Val Ala Asp Tyr Leu Asn Leu Gln Pro Thr
                245                 250                 255

Tyr Asp Ala Leu Gln Lys Ala Ile Arg Gln Val Asp Glu His Asn
            260                 265                 270

Ile Phe Phe Glu Gly Val Thr Trp Asp Phe Phe Glu Val Gly Phe Thr
        275                 280                 285

Glu Val Pro Gly Gly Lys Gln Tyr Gln Asn Arg Ser Val Leu Ser Tyr
290                 295                 300
```

-continued

```
His Tyr Tyr Glu Pro Pro Asp Phe Ser Lys Lys Leu Asn Phe Glu Ala
305                 310                 315                 320

Arg Leu Leu Asp Leu Lys Arg Leu Lys Cys Gly Gly Phe Leu Thr Glu
                325                 330                 335

Met Phe Thr Val Gly Thr Asp Phe Asn Ser Met Phe Glu Met Phe Asp
                340                 345                 350

Leu Cys Asp Lys Phe Lys Gln Ser Trp His Gly Trp Met Tyr Lys Ser
            355                 360                 365

Tyr Gly Cys Ile Glu Gln Asn Leu Gly Cys Leu Asn Met Ser Ser Pro
        370                 375                 380

Gly Lys Glu Ser Ile Gln Ile Ala Asn Thr Ser Arg Thr Tyr Pro Gln
385                 390                 395                 400

Ala Val Ala Gly Arg Thr Gln Ser Tyr Ala Phe Asp Ile Lys Thr Lys
                405                 410                 415

Val Phe Thr Leu Val Tyr Glu Thr Val Gly Ser Cys Lys Ser Gly Arg
                420                 425                 430

Thr Ile Val Tyr Phe Asn Lys Asn Leu His Tyr Pro Asn Gly Tyr Arg
            435                 440                 445

Tyr Glu Ile Asn Pro Asn Phe Lys Val Thr Pro Ser Glu Asn Glu Tyr
    450                 455                 460

Phe Leu Tyr Leu Asp Glu Val Asn Lys Val Pro Asn Thr Val Val Thr
465                 470                 475                 480

Phe Lys Leu Phe Pro Leu Ser Phe Thr Asp Ser Glu Asp Ile His Pro
                485                 490                 495

Val Thr Val Met Gly Asp Lys His Leu Ser Glu Asn His Asn Glu Asn
                500                 505                 510

Glu Lys Lys Lys Lys
            515
```

MUTANT ENDOGLYCOCERAMIDASES WITH ENHANCED SYNTHETIC ACTIVITY

CROSS-REFERENCES TO RELATED APPLICATIONS

This application is a Continuation of U.S. application Ser. No. 13/950,259, filed on Jul. 24, 2013 which is a Divisional application of U.S. application Ser. No. 11/596,942, filed on Nov. 17, 2006 which is a 371 U.S. National Phase Application from PCT/US05/019451, filed Jun. 1, 2005 which claims the benefit of U.S. Provisional Application 60/576,316, filed Jun. 1, 2004; U.S. Provisional Application 60/626,791, filed Nov. 10, 2004; and U.S. Provisional 60/666,765, filed Mar. 29, 2005, the disclosures of each of which are incorporated herein by reference in their entirety for all purposes.

REFERENCE TO SEQUENCE LISTING SUBMITTED ELECTRONICALLY

The sequence listing contained in the file named "14754310seqlist.txt", created on Oct. 7, 2015 and having a size of 265 kilobytes, has been submitted electronically herewith via EFS-Web, and the contents of the txt file are hereby incorporated by reference in their entirety.

REFERENCE TO THE SEQUENCE LISTING

SEQ ID NO:1: nucleic acid sequence of a wild-type endoglycoceramidase from *Rhodococcus* sp. M-777. GenBank Accession No. U39554.

SEQ ID NO:2: amino acid sequence encoded by nucleic acid sequence of SEQ. ID. NO.:1.

SEQ ID NO:3: amino acid sequence of a wild-type endoglycoceramidase from *Rhodococcus* sp. M-777. GenBank Accession No. AAB67050.

SEQ ID NO:4: nucleic acid sequence of a wild-type endoglycoceramidase from *Rhodococcus* sp. C9. GenBank Accession No. AB042327.

SEQ ID NO:5: amino acid sequence encoded by nucleic acid sequence of SEQ. ID. NO.:4.

SEQ ID NO:6: amino acid sequence of a wild-type endoglycoceramidase from *Rhodococcus* sp. C9. GenBank Accession No. BAB17317.

SEQ ID NO:7: nucleic acid sequence of a wild-type endoglycoceramidase from *Propionibacterium acnes* KPA171202. GenBank Accession No. gi50839098: 2281629.

SEQ ID NO:8: amino acid sequence of a wild-type endoglycoceramidase from *Propionibacterium acnes* KPA171202. GenBank Accession No. YP_056771.

SEQ ID NO:9: amino acid sequence of a wild-type endoglycoceramidase from *Propionibacterium acnes* KPA171202. GenBank Accession No. YP_056771.

SEQ ID NO:10: nucleic acid sequence of a wild-type endoglycoceramidase from *Propionibacterium acnes* KPA171202. GenBank Accession No. gi50839098: c709797-708223.

SEQ ID NO:11: amino acid sequence of a wild-type endoglycoceramidase from *Propionibacterium acnes* KPA171202. GenBank Accession No. YP_055358.

SEQ ID NO:12: amino acid sequence of a wild-type endoglycoceramidase from *Propionibacterium acnes* KPA171202. GenBank Accession No. YP_055358.

SEQ ID NO:13: nucleic acid sequence of a wild-type endoglycoceramidase from *Cyanea nozakii*. GenBank Accession No. AB047321.

SEQ ID NO:14: amino acid sequence of a wild-type endoglycoceramidase from *Cyanea nozakii*. GenBank Accession No. BAB16369.

SEQ ID NO:15: amino acid sequence of a wild-type endoglycoceramidase from *Cyanea nozakii*. GenBank Accession No. BAB16369.

SEQ ID NO:16: nucleic acid sequence of a wild-type endoglycoceramidase from *Cyanea nozakii*. GenBank Accession No. AB047322.

SEQ ID NO:17: amino acid sequence of a wild-type endoglycoceramidase from *Cyanea nozakii*. GenBank Accession No. BAB16370.

SEQ ID NO:18: amino acid sequence of a wild-type endoglycoceramidase from *Cyanea nozakii*. GenBank Accession No. BAB16370.

SEQ ID NO:19: nucleic acid sequence of a wild-type endoglycoceramidase from *Hydra magnipapillata*. GenBank Accession No. AB179748.

SEQ ID NO:20: amino acid sequence of a wild-type endoglycoceramidase from *Hydra magnipapillata*. GenBank Accession No. BAD20464.

SEQ ID NO:21: amino acid sequence of a wild-type endoglycoceramidase from *Hydra magnipapillata*. GenBank Accession No. BAD20464.

SEQ ID NO:22: nucleic acid sequence of a wild-type endoglycoceramidase from *Schistosoma japonicum*. GenBank Accession No. AY813337.

SEQ ID NO:23: amino acid sequence of a wild-type endoglycoceramidase from *Schistosoma japonicum*. GenBank Accession No. AAW25069.

SEQ ID NO:24: amino acid sequence of a wild-type endoglycoceramidase from *Schistosoma japonicum*. GenBank Accession No. AAW25069.

SEQ ID NO:25: amino acid sequence of a putative wild-type endoglycoceramidase from *Dictyostelium discoideum*. GenBank Accession No. EAL72387.

SEQ ID NO:26: amino acid sequence of a putative wild-type endoglycoceramidase from *Streptomyces avermitilis* str. MA-4680. GenBank Accession No. BAC75219.

SEQ ID NO:27: amino acid sequence of a putative wild-type endoglycoceramidase from *Leptospira interrogans serovar Copenhageni* str. Fiocruz L1-130. GenBank Accession No. YP_003582.

SEQ ID NO:28: amino acid sequence of a putative wild-type endoglycoceramidase from *Neurospora crassa*. GenBank Accession No. XP_331009.

SEQ ID NO:29: amino acid sequence of mutant endoglycoceramidase A derived from AAB67050 (E233A).

SEQ ID NO:30: amino acid sequence of mutant endoglycoceramidase A derived from AAB67050 (E233S).

SEQ ID NO:31: amino acid sequence of mutant endoglycoceramidase A derived from AAB67050 (E233G).

SEQ ID NO:32: amino acid sequence of mutant endoglycoceramidase A derived from AAB67050 (E233D).

SEQ ID NO:33: amino acid sequence of mutant endoglycoceramidase A derived from AAB67050 (E233AQ).

SEQ ID NO:34: 5' PCR primer: 5'Copt

SEQ ID NO:35: 3' PCR primer: 3'Asp PstI

SEQ ID NO:36: 3' PCR primer: 3'Gln PstI

SEQ ID NO:37: 3' PCR primer: 3'Ala PstI-11-1

SEQ ID NO:38: 3' PCR primer: 3'Gly PstI-11-1

SEQ ID NO:39: 3' PCR primer: 3'Ser PstI-11-1

SEQ ID NO:40: *Rhodococcus* EGC-E351A-forward primer

SEQ ID NO:41: *Rhodococcus* EGC-E351A-reverse primer

SEQ ID NO:42: *Rhodococcus* EGC-E351D-forward primer

SEQ ID NO:43: *Rhodococcus* EGC-E351D-reverse primer

SEQ ID NO:44: *Rhodococcus* EGC-E351G-forward primer

SEQ ID NO:45: *Rhodococcus* EGC-E351G-reverse primer

SEQ ID NO:46: *Rhodococcus* EGC-E351S-forward primer

SEQ ID NO:47: *Rhodococcus* EGC-E351S-reverse primer

SEQ ID NO:48: nucleic acid sequence encoding mutant endoglycoceramidase His E351 S, derived from GenBank Accession No. U39554.

SEQ ID NO:49: amino acid sequence encoding mutant endoglycoceramidase His E351 S, derived from GenBank Accession No. AAB67050.

SEQ ID NO:50: Endoglycoceramidase identifying motif A.

SEQ ID NO:51: Endoglycoceramidase identifying motif B, including the acid-base sequence region.

SEQ ID NO:52: Endoglycoceramidase identifying motif C.

SEQ ID NO:53: Endoglycoceramidase identifying motif D, including the nucleophilic glutamic acid residue.

SEQ ID NO:54: Endoglycoceramidase identifying motif E, including nucleophilic carboxylate glutamic acid or aspartic acid residues.

SEQ ID NO:55: amino acid sequence of a mutant endoglycoceramidase derived from *Rhodococcus* sp. M-777. GenBank Accession No. AAB67050. X=Gly, Ala, Ser, Asp, Asn, Gln, Cys, Thr, Ile, Leu or Val.

SEQ ID NO:56: amino acid sequence of a mutant endoglycoceramidase derived from *Rhodococcus* sp. C9. GenBank Accession No. BAB17317. X=Gly, Ala, Ser, Asp, Asn, Gln, Cys, Thr, Ile, Leu or Val.

SEQ ID NO:57: amino acid sequence of a mutant endoglycoceramidase derived from *Propionibacterium acnes* KPA171202. GenBank Accession No. YP_056771. X=Gly, Ala, Ser, Asp, Asn, Gln, Cys, Thr, Ile, Leu or Val.

SEQ ID NO:58: amino acid sequence of a mutant endoglycoceramidase derived from *Propionibacterium acnes* KPA171202. GenBank Accession No. YP_055358. X=Gly, Ala, Ser, Asp, Asn, Gln, Cys, Thr, Ile, Leu or Val.

SEQ ID NO:59: amino acid sequence of a mutant endoglycoceramidase derived from *Cyanea nozakii*. GenBank Accession No. BAB16369. X=Gly, Ala, Ser, Asp, Asn, Gln, Cys, Thr, Ile, Leu or Val.

SEQ ID NO:60: amino acid sequence of a mutant endoglycoceramidase derived from *Cyanea nozakii*. GenBank Accession No. BAB16370. X=Gly, Ala, Ser, Asp, Asn, Gln, Cys, Thr, Ile, Leu or Val.

SEQ ID NO:61: amino acid sequence of a mutant endoglycoceramidase derived from *Hydra magnipapillata*. GenBank Accession No. BAD20464. X=Gly, Ala, Ser, Asp, Asn, Gln, Cys, Thr, Ile, Leu or Val.

SEQ ID NO:62: amino acid sequence of a mutant endoglycoceramidase derived from *Schistosoma japonicum*. GenBank Accession No. AAW25069. X=Gly, Ala, Ser, Asp, Asn, Gln, Cys, Thr, Ile, Leu or Val.

SEQ ID NO:63: amino acid sequence of a mutant endoglycoceramidase derived from *Dictyostelium discoideum*. GenBank Accession No. EAL72387. X=Gly, Ala, Ser, Asp, Asn, Gln, Cys, Thr, Ile, Leu or Val.

SEQ ID NO:64: amino acid sequence of a mutant endoglycoceramidase derived from *Streptomyces avermitilis* str. MA-4680. GenBank Accession No. BAC75219. X=Gly, Ala, Ser, Asp, Asn, Gln, Cys, Thr, Ile, Leu or Val.

SEQ ID NO:65: amino acid sequence of a mutant endoglycoceramidase derived from *Leptospira interrogans serovar Copenhageni* str. Fiocruz L1-130. GenBank Accession No. YP_003582. X=Gly, Ala, Ser, Asp, Asn, Gln, Cys, Thr, Ile, Leu or Val.

SEQ ID NO:66: amino acid sequence of a mutant endoglycoceramidase derived from *Neurospora crassa*. GenBank Accession No. XP_331009. X=Gly, Ala, Ser, Asp, Asn, Gln, Cys, Thr, Ile, Leu or Val.

SEQ ID NO:67: predicted N-terminal signal sequence for wild-type endoglycoceramidase from *Rhodococcus* sp. M-777. GenBank Accession No. AAB67050.

SEQ ID NO:68: predicted N-terminal signal sequence for wild-type endoglycoceramidase from *Rhodococcus* sp. C9. GenBank Accession No. BAB17317.

SEQ ID NO:69: predicted N-terminal signal sequence for wild-type endoglycoceramidase from *Propionibacterium acnes* KPA171202. GenBank Accession No. YP_056771.

SEQ ID NO:70: predicted N-terminal signal sequence for wild-type endoglycoceramidase from from *Propionibacterium acnes* KPA171202. GenBank Accession No. YP_055358.

SEQ ID NO:71: predicted N-terminal signal sequence for wild-type endoglycoceramidase from *Cyanea nozakii*. GenBank Accession No. BAB16369 and BAB16370.

SEQ ID NO:72: predicted N-terminal signal sequence for wild-type endoglycoceramidase from *Hydra magnipapillata*. GenBank Accession No. BAD20464.

SEQ ID NO:73: predicted N-terminal signal sequence for wild-type endoglycoceramidase from *Schistosoma japonicum*. GenBank Accession No. AAW25069.

SEQ ID NO:74: predicted N-terminal signal sequence for wild-type endoglycoceramidase from *Dictyostelium discoideum*. GenBank Accession No. EAL72387.

SEQ ID NO:75: predicted N-terminal signal sequence for wild-type endoglycoceramidase from *Streptomyces avermitilis* str. MA-4680. GenBank Accession No. BAC75219.

SEQ ID NO:76: predicted N-terminal signal sequence for wild-type endoglycoceramidase from *Neurospora crassa*. GenBank Accession No. XP_331009.

SEQ ID NO:77: epitope tag for monoclonal anti-FLAG antibody, "FLAG tag".

SEQ ID NO:78: DDDDK epitope tag.

SEQ ID NO:79: 6 residue histidine peptide.

SEQ ID NO:80: Polyoma middle T protein epitope tag.

SEQ ID NO:81: portion of expression vector pT7-7 with T7 promoter and transcription start site.

SEQ ID NO:82: Synthetic Construct.

SEQ ID NO:83: portion of expression vector pT7-7 with transcription start site.

FIELD OF THE INVENTION

The present invention relates to the field of synthesis of saccharides, particularly those of use in preparing glycolipids, e.g., glycosphingolipids. More specifically, the invention relates to a novel approach for producing a mutant endoglycoceramidase, which has a synthetic activity that can be used to catalyze the formation of the glycosidic linkage between a monosaccharide or oligosaccharide and an aglycone to form various glycolipids.

BACKGROUND OF THE INVENTION

Glycolipids, a group of amphipathic compounds that structurally consist of a sugar chain (monosaccharide or oligosaccharide) bound to an aglycone, are important cellular membrane components known to participate in various cellular events mediating physiological processes such as the cell-cell recognition, antigenicity, and cell growth regulation (Hakomori, *Annu. Rev. Biochem.*, 50: 733-764, 1981; Makita and Taniguchi, *Glycolipid* (Wiegandt, ed.) pp 59-82, Elsevier Scientific Publishing Co., New York, 1985). Because there are no known enzymes that can universally transfer a saccharyl residue to a an aglycone (e.g., ceramide or sphingosine), synthesis of glycolipids usually requires a multi-step complex process that has the disadvantages of high cost and low yield.

Endoglycoceramidase (EC3.2.1.123), an enzyme first isolated from the Actinomycetes of *Rhodococcus* strain (Horibata, *J. Biol. Chem.* May 2004 10.1094/jbc.M401460200; Ito and Yamagata, *J. Biol. Chem.*, 261: 14278-14282, 1986), hydrolyzes the glycoside linkage between the sugar chain and the ceramide in glycolipids to produce intact monosaccharide or oligosaccharide and ceramide. To this date, several more endoglycoceramidases have been isolated and characterized (see e.g., Li et al., *Biochem. Biophy. Res. Comm.*, 149: 167-172, 1987; Ito and Yamagata, *J. Biol. Chem.*, 264: 9510-9519, 1989; Zhou et al., *J. Biol. Chem.*, 264: 12272-12277, 1989; Ashida et al., *Eur. J. Biochem.*, 205: 729-735, 1992; Izu et al., *J. Biol. Chem.*, 272: 19846-19850, 1997; Horibata et al., *J. Biol. Chem.*, 275:31297-31304, 2000; Sakaguchi et al., *J. Biochem.*, 128: 145-152, 2000; and U.S. Pat. No. 5,795,765). The active site of endoglycoceramidases has also been described by Sakaguchi et al., *Biochem. Biophy. Res. Comm.*, 260: 89-93, 1999, as including a three amino acid segment of Asn-Glu-Pro, among which the Glu residue appears to be the most important to the enzymatic activity.

Endoglycoceramidases are also known to possess an additional transglycosylation activity, which is much weaker than the hydrolytic activity (Li et al., *J. Biol. Chem.*, 266:10723-10726, 1991; Ashida et al., *Arch. Biochem. Biophy.*, 305:559-562, 1993; Horibata et al., *J. Biochem.*, 130: 263-268, 2001). This transglycosylation activity has not yet been exploited to synthesize glycolipids, because the far more potent hydrolytic activity of the enzyme counteracts this synthetic activity by quickly hydrolyzing newly made glycolipid.

In view of the deficiencies of the current methods for chemically synthesizing glycosphigolipids, a method that relies on the substrate specificity of a synthetic endoglycoceramidase would represent a significant advance in the field of saccharide (glycolipid) synthesis. The present invention provides such a synthetic endoglycoceramidase ("endoglycoceramide synthase") and methods for using this new enzyme.

BRIEF SUMMARY OF THE INVENTION

The present invention provides mutant endoglycoceramidase enzymes that have synthetic activity, assembling a saccharide and an aglycone, e.g., a ceramide or sphingosine, to form a glycolipid or a component thereof. The enzymes of the invention exploit the exquisite selectivity of enzymatic reactions to simplify the synthesis of glycolipids.

In a first aspect, the invention provides a mutant endoglycoceramidase having a modified nucleophilic carboxylate (i.e., Glu or Asp) residue, wherein the nucleophilic carboxylate residue resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54 or motif E), or conservative variants thereof, of a corresponding wild-type endoglycoceramidase, wherein the mutant endoglycoceramidase catalyzes the transfer of a saccharide moiety from a donor substrate to an acceptor substrate (e.g., an aglycone). Typically, the Glu/Asp residue is substituted with an amino acid residue other than a Glu/Asp residue, for example, a Gly, Ala, Ser, Asp, Asn, Gln, Cys, Thr, Ile, Leu or Val. In certain embodiments, the mutant endoglycoceramidase comprises any one of an amino acid sequence of SEQ ID NOs:55-66.

In a related aspect, the invention provides a mutant endoglycoceramidase characterized in that
i) in its native form the endoglycoceramidase comprises an amino acid sequence that is any one of SEQ. ID. NO.s: 2 (*Rhodococcus*) and the polypetide is encoded with nucleic acid sequence SEQ. ID. NO.: 1), 4 (*Rhodococcus*, SEQ. ID. NO.: 4 is describing the nucleic acid and the polypetide sequence), 6 (*Propionibacterium acnes*), 8 (*Propionibacterium acnes*), 10 (*Cyanea nozakii*), 12 (*Cyanea nozakii*), 14 (*Hydra magnipapillata*), 16 (*Schistosoma japonicum*), 17 (*Dictyostelium discoideum*), 18 (*Streptomyces avermitilis*), 19 (*Leptospira interrogans*), and 20 (*Neurospora crassa*); and
ii) the nucleophilic carboxylate (i.e., Glu or Asp) residue within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54) of a corresponding wild-type endoglycoceramidase is modified to an amino acid other than Glu/Asp.

In another aspect, the invention provides a method for making a mutant endoglycoceramidase having enhanced synthetic activity in comparison to a corresponding wild-type endoglycoceramidase, the method comprising modifying the nucleophilic carboxylate (i.e., Glu or Asp) residue in a corresponding wild-type endoglycoceramidase, wherein the nucleophilic Glu/Asp resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54) of a corresponding wild-type endoglycoceramidase.

In another aspect, the invention provides a method of synthesizing a glycolipid or an aglycone, the method comprising, contacting a donor substrate comprising a saccharide moiety and an acceptor substrate with a mutant endoglycoceramidase having a modified nucleophilic carboxylate residue (i.e., Glu or Asp), wherein the nucleophilic Glu/Asp resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54 or motif E) of a corresponding wild-type endoglycoceramidase, under conditions wherein the endoglycoceramidase catalyzes the transfer of a saccharide moiety from a donor substrate to an acceptor substrate, thereby producing the glycolipid or aglycone.

In a further aspect the invention provides expression vectors that comprise mutant endoglycoceramidase polynucleotide sequences; host cells that comprise the expression vectors, and methods of making the mutant endoglycoceramidase polypeptides described herein, by growing the host cells under conditions suitable for expression of the mutant endoglycoceramidase polypeptide.

Other objects, aspects and advantages of the invention will be apparent from the detailed description that follows.

Definitions

A "glycolipid" is a covalent conjugate between a glycosyl moiety and a substrate for a mutant endoglycoceramidase of the invention, such as an aglycone. An exemplary "glycolipid" is a covalent conjugate, between a glycosyl moiety and an aglycone, formed by a mutant endoglycoceramidase of the invention. The term "glycolipid" encompasses all glycosphingolipids, which are a group of amphipathic compounds that structurally consist of a sugar chain moiety (monosaccharide, oligosaccharide, or derivatives thereof) and an aglycone (i.e., a ceramide, a sphingosine, or a sphingosine analog). This term encompasses both cerebrosides and gangliosides. In certain embodiments, a glycolipid is an aglycone (non-carbohydrate alcohol (OH) or (SH)) conjugated to a non-reducing sugar and a non-glycoside.

An "aglycone," as referred to herein, is an acceptor substrate onto which a mutant endoglycoceramidase of the invention transfers glycosyl moiety from a glycosyl donor that is a substrate for said glycosyl donor. A glycosyl donor may be an activated or non-activated saccharide. An exemplary aglycone is a heteroalkyl moiety, which has the structure of, e.g., Formula Ia, Formula Ib or Formula II as shown below:

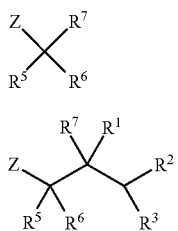

Formula Ia

Formula Ib

In Formula Ia and Formula Ib, the symbol Z represents OH, SH, or $NR^4R^{4'}$. $R^1$ and $R^2$ are members independently selected from $NHR^4$, $SR^4$, $OR^4$, $OCOR^4$, $OC(O)NHR^4$, $NHC(O)OR^4$, $OS(O)_2OR^4$, $C(O)R^4$, $NHC(O)R^4$, detectable labels, and targeting moieties. The symbols $R^3$, $R^4$ and $R^{4'}$, $R^5$, $R^6$ and $R^7$ each are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl.

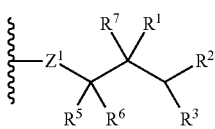

Formula II

In Formula II, $Z^1$ is a member selected from O, S, and $NR^4$; $R^1$ and $R^2$ are members independently selected from $NHR^4$, $SR^4$, $OR^4$, $OCOR^4$, $OC(O)NHR^4$, $NHC(O)OR^4$, $OS(O)_2OR^4$, $C(O)R^4$, $NHC(O)R^4$, detectable labels, and targeting moieties. The symbols $R^3$, $R^4$, $R^5$, $R^6$ and $R^7$ each are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl. Formula II is representative of certain embodiments wherein the aglycone portion is conjugated to a further substrate component, for example, a leaving group or a solid support.

The following abbreviations are used herein:
Ara=arabinosyl;
Cer=ceramide
Fm=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (N-acetylneuraminyl).

The term "sialic acid" or "sialic acid moiety" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as NeuSAc, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-NeuSAc like 9-O-lactyl-Neu5Ac or 9-O-acetyl-Neu5Ac, 9-deoxy-9-fluoro-NeuSAc and 9-azido-9-deoxy-NeuSAc. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

The term "ceramide," as used herein, encompasses all ceramides and sphingosine as conventionally defined. See, for example, Berg, et al, *Biochemistry,* 2002, 5th ed., W.H. Freeman and Co.

The term "sphingosine analog" refers to lipid moieties that are chemically similar to sphingosine, but are modified at the polar head and/or the hydrophobic carbon chain. Sphingolipid analog moieties useful as acceptor substrates in the present methods include, but are not limited to, those described in co-pending patent applications PCT/US2004/006904 (which claims priority to U.S. Provisional Patent Application No. 60/452,796); U.S. patent application Ser. No. 10/487,841; U.S. patent application Ser. Nos. 10/485,892; 10/485,195, and 60/626,678, the disclosures of each of which are hereby incorporated herein by reference in their entirety for all purposes.

In general, the sphingosine analogs described in the above-referenced applications are those compounds having the formula:

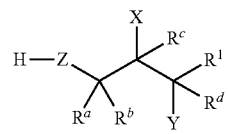

Formula III wherein Z is a member selected from O, S, $C(R^2)_2$ and $NR^2$; X is a member selected from H, —$OR^3$, —$NR^3R^4$, —$SR^3$, and —$CHR^3R^4$; $R^1$, $R^2$, $R^3$ and $R^4$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, —C(=M)$R^5$, —C(=M)-$Z^1$—$R^5$, —$SO_2R^5$, and —$SO_3$; wherein M and $Z^1$ are members independently selected from O, $NR^6$ or S; Y is a member selected from H, —$OR^7$, —$SR^7$, —$NR^7R^8$, substituted or unsubstituted alkyl, substituted or unsubstituted heteroalkyl, substituted or unsubstituted aryl, substituted or unsubstituted heteroaryl, and substituted or unsubstituted heterocycloalkyl, wherein $R^5$, $R^6$, $R^7$ and $R^8$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl; and $R^a$, $R^b$, $R^c$ and $R^d$ are each independently H, substituted or unsubstituted alkyl, substituted or unsubstituted heteroalkyl, substituted or unsubstituted aryl, substituted or unsubstituted heteroaryl, substituted or unsubstituted heterocycloalkyl.

An "acceptor substrate" for a wild-type endoglycoceramidase or a mutant endoglycoceramidase, is any aglycone moiety that can act as an acceptor for a particular endoglycoceramidase. When the acceptor substrate is contacted with the corresponding endoglycoceramidase and sugar donor substrate, and other necessary reaction mixture components, and the reaction mixture is incubated for a sufficient period of time, the endoglycoceramidase transfers sugar residues from the sugar donor substrate to the acceptor substrate. The acceptor substrate can vary for different types of a particular endoglycoceramidase. Accordingly, the term "acceptor substrate" is taken in context with the particular endoglycoceramidase or mutant endoglycoceramidase of interest for a particular application. Acceptor substrates for endoglycoceramidases and mutant endoglycoceramidases are described herein.

A "donor substrate" for wild-type and mutant endoglycoceramidases includes any activated glycosyl derivatives of anomeric configuration opposite the natural glycosidic linkage. The enzymes of the invention are used to couple α-modified or β-modified glycosyl donors, usually α-modified glycosyl donors, with glycoside acceptors. Preferred donor molecules are glycosyl fluorides, although donors with other groups which are reasonably small and which function as relatively good leaving groups can also be used. Examples of other glycosyl donor molecules include glycosyl chlorides, bromides, acetates, mesylates, propionates, pivaloates, and glycosyl molecules modified with substituted phenols. Among the α-modified or β-modified glycosyl donors, α-galactosyl, α-mannosyl, α-glucosyl, α-fucosyl, α-xylosyl, α-sialyl, α-N-acetylglucosaminyl, α-N-acetylgalactosaminyl, β-galactosyl, β-mannosyl, β-glucosyl, β-fucosyl, β-xylosyl, β-sialyl, β-N-acetylglucosaminyl and β-N-acetylgalactosaminyl are most preferred. The donor molecules can be monosaccharides, or may themselves contain multiple sugar moieties (oligosaccharides). Donor substrates of use in the particular methods include those described in U.S. Pat. Nos. 6,284,494; 6,204,029; 5,952,203; and 5,716,812, the disclosures of which are hereby incorporated herein by reference in their entirety for all purposes.

The term "contacting" is used herein interchangeably with the following: combined with, added to, mixed with, passed over, incubated with, flowed over, etc.

"Endoglycoceramidase," as used herein, refers to an enzyme that in its native or wild-type version has a primary activity of cleaving the glycosidic linkage between a monosaccharide or an oligosaccharide and a ceramide (or sphingosine) of an acidic or neutral glycolipid, producing intact monosaccharide or oligosaccharide and ceramide (Registry number: EC 3.2.1.123). The wild-type version of this enzyme may also have a secondary activity of catalyzing the formation of the glycosidic linkage between a monosaccharide or oligosaccharide and an aglycone (i.e., a ceramide or a sphingosine) to form various glycolipids. Wild-type endoglycoceramidases have at least two identifiable conserved motifs, including an acid-base region (Val-$X_1$-(Ala/Gly)-(Tyr/Phe)-(Asp/Glu)-(Leu/Ile)-$X_2$-Asn-Glu-Pro-$X_3$-$X_4$-Gly or motif B or SEQ ID NO:51), and a nucleophilic region ((Ile/Met/Leu/Phe/Val)-(Leu/Met/Ile/Val)-(Gly/Ser/Thr)-Glu-(Phe/Thr/Met/Leu)-(Gly/Leu/Phe or motif D or SEQ ID NO:53).

The terms "mutated" or "modified" as used in the context of altering the structure or enzymatic activity of a wild-type endoglycoceramidase, refers to the deletion, insertion, or substitution of any nucleotide or amino acid residue, by chemical, enzymatic, or any other means, in a polynucleotide sequence encoding an endoglycoceramidase or the amino acid sequence of a wild-type endoglycoceramidase, respectively, such that the amino acid sequence of the resulting endoglycoceramidase is altered at one or more amino acid residues. The site for such an activity-altering mutation may be located anywhere in the enzyme, including within the active site of the endoglycoceramidase, particularly involving the glutamic acid residue of the Asn-Glu-Pro subsequence of the acid-base sequence region. An artisan of ordinary skill will readily locate this Glu residue, for example, at position 233 in SEQ ID NO:3 and at position 224 in SEQ ID NO:6. Other examples of Glu residues that, once mutated, can alter the enzymatic activity of an endoglycoceramidase include a carboxylate (i.e., Glu or Asp) nucleophilic Glu/Asp residue (bolded) in the (Ile/Met/Leu/Phe/Val)-(Leu/Met/Ile/Val)-(Gly/Ser/Thr)-Glu/Asp-(Phe/Thr/Met/Leu)-(Gly/Leu/Phe) motif of a corresponding wild-type endoglycoceramidase.

A "mutant endoglycoceramidase" or "modified endoglycoceramidase" of this invention thus comprises at least one mutated or modified amino acid residue. On the other hand, the wild-type endoglycoceramidase whose coding sequence is modified to generate a mutant endoglycoceramidase is referred to in this application as "the corresponding native or wild-type endoglycoceramidase." One exemplary mutant endoglycoceramidase of the invention includes the deletion or substitution of a nucleophilic carboxylate Glu/Asp residue (bolded) in the (Ile/Met/Leu/Phe/Val)-(Leu/Met/Ile/Val)-(Gly/Ser/Thr)-Glu/Asp-(Phe/Thr/Met/Leu)-(Gly/Leu/Phe) motif of a corresponding wild-type endoglycoceramidase. One exemplary mutant endoglycoceramidase of the invention includes a mutation within the active site, e.g., the deletion or substitution of the Glu residue within the Asn-Glu-Pro subsequence of the acid-base sequence region. The mutant endoglycoceramidase exhibits an altered enzymatic activity, e.g., an enhanced glycolipid synthetic activity, in comparison with its wild-type counterpart. A mutant endoglycoceramidase that has demonstrated an increased glycolipid synthetic activity is also called an "endoglycoceramide synthase."

The term "acid-base sequence region" refers to a conserved Val-$X_1$-(Ala/Gly)-(Tyr/Phe)-(Asp/Glu)-(Leu/Ile)-$X_2$-Asn-Glu-Pro-$X_3$—$X_4$-Gly sequence (SEQ ID NO:51) in a corresponding wild-type endoglycoceramidase which includes a conserved Asn-Glu-Pro subsequence. The acid-base glutamic acid residue is located within the conserved Asn-Glu-Pro subsequence, for example, at position 233 in *Rhodococcus* sp. M-777; position 224 in *Rhodococcus* sp. C9; position 229 in *Propionibacterium acnes* EGCa; position 248 in *Propionibacterium acnes* EGCb; position 238 in *Cyanea nozakii*; at position 229 in *Hydra magnipapillata*; at postion 234 in *Dictyostelium*; at position 214 in *Schistosoma*; at position 241 in *Leptospira interrogans*; at position 272 of *Streptomyces*; and at position 247 of *Neurosporassa* (see, FIG. 15). The conserved sequence encoding a three-amino acid segment Asn-Glu-Pro was previously identified within the active site of endoglycoceramidases, and the Glu residue within the segment was thought to be connected to the hydrolytic activity of the endoglycoceramidase (Sakaguchi et al., *Biochem. Biophys. Res. Commun.*, 1999, 260: 89-93).

The term "nucleophilic residue" or "nucleophilic motif" refers to the carboxylate amino acid residue within the (Ile/Met/Leu/Phe/Val)-(Leu/Met/Ile/Val)-(Gly/Ser/Thr)-(Asp/Glu)-(Phe/Thr/Met/Leu)-(Gly/Leu/Phe) motif (SEQ ID NO:54) of a corresponding wild-type endoglycoceramidase. The nucleophilic residue can be a glutamate or an aspartate, usually a glutamate. A nucleophilic glutamic acid residue is located, for example, at position 351 in *Rhodococcus* sp. M-777; position 343 in *Rhodococcus* sp. C9; position 342 in *Propionibacterium acnes* EGCa; position 360 in *Propionibacterium acnes* EGCb; position 361 in *Cyanea nozakii*; and at position 349 in *Hydra magnipapillata*; at postion 354 in *Dictyostelium*; at position 351 in *Schistosoma*; at position 461 in *Leptospira interrogans*; at position 391of *Streptomyces*; and at position 498 of *Neurosporassa* (see, FIG. 15).

The recombinant fusion proteins of the invention can be constructed and expressed as a fusion protein with a molecular "purification tag" at one end, which facilitates purification of the protein. Such tags can also be used for immobilization of a protein of interest during the glycolipid synthesis reaction. Exemplified purification tags include MalE, 6 or more sequential histidine residues, cellulose binding protein, maltose binding protein (malE), glutathione S-transferase (GST), lactoferrin, and Sumo fusion protein cleavable sequences (commercially available from LifeSensors, Malvern, Pa. and EMD Biosciences). Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys or a substantially identical variant thereof. Other epitope tags that can be used in the invention include, e.g., myc tag, AU1, AUS, DDDDK (EC5), E tag, E2 tag, Glu-Glu, a 6 residue peptide, EYMPME, derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatureal amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic aminoacids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

A "heterologous polynucleotide," "heterologous nucleic acid", or "heterologous polypeptide," as used herein, is one that originates from a source foreign to the particular host cell, or, if from the same source, is modified from its original form. Thus, a heterologous endoglycoceramidase gene in a prokaryotic host cell includes a endoglycoceramidase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, for example over a region of at least about 25, 50, 75, 100, 150, 200, 250, 500, 1000, or more nucleic acids or amino acids, up to the full length sequence, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The phrase "stringent hybridization conditions" refers to conditions under which a nucleic acid will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes, "Overview of principles of hybridization and the strategy of nucleic acid assays"* (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short nucleic acid sequences (e.g., 10 to 50 nucleotides) and at least about 60° C. for long nucleic acid sequences (e.g., greater than 50 nucleotides). Stringent conditions may also be achieved with the addition of destabilizing agents such as formamide. For selective or specific hybridization, a positive signal is at least two times background, preferably 10 times background hybridization. Exemplary "highly stringent" hybridization conditions include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary "moderately stringent hybridization conditions" include a hybridization in a buffer of 40% formamide, 1 M NaCl, and 1% SDS at 37° C., and a wash in 1×SSC at 45° C.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and those derivatives of alkyl defined in more detail below, such as "heteroalkyl." Alkyl groups, which are limited to hydrocarbon groups, are termed "homoalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written.

Each of the above terms (e.g., "alkyl" and "heteroalkyl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Similar to the substituents described for the alkyl radical, substituents for the aryl and heteroaryl groups are varied and are selected from, for example: halogen, OR', —NR'R", —SR', -halogen, —SiR'R"R"', OC(O)R', —C(O)R', CO$_2$R', —CONR'R", —OC(O)NR'R", —NR"C(O)R', NR'C(O)NR"R"', —NR"C(O)$_2$R', NR—C(NR'R"R"')=NR"", NR C(NR'R")=NR"', —S(O)R', —S(O)$_2$R', —S(O)$_2$NR'R", NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 40. Alternatively, two of the substituents on adjacent atoms of the aryl or heteroaryl ring may optionally be replaced with a substituent of the formula -A(CH$_2$)$_r$B—, wherein A and B are independently —CRR'—, —O—, —NR—, —S—, —S(O)—, S(O)$_2$, —S(O)2NR'— or a single bond, and r is an integer of from 1 to 40. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 40, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_{40}$)alkyl.

The term "detectable label" refers to a moiety renders a molecule to which it is attached to detectable by a variety of mechanisms including chemical, enzymatic, immunological, or radiological means. Some examples of detectable labels include fluorescent molecules (such as fluorescein, rhodamine, Texas Red, and phycoerythrin) and enzyme molecules (such as horseradish peroxidase, alkaline phosphatase, and β-galactosidase) that allow detection based on fluorescence emission or a product of a chemical reaction catalyzed by the enzyme. Radioactive labels involving various isotopes, such as $^3$H, $^{125}$I, $^{35}$S, $^{14}$C, or $^{32}$P, can also be attached to appropriate molecules to enable detection by any suitable methods that registers radioactivity, such as autoradiography. See, e.g., Tijssen, "*Practice and Theory of Enzyme Immunoassays,*" *Laboratory Techniques in Biochemistry and Molecular Biology*, Burdon and van Knippenberg Eds., Elsevier (1985), pp. 9-20. An introduction to labels, labeling procedures, and detection of labels can also be found in Polak and Van Noorden, *Introduction to Immu-* nocytochemistry, 2d Ed., Springer Verlag, N.Y. (1997); and in Haugland, *Handbook of Fluorescent Probes and Research Chemicals*, a combined handbook and catalogue published by Molecular Probes, Inc. (1996).

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO, saccharides, lectins, receptors, ligand for receptors, proteins such as BSA and the like. The targeting group can also be a small molecule, a term that is intended to include both non-peptides and peptides.

The symbol ∼∼∼ whether utilized as a bond or displayed perpendicular to a bond indicates the point at which the displayed moiety is attached to the remainder of the molecule, solid support, etc.

The term "increase," as used herein, refers to a detectable positive change in quantity of a parameter when compared to a standard. The level of this positive change, for example, in the synthetic activity of a mutant endoglycoceramidase from its corresponding wild-type endoglycoceramidase, is preferably at least 10% or 20%, and more preferably at least 30%, 40%, 50%, 60% or 80%, and most preferably at least 100%.

The term "reduce" or "decrease" is defined as a detectable negative change in quantity of a parameter when compared to a standard. The level of this negative change, for example, in the hydrolytic activity of a mutant endoglycoceramidase from its corresponding wild-type endoglycoceramidase, is preferably at least 10% or 20%, and more preferably at least 30%, 40%, 50%, 60%, 80%, 90%, and most preferably at least 100%.

BRIEF DESCRIPTION OF THE DRAWINGS

FIG. 5 sets forth compounds that can be made using the enzyme of the invention.

FIGS. 12A-12C set forth compounds that can be made using the enzyme of the invention.

FIGS. 15A-15C illustrate an amino acid sequence alignment of wild-type endoglycoceramidases from *Rhodococcus, Propionibacterium, Cyanea,* and *Hydra.*

DETAILED DESCRIPTION

Introduction

Figure 1A:
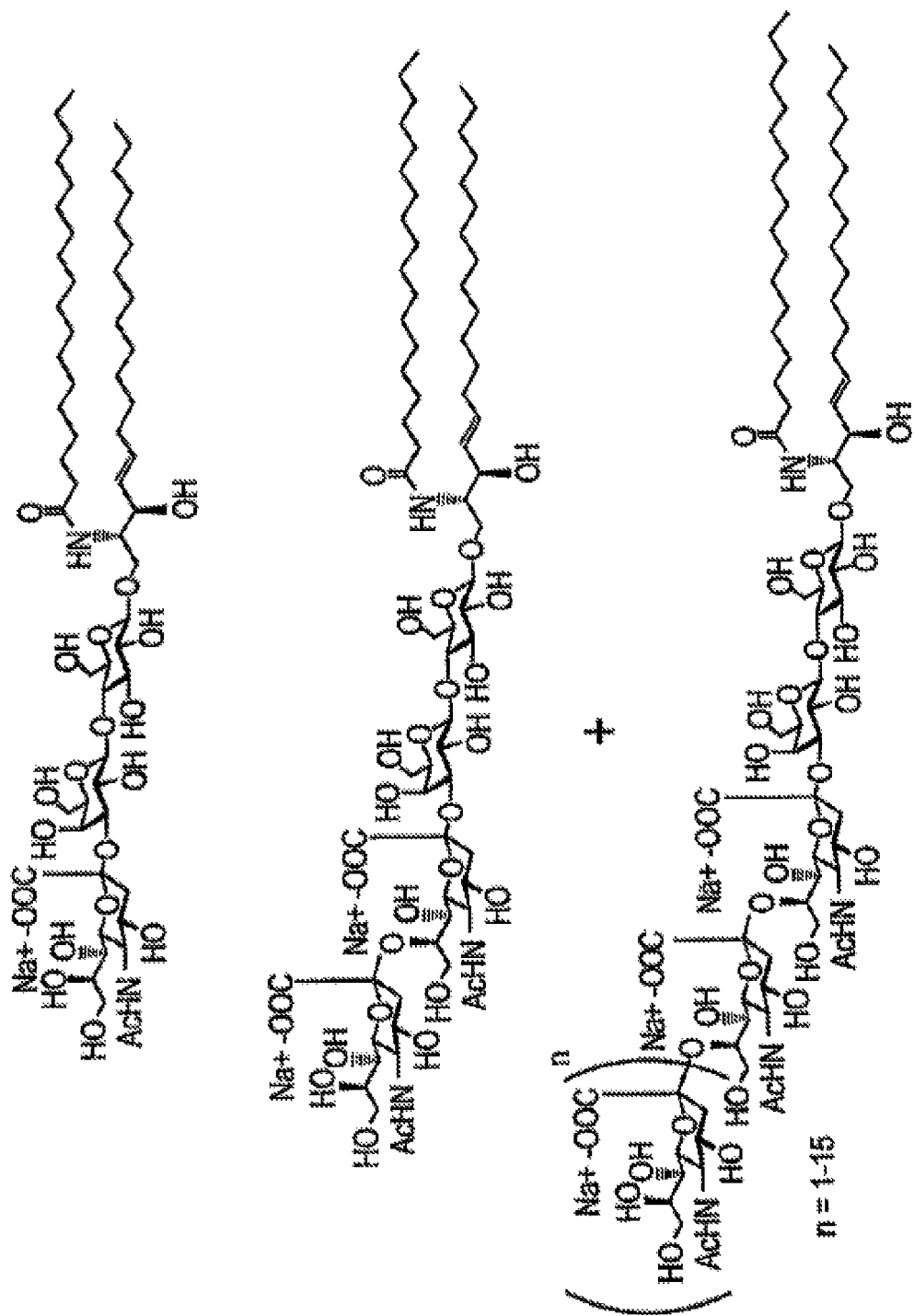
FIGS. 1A-1B set forth compounds that can be made using the enzyme of the invention.
Figure 1B:
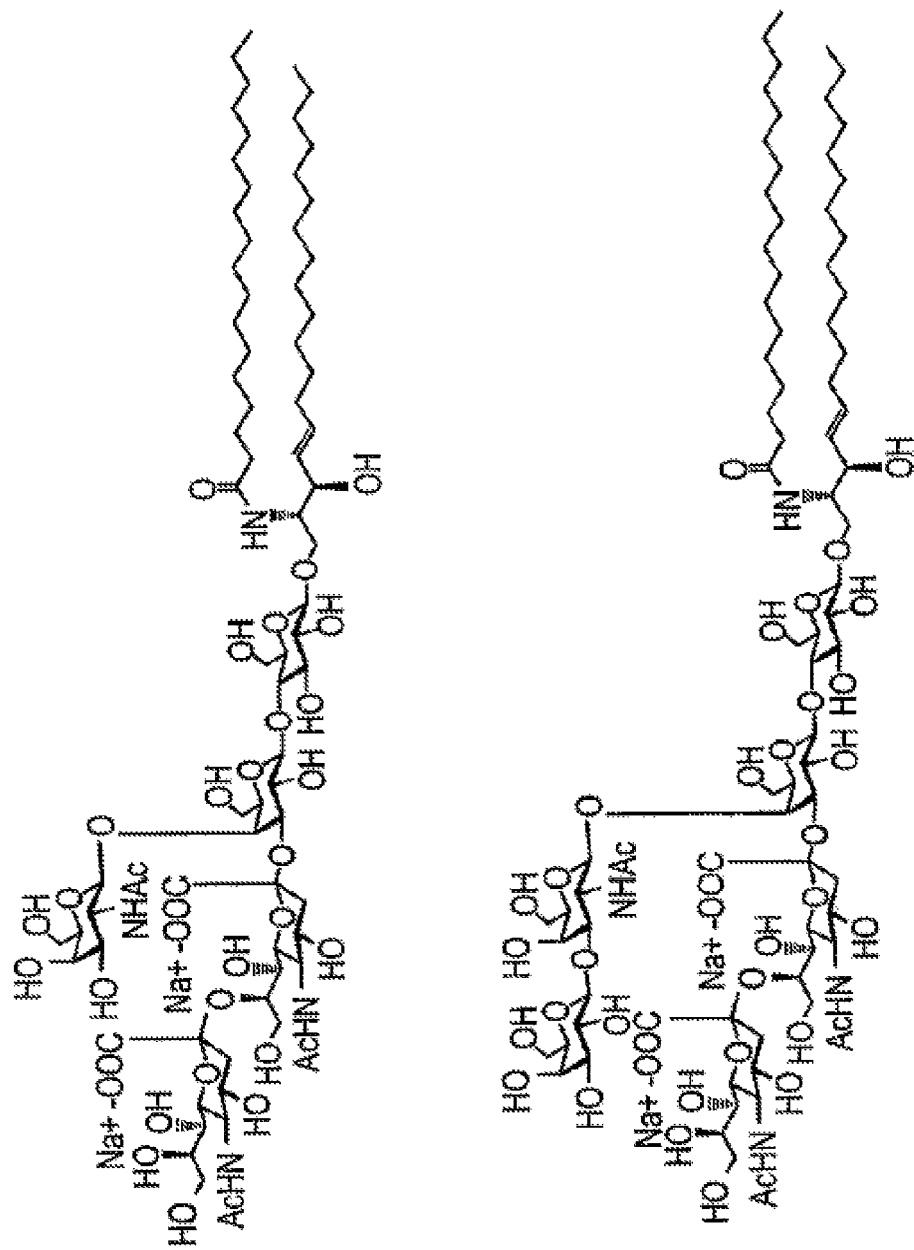
Figure 2:
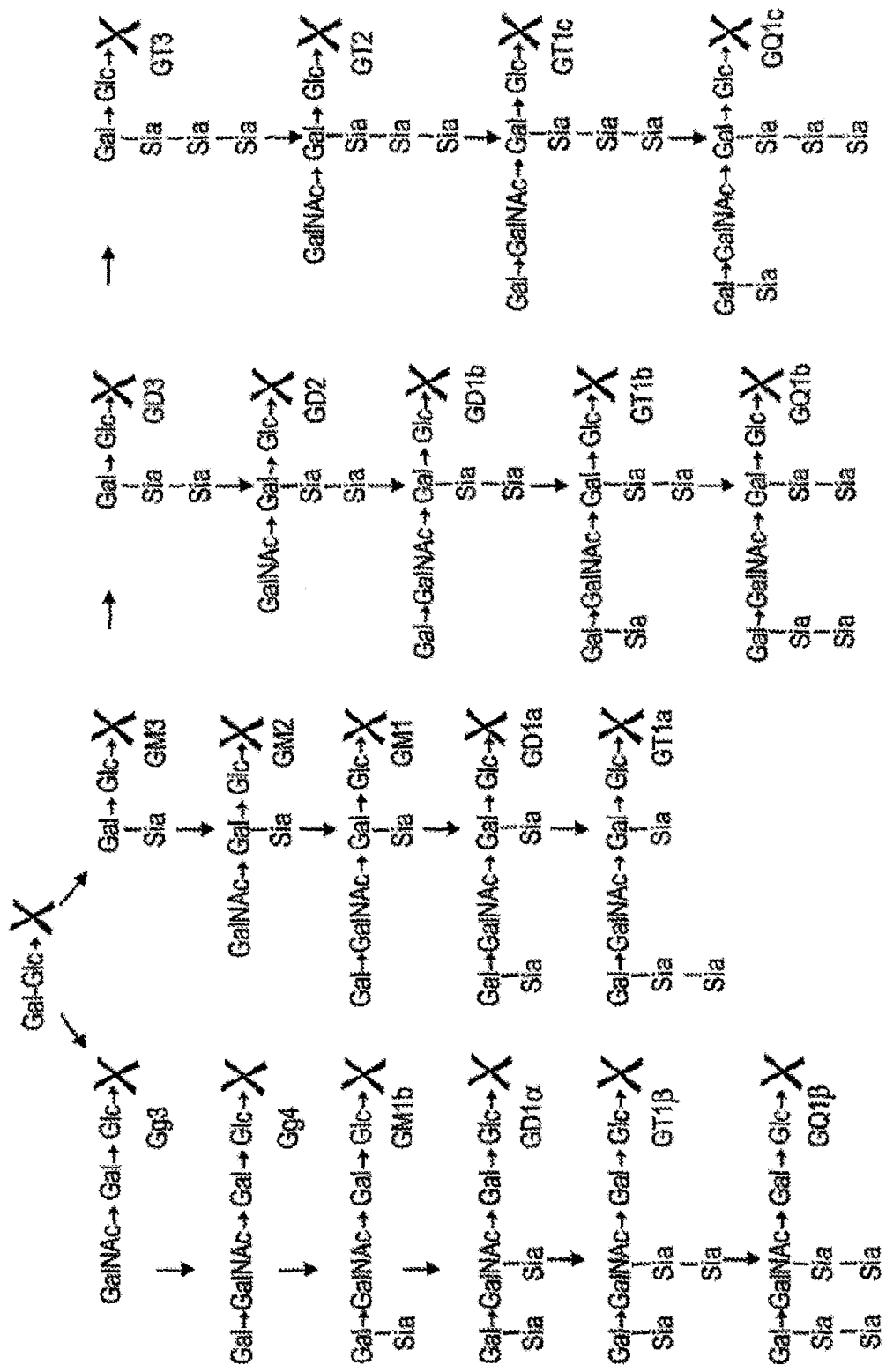
FIG. 2 sets forth compounds that can be made using the enzyme of the invention.
Figure 3A:
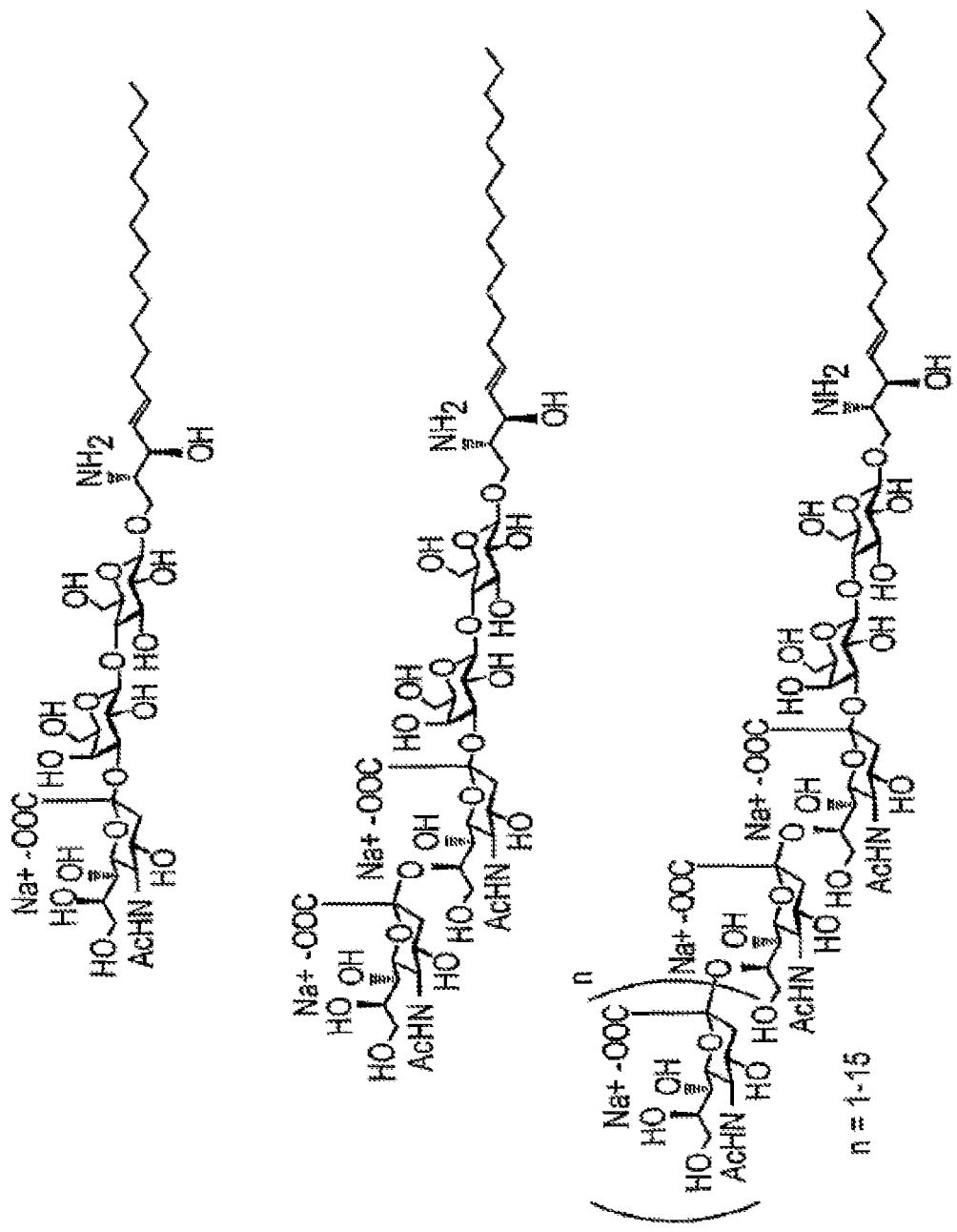
FIGS. 3A-3B set forth compounds that can be made using the enzyme of the invention.
Figure 3B:
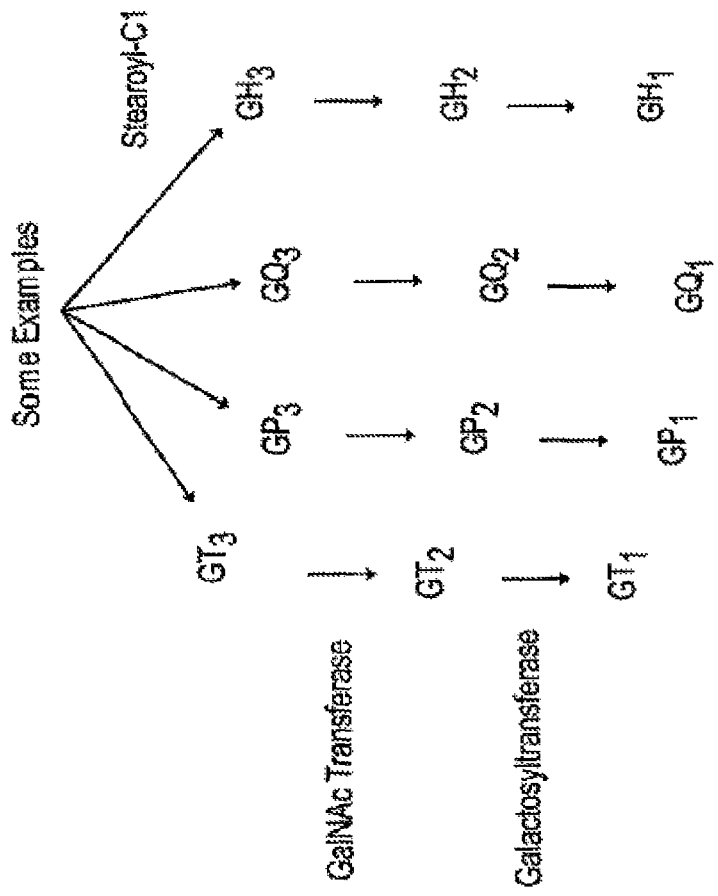
Figure 4:
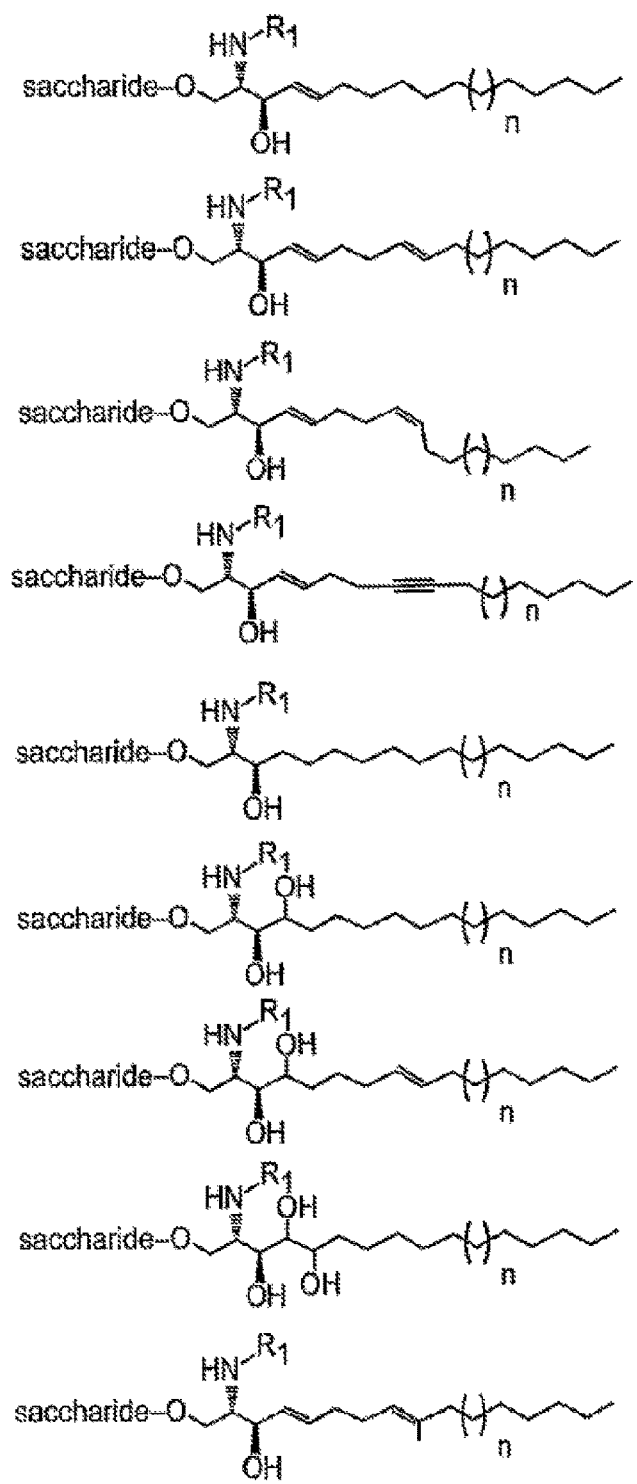
FIG. 4 sets forth compounds that can be made using the enzyme of the invention.
Figure 6:
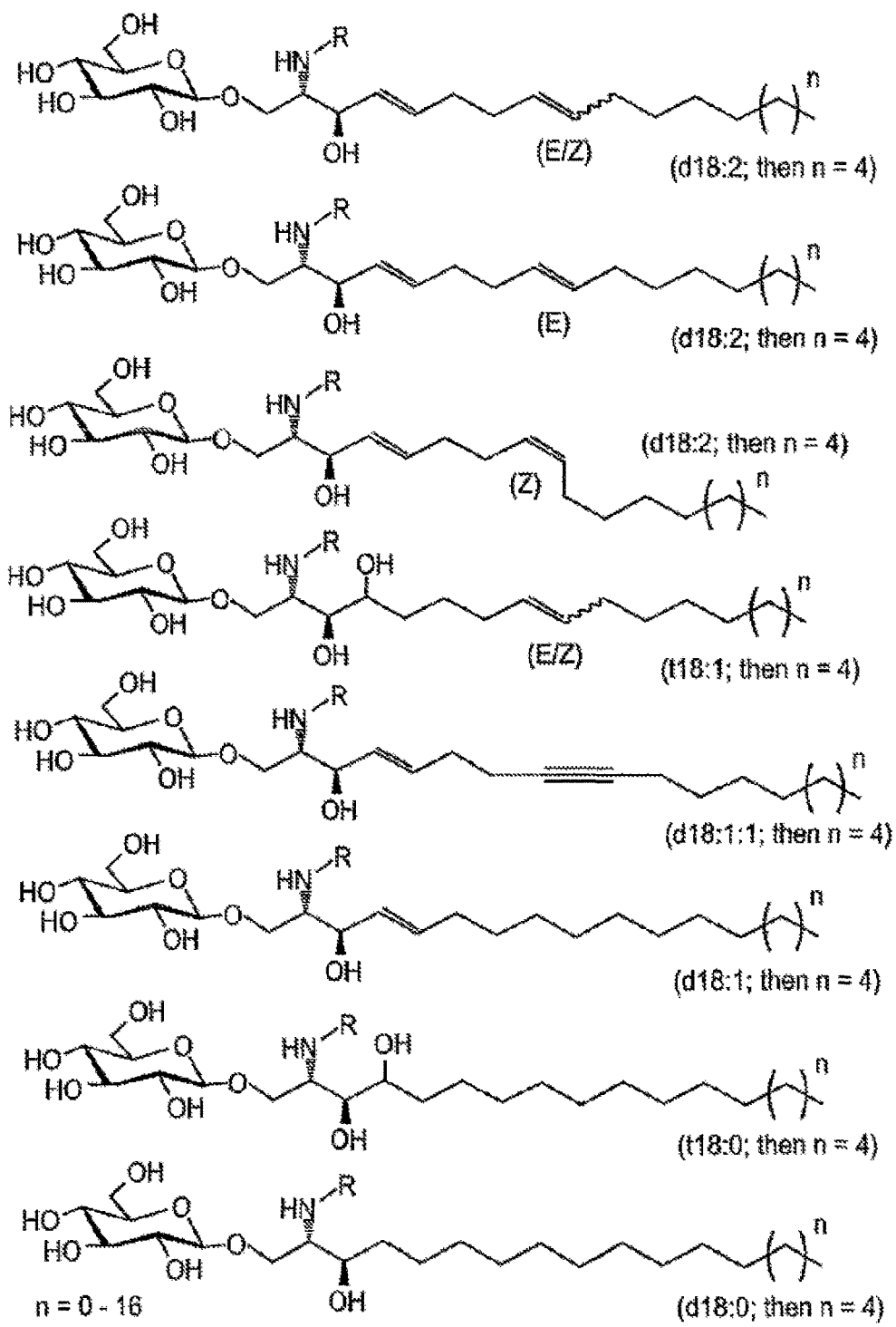
FIG. 6 sets forth compounds that can be made using the enzyme of the invention.
Figure 7:
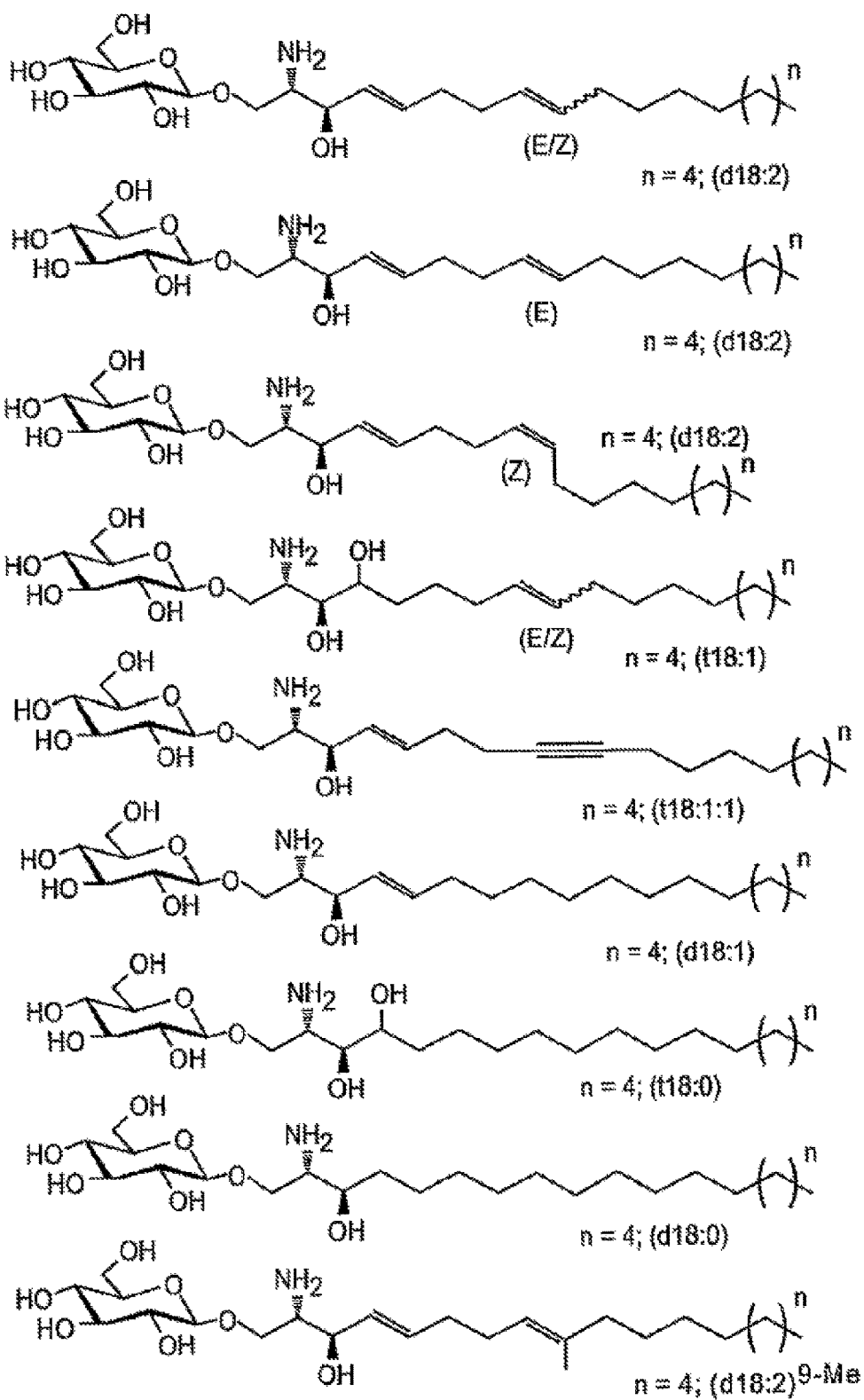
FIG. 7 sets forth compounds that can be made using the enzyme of the invention.
Figure 8A:
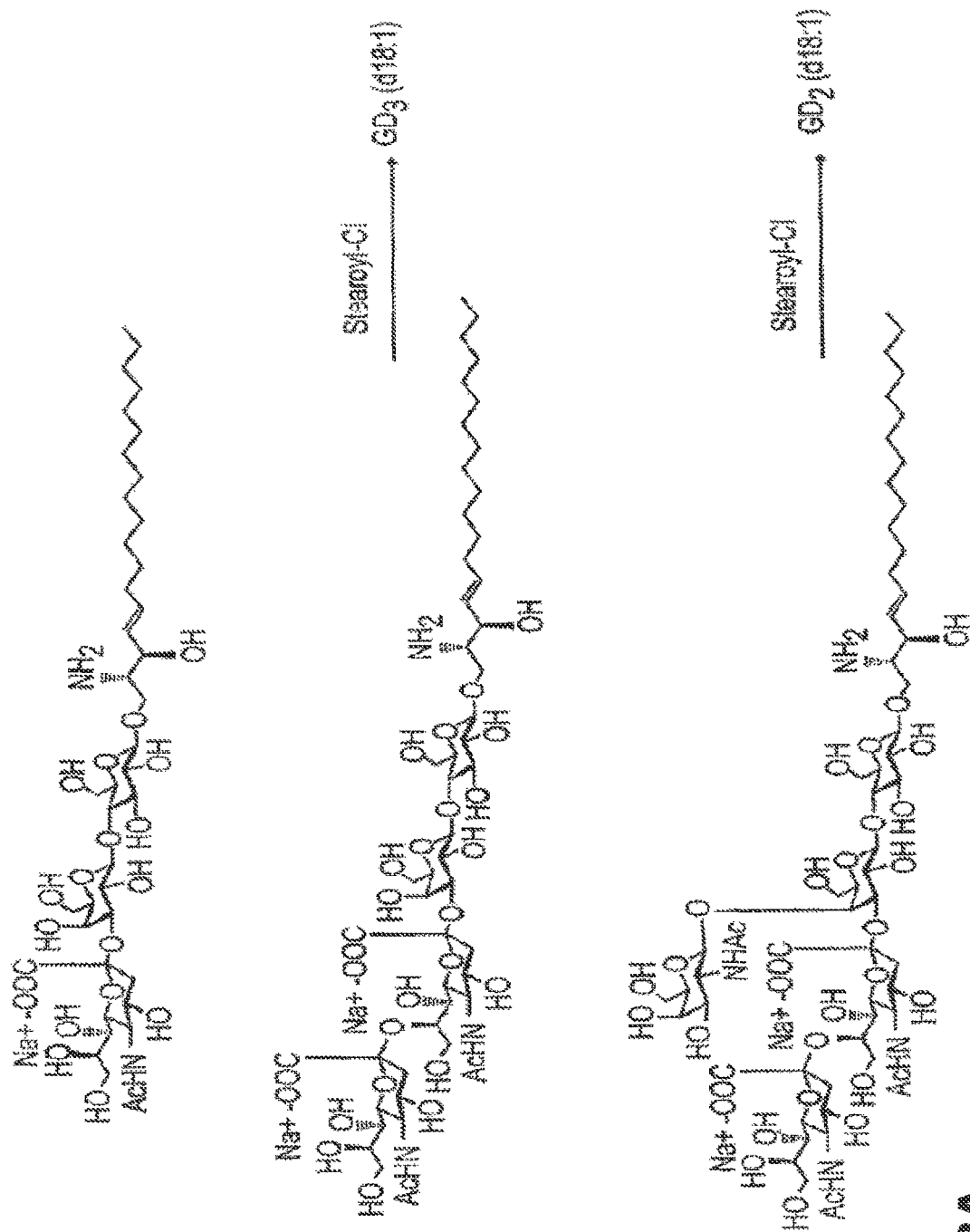
FIGS. 8A-8B set forth compounds that can be made using the enzyme of the invention.
Figure 8B:
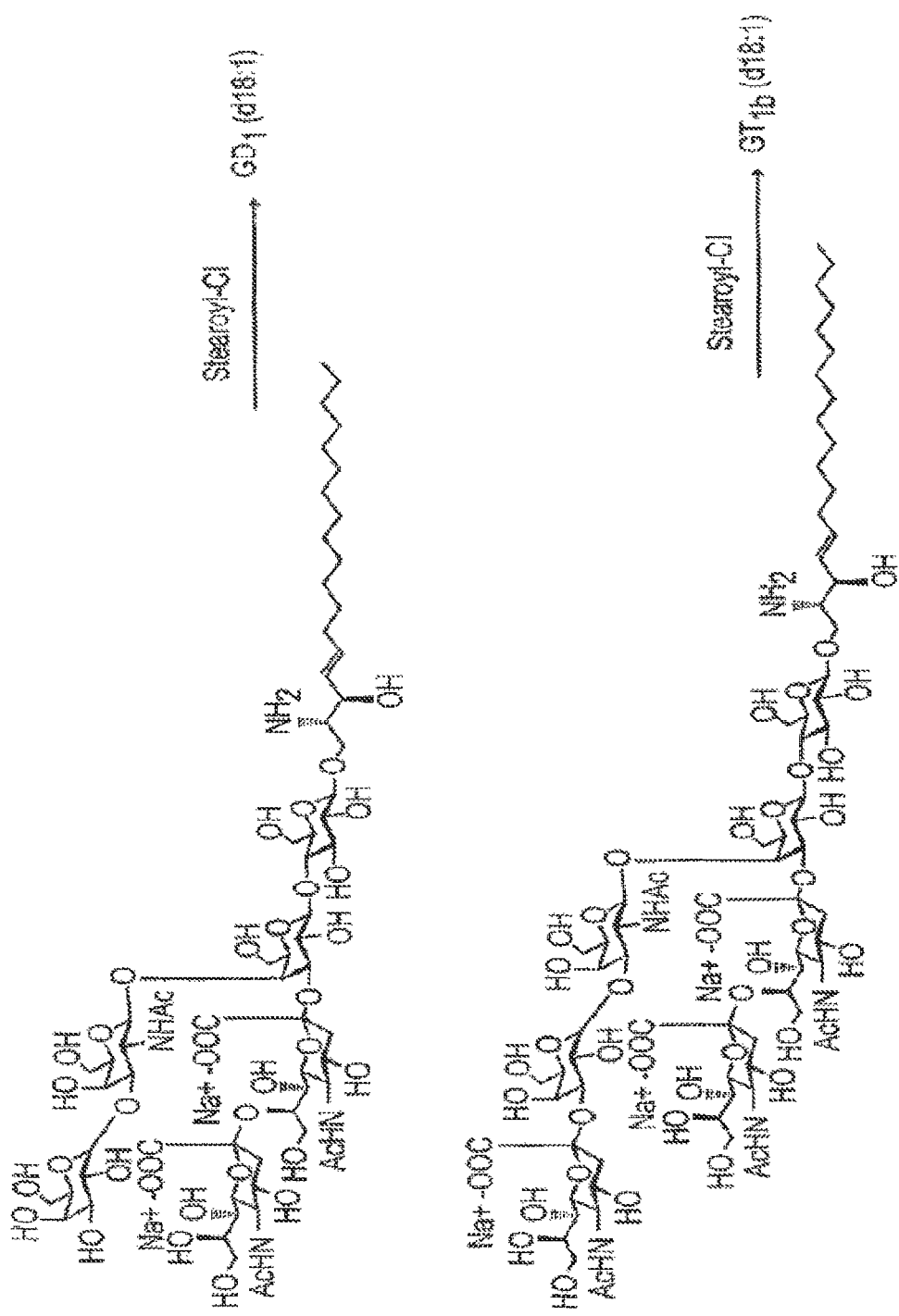
Figure 9:
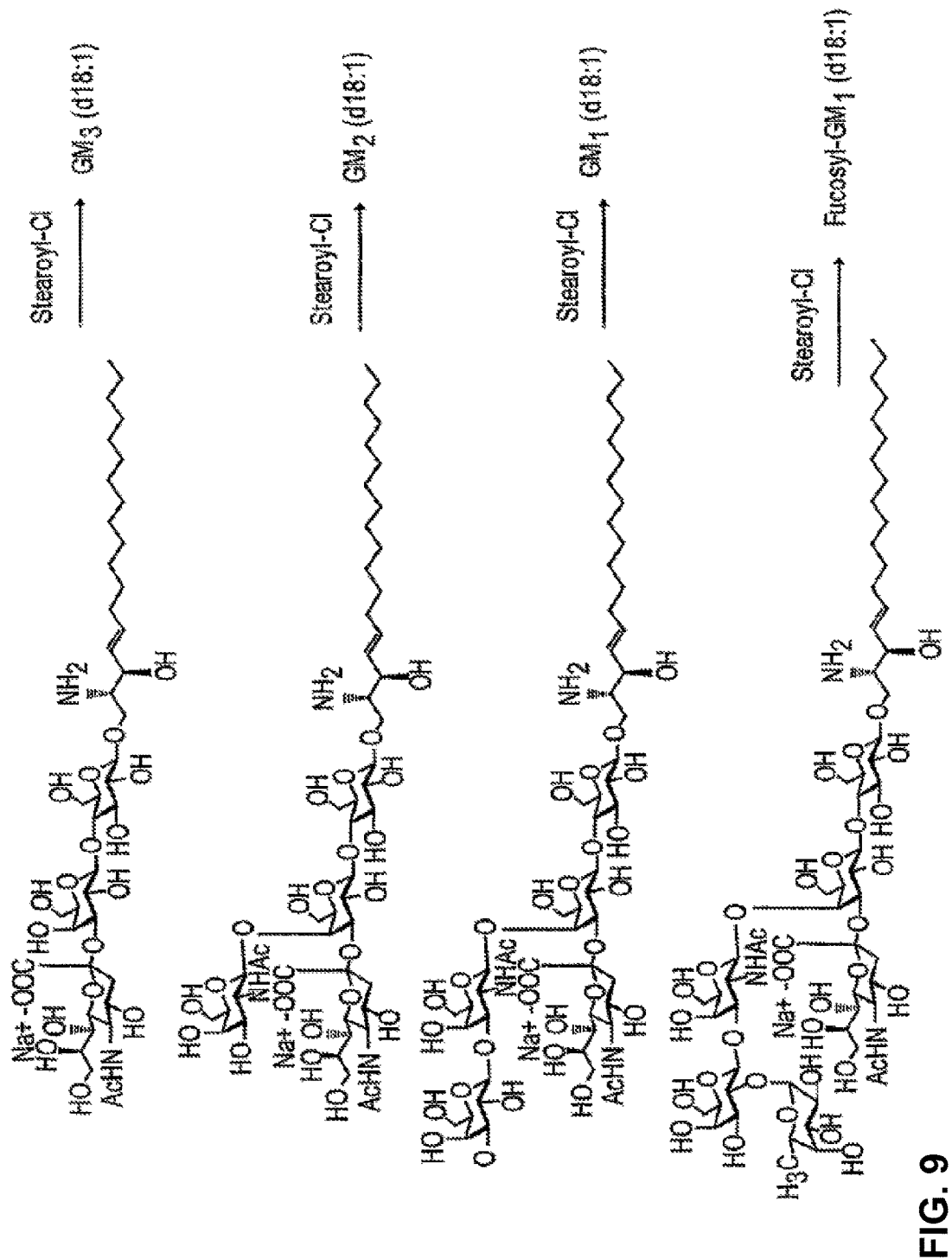
FIG. 9 sets forth compounds that can be made using the enzyme of the invention.
Figure 10A:
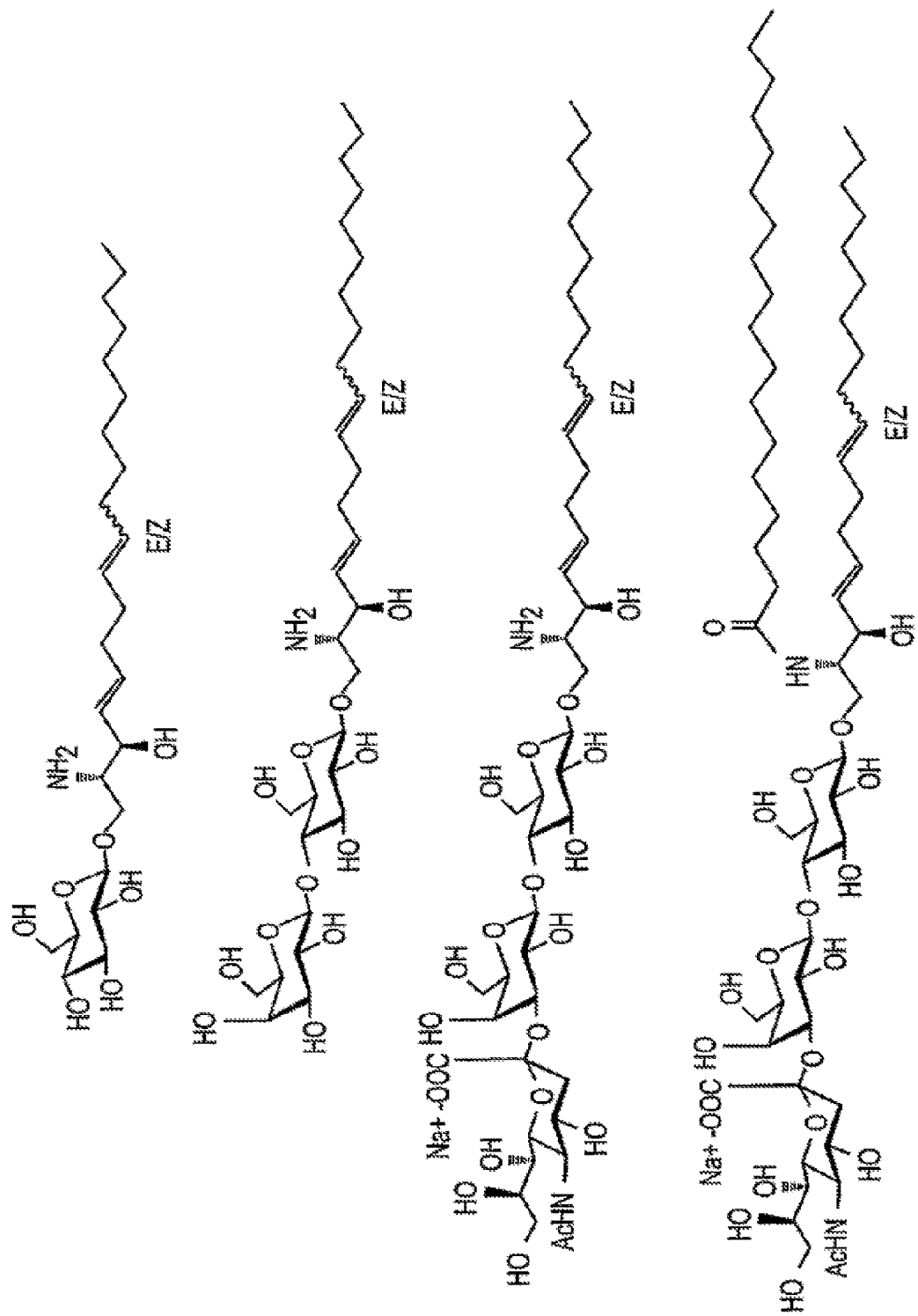
FIGS. 10A-10B set forth compounds that can be made using the enzyme of the invention.
Figure 10B:
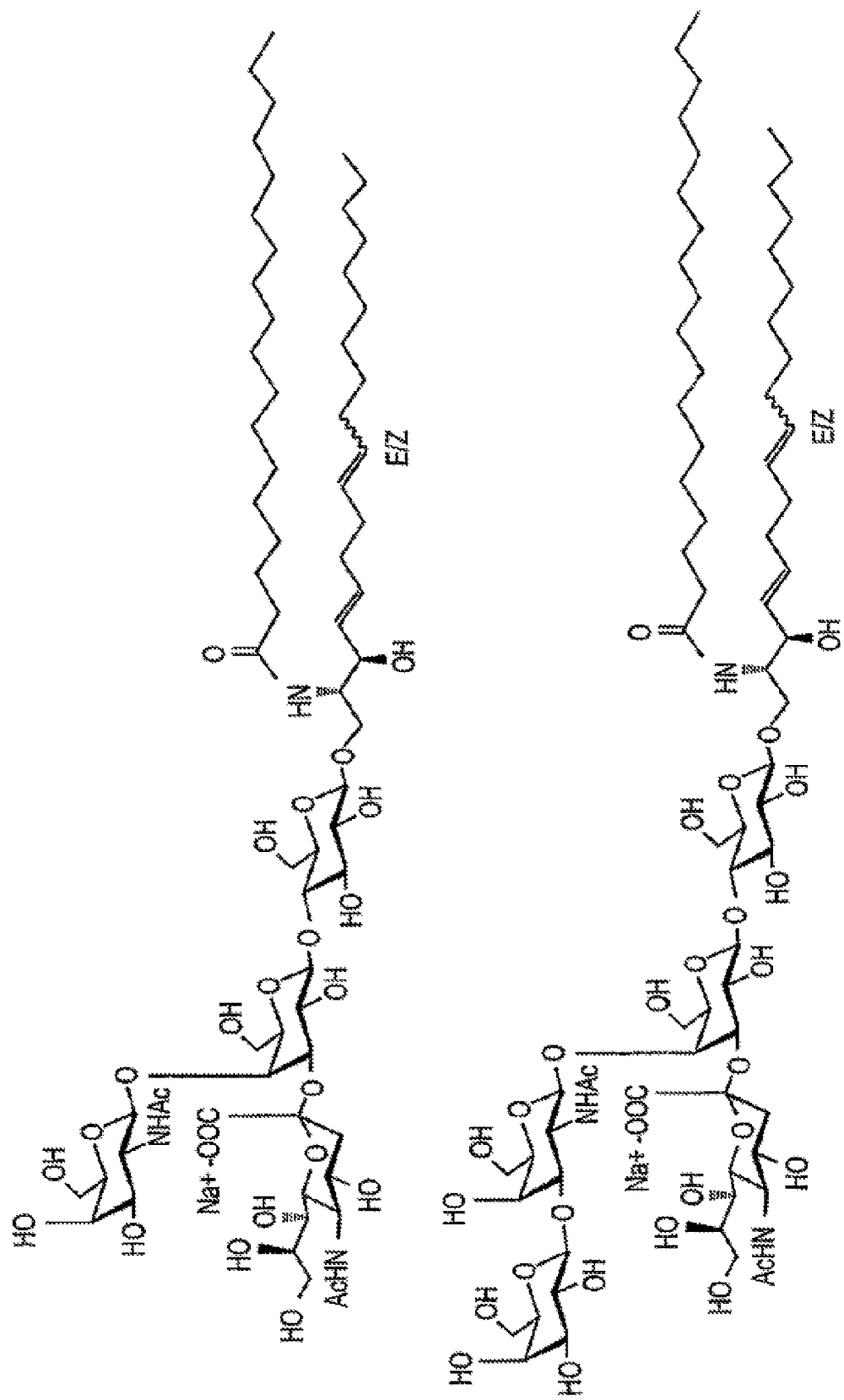
Figure 11:
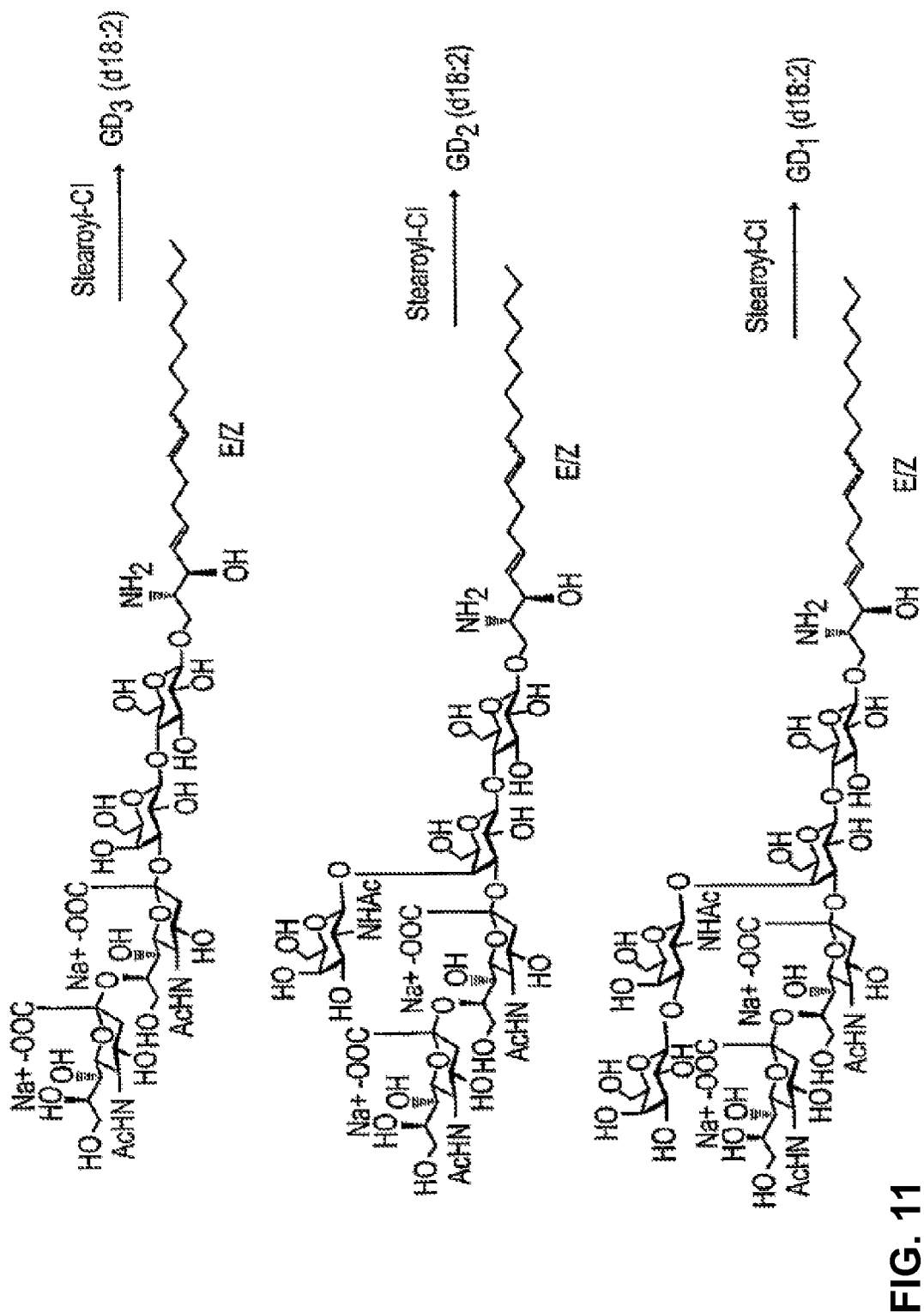
FIG. 11 sets forth compounds that can be made using the enzyme of the invention.
Figure 12A:
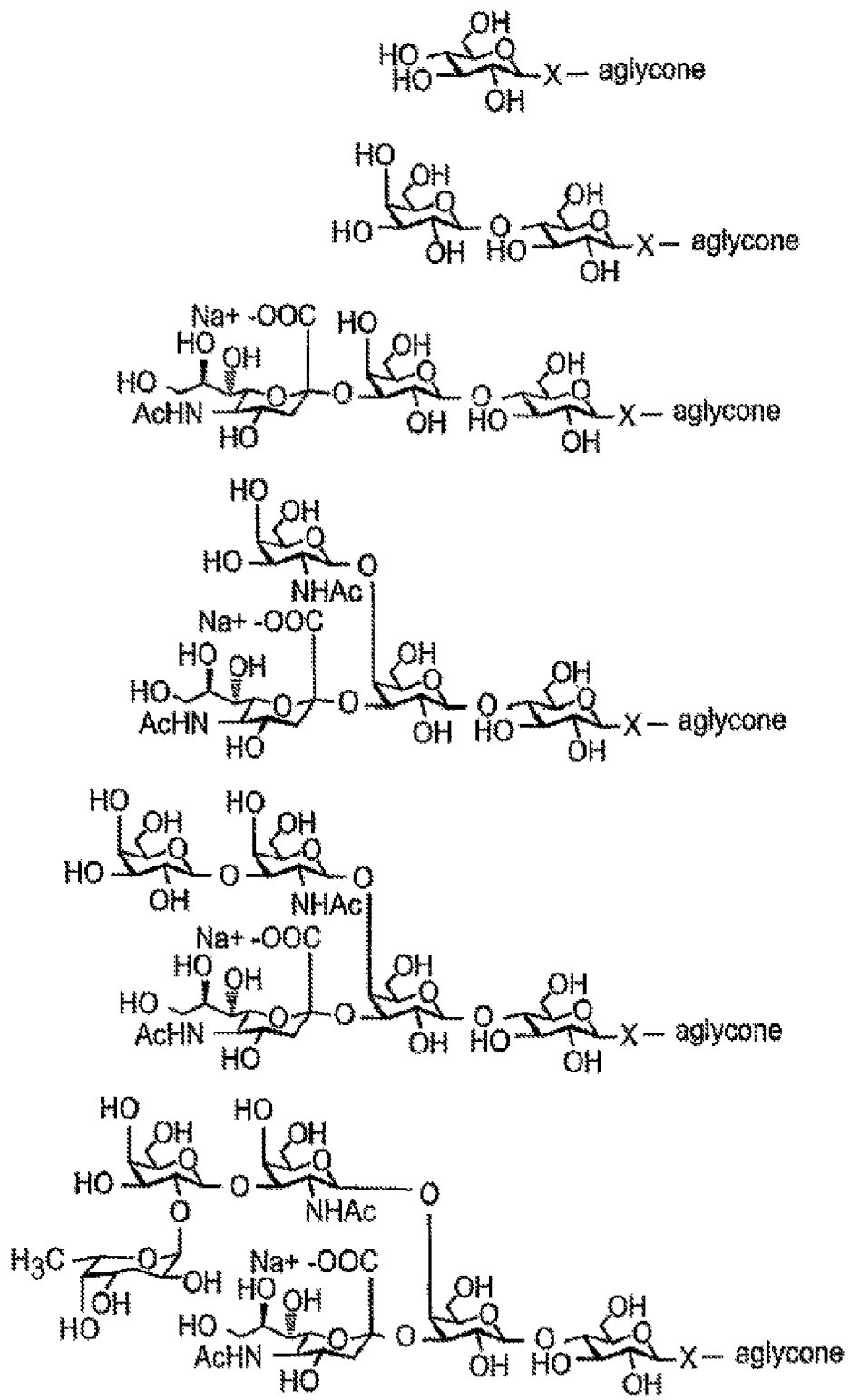
Figure 12B:
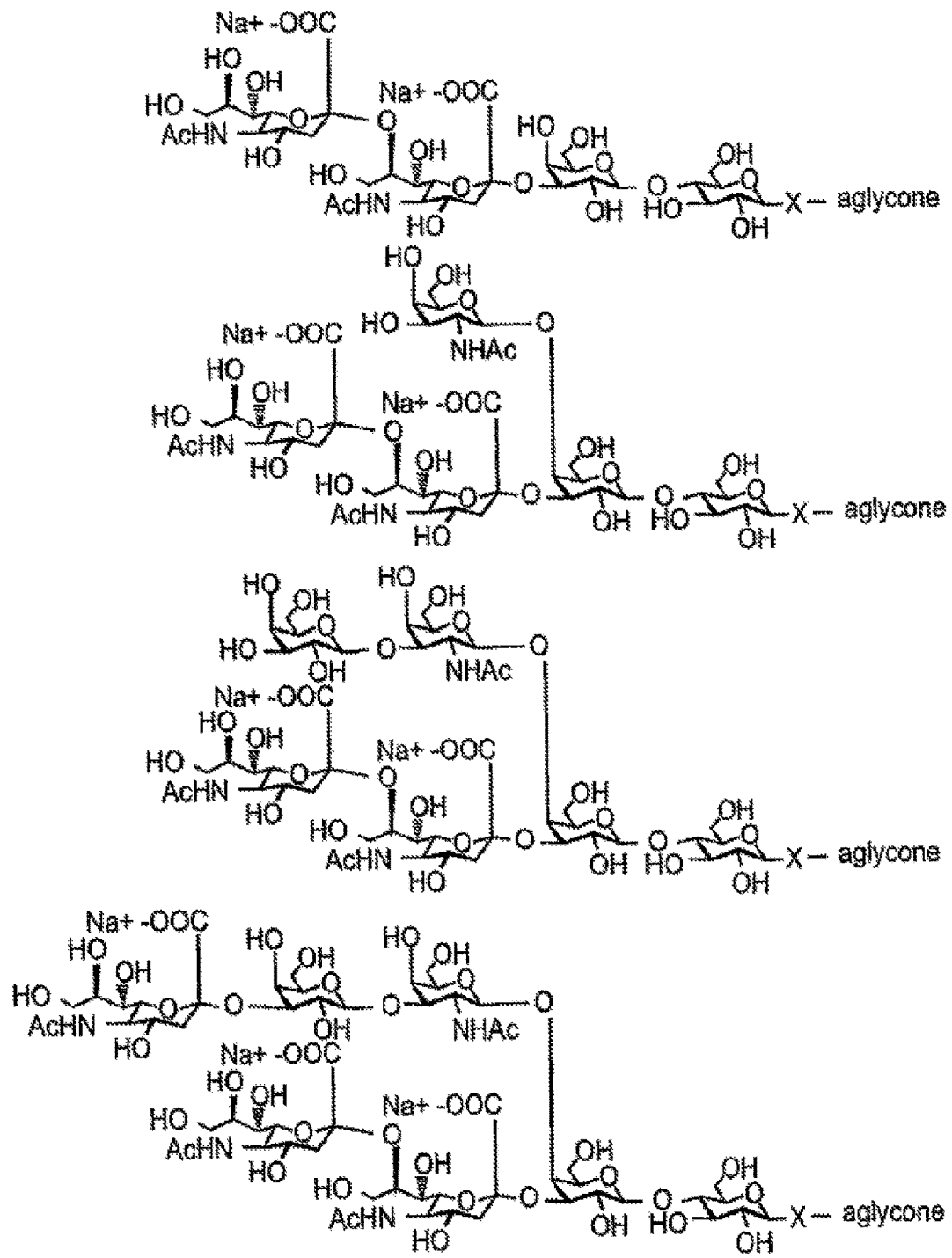
Figure 13A:
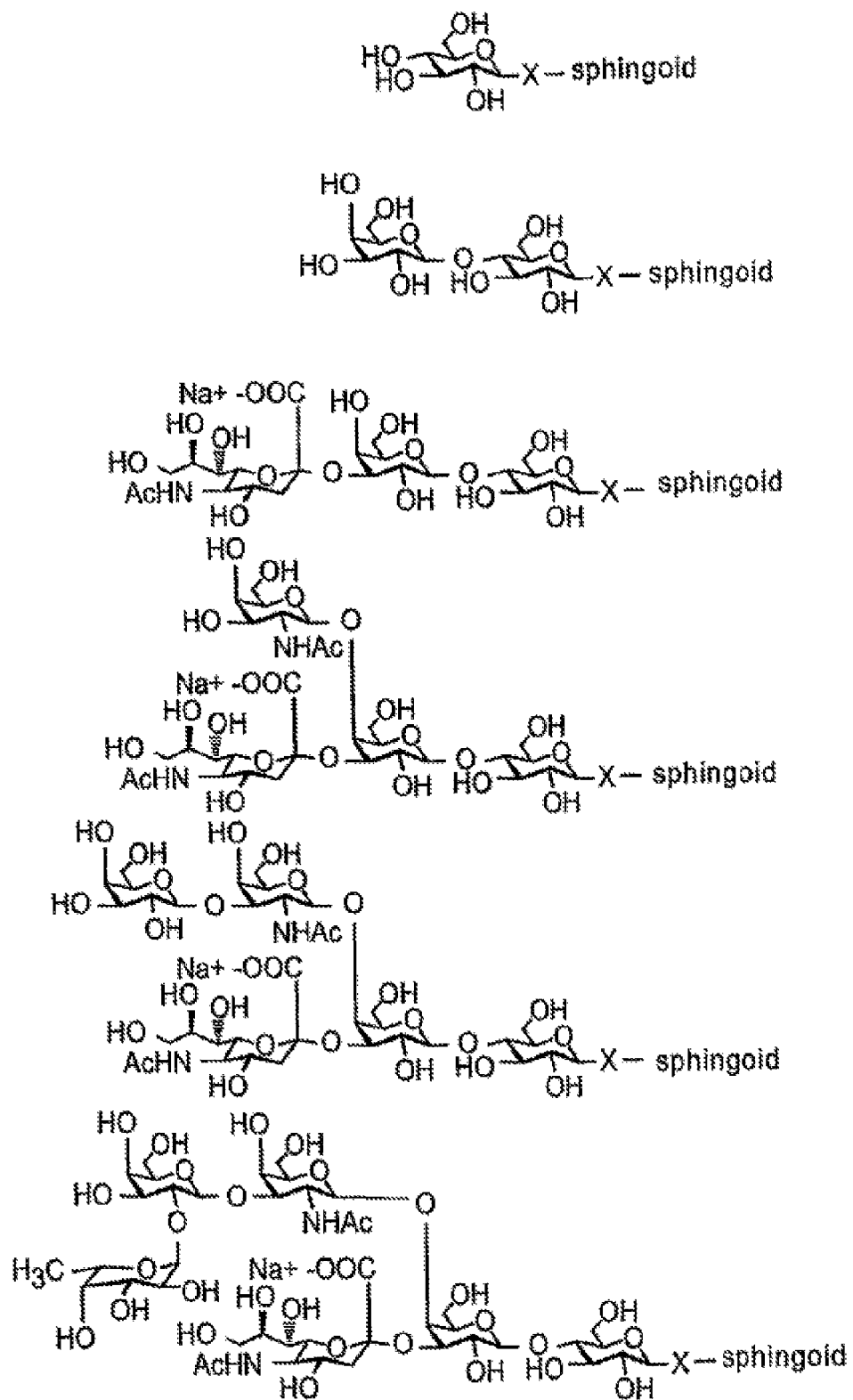
FIGS. 13A-13C set forth compounds that can be made using the enzyme of the invention.
Figure 13B:
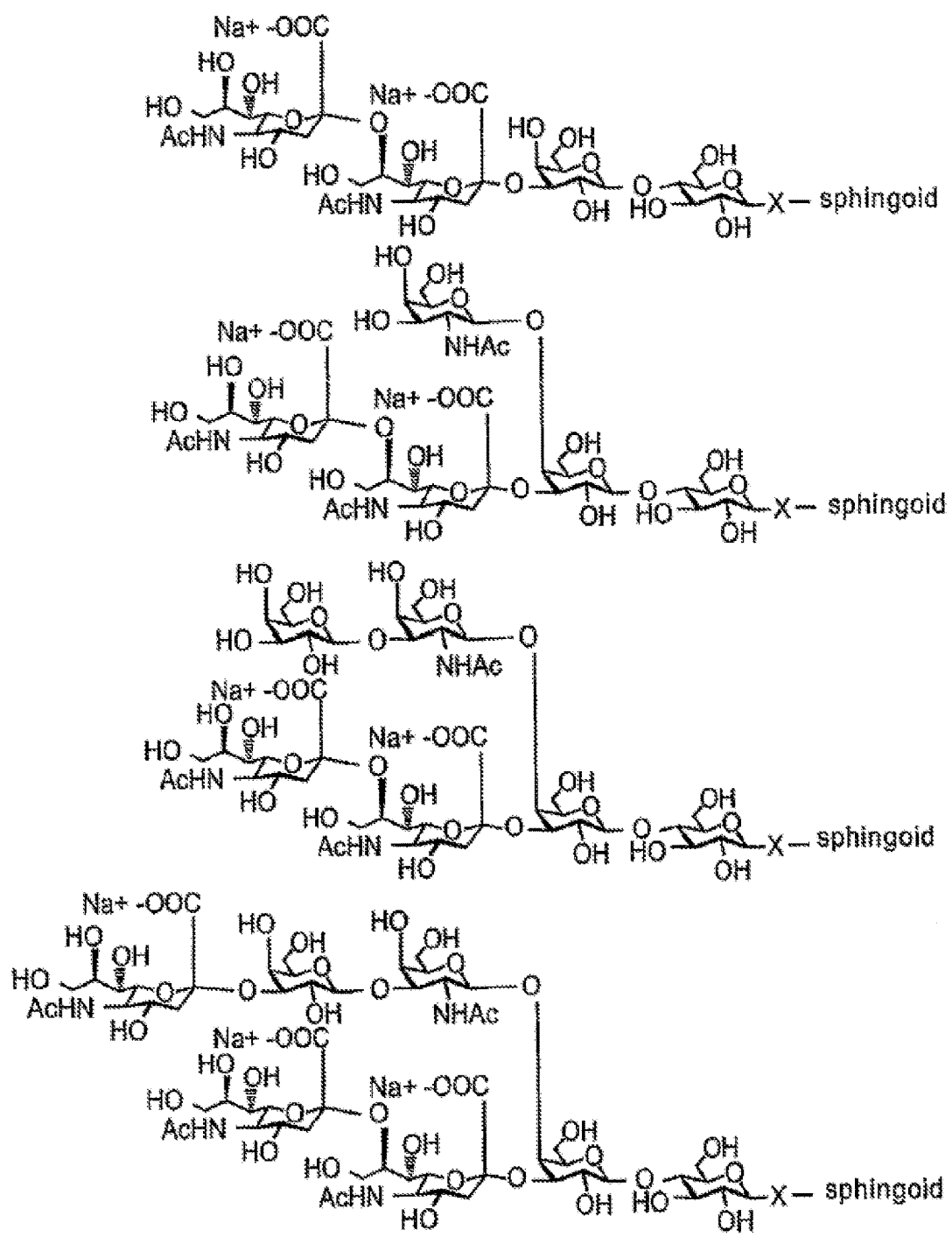
Figure 13C:
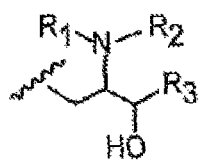

Glycolipids, each consisting of a saccharide moiety and a heteroalkyl moiety, e.g., Formula Ia, Formula Ib, Formula II or Formula III, are important constituents of cellular membranes. With their diverse sugar groups extruding outward from the membrane surface, glycolipids mediate cell growth and differentiation, recognize hormones and bacterial toxins, and determine antigenicity; some are recognized as tumor-associated antigens (Hakomori, *Annu. Rev. Biochem.,* 50:733-764, 1981; Marcus, *Mol. Immunol.* 21:1083-1091, 1984). The present invention discloses novel enzymes and methods for producing glycolipids having a saccharyl moiety of virtually any structure, making it possible to study these important molecules and develop therapeutics, e.g., anti-tumor agents, targeting certain glycolipids.

Mutant Endoglycoceramidases

The present invention provides mutant endoglycoceramidases, also termed "endoglycoceramide synthases," which have an increased synthetic activity for attaching a donor substrate comprising a saccharide moiety to an acceptor substrate (an aglycone) compared to the corresponding wild-type endoglycoceramidase. The mutant endoglycoceramidases can also have a reduced hydrolytic activity towards glycolipids compared to the corresponding wild-type endoglycoceramidase. Corresponding wild-type endoglycoceramidases have at least two identifiable conserved motifs, including an acid-base region (Val-$X_1$-(Ala/Gly)-(Tyr/Phe)-(Asp/Glu)-(Leu/Ile)-$X_2$-Asn-Glu-Pro-$X_3$-$X_4$-Gly or motif B or SEQ ID NO:51), and a nucleophilic region ((Ile/Met/Leu/Phe/Val)-(Leu/Met/Ile/Val)-(Gly/Ser/Thr)-Glu-(Phe/Thr/Met/Leu)-(Gly/Leu/Phe or motif D or SEQ ID NO:53), and hydrolyze the glycoside linkage between a sugar chain and a lipid moiety in a glycolipid.

Structurally, the invention provides a mutant endoglycoceramidase having a modified nucleophilic carboxylate Glu/Asp residue, wherein the nucleophilic Glu/Asp resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54) of a corresponding wild-type endoglycoceramidase, wherein the mutant endoglycoceramidase catalyzes the transfer of a saccharide moiety from a donor substrate to an acceptor substrate.

In a further aspect, the invention provides a mutant endoglycoceramidase having a modified Glu residue within the subsequence of Asn-Glu-Pro, wherein the subsequence resides within the acid-base sequence region of Val-$X_1$-(Ala/Gly)-(Tyr/Phe)-(Asp/Glu)-(Leu/Ile)-$X_2$-Asn-Glu-Pro-$X_3$-$X_4$-Gly sequence in the corresponding wild-type protein, wherein the mutant endoglycoceramidase catalyzes the transfer of a saccharide moiety from a donor substrate to an acceptor substrate.

In a related aspect, the invention provides a mutant endoglycoceramidase characterized in that
i) in its native form the endoglycoceramidase comprises an amino acid sequence that is any one of SEQ ID NOs: 2 (*Rhodococcus*), 4 (*Rhodococcus*), 6 (*Propionibacterium acnes*), 8 (*Propionibacterium acnes*), 10 (*Cyanea nozakii*), 12 (*Cyanea nozakii*), 14 (*Hydra magnipapillata*), 16 (*Schistosoma japonicum*), 17 (*Dictyostelium discoideum*), 18 (*Streptomyces avermitilis*), 19 (*Leptospira interrogans*), and 20 (*Neurospora crassa*); and
ii) the nucleophilic Glu/Asp residue within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence of a corresponding wild-type endoglycoceramidase is modified to an amino acid other than Glu/Asp.

In a further aspect, the invention provides a mutant endoglycoceramidase characterized in that
i) in its native form the endoglycoceramidase comprises an amino acid sequence that is any one of SEQ ID NOs: 2 (*Rhodococcus*), 4 (*Rhodococcus*), 6 (*Propionibacterium acnes*), 8 (*Propionibacterium acnes*), 10 (*Cyanea nozakii*), 12 (*Cyanea nozakii*), 14 (*Hydra magnipapillata*), 16 (*Schistosoma japonicum*), 17 (*Dictyostelium discoideum*), 18 (*Streptomyces avermitilis*), 19 (*Leptospira interrogans*), and 20 (*Neurospora crassa*); and
ii) the Glu residue within the subsequence of Asn-Glu-Pro of the acid-base sequence region Val-$X_1$-(Ala/Gly)-(Tyr/Phe)-(Asp/Glu)-(Leu/Ile)-$X_2$-Asn-Glu-Pro-$X_3$-$X_4$-Gly in the corresponding wild-type protein is modified to an amino acid other than Glu.

Typically, the mutant endoglycoceramidases of the present invention comprise a modified nucleophilic Glu/Asp residue and/or a modified acid-base sequence region Glu residue within the Asn-Glu-Pro subsequence of a corresponding wild-type endoglyoceramidase. One or both of the Glu residues are deleted or replaced with another chemical moiety that retains the integral structure of the protein such that the mutant enzyme has synthetic activity. For example, one or more of the nucleophilic and/or acid-base sequence region Glu residues (i.e., in the Asn-Glu-Pro subsequence region) can be replaced with an L-amino acid residue other than Glu, an unnatural amino acid, an amino acid analog, an amino acid mimetic, and the like. Usually, the one or more Glu residues are substituted with another L-amino acid other than Glu, for example, Gly, Ala, Ser, Asp, Asn, Gln, Cys, Thr, Ile, Leu or Val.

Functionally, the invention provides mutant endoglycoceramidases having a synthetic activity of coupling a glycosyl moiety and an aglycone substrate, forming a glycolipid. The mutant endoglycoceramidase can also have a reduced hydrolytic activity towards glycolipids compared to the corresponding wild-type endoglycoceramidase. The mutant endoglycoceramidases of the invention have a synthetic activity that is greater than the synthetic activity of the corresponding wild type endoglycoceramidase. Preferably, the synthetic activity is greater than its degradative (i.e., hydrolytic) activity in an assay. The assay for the synthetic activity of the mutant endoglycoceramidase comprises transferring a glycosyl moiety from a glycosyl donor substrate for said mutant to an aglycone (i.e., acceptor substrate). The synthetic activity can be readily measured in an assay designed to detect the rate of glycolipid synthesis by the mutant or the quantity of product synthesized by the enzyme.

In general, preferred mutant endoglycoceramidases of the invention are at least about 1.5-fold more synthetically active than their wild type analogues, more preferably, at least about 2-fold, at least about 5-fold, at least about 10-fold, at least about 20-fold, a least about 50-fold and more preferably still, at least about 100-fold. By more synthetically active is meant that the rate of starting material conversion by the enzyme is greater than that of the corresponding wild type enzyme and/or the amount of product produced within a selected time is greater than that produced by the corresponding wild type enzyme in a similar amount of time. A useful assay for determining enzyme synthetic activity includes transferring a glycosyl moiety from a glycosyl donor substrate for said mutant to an aglycone.

The corresponding wild-type endoglycoceramidase can be from a prokaryotic organism (e.g., a *Rhodococcus*, a *Propionibacterium*, a *Streptomyces*, or a *Leptospira*) or a eukaryotic organism (e.g., a *Cyanea*, a *Hydra*, a *Schistosoma*, a *Dictyostelium*, a *Neurospora*). For example, the corresponding wild-type or native endoglycoceramidase can be from an Actinobacteria, including a *Rhodococcus*, a *Propionibacterium*, or a *Streptomyces*. The corresponding wild-type or native endoglycoceramidase also can be from a Metazoan, including a *Cyanea*, a *Hydra*, or a *Schistosoma*, or from a Cnidaria, including a *Cyanea* or a *Hydra*. The corresponding wild-type or native endoglycoceramidase also can be from a Mycetozoa (e.g., a *Dictyostelium*), a Spirochete (e.g., a *Leptospira*), or a fungus, such as an Ascomycete (e.g., a *Neurospora*). In one embodiment, the corresponding wild-type endoglycoceramidase has an amino acid sequence of any one of SEQ ID NOs:2, 4, 6, 8, 10, 12, 14, 16, 17, 18, 19, or 20. In one embodiment, the corresponding wild-type endoglycoceramidase is encoded by a nucleic acid sequence of any one of SEQ ID NOs:1, 3, 5, 7, 9, 11, 13, or 15.

The corresponding wild-type endoglycoceramidase can be from any known endoglycoceramidase sequence or any endoglycoceramidase sequence which has yet to be determined. Additional corresponding wild-type endoglycoceramidases can be identified using sequence databases and sequence alignment algorithms, for example, the publicly available GenBank database and the BLAST alignment algorithm, available on the worldwide web through ncbi.nlm.nih.gov. Additional corresponding wild-type endoglycoceramidases also can be found using routine techniques of hybridization and recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994). Native or wild-type endoglycoceramidases of interest include those encoded by nucleic acid sequences that hybridize under stringent hybridization conditions to one or more of SEQ ID NOs: 1, 3, 5, 7, 9, 11, 13, or 15. Native or wild-type endoglycoceramidases of interest also include those with one or more conservatively substituted amino acids or with at least about 80%, 85%, 90%, 95%, 96%, 97%, 98% or 99% sequence identity to one or more of SEQ ID NOs:2, 4, 6, 8, 10, 12, 14, or 16-20.

Wild-type and mutant endoglycoceramidases can be further characterized by a (Met/Val/Leu)-Leu-Asp-(Met-Phe-Ala)-His-Gln-Asp-(Met/Val/Leu)-X-(Ser/Asn) motif (motif A or SEQ ID NO:50) located N-terminal to the acid-base sequence region and a C-terminal Ala-Ile-Arg-(Gln/Ser/Thr)-Val-Asp motif (motif C or SEQ ID NO:52) located C-terminal to the acid-base sequence region. For example, the (Met/Val/Leu)-Leu-Asp-(Met-Phe-Ala)-His-Gln-Asp-(Met/Val/Leu) motif is located at residues 131-140 in *Rhodococcus* sp. M-777; at residues 129-138 in *Rhodococcus* sp. C9; at residues 136-145 in *Propionibacterium acnes* EGCa; at residues 153-162 in *Propionibacterium acnes* EGCb; at residues 130-139 in *Cyanea nozakii*; and at residues 121-130 in *Hydra magnipapillata*. The Ala-Ile-Arg-(Gln/Ser/Thr)-Val-Asp motif is located at residues 259-264 in *Rhodococcus* sp. M-777; at residues 250-255 in *Rhodococcus* sp. C9; at residues 262-267 in *Propionibacterium acnes* EGCa; at residues 280-285 in *Propionibacterium acnes* EGCb; at residues 272-277 in *Cyanea nozakii*; and at residues 263-268 in *Hydra magnipapillata*.

To enhance expression of a mutant endoglycoceramidase in the soluble fraction of a bacterial host cell, the mutant endoglycoceramidases typically have had removed the native N-terminal signal peptide sequence that is expressed in the corresponding wild-type enzyme. The signal peptide sequence is typically found within the N-terminal 15, 20, 25, 30, 35, 40, 40, 45, 50 or 55 amino acid residues of a corresponding wild-type endoglycoceramidase. Predicted native N-terminal signal peptide sequences for wild-type endoglycoceramidases from *Rhodococcus, Propionibacter, Cyanea, Hydra, Schistosoma, Dyctyostelium, Streptomyces,* and *Neurospora* species are shown in SEQ ID NOs:59-68.

In addition to the amino acid sequences that comprise the mutant endoglycoceramidases, the present invention also includes nucleic acid sequences encoding a mutant endoglycoceramidase, expression vectors comprising such nucleic acid sequences, and host cells that comprise such expression vectors.

Cloning and Subcloning of a Wild-Type Endoglycoceramidase Coding Sequence

A number of polynucleotide sequences encoding wild-type endoglycoceramidases, e.g., GenBank Accession No. U39554, have been determined and can be synthesized or obtained from a commercial supplier, such as Blue Heron Biotechnology (Bothell, Wash.).

The rapid progress in the studies of organism genomes has made possible a cloning approach where an organism DNA sequence database can be searched for any gene segment that has a certain percentage of sequence homology to a known nucleotide sequence, such as one encoding a previously identified endoglycoceramidase. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding an endoglycoceramidase can be isolated from a cDNA or genomic DNA library using standard cloning techniques such as polymerase chain reaction (PCR), where homology-based primers can often be derived from a known nucleic acid sequence encoding an endoglycoceramidase. Most commonly used techniques for this purpose are described in standard texts, e.g., Sambrook and Russell, supra.

cDNA libraries suitable for obtaining a coding sequence for a wild-type endoglycoceramidase may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the wild-type endoglycoceramidase from the cDNA library. A general description of appropriate procedures can be found in Sambrook and Russell, supra.

A similar procedure can be followed to obtain a full length sequence encoding a wild-type endoglycoceramidase from a genomic library. Genomic libraries are commercially available or can be constructed according to various art-recognized methods. In general, to construct a genomic library, the DNA is first extracted from an organism where an endoglycoceramidase is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, PCR Technology, CRC Press Inc. 1994) to amplify a segment of nucleotide sequence from a cDNA or genomic library. Using the amplified segment as a probe, the full length nucleic acid encoding a wild-type endoglycoceramidase is obtained. Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

Upon acquiring a nucleic acid sequence encoding a wild-type endoglycoceramidase, the coding sequence can be subcloned into a vector, for instance, an expression vector, so that a recombinant endoglycoceramidase can be produced from the resulting construct. Further modifications to the wild-type endoglycoceramidase coding sequence, e.g., nucleotide substitutions, may be subsequently made to alter the characteristics of the enzyme.

Methods for Producing Mutant Endoglycoceramidases

In one aspect, the invention provides a method for generating a mutant endoglycoceramidase having a synthetic activity of coupling a saccharide and a substrate and forming glycolipids compared to the corresponding wild-type endoglycoceramidases. The mutant endoglycoceramidase can also have a reduced hydrolytic activity towards glycolipids compared to the corresponding wild-type endoglycoceramidase. The method includes selectively conferring synthetic activity and/or disrupting the hydrolytic activity of the corresponding wild-type endoglycoceramidase. Synthetic activity can be conferred by modifying the nucleophilic carboxylate amino acid residue (i.e., a Glu or an Asp) of a corresponding wild-type endoglycoceramidase.

Accordingly, in one aspect, the invention provides a method for making a mutant endoglycoceramidase having enhanced synthetic activity in comparison to a corresponding wild-type endoglycoceramidase, the method comprising modifying the nucleophilic carboxylate amino acid residue in a corresponding wild-type endoglycoceramidase, wherein the nucleophilic carboxylate amino acid residue resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence (SEQ ID NO:54) of a corresponding wild-type endoglycoceramidase.

In carrying out the methods of producing a mutant endoglycoceramidase, one or both of the nucleophilic carboxylate amino acid residues (i.e., a Glu or an Asp) and/or acid-base sequence region Glu residues of a corresponding endoglycoceramidase can be deleted or replaced with another chemical moiety that retains the integral structure of the protein such that the mutant enzyme has synthetic activity. For example, one or more of the nucleophilic and/or hydrolytic Glu or Asp residues can be replaced with an L-amino acid residue other than Glu or Asp, a D-amino acid residue (including a D-Glu or a D-Asp), an unnatural amino acid, an amino acid analog, an amino acid mimetic, and the like. Usually, the one or more Glu or Asp residues are substituted with another L-amino acid other than Glu or Asp, for example, Gly, Ala, Ser, Asp, Asn, Glu, Gln, Cys, Thr, Ile, Leu or Val.

Introducing Mutations into the Endoglycoceramidase Coding Sequence

Modifications altering the enzymatic activity of an endoglycoceramidase may be made in various locations within the polynucleotide coding sequence. The preferred locations for such modifications are, however, within the nucleophilic site and the acid-base sequence region of the enzyme. Conserved regions likely to contain important residues for structure or native enzymatic activity can be identified by aligning amino acid sequences of wild-type endoglycoceramidases from different organisms. Such amino acid sequences are readily available on public databases, including GenBank. Alignment of endoglycoceramidase sequences with an endoglycoceramidase sequence where the nucleophilic residue has been identified allows for the identification of the nucleophilic residue in subsequent sequences. Alternatively, the nucleophilic residue can be identified (or confirmed) via a fluorosugar labeling strategy (see, U.S. Pat. No. 5,716,812).

From an encoding nucleic acid sequence, the amino acid sequence of a wild-type endoglycoceramidase, e.g., SEQ ID NOs:2, 4, 6, 8, 10, 12, 14, 16-20 can be deduced and the presence of a nucleophilic region or an acid-base region can be confirmed. Preferably, mutations are introduced into the nucleophilic region or the acid-base region. For instance, the Glu residue located in the middle of the three-amino acid segment Asn-Glu-Pro of the acid-base sequence region, can be targeted for mutation, such as deletion or substitution by another amino acid residue. In addition, the nucleophilic carboxylate (i.e., Glu or Asp) residue (bolded) in the (Ile/Met/Leu/Phe/Val)-(Leu/Met/Ile/Val)-(Gly/Ser/Thr)-Glu/Asp-(Phe/Thr/Met/Leu)-(Gly/Leu/Phe) motif of a corresponding wild-type endoglycoceramidase is also a target for introducing mutations to alter the enzymatic activity of an endoglycoceramidase. An artisan can accomplish the goal of mutating a target Glu residue by employing any one of the well known mutagenesis methods, which are discussed in detail below. Exemplary modifications are introduced to replace the Glu residue with another amino acid residue as depicted in SEQ ID NOs:29-33.

Modifications can be directed to the nucleic acid sequence encoding a wild-type or mutant endoglycoceramidase or to one or more amino acids of an endoglycoceramidase enzyme. Typically, modifications are directed to one or more nucleic acid codons encoding one or both of the nucleophilic site and the acid-base sequence region. For example, one or more nucleic acids in the codon encoding for the Glu residue in the acid-base sequence region are modified such that the codon encodes for an amino acid other than Glu, for example, Gly, Ala, Ser, Asp, Asn, Gln, Cys, Thr, Ile, Leu or Val. In another example, one or more nucleic acids in the codon encoding for the Glu residue in the nucleophilic site are modified such that the codon encodes for an amino acid other than Glu, for example, Gly, Ala, Ser, Asp, Asn, Gln, Cys, Thr, Ile, Leu or Val. Site-directed modifications to wild-type or mutant endoglycoceramidase nucleic acid sequences can be introduced using methods well-known in the art, including overlapping PCR or overlap extension PCR (see, for example, Aiyar, et al., Methods Mol Biol (1996) 57:177-91; and Pogulis, et al., Methods Mol Biol (1996) 57:167-76). Suitable PCR primers can be determined by one of skill in the art using the sequence information provided in GenBank or other sources. Services for large-scale site-directed mutagenesis of a desired sequence are commercially available, for example, from GeneArt of Toronto, Canada.

In addition, a variety of diversity-generating protocols are established and described in the art. See, e.g., Zhang et al., Proc. Natl. Acad. Sci. USA, 94: 4504-4509 (1997); and Stemmer, Nature, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortie, Science, 229: 1193-1201 (1985)), mutagenesis using uracil-containing templates (Kunkel, Proc. Natl. Acad. Sci. USA, 82: 488-492 (1985)), oligonucleotide-directed mutagenesis (Zoller and Smith, Nucl. Acids Res., 10: 6487-6500 (1982)), phosphorothioate-modified DNA mutagenesis (Taylor et al., Nucl. Acids Res., 13: 8749-8764 and 8765-8787 (1985)), and mutagenesis using gapped duplex DNA (Kramer et al., Nucl. Acids Res., 12: 9441-9456 (1984)).

Other possible methods for generating mutations include point mismatch repair (Kramer et al., Cell, 38: 879-887 (1984)), mutagenesis using repair-deficient host strains (Carter et al., Nucl. Acids Res., 13: 4431-4443 (1985)), deletion mutagenesis (Eghtedarzadeh and Henikoff, Nucl. Acids Res., 14: 5115 (1986)), restriction-selection and restriction-purification (Wells et al., Phil. Trans. R. Soc. Lond. A, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

At the completion of modification, the mutant endoglycoceramidase coding sequences can then be subcloned into an appropriate vector for recombinant production in the same manner as the wild-type genes.

Modification of Nucleic Acids for Preferred Codon Usage in a Host Organism

The polynucleotide sequence encoding an endoglycoceramidase (either wild-type or mutant) can be altered to coincide with the preferred codon usage of a particular host. For example, the preferred codon usage of one strain of bacteria can be used to derive a polynucleotide that encodes a mutant endoglycoceramidase of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants. Services for the creation of nucleic acid sequences of preferred codon usage for optimized expression in cells of a particular desired organism (e.g., bacteria, yeast, insect, mammalian) can be commercially purchased, for example, from Blue Heron Biotechnology, Bothell, Wash.

The sequences of the cloned endoglycoceramidase genes, synthetic polynucleotides, and modified endoglycoceramidase genes can be verified using, e.g., the chain termination method for sequencing double-stranded templates as described in Wallace et al., *Gene* 16:21-26 (1981).

Expression of the Endoglycoceramidases

Following sequence verification, the wild-type or mutant endoglycoceramidase of the present invention can be produced using routine techniques in the field of recombinant genetics, relying on the polynucleotide sequences encoding the polypeptide disclosed herein.

Expression Systems

To obtain high level expression of a nucleic acid encoding a wild-type or a mutant endoglycoceramidase of the present invention, one typically subclones a polynucleotide encoding the endoglycoceramidase into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant endoglycoceramidase are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. For example, *Pichia* and Baculovirus expression systems can be purchased from Invitrogen (Carlsbad, Calif.). *Pichia* expression systems are also available for purchase from Research Corporation Technologies of Tucson, Ariz. Mammalian cells for heterologous polypeptide expression can be purchased from the American Type Culture Collection (ATCC) in Manassas, Va. and expression systems are commercially available, for example, from New England Biolabs, Beverly, Mass. In one embodiment, the eukaryotic expression vector is an adenoviral vector, an adeno-associated vector, or a retroviral vector.

The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*. Suitable mammalian cells for expression include Chinese Hamster Ovary (CHO) cells, human epithial kidney (HEK)293 cells, and NIH 3T3 cells.

A construct that includes a polynucleotide of interest operably linked to gene expression control signals that, when placed in an appropriate host cell, drive expression of the polynucleotide is termed an "expression cassette." A typical expression cassette generally contains a promoter operably linked to the nucleic acid sequence encoding the wild-type or mutant endoglycoceramidase and signals required for efficient polyadenylation of the transcript, ribosome binding sites, and translation termination. Accordingly, the invention provides expression cassettes into which the nucleic acids that encode fusion proteins are incorporated for high level expression in a desired host cell. The nucleic acid sequence encoding the endoglycoceramidase is typically linked to a cleavable signal peptide sequence to promote secretion of the endoglycoceramidase by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Typically, the polynucleotide that encodes the wild-type or mutant endoglycoceramidase polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of endoglycoceramidase proteins in host cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the endoglycoceramidase proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHOS (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Additional suitable promoters for use in yeast include the ADH2/GAPDH hybrid promoter as described in Cousens et al., *Gene* 61:265-275 (1987) and the AOX1 promoter for use in *Pichia* strains. For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions. An example of a suitable terminator is the ADH3 terminator (McKnight et al.). Recombinant protein expression in yeast host cells is well known in the art. See, for example, *Pichia Protocols*, Higgins and Cregg, eds., 1998, Humana Press; *Foreign Gene Expression in Fission Yeast: Schizosaccharomyces Pombe*, Giga-Hama and Kumagai eds., 1997, Springer Verlag. Expression of heterologous proteins in *Pichia* strains of yeast (including *Pichia pastoris, Pichia methanolica*, and *Pichia ciferrii*) is also described in U.S. Pat. Nos. 6,638,735; 6,258,559; 6,194,196; 6,001,597; and 5,707,828, the disclosures of which are hereby incorporated herein by reference in their entirety for all purposes.

Either constitutive or regulated promoters can be used in the present invention. Regulated promoters can be advantageous because the host cells can be grown to high densities before expression of the endoglycoceramidase proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the endoglycoceramidase proteins. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. One preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pUC based plasmids, pET based plasmids (i.e., pET23D, pET28A, commercially available from Novagen/EMD Biosciences) and fusion expression systems such as GST and LacZ. Epitope tags can also be added to recombinant proteins to provide convenient methods of isolation, e.g., c-myc. In yeast, vectors include Yeast Integrating plasmids (e.g., YIp5) and Yeast Replicating plasmids (the YRp series plasmids) and pGPD-2.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Mammalian host cells suitable for expression of heterologous polypeptides include, for example, Chinese Hamster Ovary (CHO) cells, human epithial kidney (HEK)293 cells, and NIH 3T3 cells. Expression of heterologous polypeptides in mammalian expression systems is reviewed in Makrides, *Gene Transfer and Expression in Mammalian Cells: New Comprehensive Biochemistry*, 2003, Elsevier Science Ltd.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant endoglycoceramidase under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The endoglycoceramidase polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the endoglycoceramidase polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Nati. Acad. Sci. USA* (1980) 77: 3988; Takahara et al., *J. Biol. Chem.* (1985) 260: 2670). In another embodiment, the fusion proteins are fused to a subsequence of protein A or bovine serum albumin (BSA), for example, to facilitate purification, secretion, or stability.

The endoglycoceramidase polypeptides of the invention can also be further linked to other bacterial proteins. This approach often results in high yields, because normal prokaryotic control sequences direct transcription and translation. In *E. coli*, lacZ fusions are often used to express heterologous polypeptides. Suitable vectors are readily available, such as the pUR, pEX, and pMR100 series (see, e.g., Sambrook et al., supra.). For certain applications, it may be desirable to cleave the non-endoglycoceramidase from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Nati. Acad. Sci. USA* (1986) 83: 561). Cleavage sites can be engineered into the gene for the fusion protein at the desired point of cleavage. The present invention further encompasses vectors comprising fusion proteins comprising the mutant endoglycoceramidases.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

As discussed above, a person skilled in the art will recognize that various conservative substitutions can be made to any wild-type or mutant endoglycoceramidase or its coding sequence while still retaining the synthetic activity of the endoglycoceramidase. Moreover, modifications of a polynucleotide coding sequence may also be made to accommodate preferred codon usage in a particular expression host without altering the resulting amino acid sequence.

When recombinantly over-expressed in bacteria, wild-type and mutant endoglycoceramidases can form insoluble protein aggregates; significant amounts of the recombinant protein will reside in the insoluble fraction during subsequent purification procedures. Expression of recombinant endoglycoceramidases in insoluble inclusion bodies can be minimized by using one or more of several strategies known to those in the art, including for example, expressing from an inducible promoter (e.g., lac, T7), adding low concentrations of inducer (e.g., IPTG), using bacterial expression strains that suppress uninduced protein expression (e.g., BL21 pLysS), using a bacterial expression strain with a heightened sensitivity to the concentration of inducer (e.g., Tuner™ host cells from Novagen/EMD Biosciences, San Diego, Calif.), using a bacterial expression strain that favors disulfide formation of expressed recombinant proteins (e.g., Origami™ host cells from Novagen), using minimal media (e.g., M9), varying induction temperatures (e.g., 16-37° C.), adding a signal sequence to direct secretion into the periplasm (e.g., pelB).

Transfection Methods

Standard transfection methods are used to produce bacterial, mammalian, yeast or insect cell lines that express large quantities of the wild-type or mutant endoglycoceramidase, which are then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the wild-type or mutant endoglycoceramidase.

Detection of the Expression of Recombinant Endoglycoceramidases

After the expression vector is introduced into appropriate host cells, the transfected cells are cultured under conditions favoring expression of the wild-type or mutant endoglycoceramidase. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding an endoglycoceramidase in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a wild-type or mutant endoglycoceramidase of the present invention, such as a polypeptide having the amino acid sequence of SEQ ID NOs:29-33, (e.g., Harlow and Lane, *Using Antibodies: A Laboratory Manual*, Cold Spring Harbor, 1998; Harlow and Lane, *Antibodies, A Laboratory Manual*, Chapter 14, Cold Spring Harbor, 1988; Kohler and Milstein, *Nature*, 256: 495-497 (1975)). Such techniques require antibody preparation by selecting antibodies with high specificity against the recombinant polypeptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*, 6: 511-519 (1976). More detailed descriptions of preparing antibody against the mutant endoglycoceramidase of the present invention and conducting immunological assays detecting the mutant endoglycoceramidase are provided in a later section.

In addition, functional assays may also be performed for the detection of a recombinant endoglycoceramidase in transfected cells. Assays for detecting hydrolytic or synthetic activity of the recombinant endoglycoceramidase are generally described in a later section.

Purification of Recombinant Endoglycoceramidases
Solubilization

Once the expression of a recombinant endoglycoceramidase in transfected host cells is confirmed, the host cells are then cultured in an appropriate scale for the purpose of purifying the recombinant enzyme.

When the endoglycoceramidases of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solubilization solvents include, but are not limited to, urea (from about 4 M to about 8 M), formamide (at least about 80%, volume/volume basis), guanidine hydrochloride (from about 4 M to about 8 M), and detergents including N-laurylsarcosine (sarkosyl), 3-(Cyclohexylamino)-1-propanesulfonic acid (CAPS), 3-[(3-Cholamidopropyl)dimethylammonio]-1-propanesulfonate (CHAPS), and lauryl maltoside. Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify recombinant polypeptides, e.g., a mutant endoglycoceramidase, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art. Proteins exported into the periplasmic space may still form inclusion bodies.

Protein Refolding

Wild-type or mutant endoglycoceramidases purified from inclusion bodies generally must be refolded after solubilization. The presence of recombinantly expressed endoglycoceramidases in inclusion bodies can be minimized and subsequent proper refolding maximized by expressing the enzymes in a bacterial strain that favors formation of disulfide bonds (e.g., Origami™ host cells from Novagen/EMD Biosciences). Alternatively, unpaired cysteines, signal peptide sequences can be removed from the recombinant sequences, for instance, using truncation and site-directed mutagenesis techniques. The presence of recombinantly expressed enzyme in inclusion bodies also can be minimized by expressing the endoglycoceramidases as a fusion protein with a maltose binding domain (see, for example, Sachdev and Chirgwin, *Protein Expr Purif.* (1998) 1:122-32). Enzyme ultimately purified from inclusion bodies can be solubilized and then subject to refolding buffers containing redox couples, for example reduced glutathione/oxidized glutathione (GSH/GSSH), or cysteine/cystamine. Described in, PCT/US05/03856 which claims priority to U.S. Provisional Patent Application Nos. 60/542,210; 60/599,406; and 60/627,406, the disclosures of each of which are hereby incorporatated herein by reference in their entirety or all purposes. Protein refolding kits are commercially available, for example, from Novagen/EMD Biosciences (see also, Frankel, et al., *Proc. Natl. Acad. Sci. USA* (1991) 88:1192-1196). Optimization of biochemical variables for proper refolding of a particular endoglycoceramidase, including protein concentration, addition of polar additives (e.g., arginine), pH, redox environment potential (the presence of redox couples), ionic strength, and species and concentration of detergent, chaotrope, divalent cations, osmolytes (e.g., polyethylene glycol (PEG)), non-polar additives (e.g., sugars) can be evaluated using a fractional factorial screen, described in Armstrong, et al., *Protein Science* (1999) 8:1475-1483. Kits for carrying out fractional factorial protein refolding optimization screens are commercially available, for example, from Hampton Research, Laguna Niguel, Calif.).

Purification of Protein

Purification Tags

The recombinant fusion protein of the invention can be constructed and expressed as a fusion protein with a molecular "purification tag" at one end, which facilitates purification of the protein. Such tags can also be used for immobilization of a protein of interest during the glycosylation reaction. Exemplified purification tags include MalE, 6 or more sequential histidine residues, cellulose binding protein, maltose binding protein (malE), glutathione S-transferase (GST), lactoferrin, and Sumo fusion protein cleavable sequences (commercially available from LifeSensors, Malvern, Pa. and EMD Biosciences). Vectors with purification tag sequences are commercially available from, for example, Novagen/EMD Biosciences. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys or a substantially identical variant thereof. Other epitope tags that can be used in the invention include, e.g., myc tag, AU1, AU5, DDDDK (EC5), E tag, E2 tag, Glu-Glu, a 6 residue histidine peptide, EYMPME, derived from the Polyoma middle T protein, HA, HSV, IRS, KT3, S tag, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

Standard Protein Separation Techniques for Purification

When a recombinant polypeptide, e.g., the mutant endoglycoceramidase of the present invention, is expressed in host cells in a soluble form, its purification can follow the standard protein purification procedures known in the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant endoglycoceramidase of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant endoglycoceramidase. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant endoglycoceramidase of the present invention) can also be separated from other proteins on the basis of their size, net surface charge, hydrophobicity, or affinity for ligands. In addition, antibodies raised against endoglycoceramidase can be conjugated to column matrices and the endoglycoceramidase immunopurified. When the enzymes are expressed as fusion proteins with purification tags, a column loaded with resin that specifically binds to the purification tag is used, for example, resin conjugated to nickel, cellulose, maltose, anti-lactoferrin antibodies, or glutathione. All of these methods are well known in the art.

It will be apparent to one of skill that chromatographic techniques can be performed at any scale and using equipment from many different manufacturers (e.g., Pharmacia Biotech).

Production of Antibodies Against Endoglycoceramidases and Immunoassays for Detection of Endoglycoceramidase Expression To confirm the production of a recombinant endoglycoceramidase, immunological assays may be useful to detect in a sample the expression of the endoglycoceramidase. Immunological assays are also useful for quantifying the expression level of the recombinant enzyme.

Production of Antibodies Against Endoglycoceramidase

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant endoglycoceramidase of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When necessary, antibodies capable of specifically recognizing a mutant endoglycoceramidase of the present invention can be tested for their cross-reactivity against the corresponding wild-type endoglycoceramidase and thus distinguished from the antibodies against the wild-type enzyme. For instance, antisera obtained from an animal immunized with a mutant endoglycoceramidase can be run through a column on which a corresponding wild-type endoglycoceramidase is immobilized. The portion of the antisera that passes through the column recognizes only the mutant endoglycoceramidase and not the corresponding wild-type endoglycoceramidase. Similarly, monoclonal antibodies against a mutant endoglycoceramidase can also be screened for their exclusivity in recognizing only the mutant but not the wild-type endoglycoceramidase.

Polyclonal or monoclonal antibodies that specifically recognize only the mutant endoglycoceramidase of the present invention but not the corresponding wild-type endoglycoceramidase are useful for isolating the mutant enzyme from the wild-type endoglycoceramidase, for example, by incubating a sample with a mutant endoglycoceramidase-specific polyclonal or monoclonal antibody immobilized on a solid support.

Immunoassays for Detecting Endoglycoceramidase Expression

Once antibodies specific for an endoglycoceramidase of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

Immunoassay Formats

Immunoassays for detecting a target protein of interest (e.g., a recombinant endoglycoceramidase) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of a wild-type or mutant endoglycoceramidase in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep antimouse antibodies) that specifically bind to the antibodies against the endoglycoceramidase.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

Methods for Synthesizing a Glycolipid Using Mutant Endoglycoceramidases

The invention also provides a method of synthesizing a glycolipid or aglycone. The method includes contacting a glycosyl donor comprising a glycosyl group, and an aglycone with a mutant endoglycoceramidase of the invention under conditions appropriate to transfer said glycosyl group to said aglycone.

In one aspect, the invention provides a method of synthesizing a glycolipid or aglycone, the method comprising, contacting a donor substrate comprising a saccharide moiety and an acceptor substrate with a mutant endoglycoceramidase having a modified nucleophilic carboxylate (i.e., Glu or Asp) residue, wherein the nucleophilic Glu/Asp resides within a (Ile/Met/Leu/Phe/Val)-(Leu/Met/Ile/Val)-(Gly/Ser/Thr)-(Glu/Asp)-(Phe/Thr/Met/Leu)-(Gly/Leu/Phe) sequence of a corresponding wild-type endoglycoceramidase, under conditions wherein the endoglycoceramidase catalyzes the transfer of a saccharide moiety from a donor substrate to an acceptor substrate, thereby producing the glycolipid or aglycone.

In a further aspect, the invention provides a method of synthesizing a glycolipid or aglycone, the method comprising, contacting a donor substrate comprising a saccharide moiety and an acceptor substrate with a mutant endoglycoceramidase having a modified Glu residue within the subsequence of Asn-Glu-Pro, wherein the subsequence resides within the acid-base sequence region of Val-$X_1$-(Ala/Gly)-(Tyr/Phe)-(Asp/Glu)-(Leu/Ile)-$X_2$-Asn-Glu-Pro-$X_3$-$X_4$-Gly sequence in the corresponding wild-type protein, under conditions wherein the endoglycoceramidase catalyzes the transfer of a saccharide moiety from a donor substrate to an acceptor substrate, thereby producing the glycolipid or aglycone.

In carrying out the methods of glycolipid synthesis, one or both of the nucleophilic carboxylate amino acid residue (i.e., a Glu or an Asp) and/or acid-base sequence region Glu residues of a corresponding wild-type endoglycoceramidase can be deleted or replaced with another chemical moiety that retains the integral structure of the protein such that the mutant enzyme has synthetic activity. For example, one or more of the nucleophilic carboxylate amino acid residues (Glu or Asp) and/or acid-base sequence region Glu residues can be replaced with an L-amino acid residue other than Glu or Asp, a D-amino acid residue (including a D-Glu or a D-Asp), an unnatural amino acid, an amino acid analog, an amino acid mimetic, and the like. Usually, the one or more carboxylate amino acid residues (Glu or Asp) are substituted with another L-amino acid other than Glu or Asp, for example, Gly, Ala, Ser, Asp, Asn, Glu, Gln, Cys, Thr, Ile, Leu or Val.

In one embodiment, the mutant enzymes of the invention converts at least about 50% of the starting materials, based upon the limiting reagent, to a desired glycolipid, more preferably, at least about 60%, 70%, 80% or 90%. In another preferred embodiment, the conversion of the limiting reagent to glycolipid is virtually quantitative, affording a conversion that is at least about 90%, and more preferably, at least about 92%, 94%, 96%, 98% and even more preferably, at least about 99%.

In another exemplary embodiment, the glycosyl donor and the acceptor substrate (i.e., aglycone) are present in an approximately 1:1 molar ratio and the enzyme of the invention, acting catalytically, converts the two reagents to a glycolipid in at least about 50% yield, more preferably at least about 60%, 70%, or 80%. In a further exemplary embodiment, the conversion is essentially quantitative as discussed above.

In one embodiment, the synthesized glycolipid is an aglycone (non-carbohydrate alcohol (OH) or (SH)) conjugated to a non-reducing sugar and a non-glycoside.

Donor Substrates

Donor substrates for wild-type and mutant endoglycoceramidases include any activated glycosyl derivatives of anomeric configuration opposite the natural glycosidic linkage. The enzymes of the invention are used to couple α-modified or β-modified glycosyl donors, usually α-modified glycosyl donors, with glycoside acceptors. Preferred donor molecules are glycosyl fluorides, although donors with other groups which are reasonably small and which function as relatively good leaving groups can also be used. Examples of other glycosyl donor molecules include glycosyl chlorides, bromides, acetates, mesylates, propionates, pivaloates, and glycosyl molecules modified with substituted phenols. Among the α-modified or β-modified glycosyl donors, α-galactosyl, α-mannosyl, α-glucosyl, α-fucosyl, α-xylosyl, α-sialyl, α-N-acetylglucosaminyl, α-N-acetylgalactosaminyl, β-galactosyl, β-mannosyl, β-glucosyl, β-fucosyl, β-xylosyl, β-sialyl, β-N-acetylglucosaminyl and β-N-acetylgalactosaminyl are most preferred. Additional donor substrates include ganglioside head groups, for example, those listed in Table 2, below, and those depicted in FIGS. 1-13. Accordingly, in one embodiment, the donor substrate can be one or more ganglioside glycosyl head groups selected from the group consisting of $GD_{1a}$, $GD_{1\alpha}$, $GD_{1b}$, $GD_2$, $GD_3$, Gg3, Gg4, $GH_1$, $GH_2$, $GH_3$, $GM_1$, $GM_{1b}$, $GM_2$, $GM_3$, Fuc-$GM_1$, $GP_1$, $GP_2$, $GP_3$, $GQ_{1b}$, $GQ_{1B}$, $GQ_{1\beta}$, $GQ_{1c}$, $GQ_2$, $GQ_3$, $GT_{1a}$, $GT_{1b}$, $GT_{1c}$, $GT_{1\beta}$, $GT_{1c}$, $GT_2$, and $GT_3$. The donor molecules can be monosaccharides, or may themselves contain multiple sugar moieties (oligosaccharides). Donor substrates of use in the particular methods include those described in U.S. Pat. Nos. 6,284,494; 6,204,029; 5,952,203; and 5,716,812.

Glycosyl fluorides can be prepared from the free sugar by first acetylating the sugar and then treating it with HF/pyridine. This will generate the thermodynamically most stable anomer of the protected (acetylated) glycosyl fluoride. If the less stable anomer is desired, it may be prepared by converting the peracetylated sugar with HBr/HOAc or with HCL to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g., NaOMe/MeOH). In addition, glycosyl donor molecules, including many glycosyl fluorides can be purchased commercially. Thus a wide range of donor molecules are available for use in the methods of the present invention.

Acceptor Substrates

Suitable acceptor substrates include any aglycone that the mutant endoceramidases can conjugate with a saccharide moiety. For example, the mutant endoglycoceramide synthases are capable of synthesizing a glycolipid or aglycone by coupling a saccharide and a heteroalkyl substrate with a structure as shown in Formula Ia, Formula Ib, Formula II or Formula III as shown below:

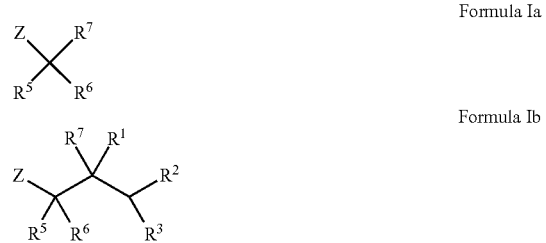

Formula Ia

Formula Ib

In Formula Ia and Formula Ib, the symbol Z represents OH, SH, or $NR^4R^{4'}$. $R^1$ and $R^2$ are members independently selected from $NHR^4$, $SR^4$, $OR^4$, $OCOR^4$, $OC(O)NHR^4$, $NHC(O)OR^4$, $OS(O)_2OR^4$, $C(O)R^4$, $NHC(O)R^4$, detectable labels, and targeting moieties. The symbols $R^3$, $R^4$ and $R^{4'}$, $R^5$, $R^6$ and $R^7$ each are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl.

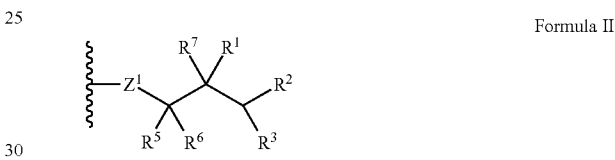

Formula II

In Formula II, $Z^1$ is a member selected from O, S, and $NR^4$; $R^1$ and $R^2$ are members independently selected from $NHR^4$, $SR^4$, $OR^4$, $OCOR^4$, $OC(O)NHR^4$, $NHC(O)OR^4$, $OS(O)_2OR^4$, $C(O)R^4$, $NHC(O)R^4$, detectable labels, and targeting moieties. The symbols $R^3$, $R^4$, $R^5$, $R^6$ and $R^7$ each are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl. Formula II is representative of certain embodiments wherein the aglycone portion is conjugated to a further substrate component, for example, a leaving group or a solid support.

In certain embodiments, acceptor substrates such as those depicted in Table 1 below are used in the methods of glycolipid or aglycone synthesis employing the mutant endoglycoceramidases.

TABLE 1

Representative Acceptor Substrates For Glycosynthase Synthesis Reactions

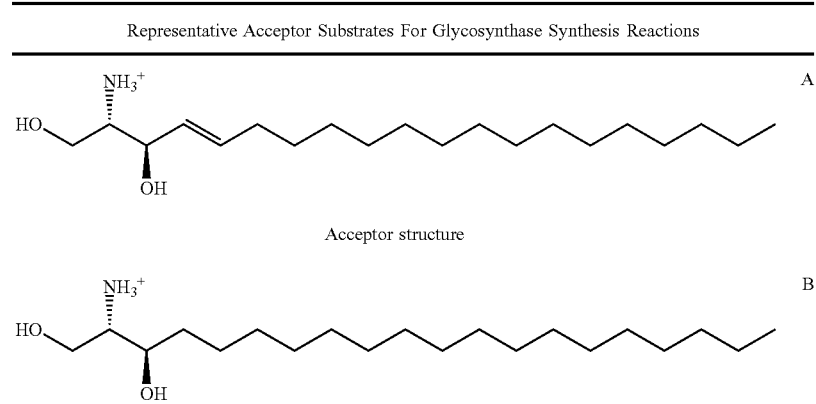

Acceptor structure

TABLE 1-continued

Representative Acceptor Substrates For Glycosynthase Synthesis Reactions

[Structures C through J showing sphingosine and ceramide analogs]

In certain embodiments, the acceptor substrate is a sphingosine, a sphingosine analog or a ceramide. In certain embodiments, the acceptor substrate is one or more sphingosine analogs, including those described in co-pending patent applications PCT/US2004/006904 (which claims priority to U.S. Provisional Patent Application No. 60/452,796); U.S. patent application Ser. No. 10/487,841; U.S. patent application Ser. Nos. 10/485,892; 10/485,195, and 60/626,678.

In general, the sphingosine analogs described in the above-referenced applications are those compounds having the formula:

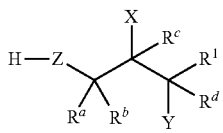

Formula III wherein Z is a member selected from O, S, C(R$^2$)$_2$ and NR$^2$; X is a member selected from H, —OR$^3$, —NR$^3$R$^4$, —SR$^3$, and —CHR$^3$R$^4$; R$^1$, R$^2$, R$^3$ and R$^4$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, —C(=M)R$^5$, —C(=M)-Z$^1$—R$^5$, —SO$_2$R$^5$, and —SO$_3$; wherein M and Z$^1$ are members independently selected from O, NR$^6$ or S; Y is a member selected from H, —OR$^7$, —SR$^7$, —NR$^7$R$^8$, substituted or unsubstituted alkyl, substituted or unsubstituted heteroalkyl, substituted or unsubstituted aryl, substituted or unsubstituted heteroaryl, and substituted or unsubstituted heterocycloalkyl, wherein R$^5$, R$^6$, R$^7$ and R$^8$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl; and R$^a$, R$^b$, R$^c$ and R$^d$ are each independently H, substituted or unsubstituted alkyl, substituted or unsubstituted heteroalkyl, substituted or unsubstituted aryl, substituted or unsubstituted heteroaryl, substituted or unsubstituted heterocycloalkyl.

In certain embodiments, the acceptor substrate can be one or more sphingosine analogs including D-erythro-sphingosine, D-erythro-sphinganine, L-threo-sphingosine, L-threo-dihydrosphingosine, D-erythro-phytosphingosine, or N-ocatanoyl-D-erythro-sphingosine.

Production of Glycolipids

Wild-type and mutant endoglycoceramidase polypeptides can be used to make glycolipid products in in vitro reactions mixes or by in vivo reactions, e.g., by fermentative growth of recombinant microorganisms that comprise nucleotides that encode endoglycoceramidase polypeptides.

A. In Vitro Reactions

The wild-type and mutant endoglycoceramidase polypeptides can be used to make sialylated products in in vitro reactions mixes. The in vitro reaction mixtures can include permeabilized microorganisms comprising the wild-type or mutant endoglycoceramidase polypeptides, partially purified endoglycoceramidase polypeptides, or purified endoglycoceramidase polypeptides; as well as donor substrates, acceptor substrates, and appropriate reaction buffers. For in vitro reactions, the recombinant wild-type or mutant endoglycoceramidase proteins, acceptor substrates, donor substrates and other reaction mixture ingredients are combined by admixture in an aqueous reaction medium. Additional glycosyltransferases can be used in combination with the endoglycoceramidase polypeptides, depending on the desired glycolipid end product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular endoglycoceramidase and other enzymes used.

Enzyme amounts or concentrations are expressed in activity units, which is a measure of the initial rate of catalysis. One activity unit catalyzes the formation of 1 µmol of product per minute at a given temperature (typically 37° C.) and pH value (typically 7.5). Thus, 10 units of an enzyme is a catalytic amount of that enzyme where 10 µmol of substrate are converted to 10 µmol of product in one minute at a temperature of 37° C. and a pH value of 7.5.

The reaction mixture may include divalent metal cations (Mg$^{2+}$, Mn$^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired glycolipid determinants. For large-scale preparations, the reaction will often be allowed to proceed for between about 0.5-240 hours, and more typically between about 1-18 hours.

Preferably, the concentrations of activating donor substrates and enzymes are selected such that glycosylation proceeds until the acceptor substrate is consumed.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

B. In Vivo Reactions

The mutant endoglycoceramidase polypeptides can be used to make glycolipid products by in vivo reactions, e.g., fermentative growth of recombinant microorganisms comprising the endoglycoceramidase polypeptides. Fermentative growth of recombinant microorganisms can occur in the presence of medium that includes an acceptor substrate and a donor substrate or a precursor to a donor substrate. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein.

For glycosyltransferase cycles carried out in vitro, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Functional Assays for the Endoglycoceramidases

In addition to immunological assays, enzymatic assays can be used for detecting the presence and/or activity of the endoglycoceramidase of the present invention. These enzymatic assays are useful to establish the distinct functional characteristics of the wild-type and mutant endoglycoceramidases of the present invention. The production of glycolipid end products can be monitored by e.g., determining that production of the desired product has occurred or by determining that a substrate such as the acceptor substrate has been depleted. Those of skill will recognize that glycolipid end products including gangliosides or glycosphingolipid analogs can be identified using techniques such as chromatography, e.g., using paper or TLC plates, or by mass spectrometry, e.g., MALDI-TOF spectrometry, or by NMR spectroscopy.

Assays for Hydrolytic Activity

To test the hydrolytic activity of an endoglycoceramidase, either the wild-type or a modified version of the enzyme, a glycolipid can be used as a substrate. Upon incubation of the substrate (e.g., lyso-$GM_2$, $GM_2$, or $GM_3$) with the endoglycoceramidase under appropriate conditions, assays are performed to detect the presence of hydrolytic products such as an oligosaccharide and an aglycone (e.g., C-18 ceramide), which indicates that the endoglycoceramidase is hydrolytically active. To facilitate the detection of hydrolytic products, the substrate for a hydrolytic assay may be labeled with a detectably moiety, for instance, a fluorescent or radioactive label. Sugars which release a fluorescent or chromophoric group on hydrolysis (i.e., dinitrophenyl, p-nitrophenyl, or methylumbelliferyl glycosides) can also be used to test for hydrolytic activity. A preferred assay format for detecting hydrolytic products includes various chromatographic methods, such as thin-layer chromatography (TLC).

An appropriate control is preferably included in each hydrolytic activity assay such that the activity level of a mutant endoglycoceramidase can be assessed in comparison with that of a wild-type endoglycoceramidase.

Assays for Synthetic Activity

To test the synthetic activity of an endoglycoceramidase, particularly a mutant endoglycoceramidase (or an "endoglycoceramide synthase"), an oligosaccharide and a heteroalkyl substrate, e.g., of Formula I and Formula II, can be used as substrates. Upon incubation of the two substrates with the "endoglycoceramide synthase" under appropriate conditions, assays are performed to detect the presence of glycolipid formed by reaction between the oligosaccharide and the heteroalkyl substrate, e.g., an aglycone including a ceramide or a sphingosine, which indicates that the "endoglycoceramide synthase" is synthetically active. To facilitate the detection of the synthetic process, at least one of the two substrates for the synthetic assay may be labeled with a detectably moiety, for instance, a fluorescent or radioactive label. The same assay format, such as TLC, for detecting hydrolytic products can be used for detecting synthetic products.

An appropriate control is preferably included in each assay such that the activity level of an endoglycoceramide synthase can be assessed in comparison with that of a wild-type endoglycoceramidase.

Synthesis of Glycolipids Using Mutant Endoglycoceramide Synthases

Upon identifying a mutant endoglycoceramidase that is synthetically active, this enzyme can be used for production of a large variety of glycolipids based on different combinations of heteroalkyl substrates. End products of particular interest are glycosylated aglycones, including glycosylated sphingosines, glycosylated sphingosine analogs, and glycosylated ceramides (i.e., cerebrosides and gangliosides). The methods of the invention are useful for producing any of a large number of gangliosides and related structures. Many gangliosides of interest are described in Oettgen, H. F., ed., *Gangliosides and Cancer*, VCH, Germany, 1989, pp. 10-15, and references cited therein. The end product can be a glycosylsphingosine, a glycosphingolipid, a cerebroside or a ganglioside. Exemplified ganglioside end products include those listed in Table 2, below. Accordingly, in one embodiment, the synthesized glycolipid can be one or more of $GD_{1a}$, $GD_{1\alpha}$, $GD_{1b}$, $GD_2$, $GD_3$, Gg3, Gg4, $GH_1$, $GH_2$, $GH_3$, $GM_1$, $GM_{1b}$, $GM_2$, $GM_3$, Fuc-$GM_1$, $GP_1$, $GP_2$, $GP_3$, $GQ_{1b}$, $GQ_{1B}$, $GQ_{1\beta}$, $GQ_{1c}$, $GQ_2$, $GQ_3$, $GT_{1a}$, $GT_{1b}$, $GT_{1c}$, $GT_{1\beta}$, $GT_{1c}$, $GT_2$, $GT_3$, or polysialylated lactose.

TABLE 2

Exemplified Ganglioside Formulas and Abbreviations

| Structure | Abbreviation |
|---|---|
| Neu5Ac3Gal4GlcCer | GM3 |
| GalNAc4(Neu5Ac3)Gal4GlcCer | GM2 |
| Gal3GalNAc4(Neu5Ac3)Gal4GlcCer | GM1a |
| Neu5Ac3Gal3GalNAc4Gal4GlcCer | GM1b |
| Neu5Ac8Neu5Ac3Gal4GlcCer | GD3 |
| GalNAc4(Neu5Ac8Neu5Ac3)Gal4GlcCer | GD2 |
| Neu5Ac3Gal3GalNAc4(Neu5Ac3)Gal4GlcCer | GD1a |
| Neu5Ac3Gal3(Neu5Ac6)GalNAc4Gal4GlcCer | GD1α |
| Gal3GalNAc4(Neu5Ac8Neu5Ac3)Gal4GlcCer | GD1b |
| Neu5Ac8Neu5Ac3Gal3GalNAc4(Neu5Ac3)Gal4GlcCer | GT1a |
| Neu5Ac3Gal3GalNAc4(Neu5Ac8Neu5Ac3)Gal4GlcCer | GT1b |
| Gal3GalNAc4(Neu5Ac8Neu5Ac8Neu5Ac3)Gal4GlcCer | GT1c |
| Neu5Ac8Neu5Ac3Gal3GalNAc4(Neu5Ac8Neu5c3)Gal4GlcCer | GQ1b |

*Nomenclature of Glycolipids*, IUPAC-IUB Joint Commission on Biochemical Nomenclature (Recommendations 1997); *Pure Appl. Chem.* (1997) 69: 2475-2487; *Eur. J. Biochem* (1998) 257: 293-298) (see, the worldwide web at chem.qmw.ac.uk/iupac/misc/glylp.html).

Exemplified end products further include those depicted in FIGS. 1-13. Additional end product glycolipids that can be produced using the mutant endoglycoceramidases of the present invention include the glycosphingolipids, glycosylsphingosines and ganglioside derivatives disclosed in co-pending patent applications PCT/US2004/006904 (which claims priority to U.S. Provisional Patent Application No. 60/452,796); U.S. patent application Ser. No. 10/487,841; U.S. patent application Ser. Nos. 10/485,892; 10/485,195, and 60/626,678.

Further modifications can be made to the glycolipids synthesized using the endoglycoceramide synthase of the present invention. Exemplary methods of further elaborating glycolipids produced using the present invention are set forth in WO 03/017949; PCT/US02/24574; US2004063911 (although each is broadly directed to modification of peptides with glycosyl moieties, the methods disclosed therein are equally applicable to the glycolipids and method of producing them set forth herein). Moreover, the glycolipid compositions of the invention can be subjected to glycoconjugation as disclosed in WO 03/031464 and its progeny (although each is broadly directed to modification of peptides with glycosyl moieties, the methods disclosed therein are equally applicable to the glycolipids and method of producing them set forth herein).

EXAMPLES

The following examples are provided by way of illustration only and not by way of limitation. Those of skill in the art will readily recognize a variety of non-critical parameters that could be changed or modified to yield essentially similar results.

Example I: Generating Mutant Endoglycoceramidases

Figure 14:
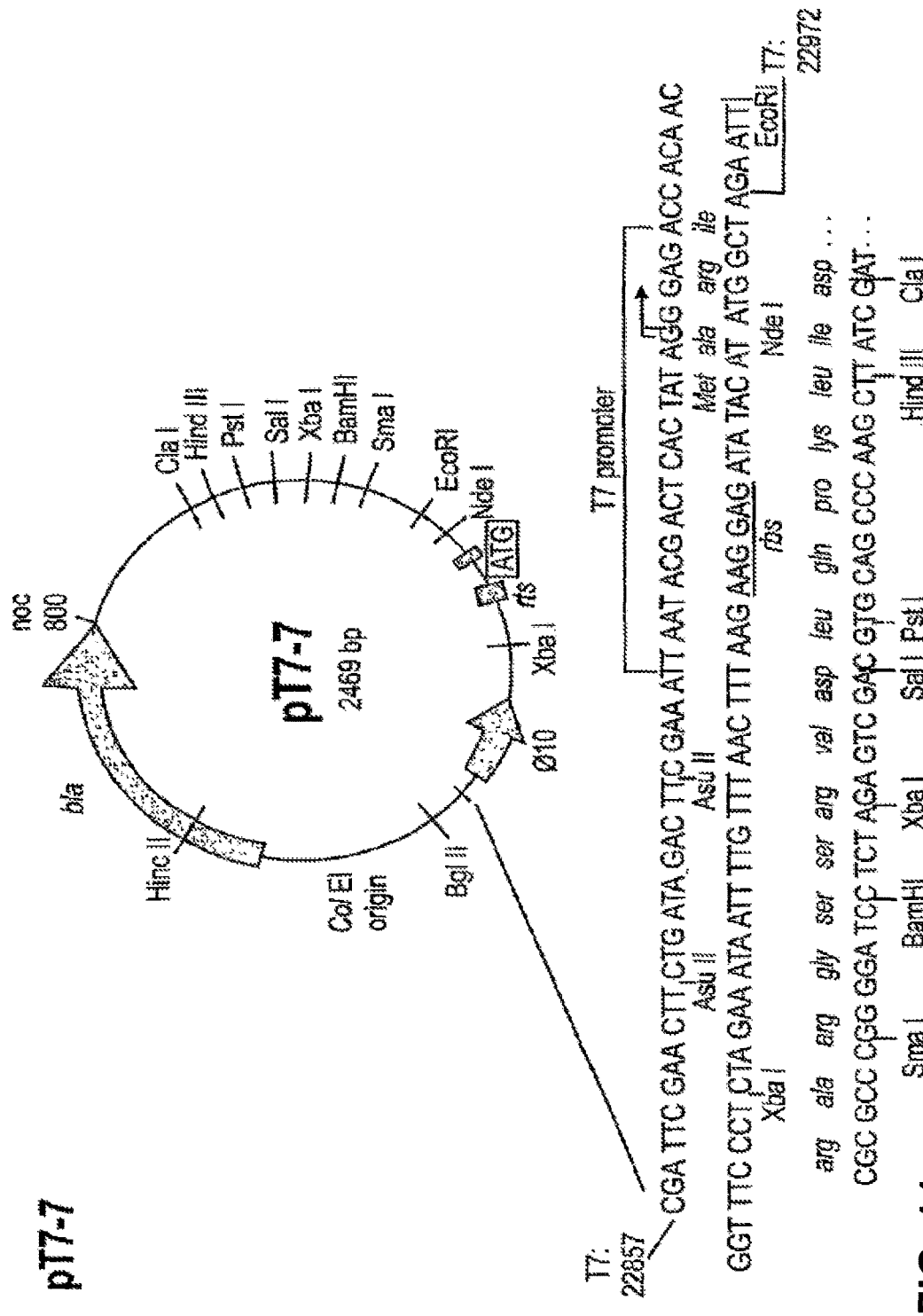
FIG. 14 is a schematic depiction of expression vector pT7-7, indicating restriction enzyme sites.

A synthetic endoglycoceramidase gene was produced by Blue Heron Biotechnology (EGCase1395). Subsequently the gene was subcloned into a pT7-7 expression vector (FIG. 14). Mutations at one of the nucleotides encoding Glu233 of endoglycoceramidase derived from *Rhodococcus* sp. M-777 (GenBank Accession No. AAB67050, SEQ ID NO:3), were introduced into the EGCase gene by a PCR-based method using five primer sets by combining the same 5' primer with five different 3' primers:

```
The 5' primer:
5'Copt
                                        (SEQ ID NO: 34)
AATTCGATTGGATCCCATATGAGCGGAAGCG The 3' primers:
3'Asp PstI
                                        (SEQ ID NO: 35)
TCGATTCTGCAGGGAGCCACCAAACGGGTCATTCATCAG 3'Gln PstI
                                        (SEQ ID NO: 36)
TCGATTCTGCAGGGAGCCACCAAACGGCTGATTCATCAG 3'Ala PstI-11-1
                                        (SEQ ID NO: 37)
CGGTCCCTGCAGGGAGCCACCAAACGGCGCATTCATCAG 3'Gly PstI-11-1
                                        (SEQ ID NO: 38)
CGGTCCCTGCAGGGAGCCACCAAACGGCCCATTCATCAG 3'Ser PstI-11-1
                                        (SEQ ID NO: 39)
CGGTCCCTGCAGGGAGCCACCAAACGGCGAATTCATCAG
```

The PCR program used for generating mutations was essentially as follows: the template and primers were first incubated at 95° C. for 5 minutes, Vent DNA polymerase (New England Biolabs) was then added, which was followed by 30 cycles of amplification: 94° C. for 1 minute, 55° C. for 1 minute, and 72° C. for 2 minutes.

PCR products were digested with NdeI and PstI, and pT7-7 vector was digested with NdeI, EcoRI, and PstI. Following purification of the digestion products from a 0.8% TAE agarose gel, the PCR products were subcloned into pT7-7 vector via a ligation reaction. Upon completion of the ligation reaction, the ligation product was electroporated into BL21DE3 LacZ⁻ cells, which were prepared from BL21DE3 cells (William Studier, Brookhaven National Laboratories, Upton, N.Y.) by disrupting the LacZ gene with a tetracycline or kanamycin resistance gene (generated at Neose Technologies, Inc.). Colonies were screened for PCR product insert. All EGCase mutants were confirmed by sequencing.

Example II: Hydrolytic Assays

An exemplary hydrolytic reaction had a volume of 50 μL, containing 20 μg of substrate (pre-dried lyso-GM2, GM2, or GM3, generated at Neose Technologies, Inc.), 25 μg of Taurodeoxycholic acid (Sigma, Cat #T-0875), 50 mM sodium acetate (pH 5.2), and 5-10 μL of crude cell lysate containing a wild-type or mutant EGCase. The hydrolytic mixture was incubated at 37° C. for 10 to 120 minutes.

Example III: Synthetic Assays

An exemplary synthetic reaction had a volume of 50 μL, containing 5 mM $MgCl_2$, 0.5% detergent, 0.3 mM ceramide-C-18 (pre-dried), 20 mM Tris-HCl (pH 7.5), and 0.36 mM 3' sialyl lactose fluoride (3' SLF). The detergents used in the reaction were Triton-X100 (0.5%), Taurodeoxycholic acid (25 μg), NP-40 (0.5%), Tween-80 (0.5%), 3-14 Zwittergent (0.5%), and Triton-CF54 (0.5%). The reaction times ranged from 2 to 16 h in various buffers ranging in pH from 5.2 to 8.0.

Example IV: TLC Analysis

5 μL of a hydrolytic or synthetic reaction was spotted on a TLC plate. The plate was then dried with a hair dryer set on low. The plate was run in an appropriate solvent system (solvent A: chloroform/methanol at 95:5 v/v, solvent B: 1-butyl alcohol/acetic acid/$H_2O$ at 2:1:1 v/v, solvent C: chloroform/methanol/$H_2O$/ammonium hydroxide at 60:40:5:3). The plate was then dried and stained with anisaldehye. The TLC plate was subsequently developed by heating on a hot plate set at three.

Example V

The following example illustrates the successful generation of a glycosynthase enzyme capable of performing the efficient glycosidic coupling between 3'-sialyllactosyl fluoride and a variety of lipid acceptors by performing selected modifications on the endoglycoceramidase II enzyme from *Rhodococcus* M-777 (SEQ ID NO:3).

Cloning of Exemplified Mutant Endoglycoceramidase E351S

The DNA sequence of the wild-type EGCase gene from *Rhodococcus* was used as a template for the design of the construct. Using an overlapping PCR strategy, an amino acid substitution of serine for glutamic acid at amino acid position 351 relative to the wild-type enzyme was engineered into the coding sequence (see, primer sequences SEQ ID NOs:40-47). The final coding sequence was also truncated at amino acid 29 relative to the wild-type enzyme in order to mimic the mature version of the enzyme that is normally generated during secretion (SEQ ID NOs:48 and 49). Restriction sites were engineered onto the ends of the coding sequence (NdeI and XhoI, respectively) in order to ligate to the corresponding sites in frame with the six his tag from the pET28A vector (Novagen/EMD Biosciences, San Diego Calif.). This construct was confirmed to be correct by restriction and sequence analysis and then was used to transform the E.coli strain BL21(DE3) (Novagen) using 50 mcg/ml Kanamycin selection. An individual colony was used to inoculate a culture of Maritone-50 mcg/ml Kanamycin that was incubated for 16 hrs at 37° C. A sample of culture was mixed to achieve 20% glycerol and aliquots were frozen at −80° C. and referred as stock vials.

Mutant Endoglycoceramidase (EGC) Expression and Purification

Wild-type EGC and the following EGC mutants; E351A, E351D, E351D, E351G, and E351S have been successfully expressed and purified. The expression levels for the EGC variants are quite high, therefore cell cultures of 50 ml were used to produce the enzymes.

Cells from a −80° C. freezer stock were directly inoculated into 50 ml Typ broth and were grown at 37° C. to saturation. The temperature was then lowered to 20° C. and protein production was induced by addition of IPTG to 0.1 mM (due to solubility issues, the E351G mutant was expressed at an IPTG concentration of 0.05 mM to prevent aggregation). After 8-12 hours, the cells are harvested by centrifugation and the pellet was resuspended in 2.5 ml BugBuster protein extraction reagent (Novagen). Cell lysis was allowed to proceed for 20 min, and the cell debris was then removed by centrifugation.

The cell lysate was then applied to a 1 ml Ni-NTA column (Amersham), which was then washed with two column volumes of binding buffer (20 mM sodium phosphate, pH 7.0, containing 0.5 M NaCl). EGC was eluted by the stepwise addition of imidazole to a final concentration of 0.5

Figure 16:
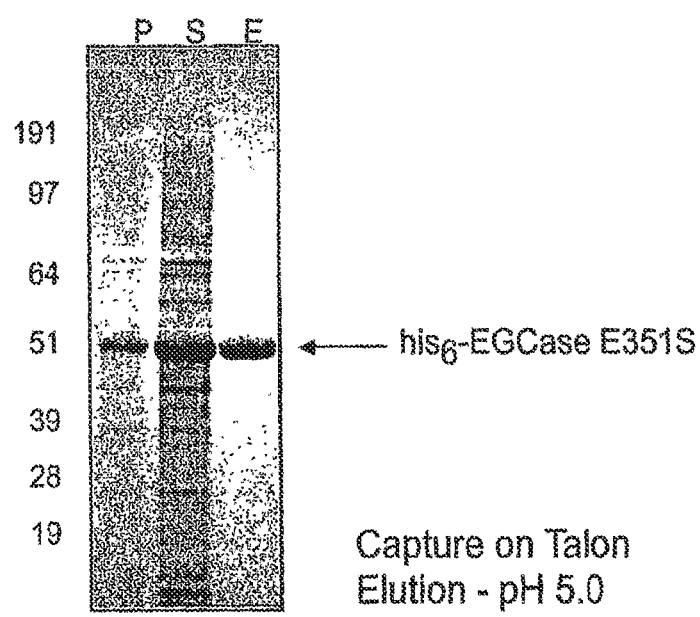
FIG. 16 illustrates SDS-PAGE analysis of EGCase purification. Lanes: 1) insoluble pellet fraction; 2) lysate soluble fraction; and 3) purified fraction.

M (EGC elutes between 0.2 and 0.3 M imidazole). Fractions containing EGC were identified by SDS-PAGE. The purification gave a protein of >95% purity after a single step. The expression and purification of exemplified *Rhodococcus* EGC mutant E351S is depicted in FIG. 16.

Fractions containing EGC were pooled and the buffer was changed to 25 mM NaOAc, pH 5.0, containing 0.2% Triton X-100 using an Amicon centrifugal ultrafiltration device (MWCO=10, 000 Da). At this time, the protein was concentrated to a final volume of approximately 2 ml.

Protein concentration was then assessed using the Bradford method. The purification generally yielded about 10 mg EGC (180-200 mg per liter of expression culture). The enzyme was stable in this form for at least 3 months.

Enzymatic Synthesis of Lyso-$GM_1$ by Mutant EGC Enzymes

Figure 17:
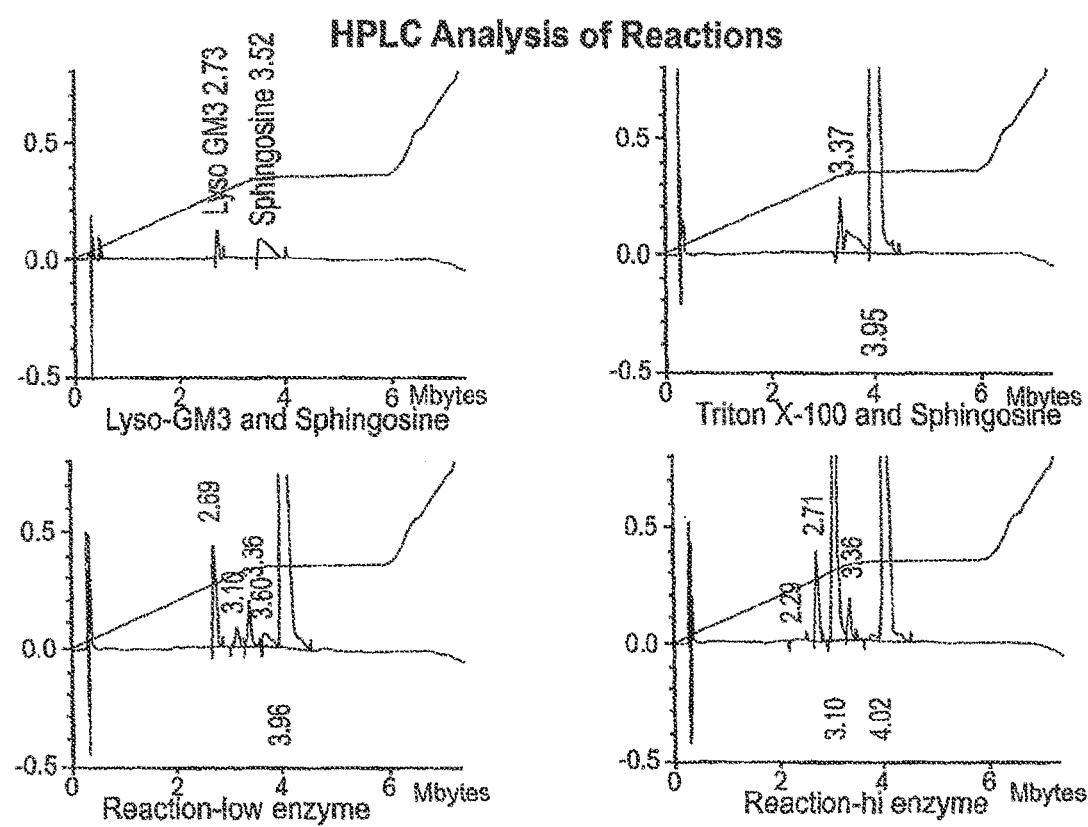
FIG. 17 illustrates a reaction analysis by HPLC showing the synthesis of Lyso-GM3 after 12 hrs. Top panels: control runs. Bottom panels: reaction runs.

Reactions were performed in 25 mM NaOAc (pH 5.0) containing 0.1-0.2% Triton X-100. A typical reaction mixture contained approximately 50 mg/ml of a fluorinated GM1 sugar donor (GM1-F), 15 mg/ml of an acceptor sphingosine, and 2.0 mg/ml of the appropriate EGC mutant in a total reaction volume of 50 µl. Under these conditions, the reaction proceeds to >90% completion within 12 hours at 37° C. based on TLC analysis. Transfer of the fluorinated GM1 sugar donor was monitored using an HPLC reverse phase method on a Chromolith RP-8e column with eluants of 0.1% trifluoroacetic acid (TFA) in acetonitrile (ACN) to 0.1% TFA in $H_2O$. Exemplified results of HPLC monitoring of a glycosynthase reaction for a *Rhodococcus* E351S mutant is depicted in FIG. 17.

Enzymatic Synthesis of Lyso-$GM_3$ by Mutant EGC Enzymes

Reactions were performed in 25 mM NaOAc (pH 5.0) containing 0.2% Triton X-100. A typical reaction mixture contained approximately 10 mM 3'-sialyllactosyl fluoride (3'-SLF), 20 mM of the acceptor D-erythro-sphingosine, and 0.5 mg/ml of the appropriate EGC mutant in a total reaction volume of 100 µl. Under these conditions, the reaction proceeds to >90% completion within 12 hours at 37° C. based on TLC analysis. In addition to D-erythro-sphingosine, Table 1, above, shows the structures of other acceptor species that have been used in glycosynthase reactions with 3'-SLF.

Essentially all of the 3'-SLF was consumed in the enzymatic reaction with D-erythro-sphingosine. Thus this reaction delivered a conservative estimate of a minimum of 90% turnover with respect to 3'-SLF. Running solvent was $CHCl_3$/MeOH/0.2% $CaCl_2$ (5:4:1), with detection by orcinol-$H_2SO_4$ stain. Purification of the lyso-$GM_3$ product was achieved using a combination of normal phase and reversed phase SepPak cartridges (Waters). The identity of the product as lyso-$GM_3$ was supported by mass spectrometry and NMR.

Figure 18:
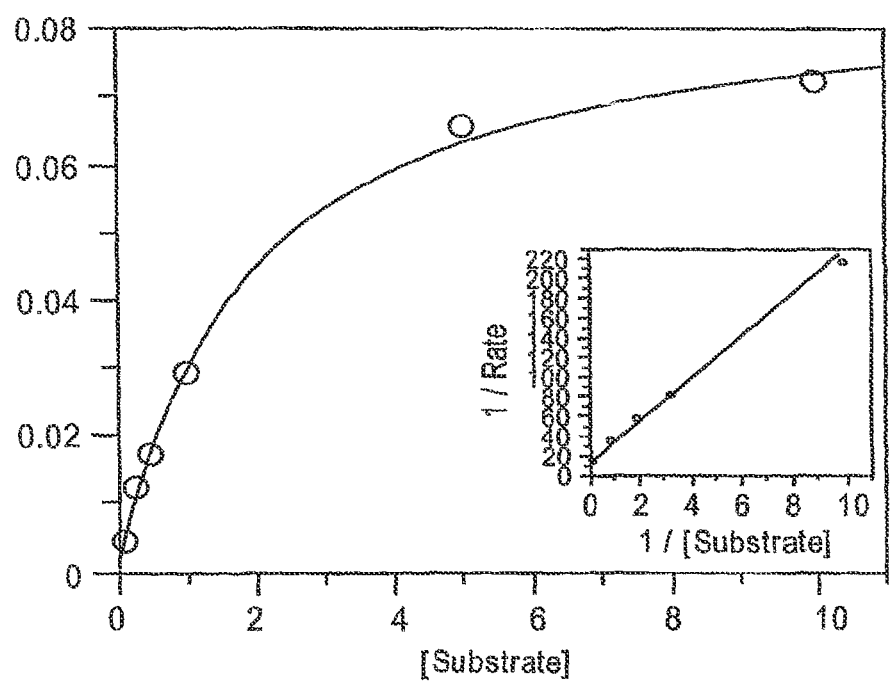
FIG. 18 illustrates a Michaelis-Menten curve for wild-type *Rhodococcus* EGC using 2,4-dinitrophenyl lactoside as the substrate.
Figure 19A:
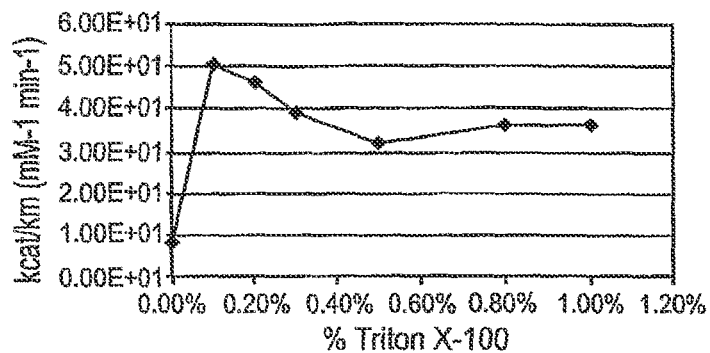
FIGS. 19A-19C illustrate variation of kcat, Km, and kcat/Km with increasing detergent concentration for wild-type *Rhodococcus* EGC.
Figure 19B:
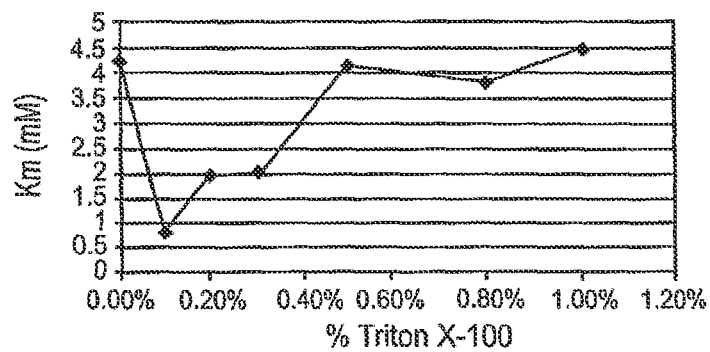
Figure 19C:
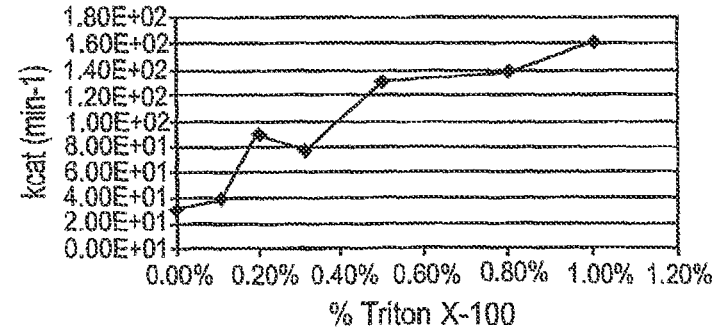
Figure 20:
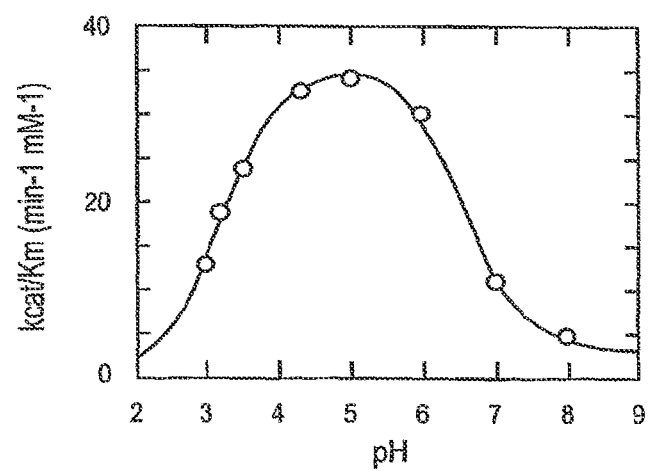
FIG. 20 illustrates pH rate profile for wild-type *Rhodococcus* EGC. Estimated pKa values for the catalytic glutamate residues are 3.2 and 6.5.

Example VI: Kinetic Parameters of Wild-Type *Rhodococcus* M-777 Endoglycoceramidase Using 2,4-dinitrophenyl lactoside as a substrate, the *Rhodococcus* M-777 EGC enzyme has a Km of approximately 2 mM, and a kcat of 90 min-1 (FIG. 18). The dependence of the activity on detergent concentration was also investigated. It was found that in the absence of detergent, the rate of hydrolysis was very low. With the addition of Triton X-100 to 0.1%, the kcat/Km increased dramatically, and gradually decreased with further additions of detergent. The dependence of kcat/Km on detergent concentration leveled off at concentrations greater than 0.5%; increasing the detergent concentration caused a steady increase in both kcat and Km up to a concentration of 1% (FIGS. 19A-C). The pH dependence of the hydrolysis activity was also investigated. As expected, the maximal kcat/Km is observed around pH 5 (FIG. 20).

Example VII: Expression of Wild-Type *Propionibacterium* Acnes Endoglycoceramidase in *E. coli*

The expression level of *P. acnes* EGC enzyme was extremely high, likely exceeding 200 mg/l. However, the expressed protein exclusively formed inclusion bodies under a variety of conditions. This propensity to form inclusion bodies is also observed for the *Rhodococcus* enzyme, but it is possible to minimize this tendency using Tuner cells in conjunction with a low induction temperature (<20° C.) and low concentration of IPTG (0.1 mM). These tactics proved unsuccessful with the *P. acnes* enzyme. Furthermore, the *P. acnes* enzyme was found to express at a very high level even in the absence of IPTG, with inclusion bodies forming during the pre-induction growth phase.

A series of experiments was performed to try to bring at least some protein into the soluble fraction, including:

variation of induction temperature (16-37° C.) in conjunction with variation of [IPTG] (0-0.1 mM);

pre-induction growth at room temperature to lower the levels of background expression;

transformation into BL21 pLysS (to suppress background expression) with variation of conditions as described above;

expression from a lac promoter rather than the T7 system with the above variations;

heat shock of the cells prior to induction (42° C. and 60° C. for 2 min in separate experiments) to induce chaperone expression;

adding a pelB signal sequence to direct secretion into the periplasm; and attempts were also made to resolubilize the inclusion by denaturation with either urea (8 M) or guanidinium HCL (2 M) as the chaotropic agent followed by either iterative lowering of the denaturant concentration by dialysis or removal of the denaturant by first adsorbing the protein onto a Ni-NTA column and then decreasing the denaturant concentration using a linear gradient.

Figure 21:
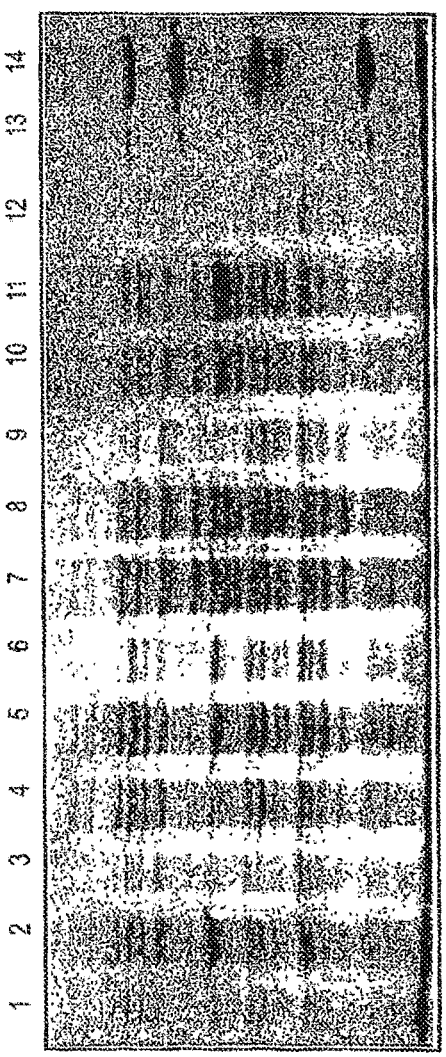
FIG. 21 illustrates expression in *E. coli* of *Propionibacterium acnes* wild-type EGC under a variety of conditions. In each series of three lanes, the first shows the pre-induction expression level, the second the total cell fraction after induction, and the third the soluble fraction of the cell lysate. In all cases, induction was performed at 18° C. Lanes 1-3: BL21 pLysS, 0.1 mM IPTG, M9 media. Lanes 4-6: Tuner, 0.1 mM IPTG, M9. Lanes 7-9: BL21 pLysS, 0.01 mM IPTG, Typ media. Lanes 10-12: Tuner, 0.1 mM IPTG, Typ media. Lane 14: Molecular weight standards.

Soluble *P. acnes* EGC was obtained by performing the growth and induction steps in M9 minimal medium using Tuner cells with induction overnight at 18° C. in the presence of 0.1 mM IPTG (essentially the same conditions used for the *Rhodococcus*, except with minimal media rather than rich) (FIG. 21, lane 6). In a simultaneous experiment using BL21 pLysS as the expression strain, inclusion bodies were formed, presumably due to the action of the lactose permease in increasing the internal IPTG concentration to a level where expression still proceeds at a very high rate even in minimal media. Simultaneously employing the following three tactics lowered the rate of protein production sufficiently to obtain soluble *P. acnes* EGC enzyme while retaining the Histag: (i) minimal media for growth and expression, (ii) a very low IPTG concentration, and (iii) expression in the lactose permease deficient Tuner cells. Under these conditions, hydrolysis activity on both 2,4-dinitrophenyl lactoside and GM3 ganglioside in the cell extract was detected.

A gene construct for an E319S mutant EGC was prepared in parallel with the wild-type sequence. This mutant enzyme catalyzed the glycosynthase reaction as well.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A method of producing a glycolipid, the method comprising:
    contacting a donor substrate having an activated saccharide moiety and an acceptor substrate with a variant of a wild-type endoglycoceramidase in a reaction mixture, wherein the variant catalyzes the transfer of the saccharide moiety from the donor substrate to the acceptor substrate at a rate that exceeds hydrolysis of the glycolipid, wherein the wild-type endoglycoceramidase has a nucleophilic region comprising a (Ile/Met/Leu/Phe/Val)-(Leu/Met/Ile/Val)-(Gly/Ser/Thr)-Glu/Asp)-(Phe/Thr/Met/Leu)-(Gly/Leu/Phe) sequence, said variant comprises an amino acid substitution of the Glu residue within said sequence of SEQ ID NO: 6, wherein the amino acid substitution is selected from Ser, Gly, and Ala, and wherein said variant comprises a (Met/Val/Leu)-Leu-Asp-(Met/Phe/Ala)-His-GlnAsp-(Met/Val/Leu)-X-(Ser/Asn) sequence at amino acid residues 129-138 of SEQ ID NO: 6 and X can be any amino acid.

2. The method of claim 1, wherein said variant endoglycoceramidase exhibits increased catalytic activity in the transfer of the saccharide moiety from the donor substrate to the acceptor substrate as compared to the wild-type endoglycoceramidase.

3. The method of claim 1, wherein said variant exhibits decreased catalytic activity in hydrolyzing the glycolipid as compared to the wild-type endoglycoceramidase.

4. The method of claim 1, wherein the acceptor substrate is sphingosine.

5. The method of claim 1, wherein the acceptor substrate is a sphingosine analog having a structure defined by the formula:

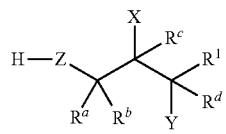

Formula III wherein Z is a member selected from O, S, $C(R^2)_2$ and $NR^2$; X is a member selected from H, $-OR^3$, $-NR^3R^4$, $CR^3$, and $-CHR^3R^4$; $R^2$, $R^3$ and $R^4$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, $-C(=M)R^5$, $-C(=M)-Z^1-R^5$, $-SO_2R^5$, and $SO_3$; wherein M and $Z^1$ are members independently selected from O, $NR^6$ or S; Y is a member selected from H, $-OR^7$, $-SR^7$, $-NR^7R^8$, substituted or unsubstituted alkyl, substituted or unsubstituted heteroalkyl, substituted or unsubstituted aryl, substituted or unsubstituted heteroaryl, and substituted or unsubstituted heterocycloalkyl, wherein $R^5$, $R^6$, $R^7$ and R[8] are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl; and R[a], R[b], R[c] and R[d] are each independently H, substituted or unsubstituted alkyl, substituted or unsubstituted heteroalkyl, substituted or unsubstituted aryl, substituted or unsubstituted heteroaryl, and substituted or unsubstituted heterocycloalkyl.

6. The method of claim 1, wherein the acceptor substrate is a sphingosine analog selected from D-erythro-sphingosine, D-erythro-sphinganine, L-threo-sphingosine, L-threo-dihydrosphingosine, D-erythro-phytosphingosine, and N-ocatanoyl-D-erythro-sphingosine.

7. The method of claim 1, wherein the acceptor substrate is a molecule having a formula selected from:

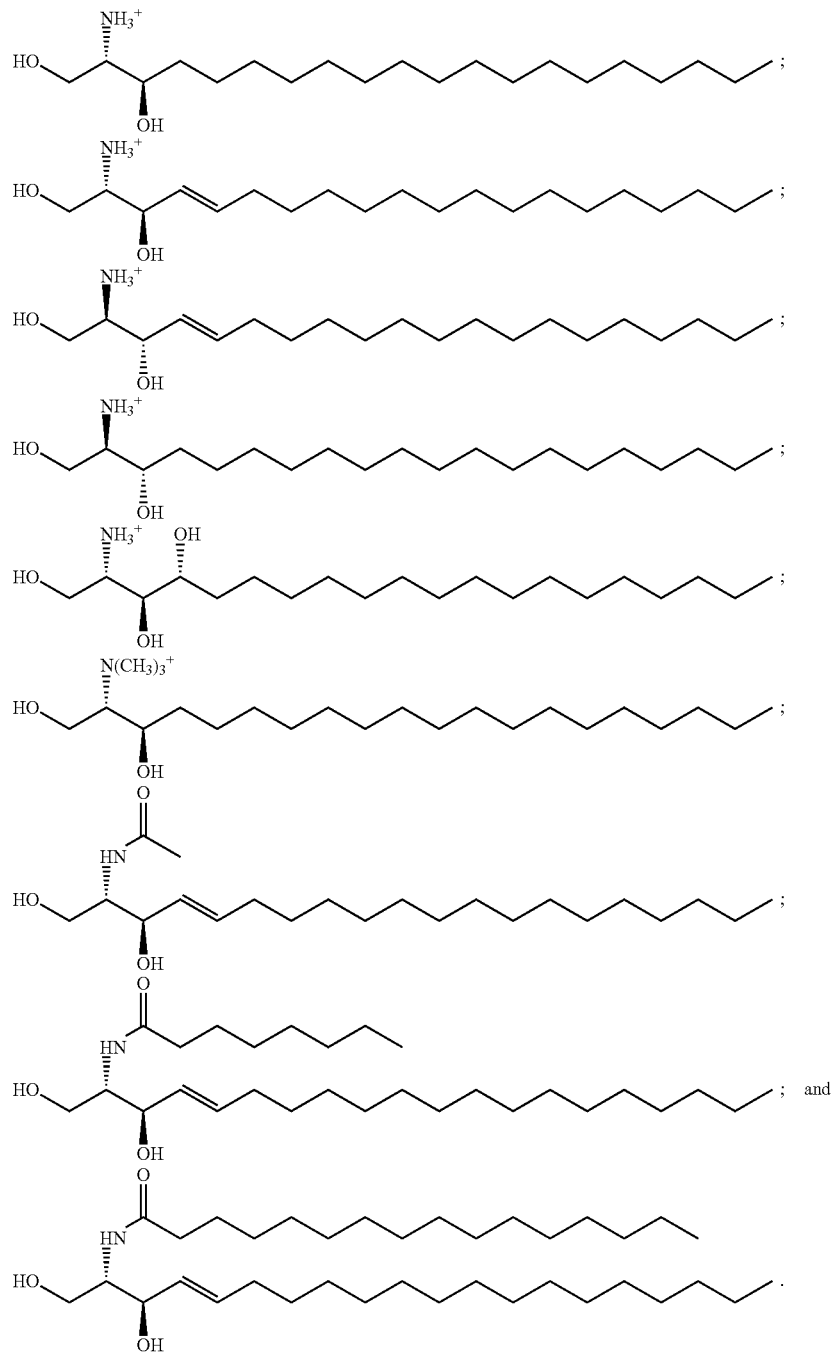

8. The method of claim 1, wherein the donor substrate is a glycosyl fluoride.

9. The method of claim 1, wherein said variant achieves a reaction yield of at least about 70%.

10. The method of claim 1, wherein the donor substrate and acceptor substrate are contacted with the variant at a temperature ranging from about 20° C. to 37° C.

11. The method of claim 1, wherein the reaction mixture comprises a solubilizing detergent.

12. The method of claim 11, wherein the solubilizing detergent is Triton X-100.

13. The method of claim 1, wherein said method further comprises purifying said glycolipid from the reaction mixture.

14. The method of claim 1, wherein the glycolipid is a ganglioside selected from disialoganglioside ($GD_{1a}$, $GD_{1\alpha}$, $GD_{1b}$, $GD_2$, $GD_3$), galactosylganglioside ($Gg_3$, $Gg_4$), monosialyltetrahexosylceramide ($GH_1$, $GH_2$, $GH_3$), monosialoganglioside ($GM_1$, $GM_{1b}$, $GM_2$, $GM_3$, Fuc-$GM_1$), pentasialoganglioside ($GP_1$, $GP_2$, $GP_3$), tetrasialoganglioside ($GQ_{1b}$, $GQ_{1B}$, $GQ_{1\beta}$, $GQ_{1c}$, $GQ_2$, $GQ_3$), trisialoganglioside ($GT_{1a}$, $GT_{1b}$, $GT_{1c}$, $GT_{1\beta}$, $GT_{1c}$, $GT_2$, and $GT_3$).

15. The method of claim 1, wherein the glycolipid is monosialoganglioside 1 ($GM_1$).

16. The method of claim 15, wherein the glycolipid is lysomonosialoganglioside 1 (lyso-$GM_1$).

* * * * *